US011225480B2

(12) United States Patent
Sheth et al.

(10) Patent No.: US 11,225,480 B2
(45) Date of Patent: Jan. 18, 2022

(54) MALIC ENZYME INHIBITORS

(71) Applicant: SUN PHARMA ADVANCED RESEARCH COMPANY LTD, Mumbai (IN)

(72) Inventors: Gaurav Sanjivkumar Sheth, Vadodara (IN); Sabbirhusen Yusufbhai Chimanwala, Vadodara (IN); Tushar Mukund Jarag, Vadodara (IN); Aishwarya Hampiholi, Pune (IN); Saikat Maity, Medinipur (IN); Prabal Sengupta, Vadodara (IN); Gulamnizami Abdulsattar Qureshi, Vadodara (IN); Umesh Vishnu Chaudhari, Vadodara (IN); Raj Gopal Venkat, Hyderabad (IN); V. S. N. Murty Kadiyala, Vadodara (IN); Sairam V V M Kalapatapu, Hyderabad (IN); Vaibhav Jain, Sagar (IN); Trinadha Rao Chitturi, Vadodara (IN)

(73) Assignee: SUN PHARMA ADVANCED RESEARCH COMPANY LTD, Mumbai (IN)

( * ) Notice: Subject to any disclaimer, the term of this patent is extended or adjusted under 35 U.S.C. 154(b) by 0 days.

(21) Appl. No.: 17/073,017

(22) Filed: Oct. 16, 2020

(65) Prior Publication Data
US 2021/0115038 A1    Apr. 22, 2021

(30) Foreign Application Priority Data

Oct. 17, 2019    (IN) .............................. 201921033255

(51) Int. Cl.
| | | |
|---|---|---|
| *C07D 401/12* | (2006.01) | |
| *C07D 401/14* | (2006.01) | |
| *C07D 409/12* | (2006.01) | |
| *C07D 413/14* | (2006.01) | |
| *C07D 471/04* | (2006.01) | |
| *C07D 209/08* | (2006.01) | |
| *C07D 209/18* | (2006.01) | |
| *C07D 209/42* | (2006.01) | |
| *C07D 213/74* | (2006.01) | |
| *C07D 213/81* | (2006.01) | |
| *C07D 295/182* | (2006.01) | |
| *C07D 493/08* | (2006.01) | |

(52) U.S. Cl.
CPC ......... *C07D 471/04* (2013.01); *C07D 209/08* (2013.01); *C07D 209/18* (2013.01); *C07D 209/42* (2013.01); *C07D 213/74* (2013.01); *C07D 213/81* (2013.01); *C07D 295/182* (2013.01); *C07D 401/12* (2013.01); *C07D 401/14* (2013.01); *C07D 409/12* (2013.01); *C07D 493/08* (2013.01)

(58) Field of Classification Search
CPC ................ C07D 401/14; C07D 401/12; C07D 409/12; C07D 413/14; C07D 471/04
See application file for complete search history.

(56) References Cited

U.S. PATENT DOCUMENTS 9,539,323 B2    1/2017 Sukhatme et al.

FOREIGN PATENT DOCUMENTS

| CN | 107721975 | * | 2/2018 |
| EP | 0595241 A2 |   | 5/1994 |

OTHER PUBLICATIONS

Hsieh, et al., A Small-molecule Inhibitor Suppresses the Tumor-associated Mitochondrial NAD(P)+-dependent Malic Enzyme (ME2) and Induces Cellular Senescence, Oncotarget, 2015, 6:24, 20084-20098.
Wen, et al., Discovery of a Novel Inhibitor of NAD(P)+-dependent Malic Enzyme (ME2) by High-Throughput Screening, Acta Pharmacologica Sinica, 2014, 35:674-684.
International Search Report issued in PCT/IB2020/059785 dated Jan. 29, 2021.

* cited by examiner

*Primary Examiner* — Brian E McDowell
(74) *Attorney, Agent, or Firm* — Blank Rome LLP

(57) ABSTRACT

The present invention relates to novel compounds useful as malic enzyme (ME) inhibitors, processes for their preparation and use of these compounds for the therapeutic treatment of disorders mediated by ME such as cancers (e.g. pancreatic ductal adenocarcinoma (PDAC)) in humans. The novel compounds have a structure according to Formula I Formula I or a pharmaceutically acceptable salt, stereoisomer or deuterated analog thereof, wherein X, $R_1$, $R_2$ and Y are as described herein.

11 Claims, No Drawings

MALIC ENZYME INHIBITORS

RELATED APPLICATIONS

This application claims priority to Indian Provisional Patent Application No. 201921033255 filed on Oct. 17, 2019, the contents of which is hereby incorporated by reference in its entirety.

FIELD OF THE INVENTION

The present invention relates to compounds useful as malic enzyme (ME) inhibitors, process for their preparation, and use of the compounds for the therapeutic treatment of disorders mediated by ME, such as cancer (e.g., in humans).

BACKGROUND OF THE INVENTION

One hallmark of cancer is excessive growth and uncontrolled proliferation. Cancer cells need energy and, using this energy, cell membranes, nucleotides, and proteins grow in cells and proliferate. Once cancer is initiated, alterations in key signaling pathways accumulate and lead to loss of control over metabolism as well as proliferation (Hanahan D, Weinberg R A., Hallmarks of Cancer: the next generation. Cell, 2011; 144(5): 646-74).

Metabolic alterations provide the energetic and anabolic demands of enhanced cell proliferation. In order to meet these requirements, cancer cells use various metabolic approaches, such as high aerobic glycolysis, glutaminolysis, and fatty acid synthesis. Pyruvate, NAD, and NADPH have key roles in supporting the advancement of glycolysis and fatty acid synthesis. Malic enzyme is an important enzyme in metabolism that catalyzes the conversion of malate to pyruvate with the concomitant regeneration of NADPH. Malic enzyme, by producing pyruvate and NADPH, provides abundant vital resources for glycolysis and fatty acid synthesis. Malic enzyme expression is significantly up-regulated in different types of human cancers.

Malic enzymes are oxidative decarboxylases that catalyze the conversion of L-malate to pyruvate and $CO_2$ and use NAD+ or NAD(P)+ as a cofactor. In mammals, there are three malic enzyme isoforms with different cofactor specificities: the cytosolic NADP+-dependent malic enzyme 1 (ME1), the mitochondrial NAD(P)+-dependent malic enzyme 2 (ME2), and the mitochondrial NADP+-dependent malic enzyme 3 (ME3).

Cytoplasmic ME1 decarboxylates malate to form pyruvate and ultimately NADPH. In cancer cells, pyruvate generated in this manner is utilized for lactate fermentation. It has been reported that wild-type p53 represses ME1 expression and hence ME1 overexpression is associated with cancers carrying mutated p53. Malic enzyme 1 is the link to energy metabolism, redox status, and EMT specifically in cancers of squamous cell (oral, head and neck), nasopharynx, synovium, lung, pancreas, gastric, oesophageal, liver and breast (see, e.g., Ruocen Liao et al., ME1 promotes basal-like breast cancer progression and associates with poor prognosis, Sci. Rep., 2018, 8:16743).

It has also been reported that ME2 enzyme activity increased with progression to neoplasia in a rat tracheal epithelial line and in Morris hepatomas (see, e.g., Jian-Guo Ren et al., Knockdown of Malic Enzyme 2 Suppresses Lung Tumor Growth, Induces Differentiation and Impacts PI3K/AKT Signaling, Sci. Rep., 2014, 4:5414). The first functional connection between ME2 expression and cancer was reported in ME2 knockdown (KD) in K562 cells and this led to erythroid differentiation in chronic myelogenous leukemia in K562 cells. ME2 also plays a more important role in A549 cell survival in tumor cells than in normal lung cells. ME2 depletion also induced senescence and suppressed tumor growth in the p532/2 HCT1 16 xenograft model.

Genomic deletions are a key driver of virtually all cancers. During cancer progression, many cancer cells delete tumour-suppressor genes that block tumour development. This deletion process often also removes some neighbouring genes. The partial or complete loss of these neighbouring genes can make cancer cells vulnerable to therapeutic targeting—a concept known as collateral lethality.

In mammals, there is a third malic enzyme (ME3) which is NADP+-dependent. Dey et al., (Nature, 2017 Feb. 2; 542(7639):119-123) report that silencing of ME3 when Smad4 and ME2 are co-deleted leads to collateral lethality. There could be several possible unexplored independent functions of ME3 and whence ME3 inhibitors can be useful in several cancers as well.

Pancreatic cancer is one of the leading causes of cancer deaths in western societies, with the worst prognosis. It is the third leading cause of cancer deaths in the United States (US) alone (Lancet Oncol. 2017 June; 18(6):770-778) and is projected to be the second leading cause of cancer-related deaths in US by 2030 (Endosc Ultrasound, 2017 December; 6 (Suppl 3): S58-S61). Even for early-stage disease, recurrence is high. Although recent combination therapies for metastatic pancreatic ductal adenocarcinoma (PDAC) have improved the median overall survival (mOS) by up to 5 months, the overall prognosis remains almost unchanged, and novel therapies are desperately needed. The majority of patients at diagnosis are unresectable, as the disease remains symptomatically silent during the early stages, and no effective screening test exists (Clin Cancer Res., 2017 Apr. 1; 23(7):1670-1678).

Pancreatic cancer originates from exocrine cells of the pancreas, and among all exocrine tumors, pancreatic ductal adenocarcinoma (PDAC) is the most common type of pancreatic neoplasm, accounting for more than 90% of pancreatic tumors (Prog. Mol. Biol. Transl. Sci., 2016; 144:241-275). In spite of intense research efforts and the development of numerous new cancer drugs and treatment strategies over the past four decades, there has been no significant improvement in overall patient survival, and death rates are almost equivalent to incidence rates.

Pancreatic cancers are accompanied by activating mutations in KRAS oncogene in >90% of cases, and subsequent loss of tumor suppressors INK4A/ARF, TP53 and SMAD4 (Genes Dev., 2003 Dec. 15; 17(24):3112-26). Oncogenic Kras (KrasG12D) is a major driver in PDAC initiation, with loss in tumor suppressor genes. Constitutive KrasG12D signaling drives uncontrolled proliferation and enhances survival of cancer cells through the activation of its downstream signaling pathways, such as the MAPK and PI3K-mTOR pathways. To meet the increased anabolic needs of enhanced proliferation, cancer cells require both sufficient energy and biosynthetic precursors as cellular building blocks to fuel cell growth. In cancer cells, metabolic pathways are rewired in order to divert nutrients, such as glucose and glutamine, into anabolic pathways to satisfy the demand for cellular building blocks. It has been reported that the reprogramming of tumor metabolism is under the control of various oncogenic signals (J. Oral Maxillofac Pathol., 2017 May-August; 21(2):244-251). The Ras oncogene in particular has been shown to promote glycolysis.

European Patent Publication No. EP 0595241 A2 discloses a method for inhibiting the growth and proliferation of mammalian tumor cells by examining the expression of specific isoforms of malic enzyme and specifically inhibiting the malate enzyme isoform which is overexpressed.

U.S. Pat. No. 9,539,323 discloses the use of a malic enzyme 2 inhibitor for treating a subject having cancer.

There is a continuing need for new compounds useful as malic enzyme (especially ME3) inhibitors.

SUMMARY OF THE INVENTION

In one aspect, the present invention provides a method of inhibiting a malic enzyme in a subject comprising administering to the subject in need thereof a compound of Formula I

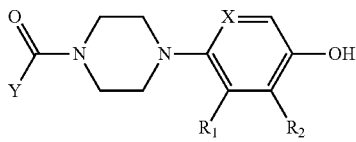

Formula I or a pharmaceutically acceptable salt, stereoisomer or deuterated analog thereof, wherein
X is CH or nitrogen;
$R_1$ is selected from hydrogen, $CH_3$, —COOH, fluoro and CN;
$R_2$ is selected from hydrogen, $CH_3$, —COOH, fluoro and CN; and
Y is selected from substituted or unsubstituted $C_{1-5}$ alkyl, substituted or unsubstituted $C_{2-4}$ alkenyl, substituted or unsubstituted 5 to 14 membered heteroaryl ring containing one, two or three heteroatoms each independently selected from nitrogen, oxygen, and sulfur, substituted or unsubstituted 5 to 14 membered heterocycloalkyl group containing one, two or three heteroatoms each independently selected from nitrogen and oxygen, substituted or unsubstituted $C_{3-15}$ cycloalkyl, substituted or unsubstituted $C_{3-15}$ cycloalkyl$C_{1-6}$alkyl, substituted or unsubstituted $C_{6-14}$ aryl, substituted or unsubstituted $C_{6-14}$aryl$C_{1-6}$alkyl, substituted or unsubstituted $C_{6-14}$aryl$C_{2-5}$alkenyl, substituted or unsubstituted 5 to 14 membered heteroaryl$C_{1-6}$alkyl, and substituted or unsubstituted 5 to 14 membered heterocycloalkyl$C_{1-6}$alkyl.

In another aspect, the present invention provides a compound of Formula I

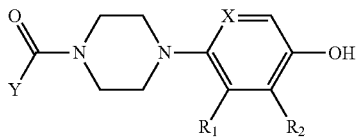

Formula I or a pharmaceutically acceptable salt, stereoisomer or deuterated analog thereof, wherein
X is CH or nitrogen;
$R_1$ is selected from hydrogen, $CH_3$, —COOH, fluoro and CN;
$R_2$ is selected from hydrogen, $CH_3$, —COOH, fluoro and CN;
Y is selected from substituted or unsubstituted $C_{1-5}$ alkyl, substituted or unsubstituted $C_{2-4}$ alkenyl, substituted or unsubstituted 5 to 14 membered heteroaryl ring containing one, two or three heteroatoms each independently selected from nitrogen, oxygen, and sulfur, substituted or unsubstituted 5 to 14 membered heterocycloalkyl group containing one, two or three heteroatoms each independently selected from nitrogen and oxygen, substituted or unsubstituted $C_{3-15}$ cycloalkyl, substituted or unsubstituted $C_{3-15}$ cycloalkyl$C_{1-6}$alkyl, substituted or unsubstituted $C_{6-14}$ aryl, substituted or unsubstituted $C_{6-14}$aryl$C_{1-6}$alkyl, substituted or unsubstituted $C_{6-14}$aryl$C_{2-5}$alkenyl, substituted or unsubstituted 5 to 14 membered heteroaryl$C_{1-6}$alkyl, and substituted or unsubstituted 5 to 14 membered heterocycloalkyl$C_{1-6}$alkyl;

with the proviso that (i) when X is CH, then Y is selected from:

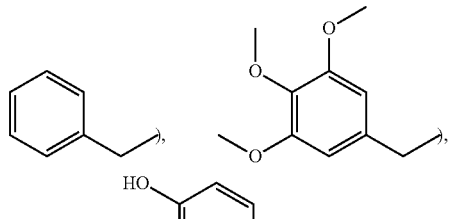

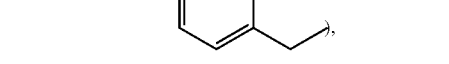

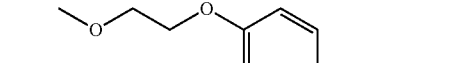

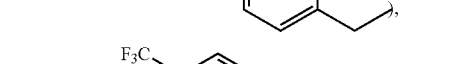

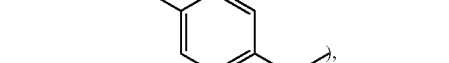

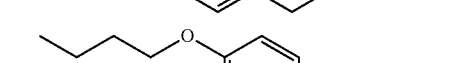

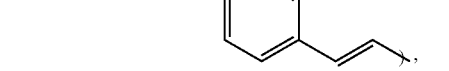

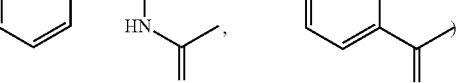

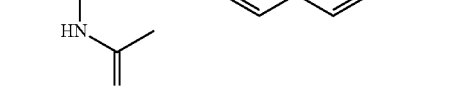

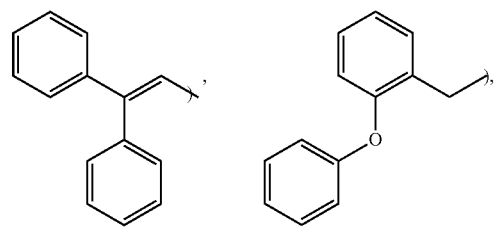
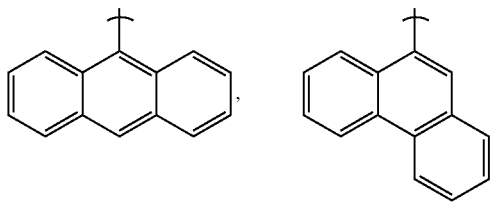
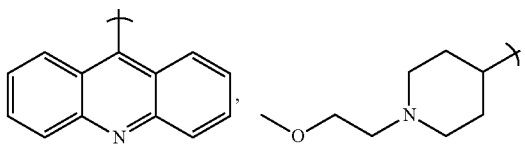
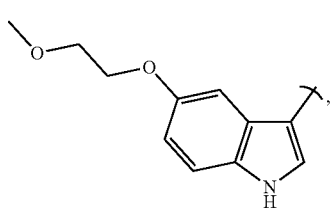
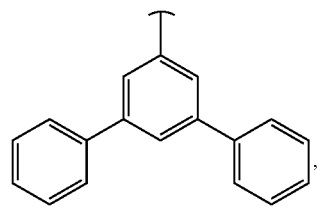
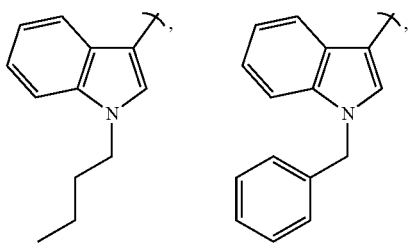
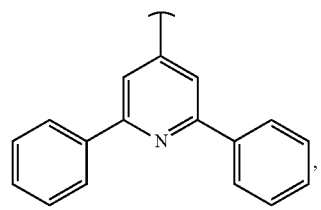
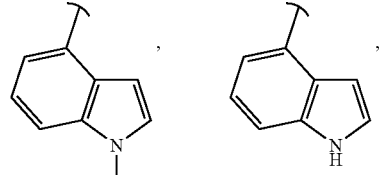
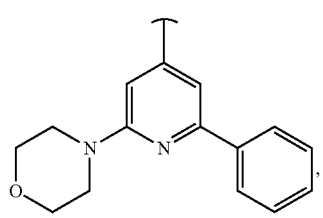
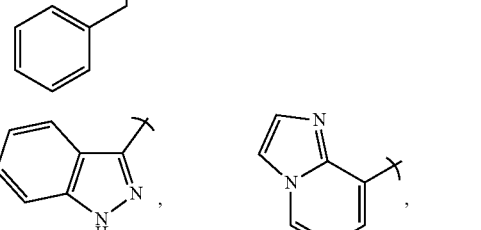
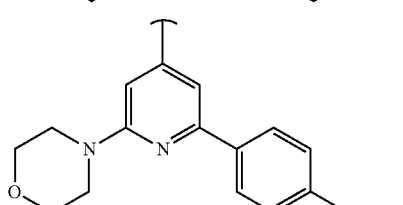
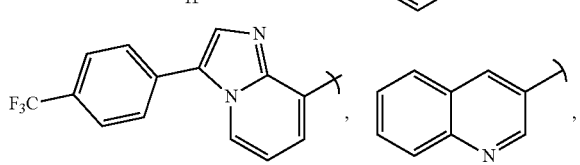
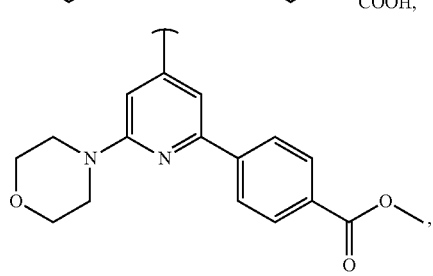
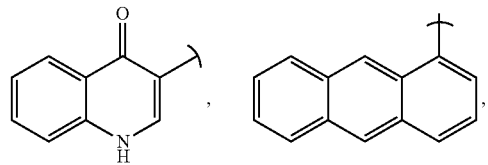
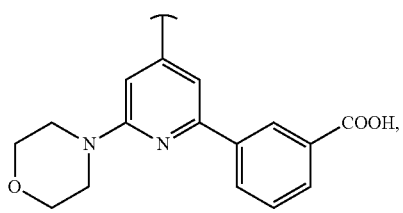

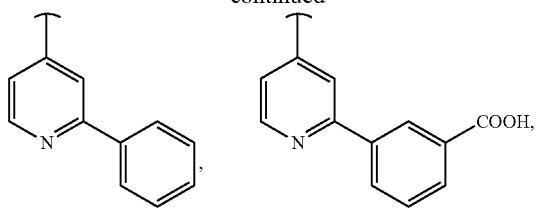
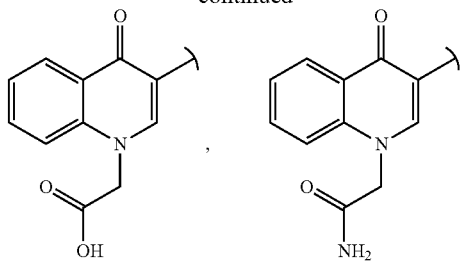
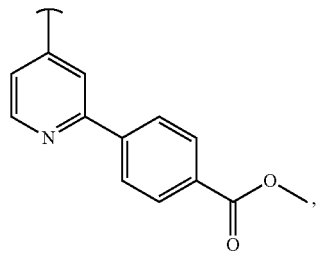
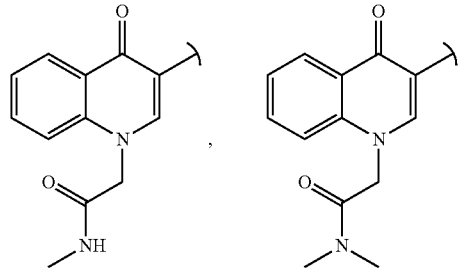
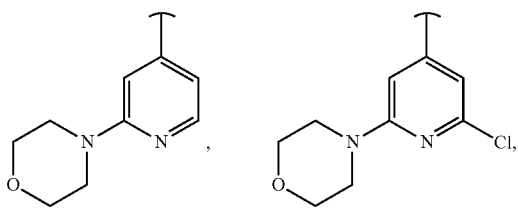
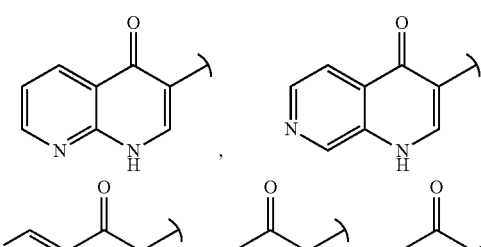
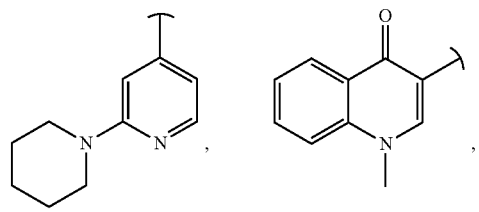
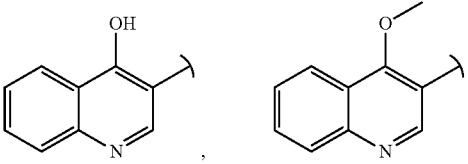
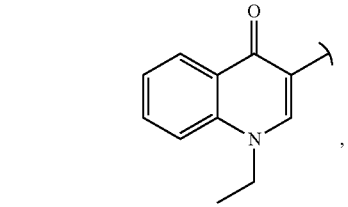
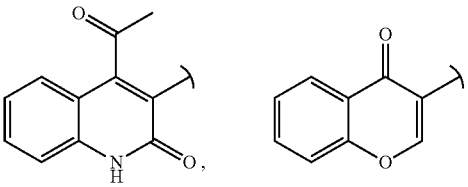
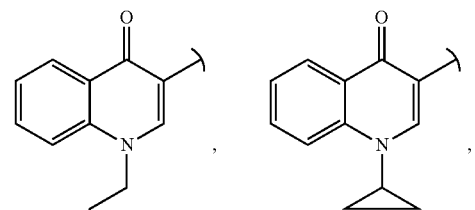
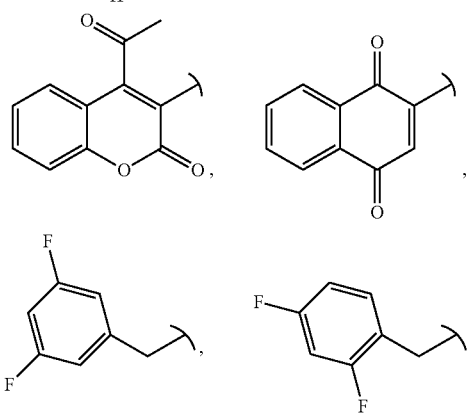
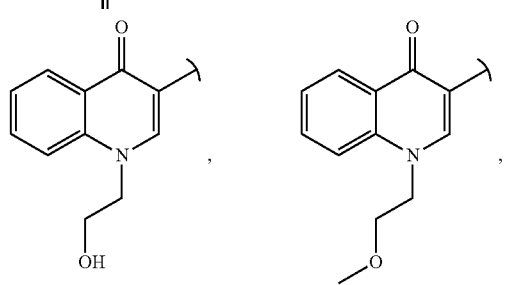
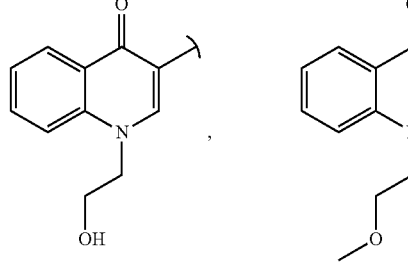

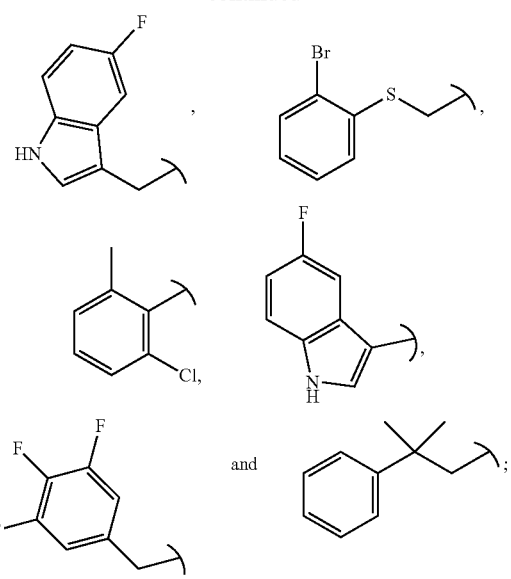
and (ii) when X is nitrogen, then Y is selected from:
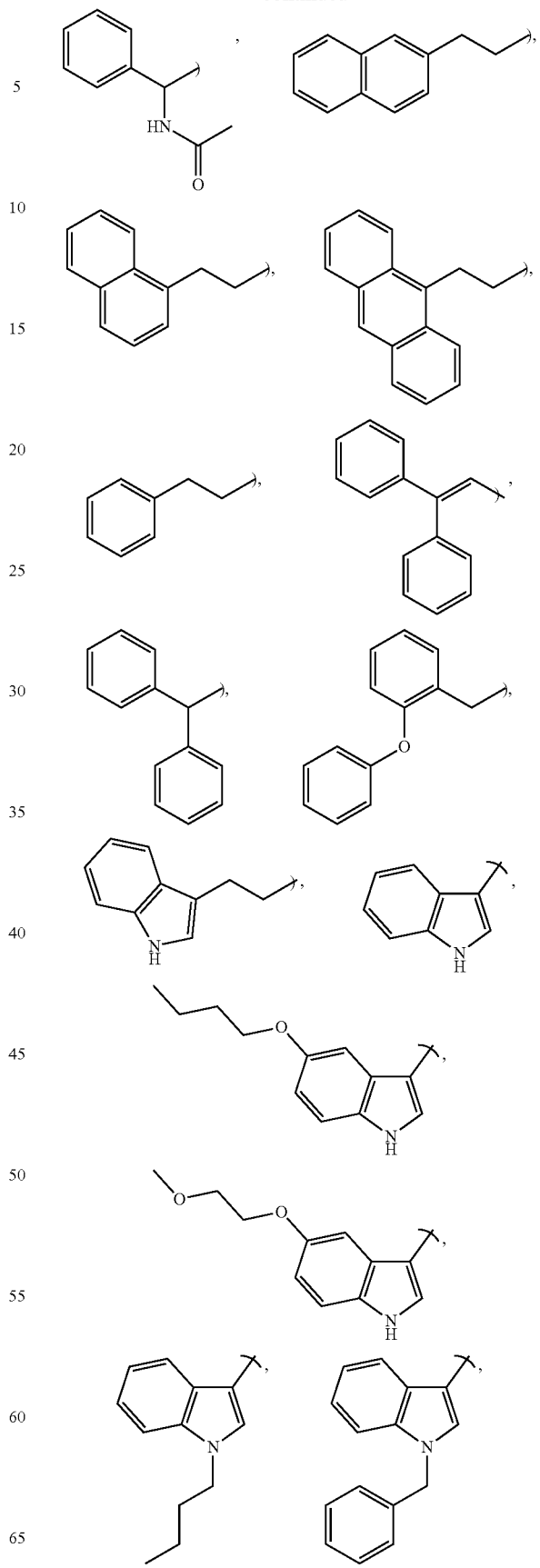

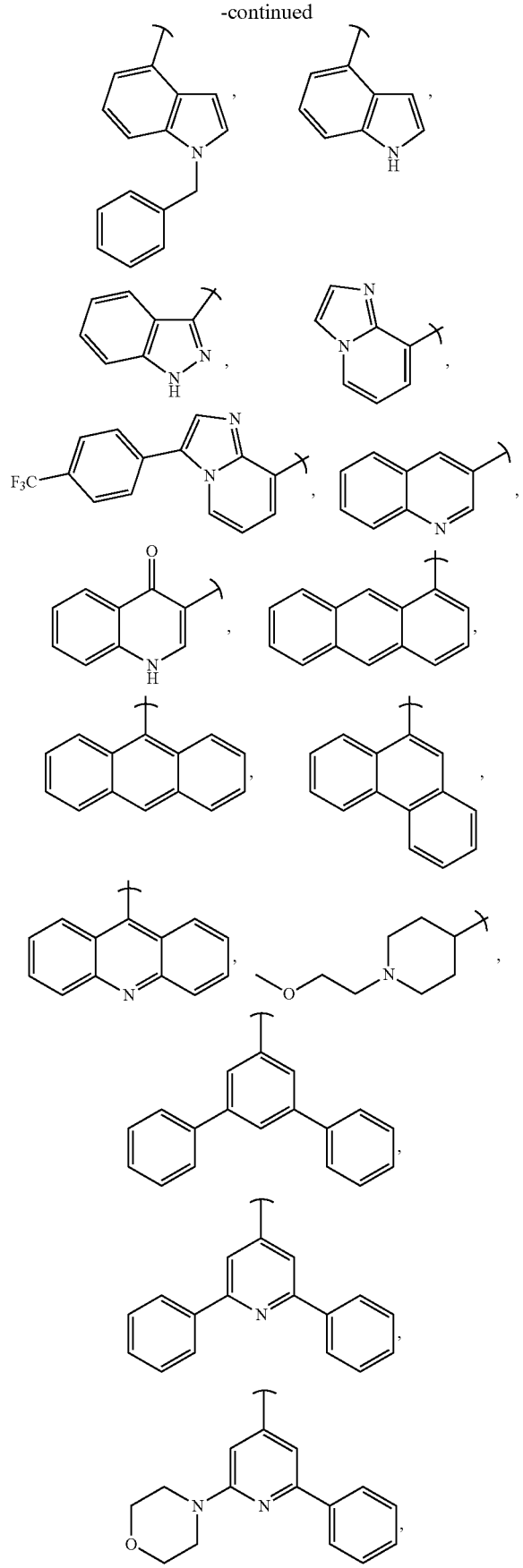
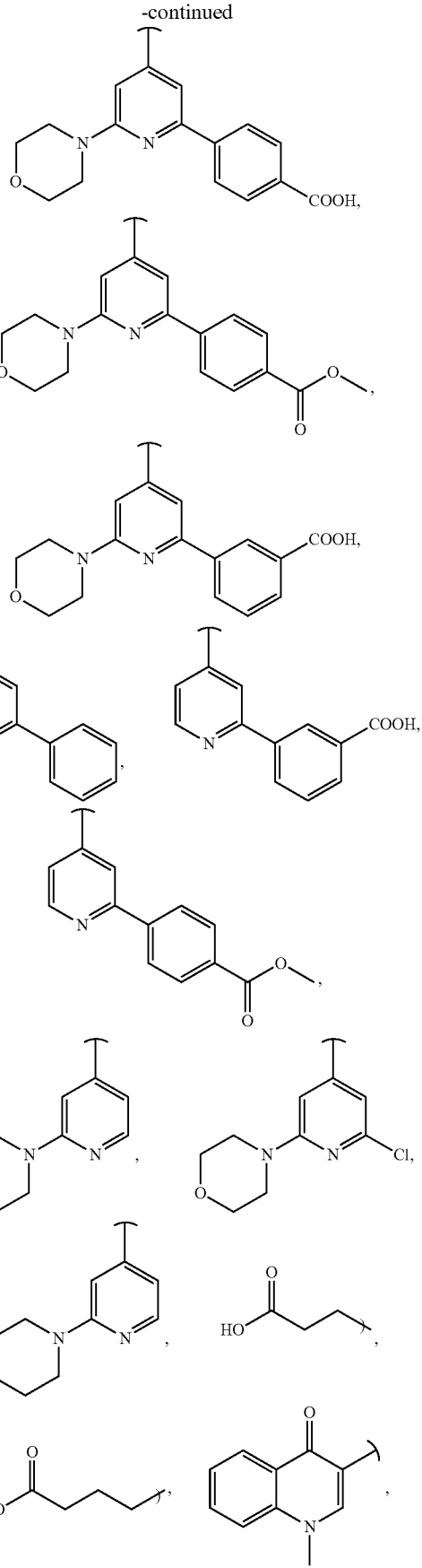

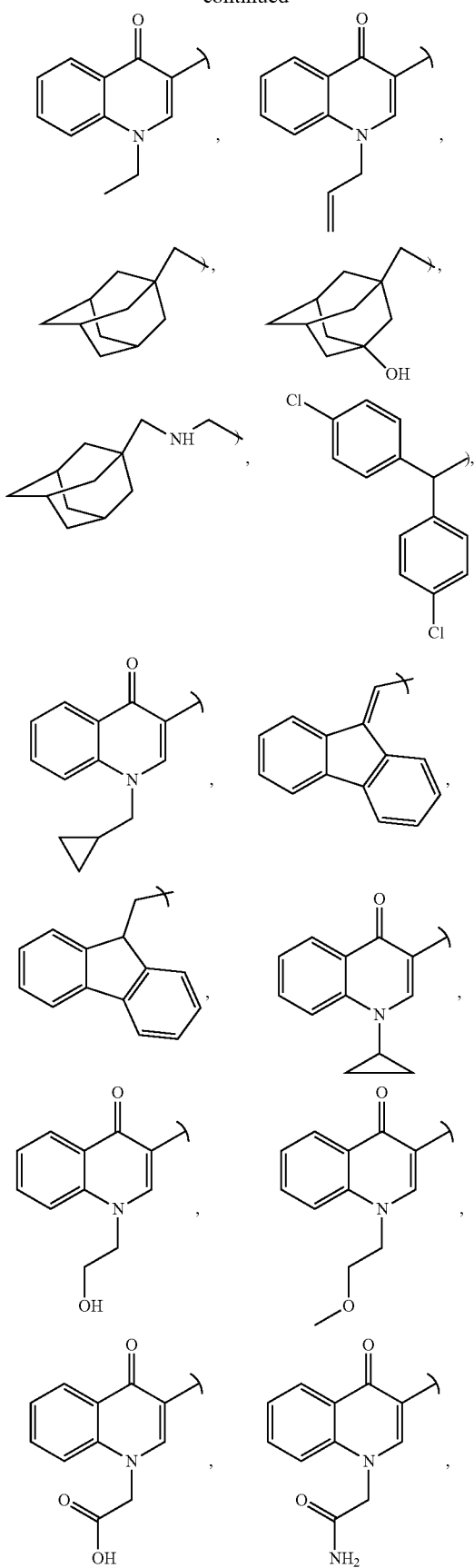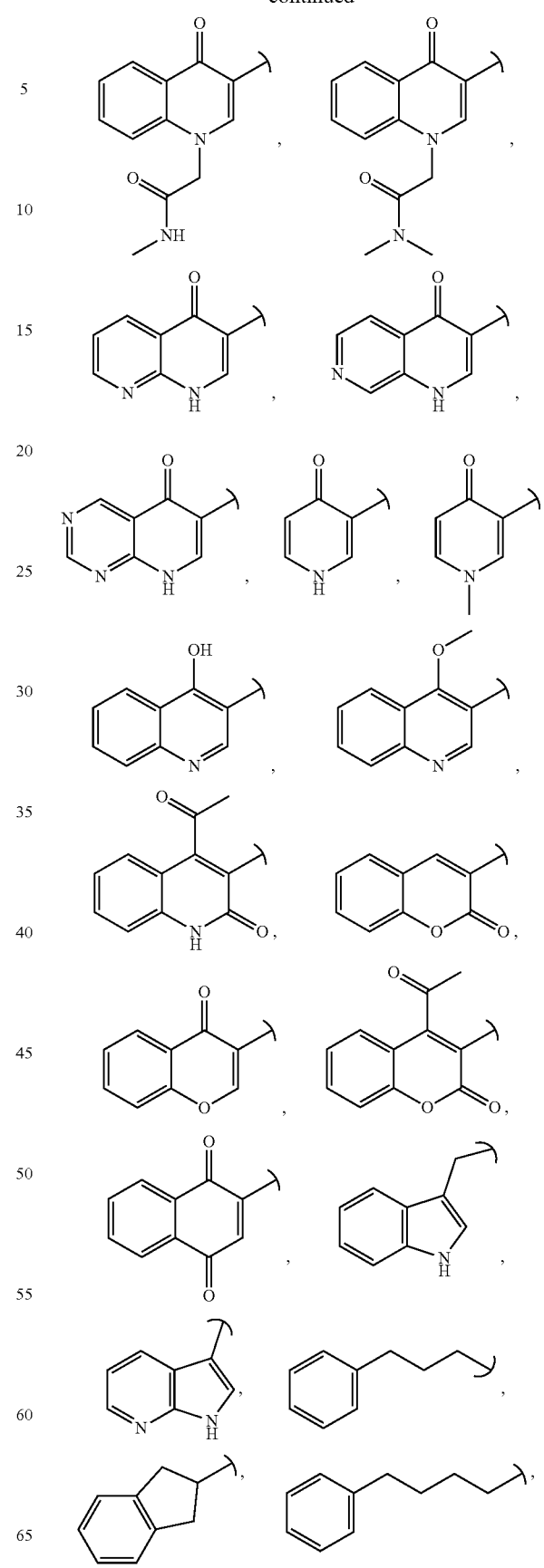

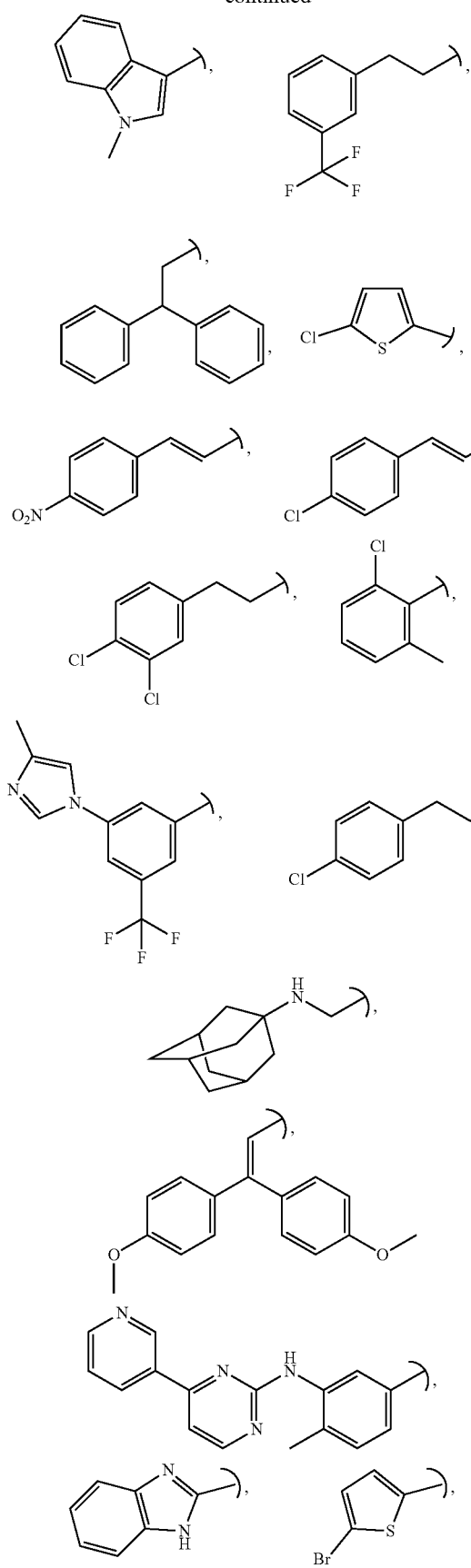
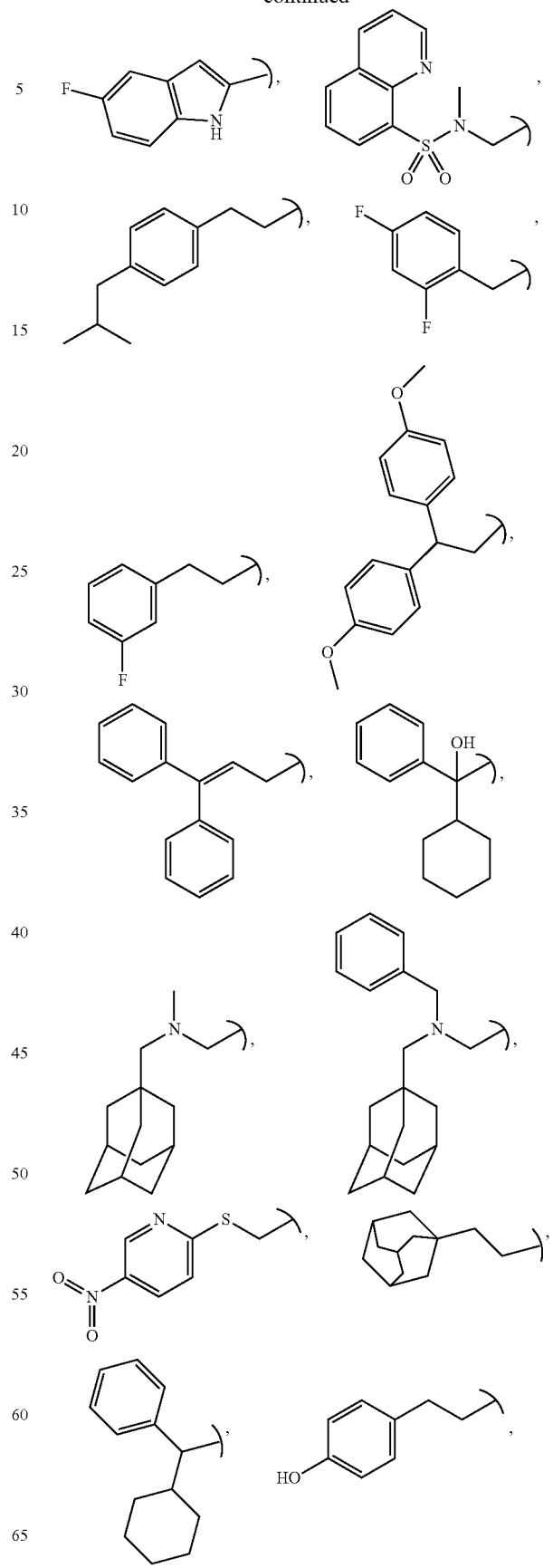

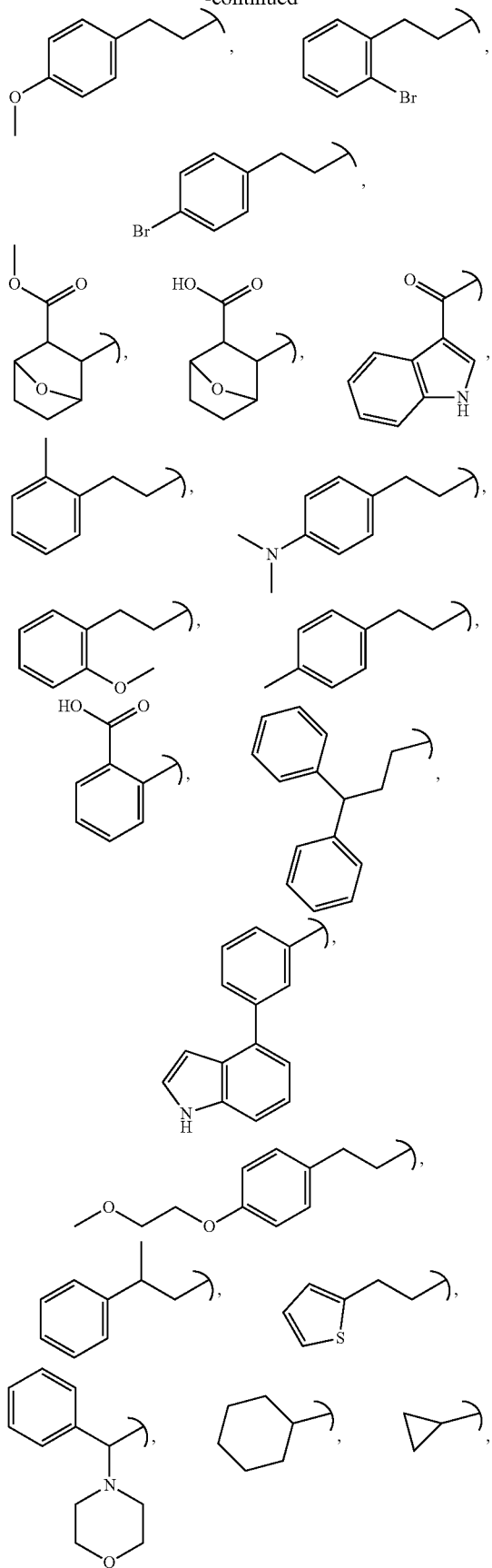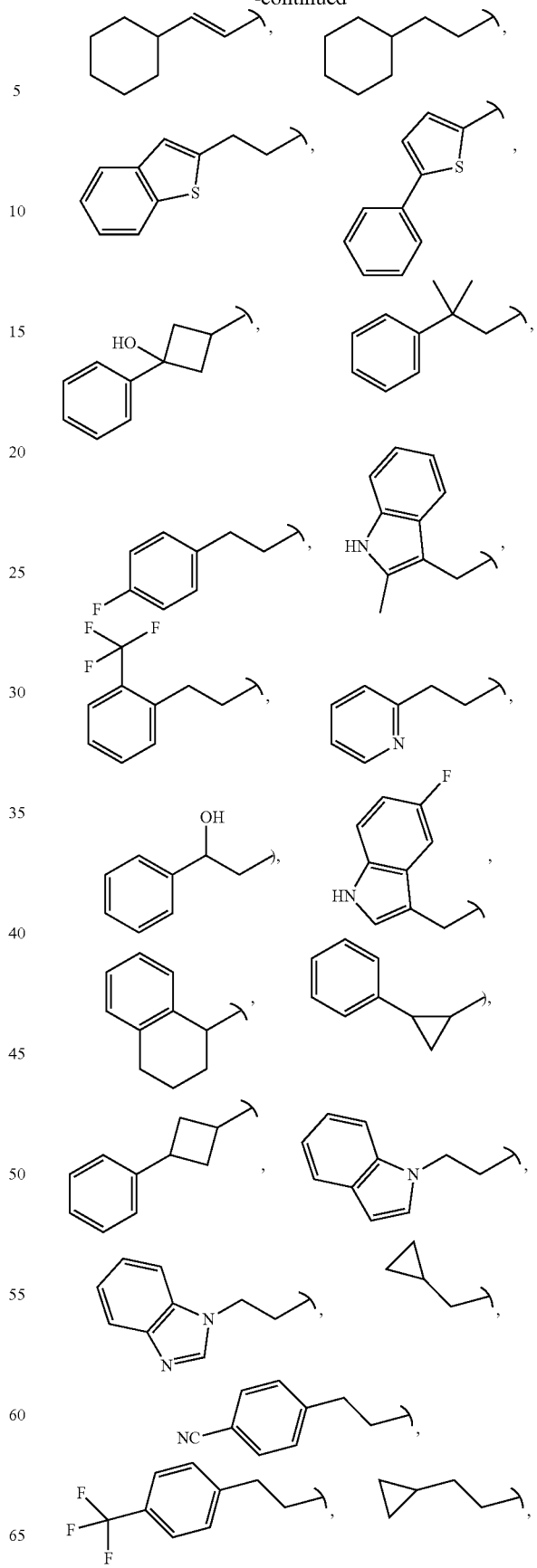

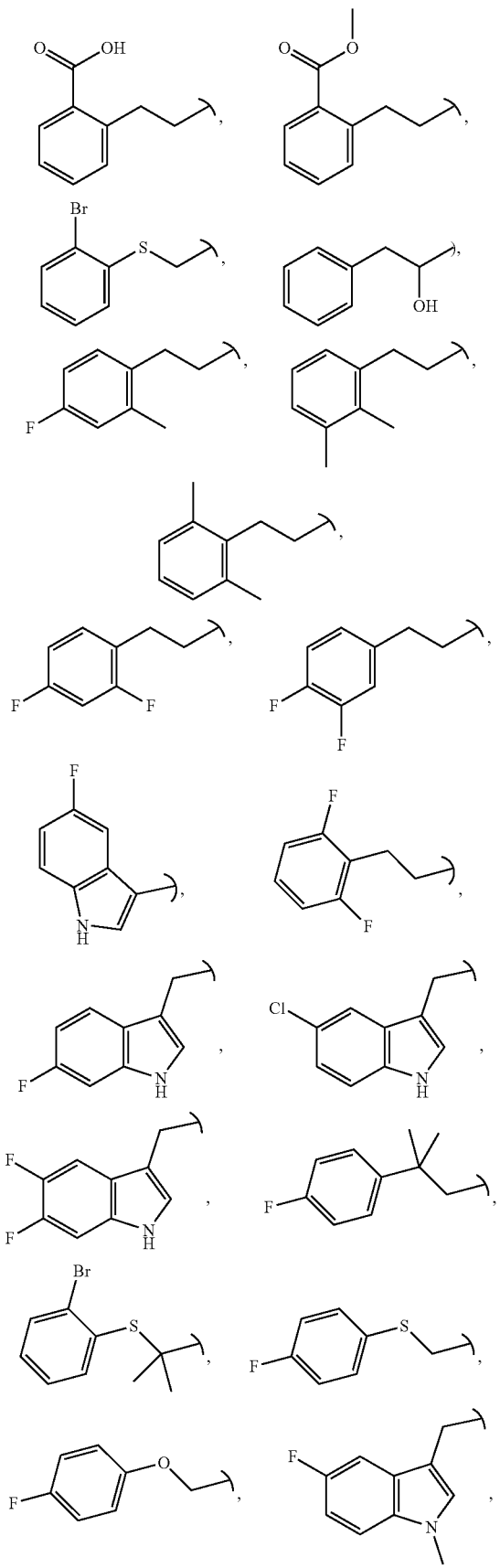
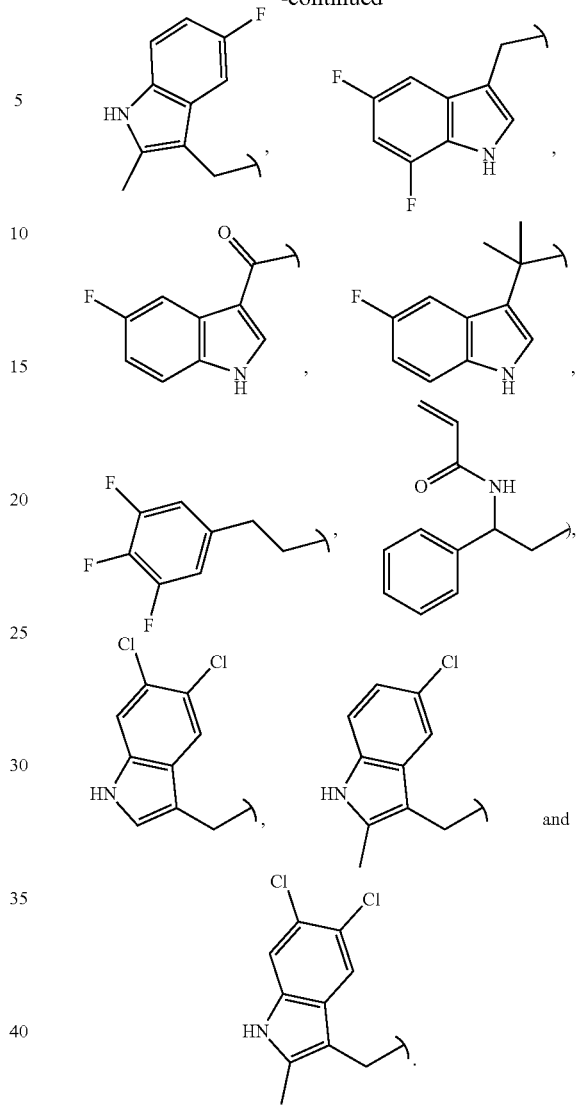

The compounds of the present invention are potent ME inhibitors and are useful in the treatment of diseases mediated by ME such as cancer (e.g., a non-solid or a solid cancer) particularly PDAC.

DETAILED DESCRIPTION OF THE INVENTION

Definitions

The term "pharmaceutically acceptable salt" as used herein includes acid addition salts formed with either organic or inorganic acids. Suitable pharmaceutically acceptable salts include, but not limited to, acid addition salts which may be salts of inorganic acids such as hydrochloric acid, hydrobromic acid, phosphoric acid, or of organic acids such as, for example, acetic acid, benzenesulfonic acid, methanesulfonic acid, benzoic acid, citric acid, glycolic acid, lactic acid, fumaric acid, succinic acid, adipic acid, pimelic acid, suberic acid, azelaic acid, malic acid, tartaric acid, and amino acids such as glutamic acid or aspartic acid. The pharmaceutically acceptable acid addition salts also include salts formed with the addition of one or more equivalents of acids, for example, monohydrochloride, and dihydrochloride salts.

The term "treating or treatment" as used herein refers to completely or partially curing, alleviating, ameliorating, improving, relieving, delaying the onset of, inhibiting progression of, reducing severity of, and/or reducing incidence of one or more symptoms or features of a particular disease, disorder, and/or condition.

The term "subject" as used herein refer to either a human or a non-human animal. These terms include mammals such as humans, primates, livestock animals (e.g., bovines and porcines), companion animals (e.g., canines and felines) and rodents (e.g., mice and rats).

The term "deuterated analog" as used herein refers to compounds described herein wherein at least one hydrogen atom has been replaced by a deuterium atom. The deuterated analog may be a fully or partially deuterium substituted derivative.

The term "alkyl" as used herein refers to a saturated hydrocarbon chain radical that includes solely carbon and hydrogen atoms in the backbone, either linear or branched, having from 1 to 6 carbon atoms, both inclusive unless defined otherwise and which is attached to the rest of the molecule by a single bond. Suitable non-limiting examples of alkyl groups include, e.g., methyl, ethyl, n-propyl, 1-methylethyl (isopropyl), n-pentyl, n-hexyl, etc. Unless set forth or recited to the contrary, all alkyl groups described herein may be unsubstituted or substituted.

For example, an alkyl group can be substituted with one or more groups independently selected from:

$C_{6-14}$ aryl (for example, phenyl, naphthyl, anthracenyl) which is optionally further substituted with one or more groups independently selected from $C_{1-4}$ alkoxy (for example, methoxy, propoxy and butoxy), hydroxyl, $C_{1-4}$ alkyl optionally substituted with $C_{1-3}$ alkoxy, $C_{1-3}$ haloalkyl (for example, trifluoromethyl), NHC(O)Me, C(O), phenoxy, halogen (for example, chloro, fluoro, iodo or bromo), $N(Me)_2$, COOH, COOMe and nitrile (CN);

6 to 14 membered heteroaryl (for example pyridine);

COOH;

hydroxyl;

benzenethiolyl, optionally substituted with one or more halogen (for example, chloro, fluoro, iodo or bromo);

$C_{3-14}$ cycloalkyl (for example, cyclopropyl, cyclobutyl, cyclohexyl, tricyclo[3.3.1.1$^{3,7}$]decane, 9H-fluorene), each of which may be optionally further substituted with one or more groups selected from hydroxyl; and amino group, optionally further substituted with one or more groups selected from (a) $C_{6-14}$ cycloalkyl (for example tricyclo[3.3.1.1$^{3,7}$]decane), (b) $C_{1-4}$ alkyl optionally substituted with phenyl or $C_{6-14}$ cycloalkyl (for example tricyclo [3.3.1.1$^{3,7}$]decane) and (c) —S(O)$_2$-heteroaryl(5-14)membered.

The numerical in phrases like "$C_{1-4}$", refers to the number of carbon atoms in the chain. For example, the phrase "$C_{1-4}$ alkyl" refers to an alkyl chain having 1 to 4 carbon atoms.

The term "alkenyl" as used herein refers to a hydrocarbon chain containing at least one carbon-carbon double bond, and may have (E) or (Z) configuration. An alkenyl group may contain 2 to 8 carbon atoms unless specified otherwise. Unless set forth or recited to the contrary, all alkenyl groups described herein may form part of a straight or branched chain. Suitable non-limiting examples of alkenyl groups include, e.g., ethylene, 2-propenyl (allyl), 2-methyl-2-propenyl and 2-butenyl. Unless set forth or recited to the contrary, all alkenyl groups described herein may be unsubstituted or substituted. For example, an alkenyl group can be substituted with one or more group selected from:

$C_{6-14}$ aryl (for example phenyl) optionally substituted with one or more group independently selected from $C_{1-4}$ alkoxy (for example methoxy, propoxy, butoxy), and nitro;

$C_{6-14}$ cycloalkyl (for example cyclopropane, cyclobutane, cyclohexane, 9H-fluorene); and N(Me)S(O)$_2$heteroaryl.

The term "cycloalkyl" as used herein refers to a non-aromatic mono, multicyclic, bridged multicyclic or spiro-multicyclic ring system of 3 to 15 carbon atoms unless specified otherwise. Monocyclic ring include, but are not limited to, cyclopropyl, cyclobutyl, cyclopentyl and cyclohexyl. Examples of simple multicyclic cycloalkyl groups include, but are not limited to, perhydronapththyl, and perhydroindenyl. Bridged multicyclic groups include, but are not limited to, adamantyl and norbornyl. Spiromulticyclic groups include, but are not limited to, spiro(4,4)non-2-yl. Unless set forth or recited to the contrary, all cycloalkyl groups described herein may be unsubstituted or substituted. For example, a cycloalkyl group can be substituted with one or more groups selected from oxo (=O), hydroxyl, and $C_{6-14}$ aryl (for example, phenyl).

The term "aryl" as used herein refers to an aromatic radical having 6 to 14 carbon atoms, including monocyclic, bicyclic or tricyclic aromatic systems. A bicyclic aryl group includes an aromatic ring fused to a saturated, partially unsaturated ring, or aromatic ring.

The bicyclic aryl group may be attached to the rest of the molecule at any suitable position including the position on the aromatic ring or saturated or partially unsaturated ring. Typical aryl groups include, but are not limited to, phenyl, naphthyl, indanyl (for e.g. 1-indanyl, 5-indanyl), indenyl, anthracenyl and phenanthrenyl. Unless set forth or recited to the contrary, all aryl groups described herein may be unsubstituted or substituted. For example, an aryl group can be substituted with one or more groups independently selected from:

$C_{1-4}$ alkyl (for example, methyl, ethyl, propyl and butyl) optionally substituted with one more halogen (for example, chloro, fluoro, iodo or bromo); phenyl;

halogen (for example, chloro, fluoro, iodo or bromo);

5 to 10 membered heteroaryl ring optionally substituted with one or more groups selected from $C_{1-4}$ alkyl;

amino group, optionally further substituted with a substituted heteroaryl group; and

COOH.

The term "heteroaryl ring" refers to a 5 to 14 membered aromatic heterocyclic ring containing one or more (such as 1, 2 or 3) heteroatoms, each independently selected from nitrogen, oxygen and sulfur. The heteroaryl ring may be a mono-, bi- or tri-cyclic ring system and includes fused ring systems (at least one of which is aromatic). The heteroaryl ring radical may be attached to the main structure at any heteroatom or carbon atom that results in the creation of a stable structure. Suitable examples of heteroaryl rings include, but are not limited to oxazolyl, isoxazolyl, imidazolyl, furyl, indolyl, isoindolyl, pyrrolyl, triazolyl, triazinyl, tetrazoyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, benzopyranyl, carbazolyl, quinolinyl, isoquinolinyl, quinazolinyl, purinyl, quinoxalinyl, quinolinyl, isoquinolinyl, thiadiazolyl, indolizinyl, imidazo[1,2-a]pyridyl and phthalazinyl. Unless set forth or recited to the contrary, all heteroaryl groups described or claimed herein may be unsubstituted or substituted.

For example, a heteroaryl ring can be substituted with one or more groups selected from:

$C_{1-4}$ alkoxy (for example, methoxy, propoxy, butoxy) optionally substituted with one or more $C_{1-4}$ alkoxy or $C_{1-4}$ alkyl, benzyl, phenyl, wherein the phenyl may be optionally further substituted with one or more $C_{1-3}$ haloalkyl (for example trifluoromethyl), and/or COOH and/or COOMe, hydroxyl, morpholinyl, halogen (for example, chloro, fluoro, iodo or bromo), and $C_{6-14}$ heterocyclyl (for example piperidine).

The term "heterocycloalkyl" refers to a cycloalkyl ring containing one, two or three heteroatoms, each independently selected from nitrogen or oxygen. Suitable non-limiting examples of heterocycloalkyl groups include, but are not limited to, pyrrolidinyl, piperidine, piperazinyl, morpholinyl, thiomorpholine and 1,3-oxazine. Unless set forth or recited to the contrary, a heterocycloalkyl ring described herein may be unsubstituted or substituted. For example, a heterocycloalkyl ring can be substituted with one or more groups selected from:

$C_{1-4}$ alkoxy (for example, methoxy, propoxy, butoxy) optionally substituted with one or more $C_{1-4}$ alkoxy and/or $C_{1-4}$ alkyl;

benzyl;

phenyl, wherein the phenyl group may be optionally further substituted with one or more $C_{1-3}$ haloalkyl (for example, trifluoromethyl) and/or COOH and/or COOMe;

$C_{1-4}$ alkyl which may be optionally further substituted with one or more groups selected from $C_{1-4}$ alkoxy (for example, methoxy, propoxy and butoxy), COOH, $CONH_2$, CONHMe, $CONH(Me)_2$, and $C_{3-6}$ cycloalkyl (for example, cycloalkyl, cyclopropyl, cyclobutyl);

$C_{2-4}$ alkenyl;

oxo (=O);

$C_{3-6}$ cycloalkyl (for example, cyclopropyl);

$C_{1-4}$ alkanol (for example $CH_2CH_2OH$);

C(O)Me;

COOMe;

COOH;

hydroxyl;

morpholinyl;

halogen (for example, chloro, fluoro, iodo or bromo); and 6 to 14 membered heterocyclyl ring (for example piperidine).

Thus, in one aspect, the present invention relates to a compound of Formula I

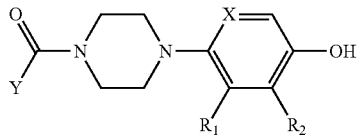

Formula I or a pharmaceutically acceptable salt, stereoisomer or deuterated analog thereof, wherein X is CH or nitrogen;

$R_1$ is selected from hydrogen, —$CH_3$, —COOH, fluoro and —CN;

$R_2$ is selected from hydrogen, —$CH_3$, —COOH, fluoro and —CN;

Y is selected from substituted or unsubstituted $C_{1-5}$ alkyl, substituted or unsubstituted $C_{2-4}$ alkenyl, substituted or unsubstituted 5 to 14 membered heteroaryl ring containing one, two or three heteroatoms each independently selected from nitrogen, oxygen, and sulfur, substituted or unsubstituted 5 to 14 membered heterocycloalkyl group containing one, two or three heteroatoms each independently selected from nitrogen and oxygen, substituted or unsubstituted $C_{3-15}$ cycloalkyl, substituted or unsubstituted $C_{3-15}$ cycloalkyl$C_{1-6}$alkyl, substituted or unsubstituted $C_{6-14}$ aryl, substituted or unsubstituted $C_{6-14}$aryl$C_{1-6}$alkyl, substituted or unsubstituted $C_{6-14}$aryl$C_{2-5}$alkenyl, substituted or unsubstituted 5 to 14 membered heteroaryl$C_{1-6}$alkyl, and substituted or unsubstituted 5 to 14 membered heterocycloalkyl$C_{1-6}$alkyl;

with the proviso that (i) when X is CH then Y is selected from:

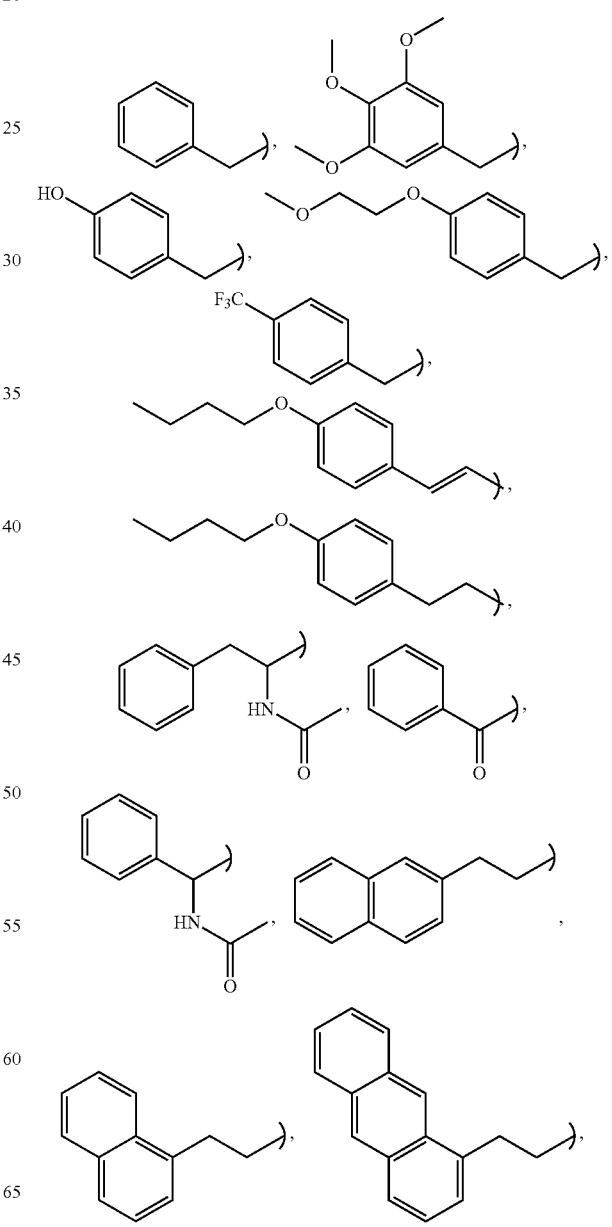

25
-continued
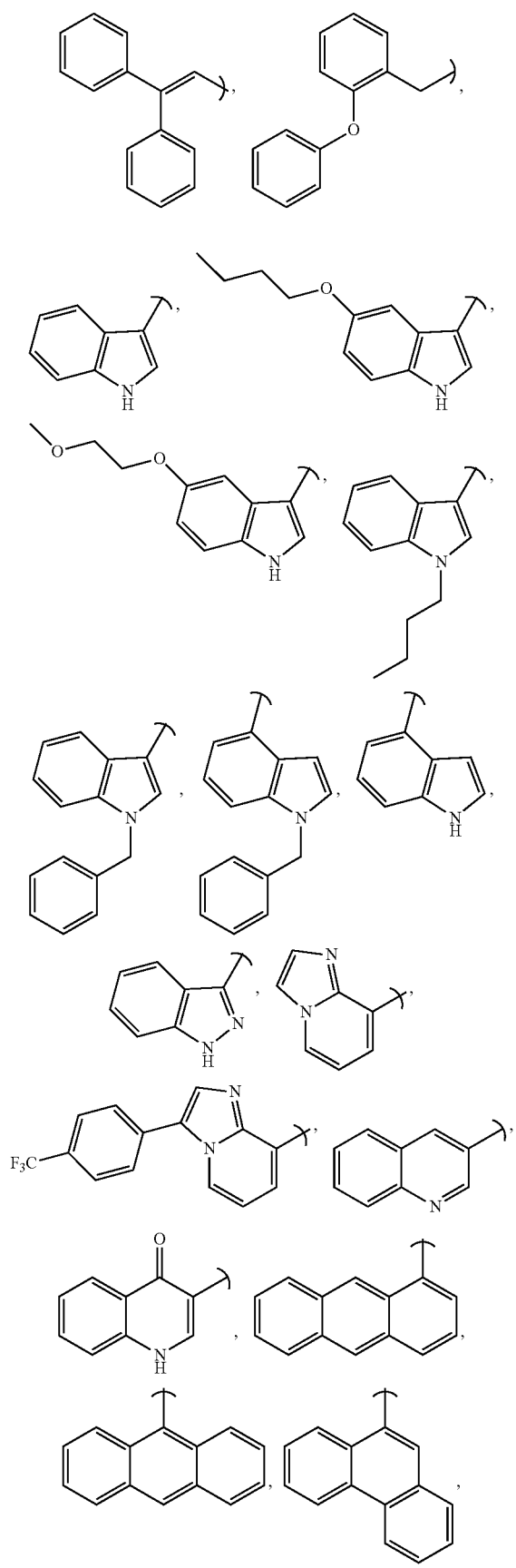
26
-continued
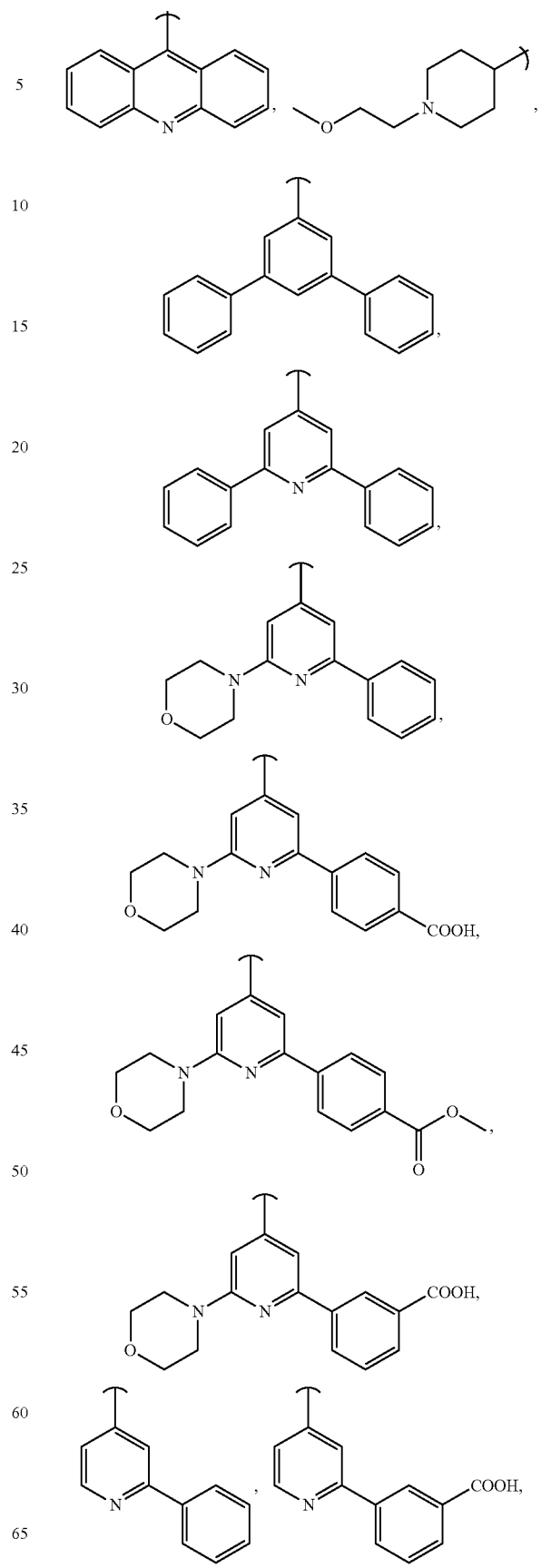

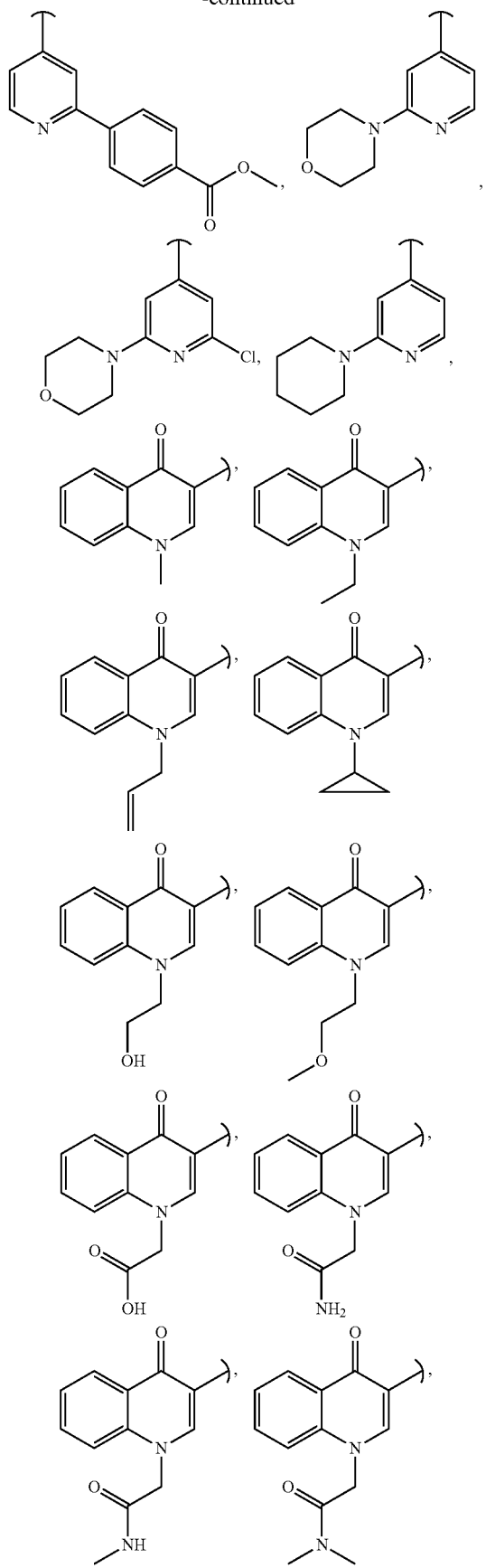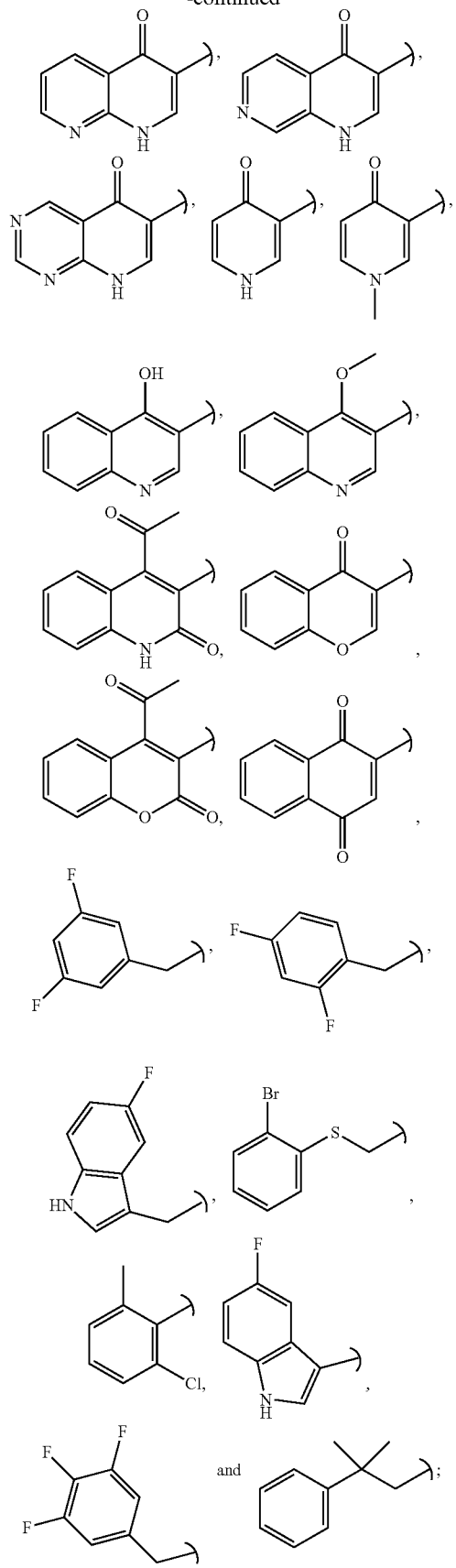

and (ii) when X is nitrogen then Y is selected from:
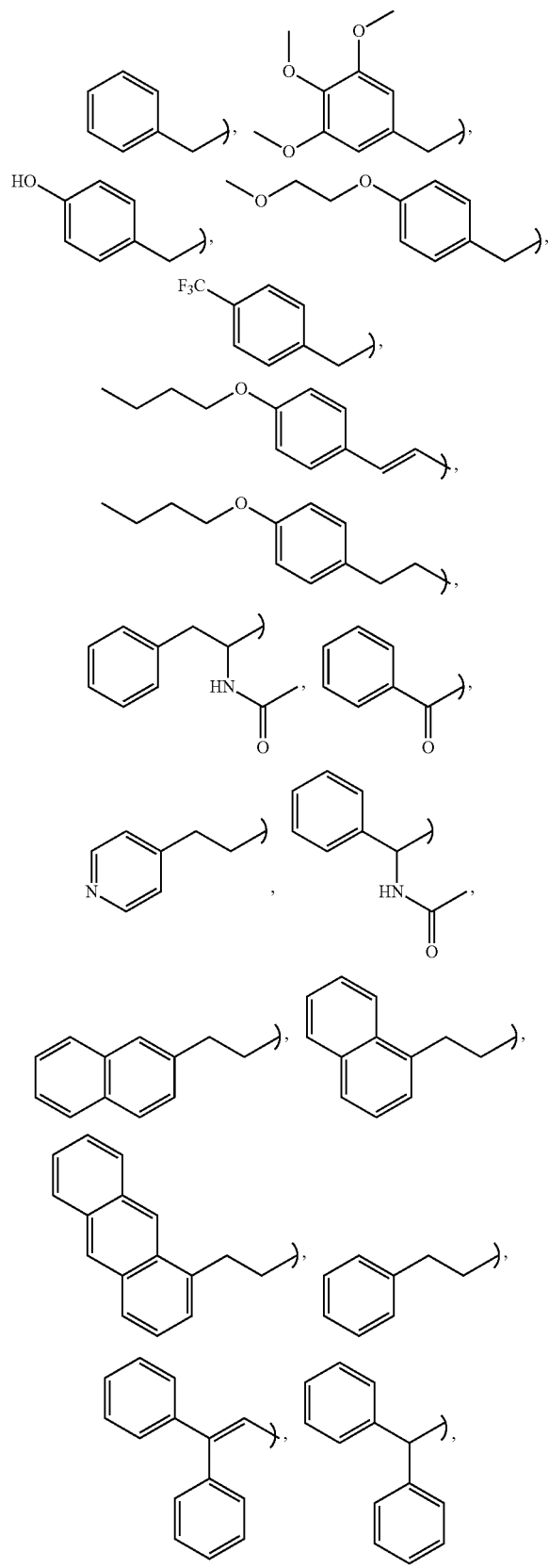
-continued
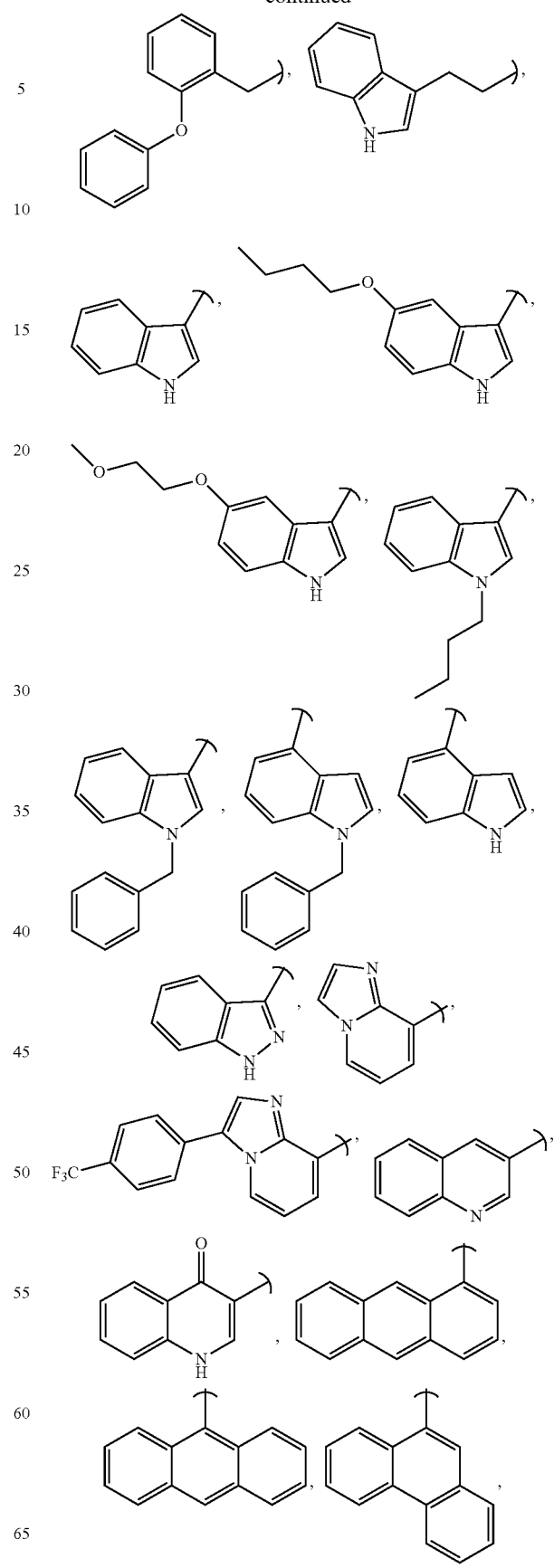

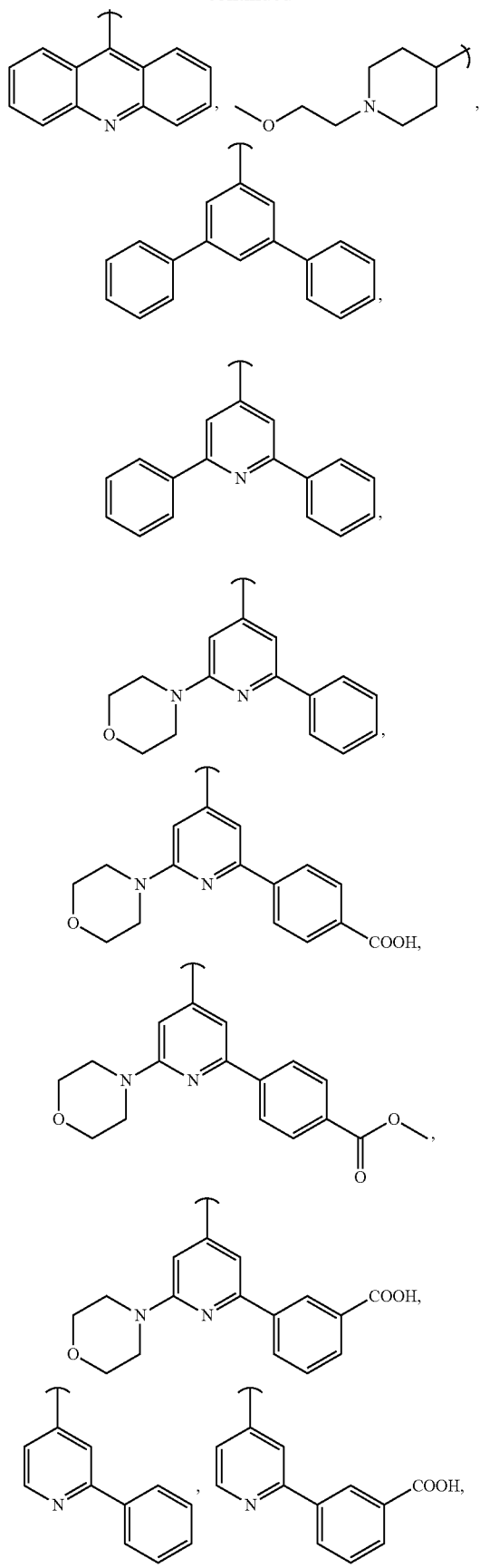
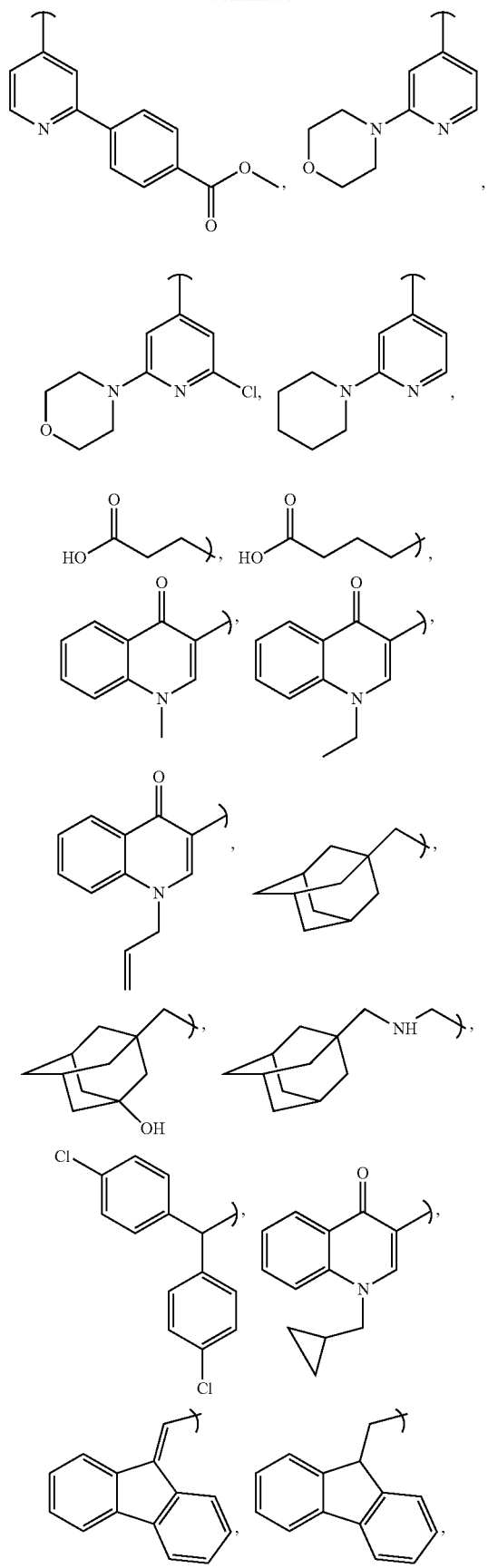

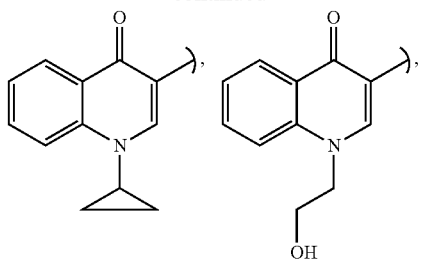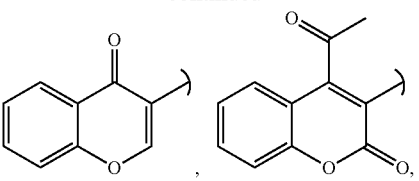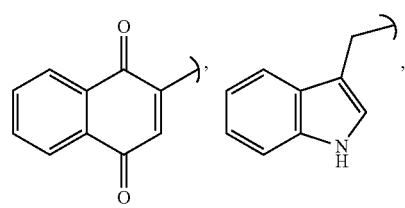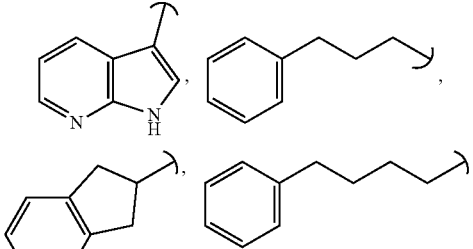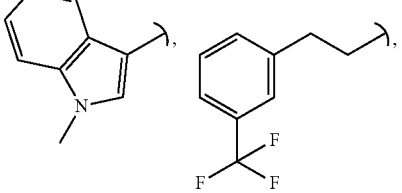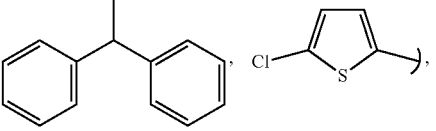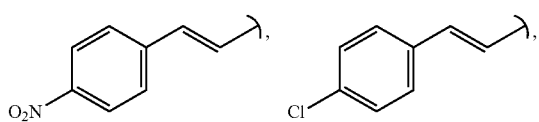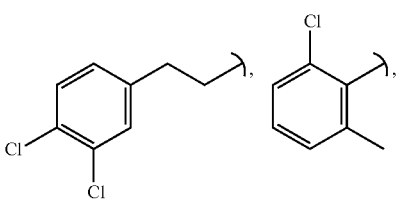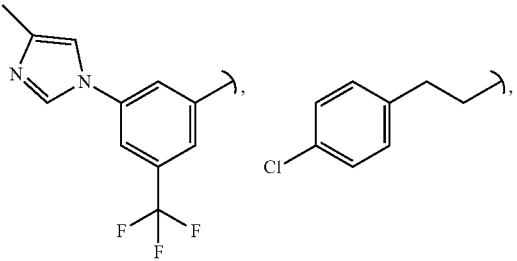

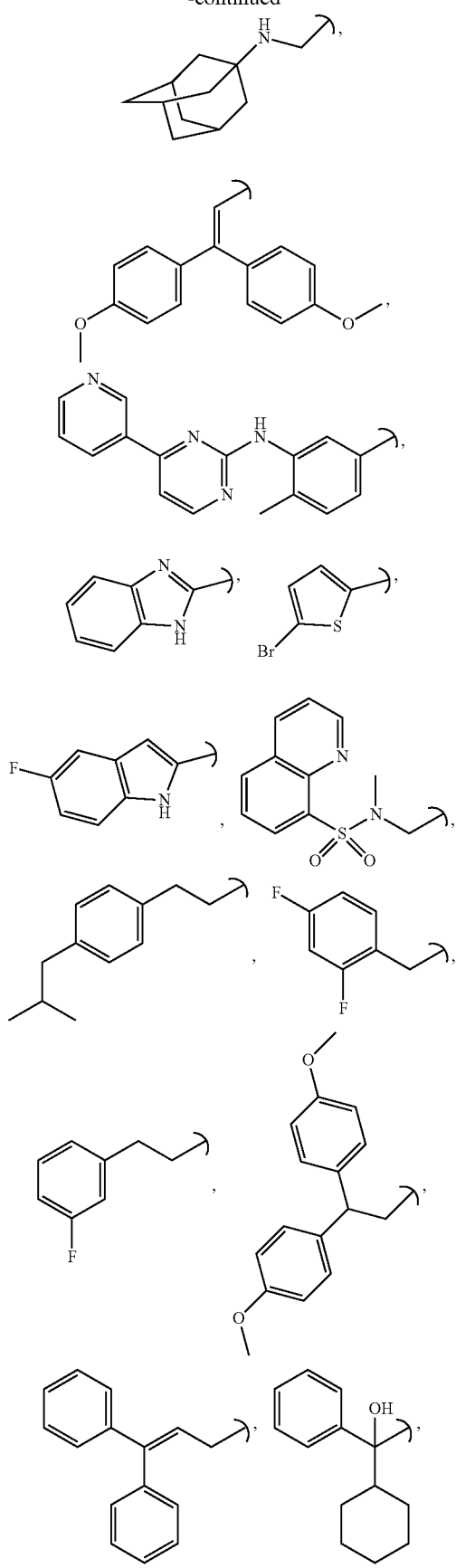
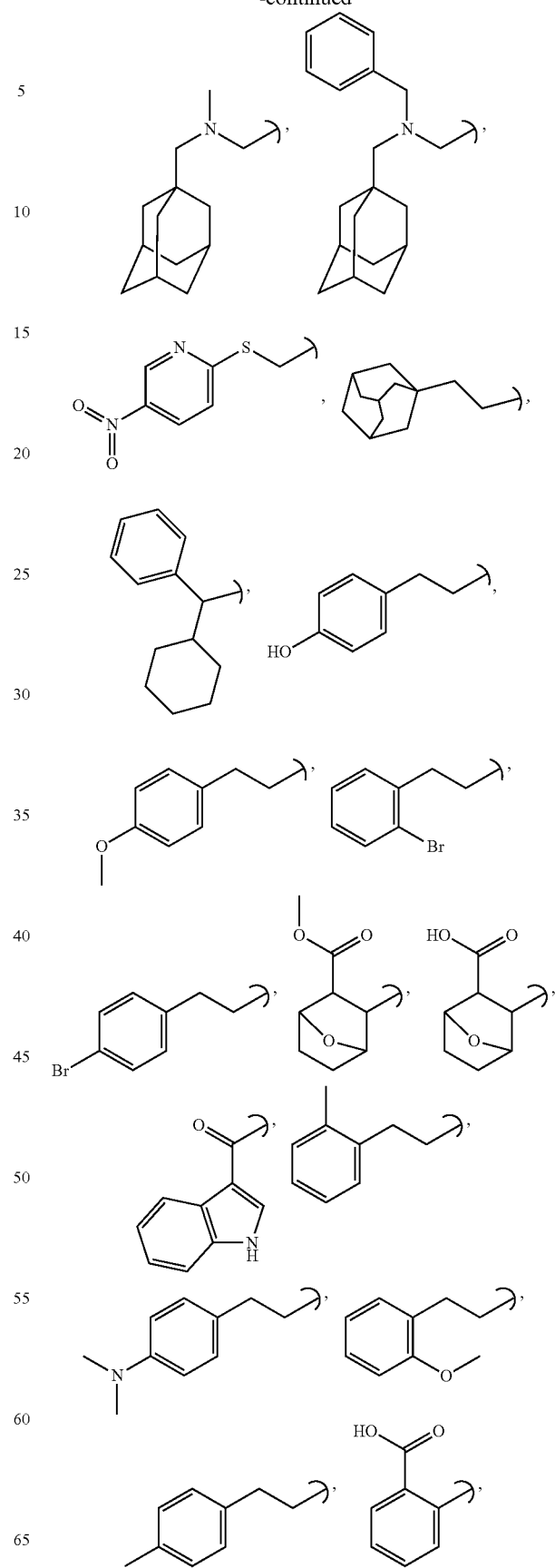

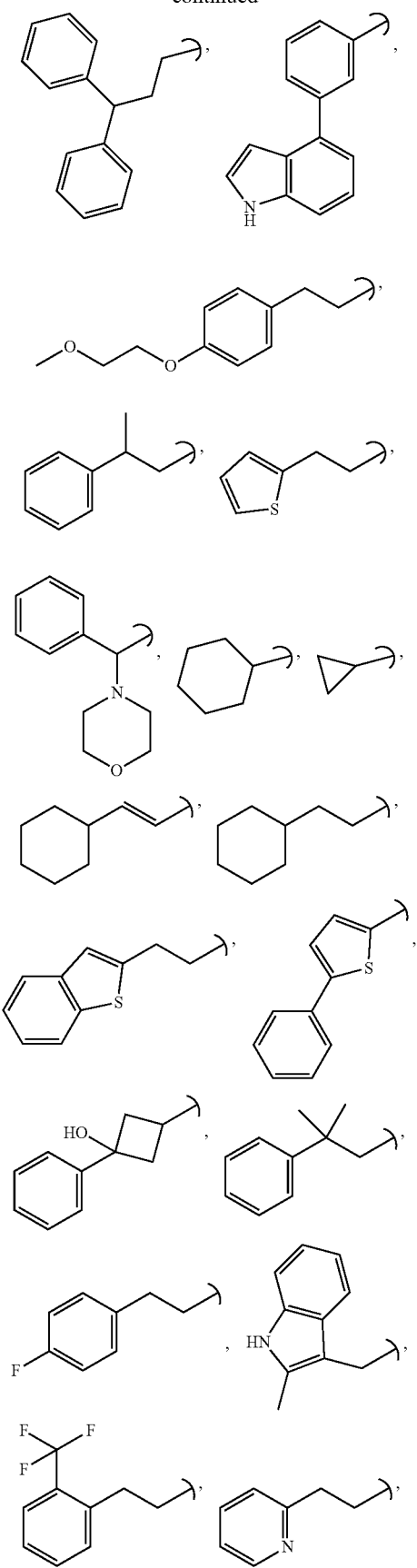
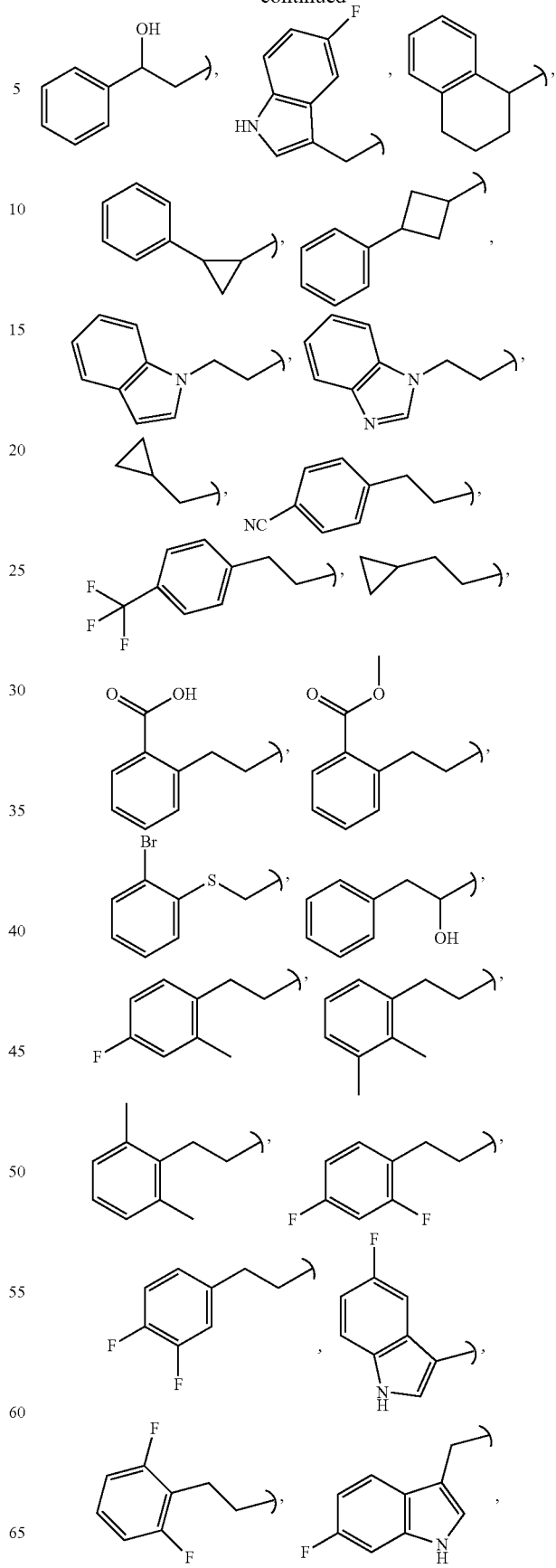

-continued

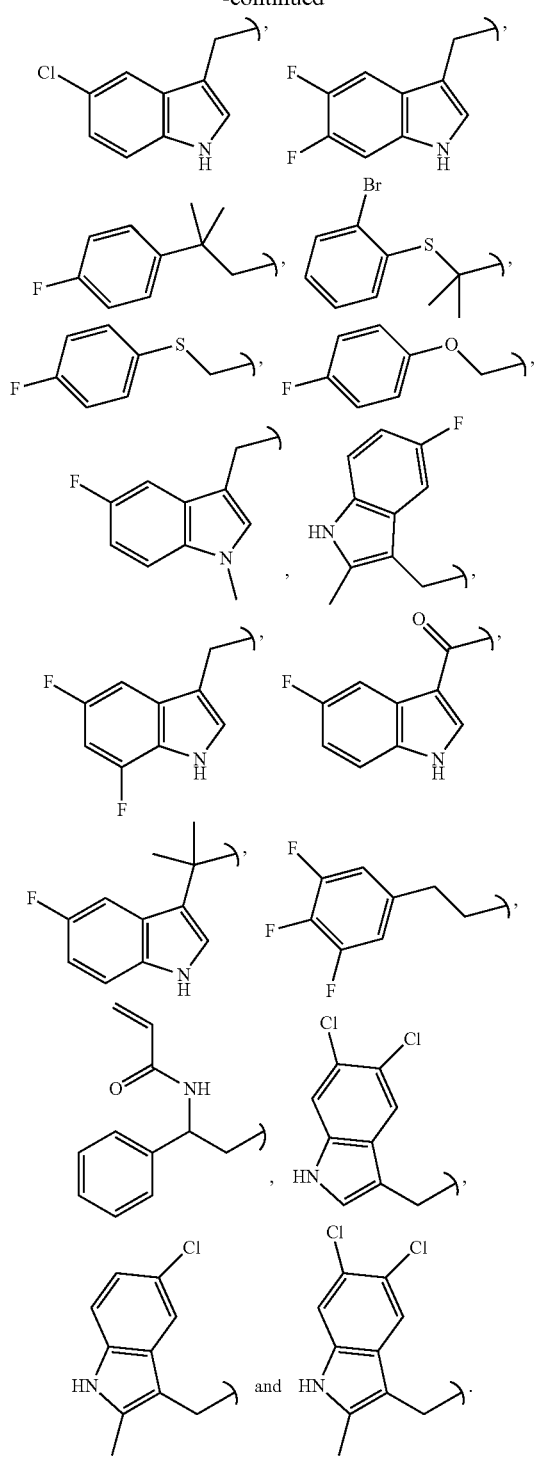

The compounds of Formula I may be described in one or more embodiments. It is to be understood that the embodiments described herein are illustrative of the present invention and are not intended to be limiting. It is also to be understood that the embodiments described herein may be used independently or in conjunction with any definition, or any other embodiment defined herein. Thus, the invention contemplates all possible combinations and permutations of the various independently described embodiments.

According to one embodiment, the present invention provides a compound of Formula I or a pharmaceutically acceptable salt, stereoisomer or deuterated analog thereof, wherein X is CH;

$R_1$ is selected from hydrogen, —$CH_3$, —COOH, fluoro and —CN;

$R_2$ is selected from hydrogen, —$CH_3$, —COOH, fluoro and —CN;

Y is selected from:

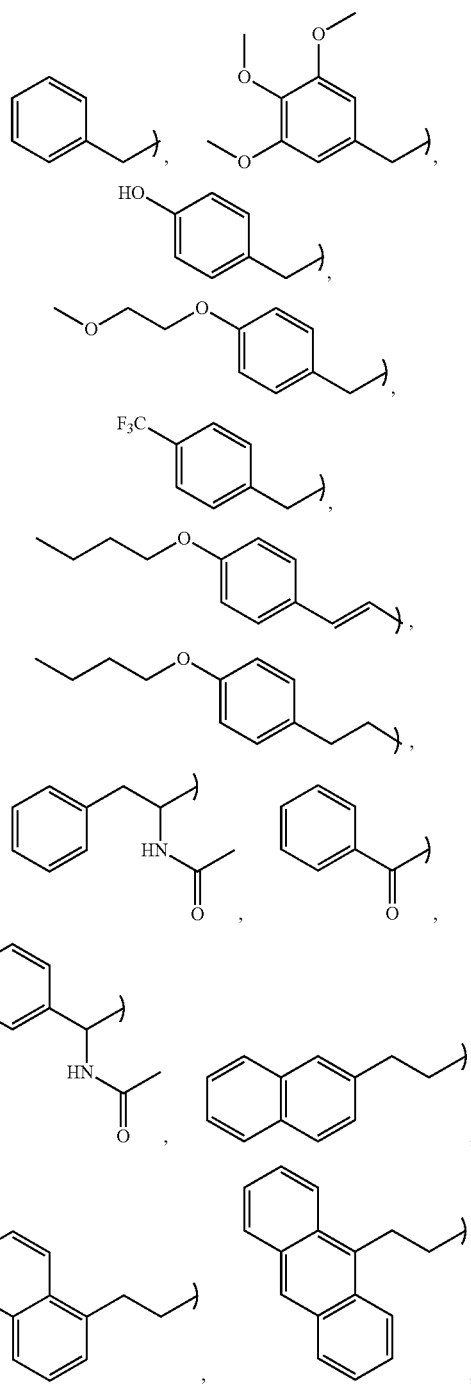

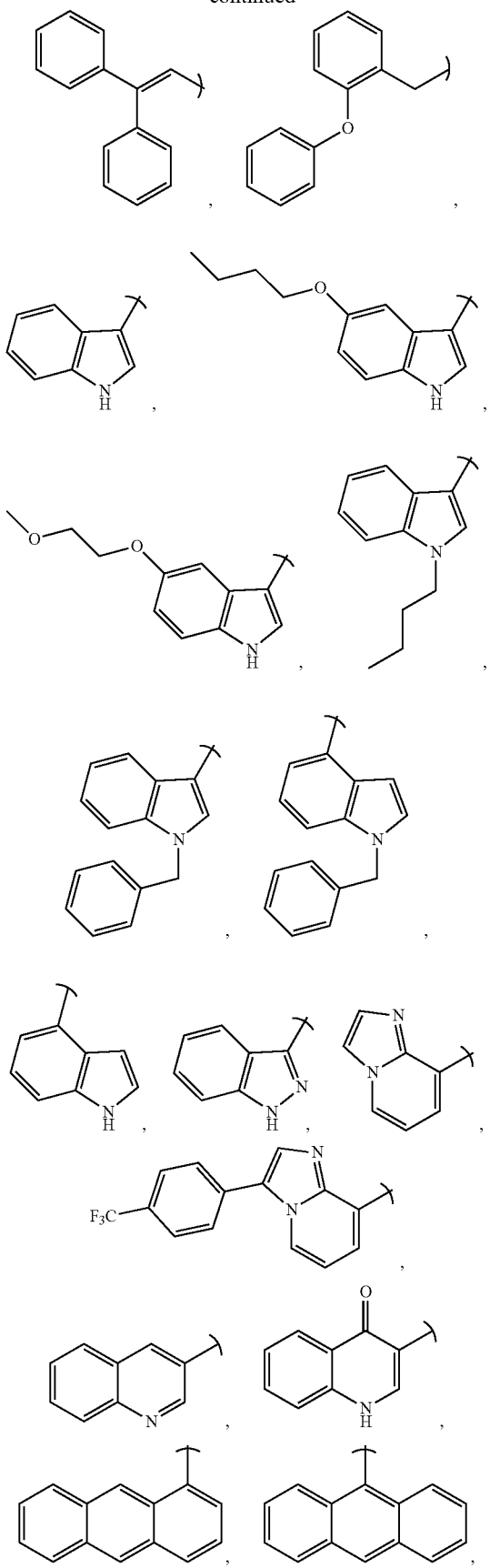
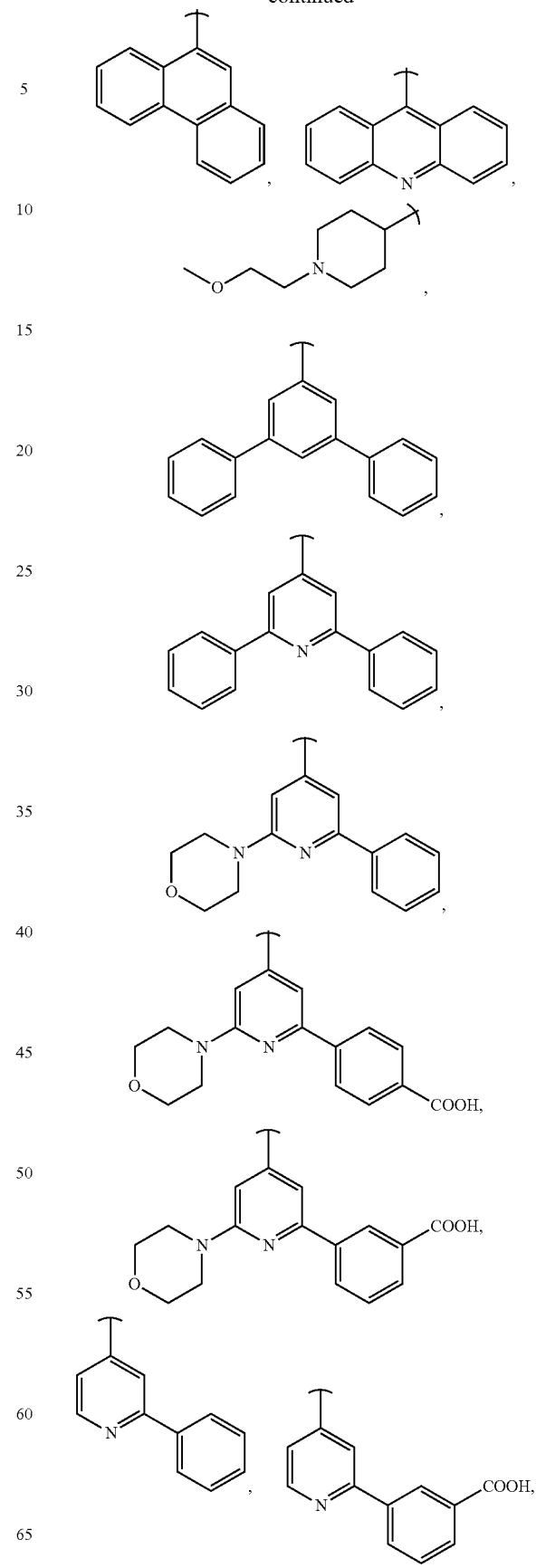

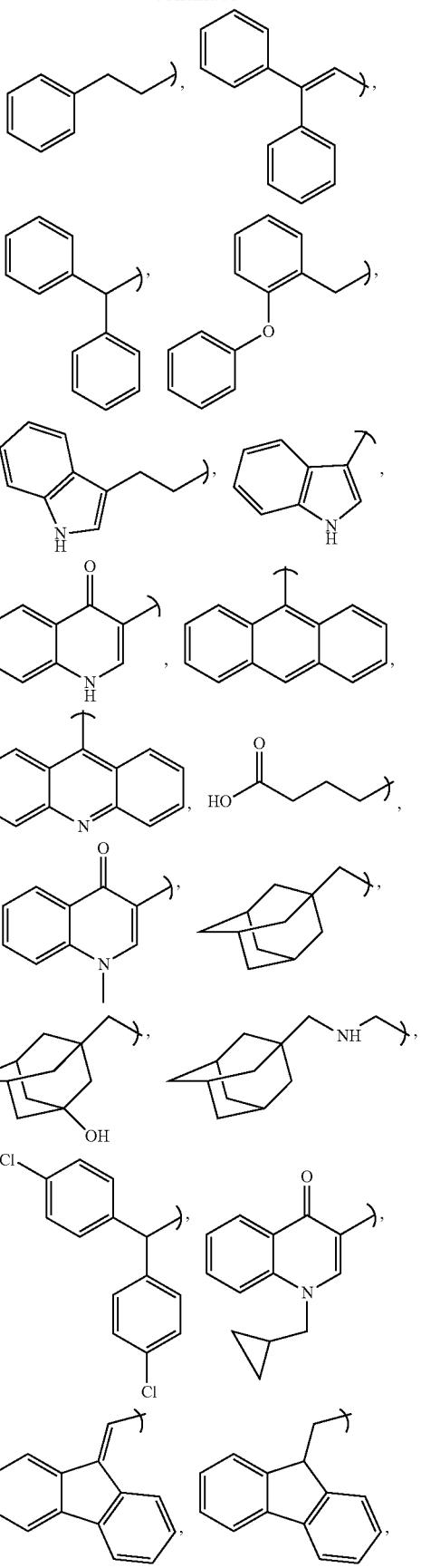
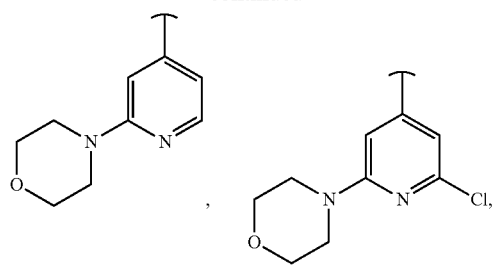
In another embodiment, the present invention provides a compound of Formula I or a pharmaceutically acceptable salt, stereoisomer or deuterated analog thereof, wherein
X is nitrogen;
$R_1$ is selected from hydrogen, —$CH_3$, —COOH, fluoro and —CN;
$R_2$ is selected from hydrogen, —$CH_3$, —COOH, fluoro and —CN;
Y is selected from:
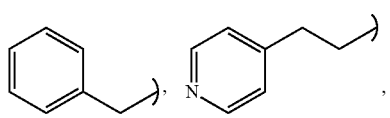

-continued
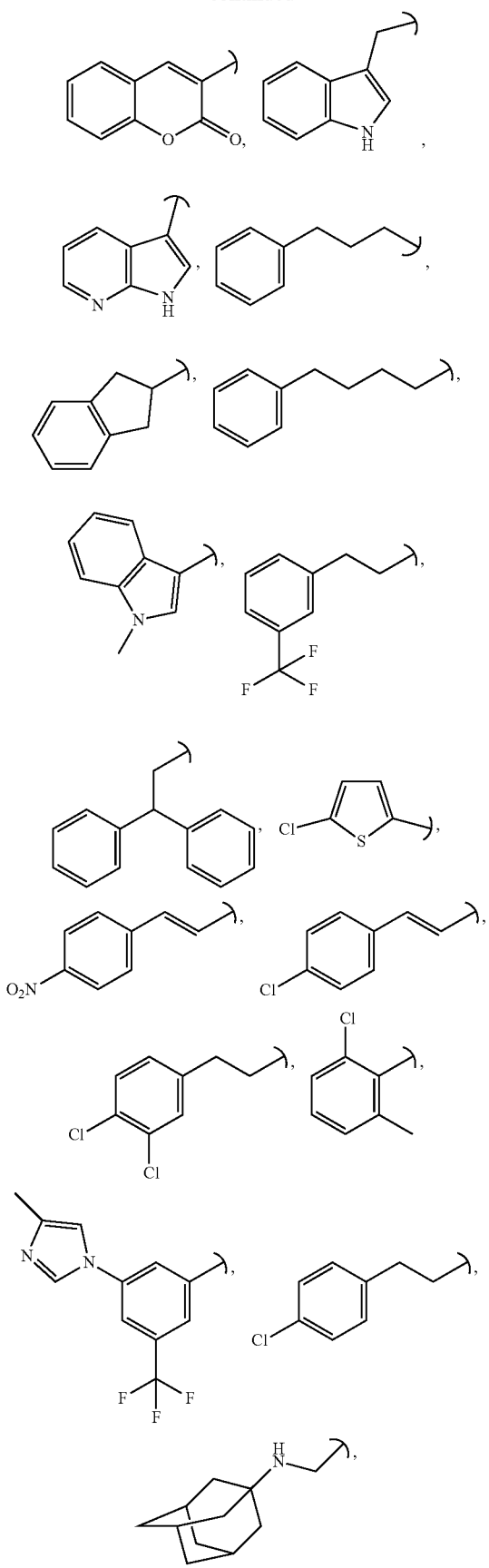
-continued
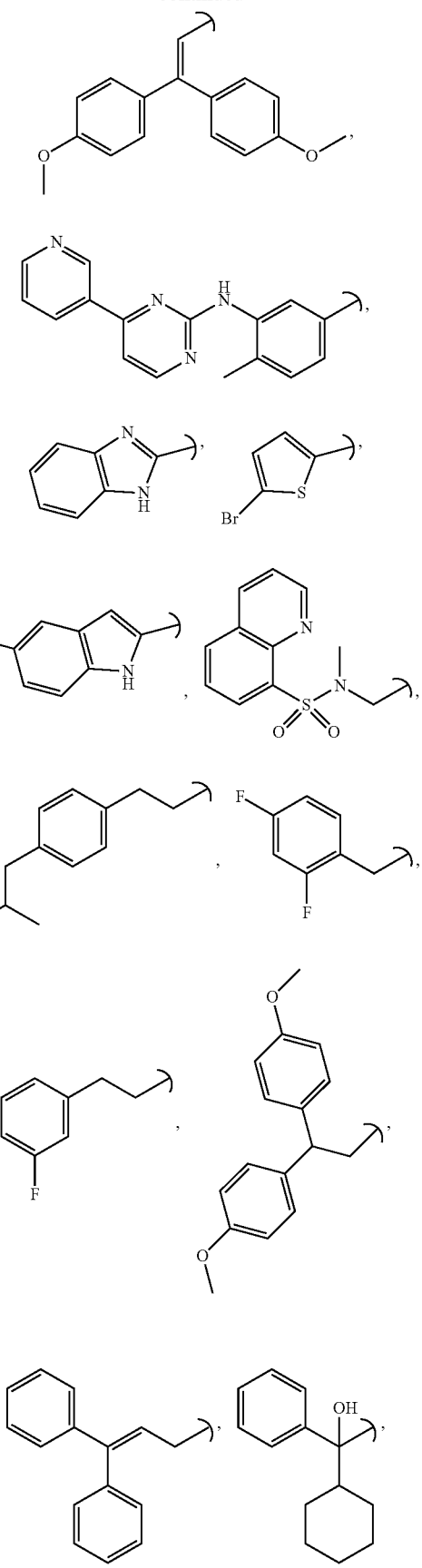

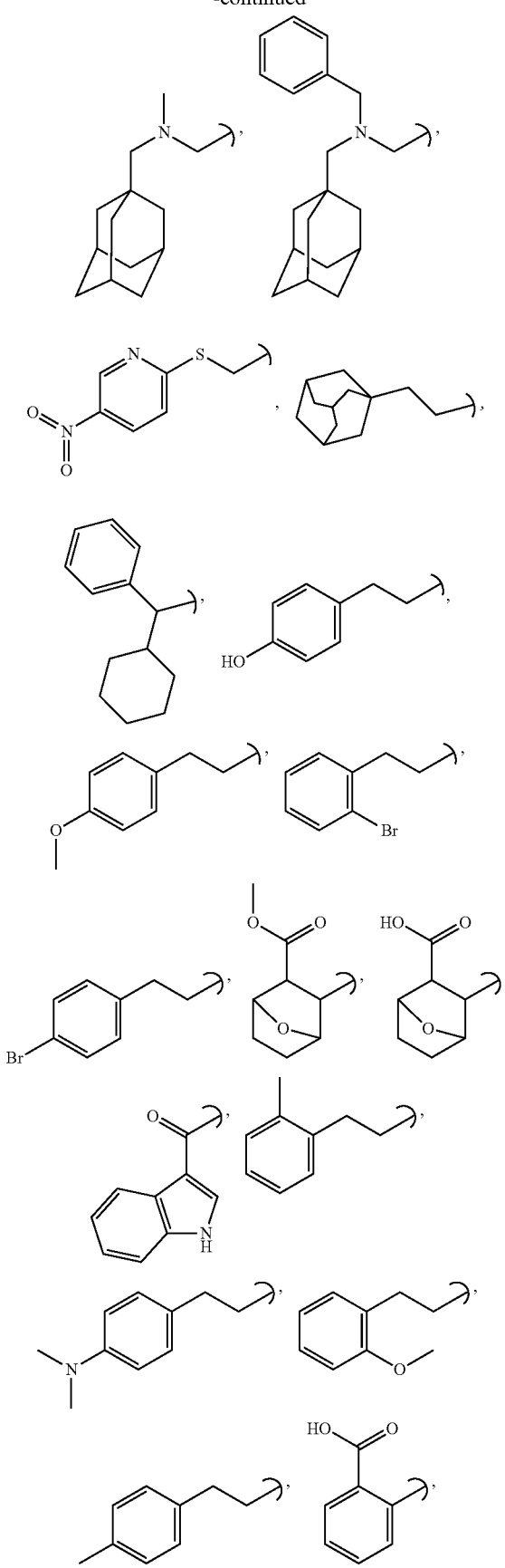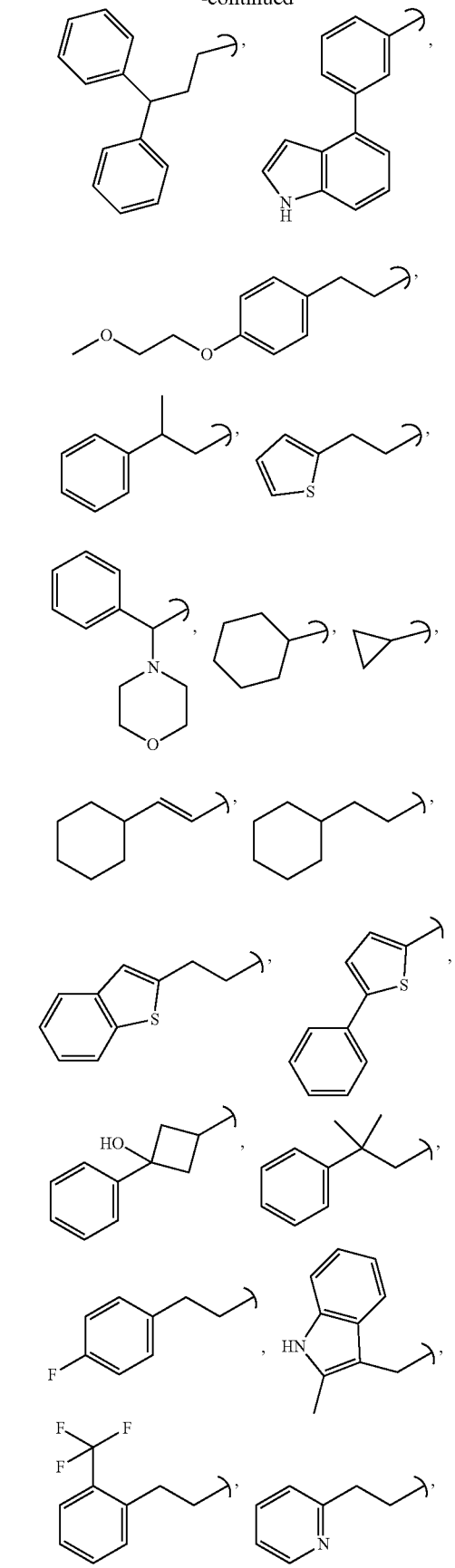

-continued
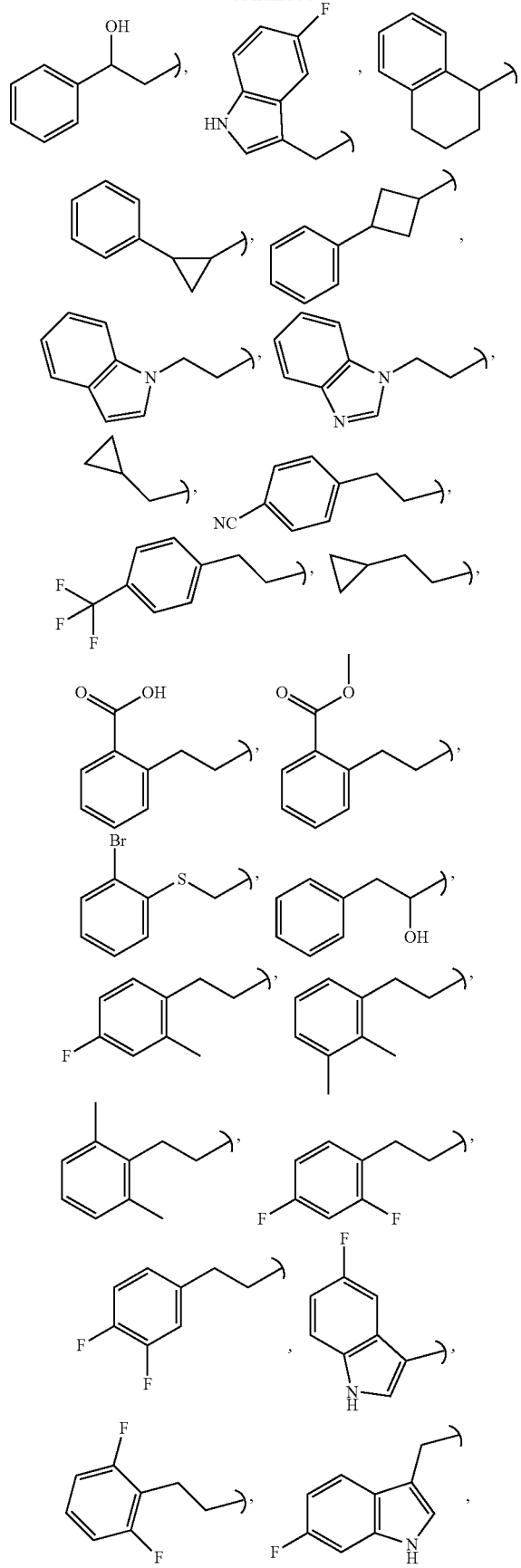
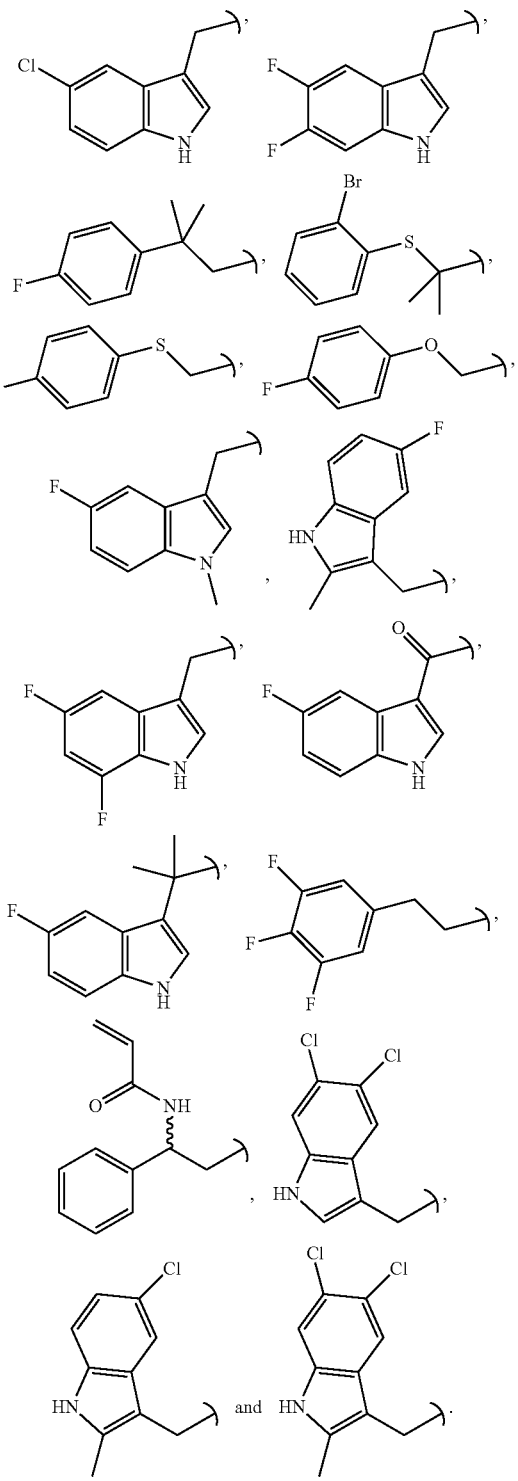
In another embodiment, the present invention provides a compound of Formula I wherein $R_1$ and $R_2$ are hydrogen.
In another embodiment, the present invention provides a compound of Formula I, or a pharmaceutically acceptable salt, stereoisomer or deuterated analog thereof, wherein
$R_1$ and $R_2$ are hydrogen,
X is CH or nitrogen, and when X is CH then Y is selected from:
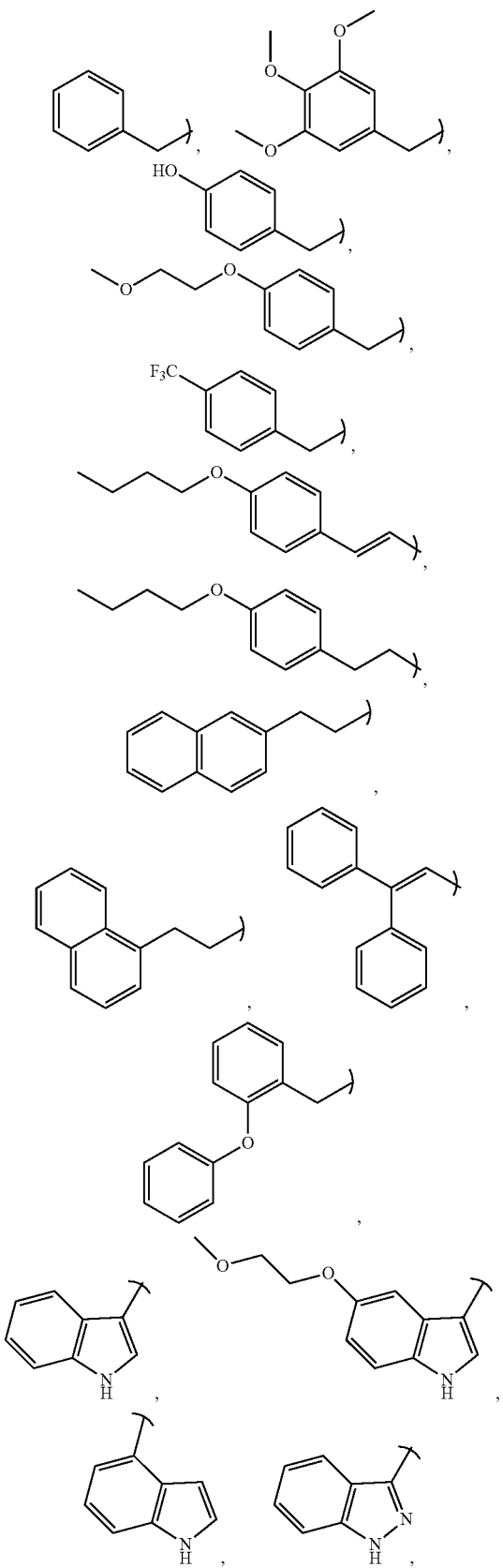
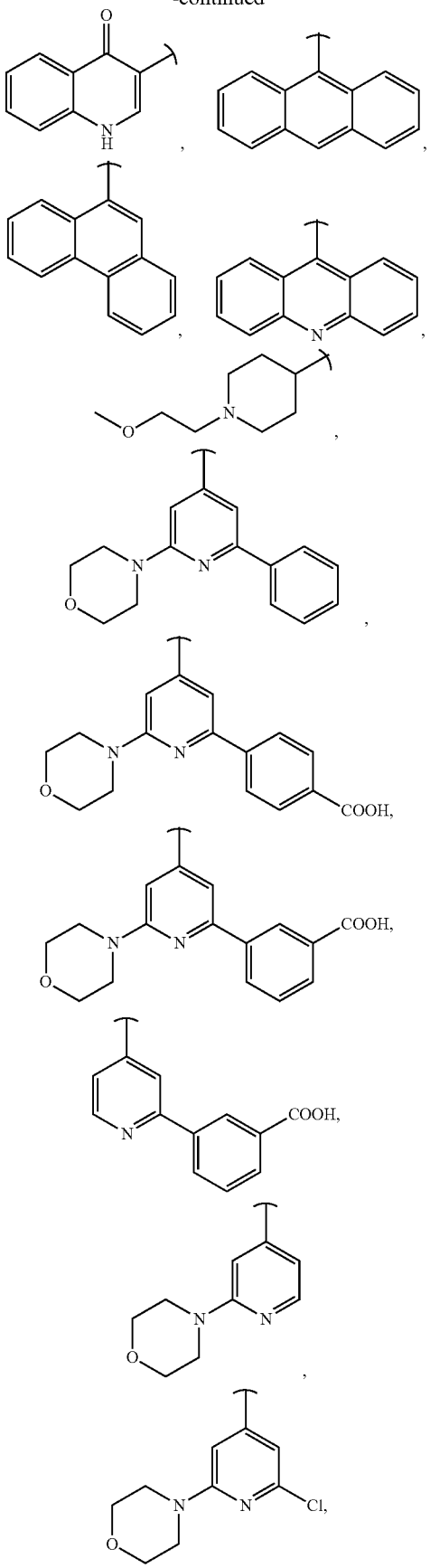

-continued

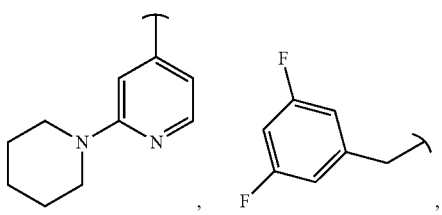

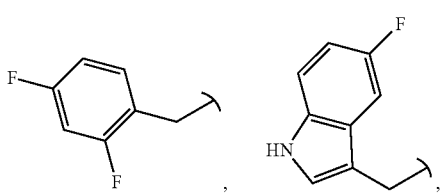

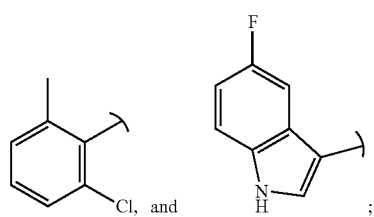

and when X is nitrogen then Y is selected from:

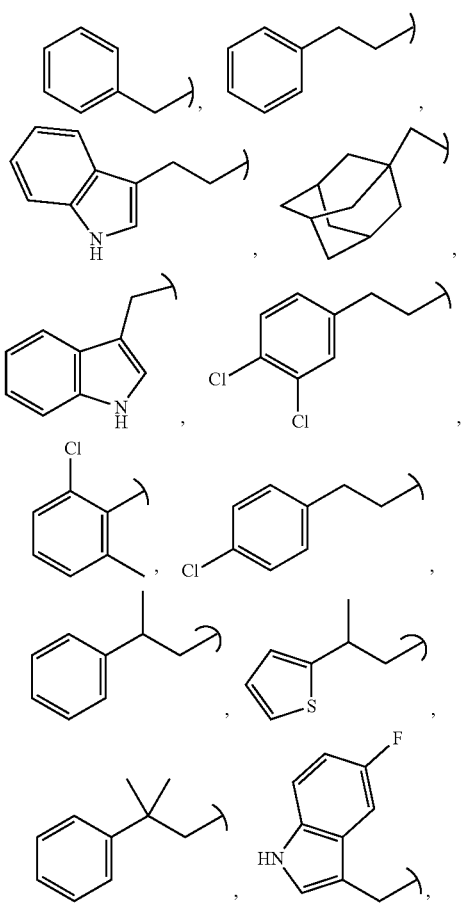

-continued

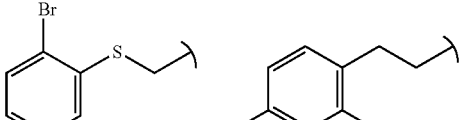

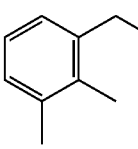, and

In another embodiment, the present invention provides a compound of Formula I, or a pharmaceutically acceptable salt, stereoisomer or deuterated analog thereof, wherein
$R_1$ and $R_2$ are hydrogen; and
X is CH or nitrogen,
wherein when X is CH, Y is selected from:

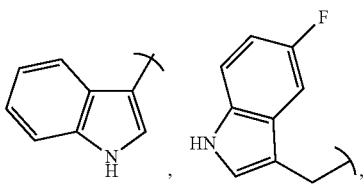

and when X is nitrogen, Y is selected from:

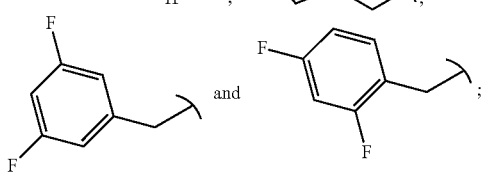

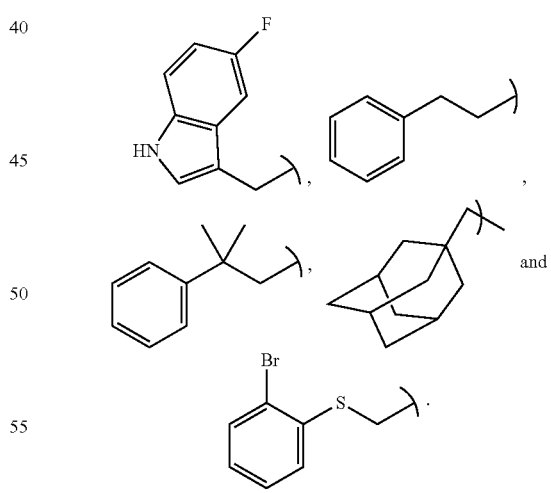

In another embodiment, the present invention provides a compound of Formula I, or a pharmaceutically acceptable salt, stereoisomer or deuterated analog thereof, wherein
$R_1$ is selected from hydrogen, $CH_3$, —COOH, fluoro and CN (e.g., hydrogen);
$R_2$ is selected from hydrogen, $CH_3$, —COOH, fluoro and CN (e.g., hydrogen);
X is CH, and Y is selected from:

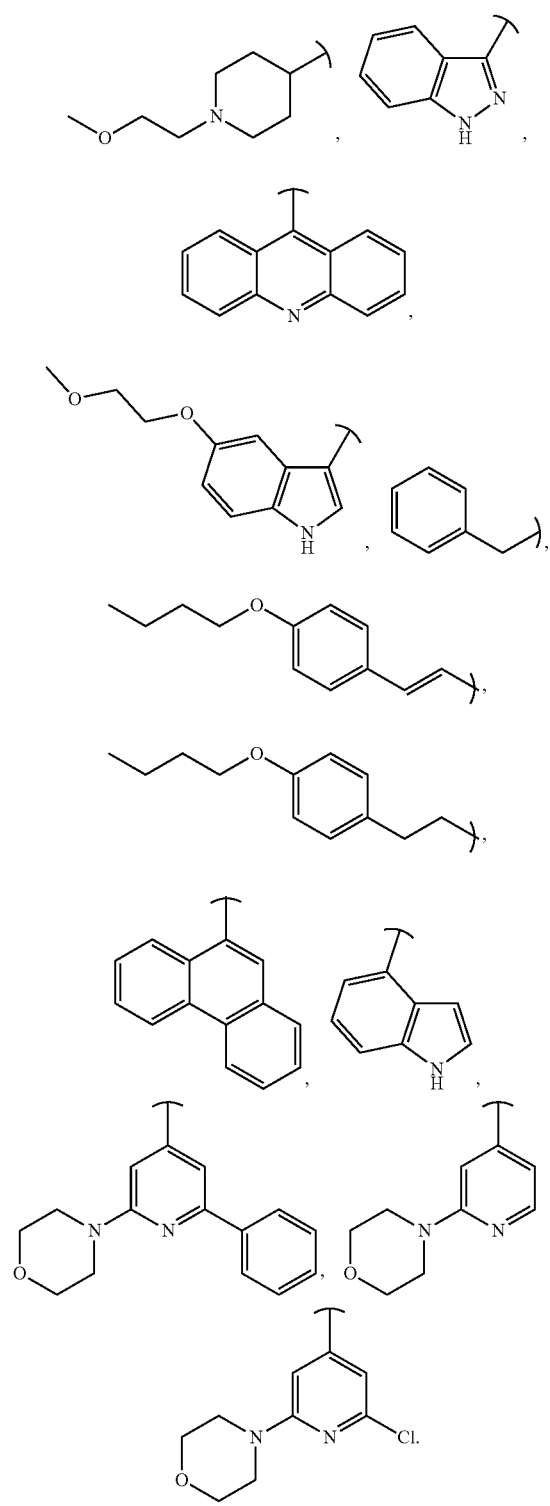

In another embodiment, the present invention provides a compound of Formula I, or a pharmaceutically acceptable salt, stereoisomer or deuterated analog thereof, wherein $R_1$ and $R_2$ both are hydrogen, X is nitrogen and Y is selected from the group consisting of:

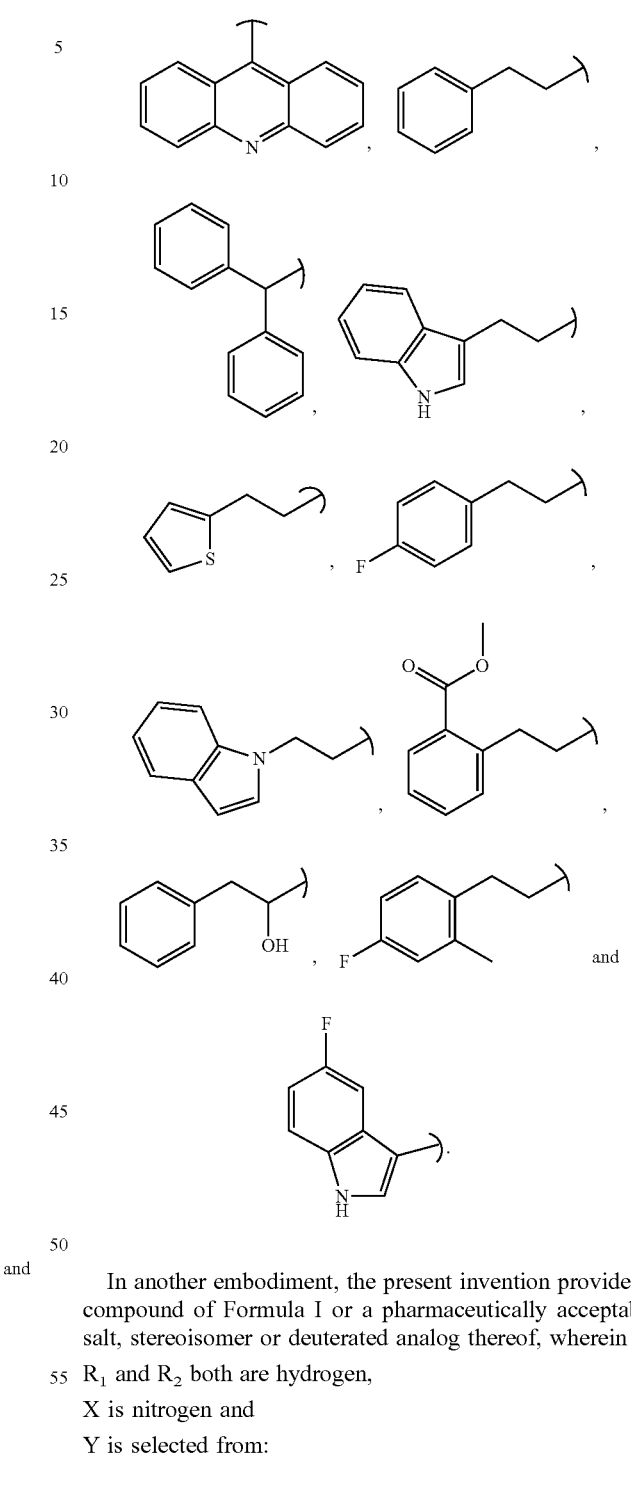

In another embodiment, the present invention provides a compound of Formula I or a pharmaceutically acceptable salt, stereoisomer or deuterated analog thereof, wherein $R_1$ and $R_2$ both are hydrogen, X is nitrogen and Y is selected from:

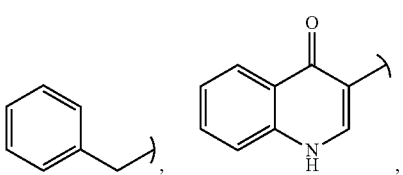

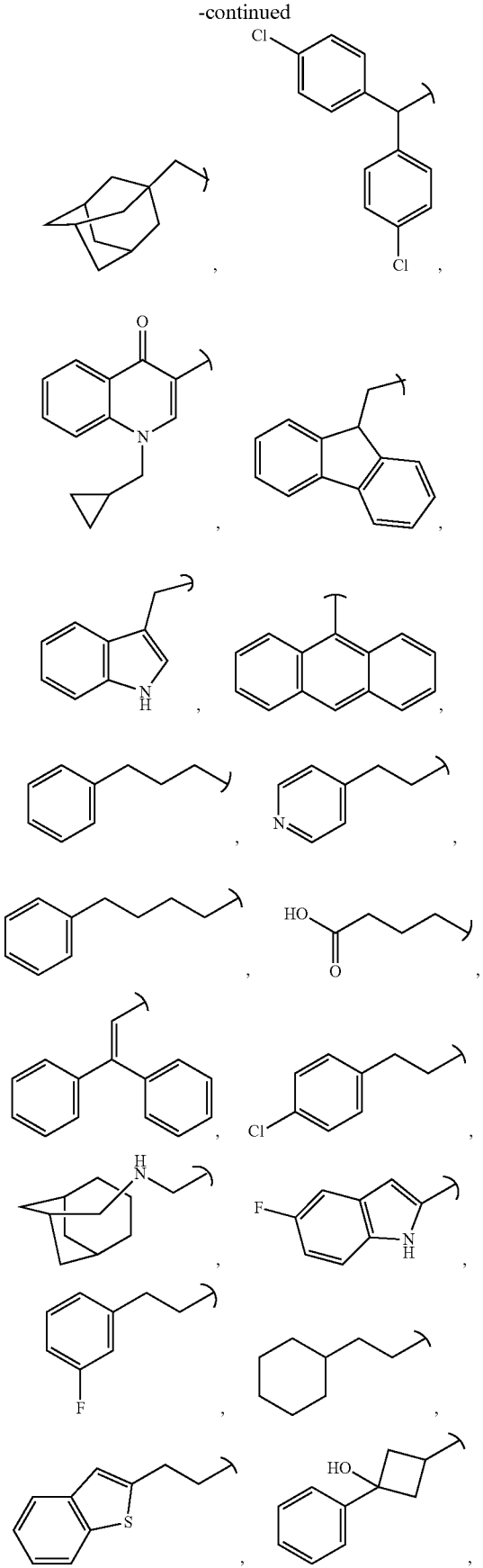
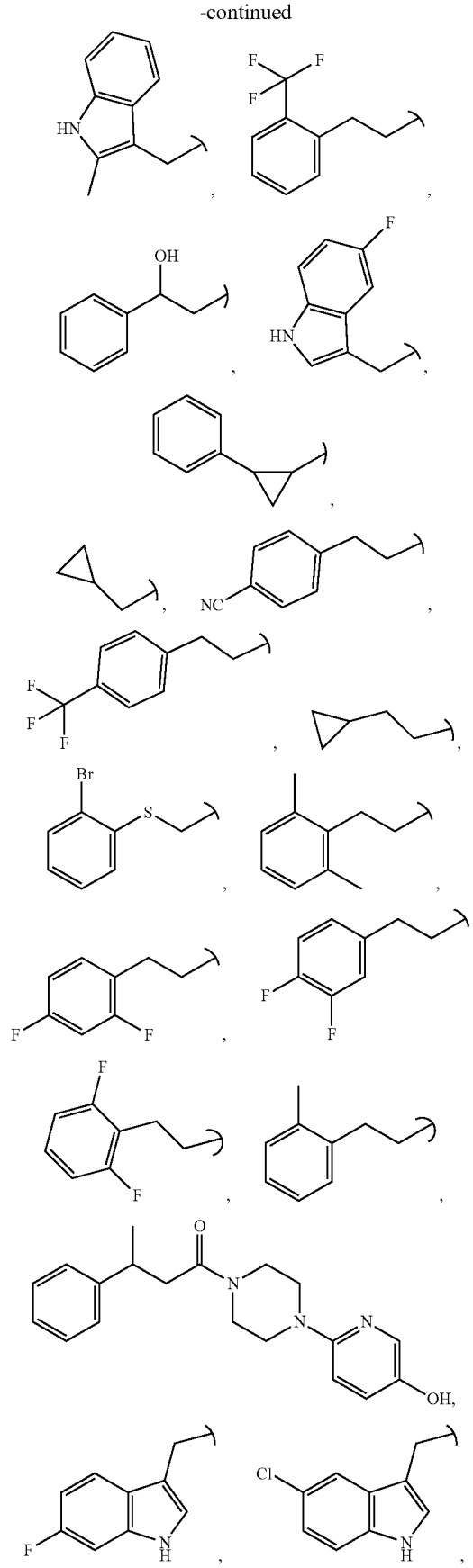

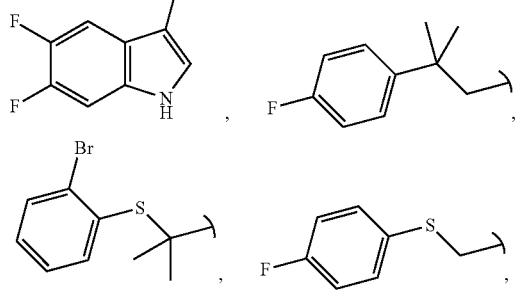
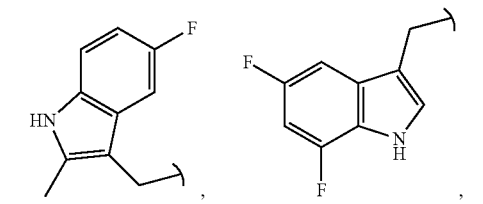
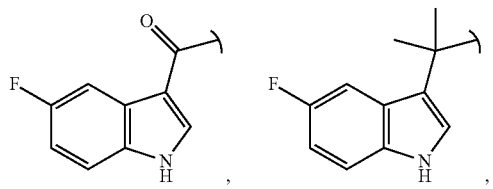
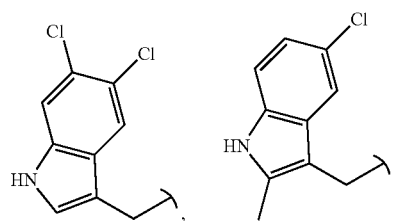
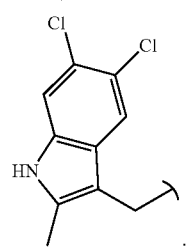 and
In another embodiment, the present invention provides a compound of Formula I or a pharmaceutically acceptable salt, stereoisomer or deuterated analog thereof, wherein
$R_1$ is selected from hydrogen, $CH_3$, —COOH, fluoro and CN (e.g., hydrogen);
$R_2$ is selected from hydrogen, $CH_3$, —COOH, fluoro and CN (e.g., hydrogen);
X is CH; and
Y is selected from:
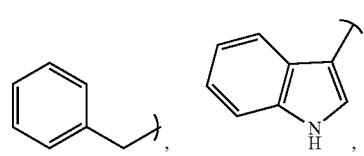
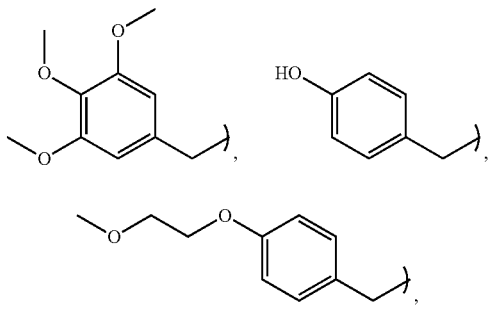
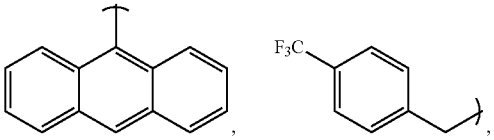
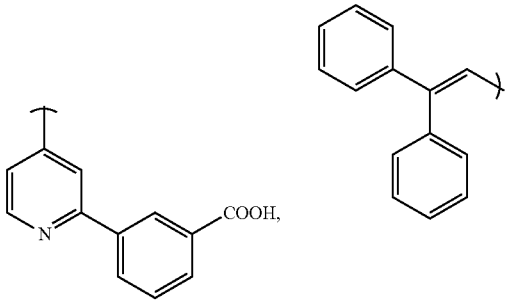
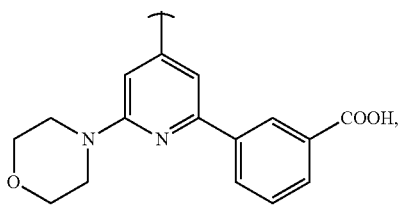
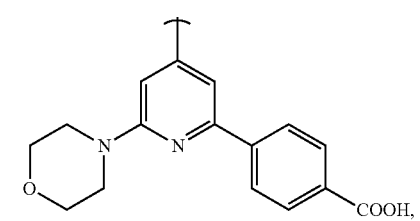
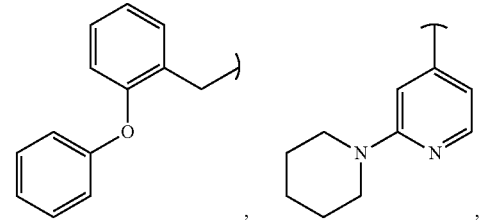

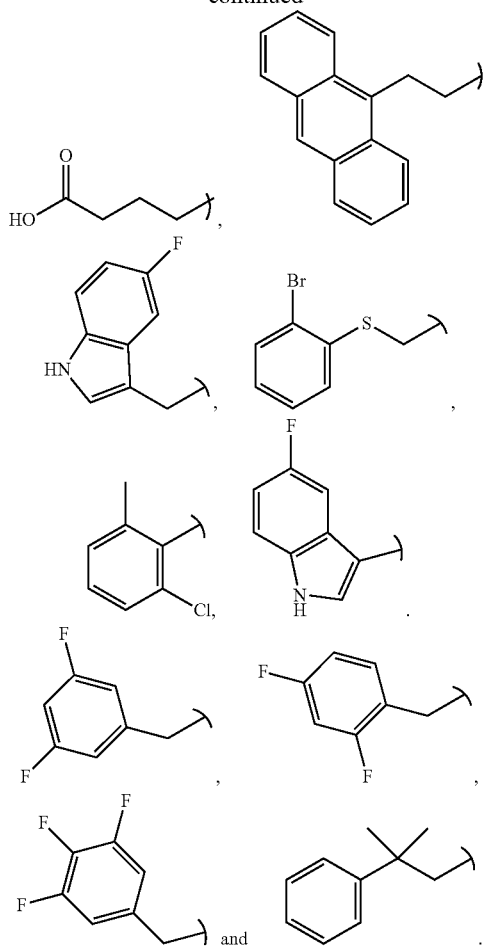
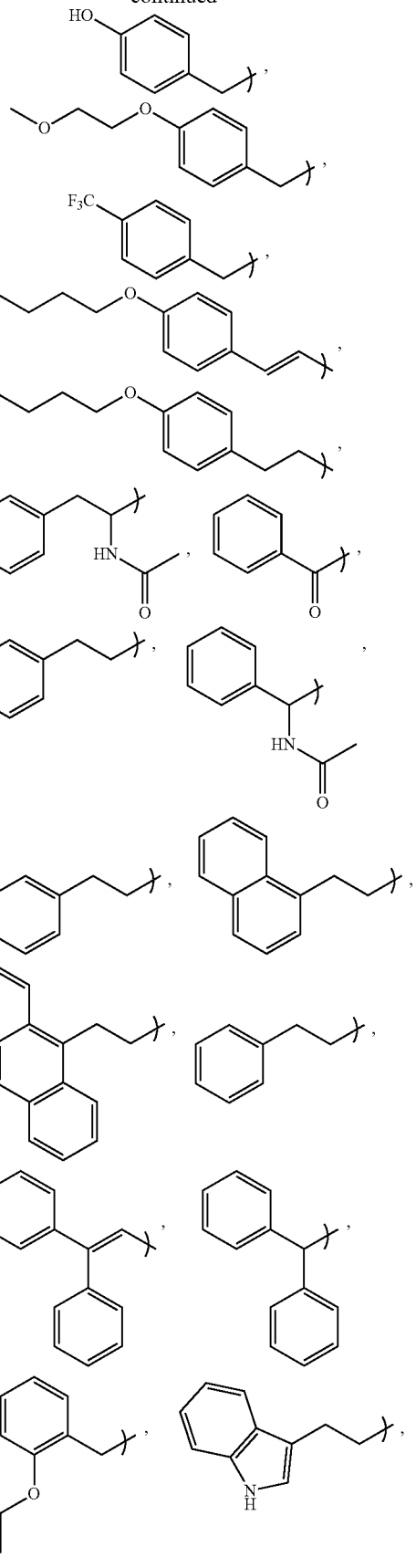
In another aspect, the present invention provides a compound of Formula Ia
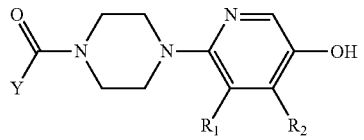
Formula Ia
or a pharmaceutically acceptable salt, stereoisomer or deuterated analog thereof, wherein
$R_1$ is selected from hydrogen, —$CH_3$, —COOH, fluoro and —CN;
$R_2$ is selected from hydrogen, —$CH_3$, —COOH, fluoro and —CN; and
Y is selected from:

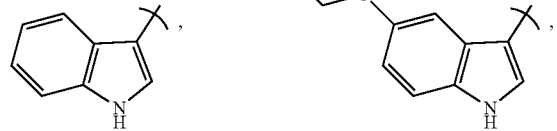
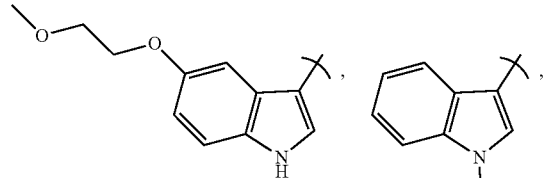

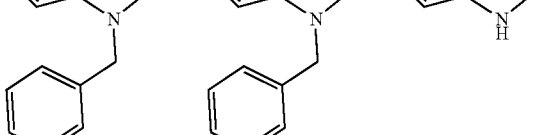
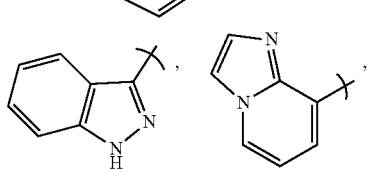
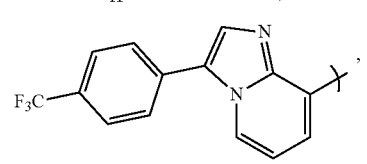
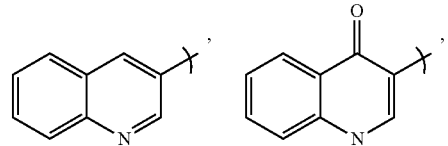
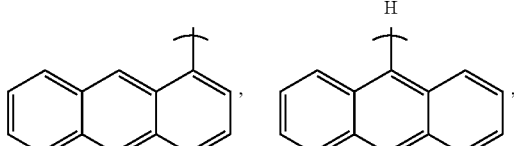
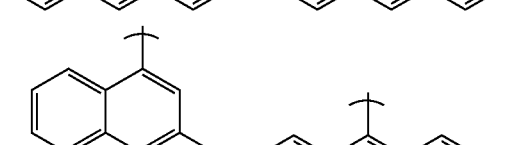
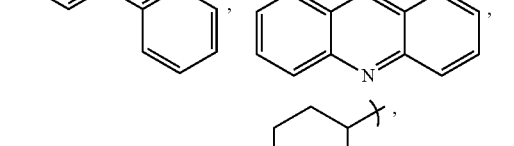
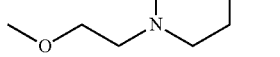
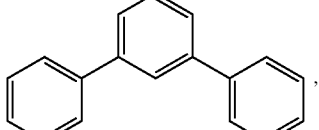
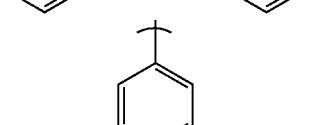
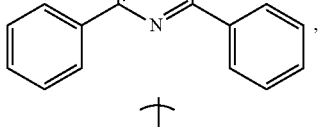
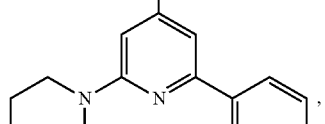
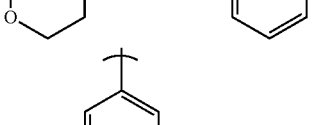
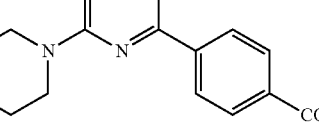
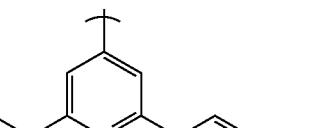
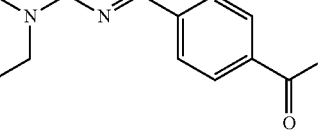
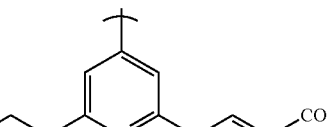
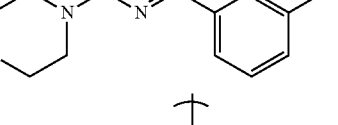
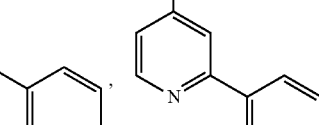
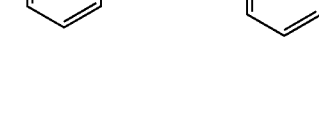
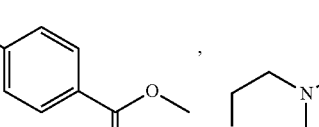

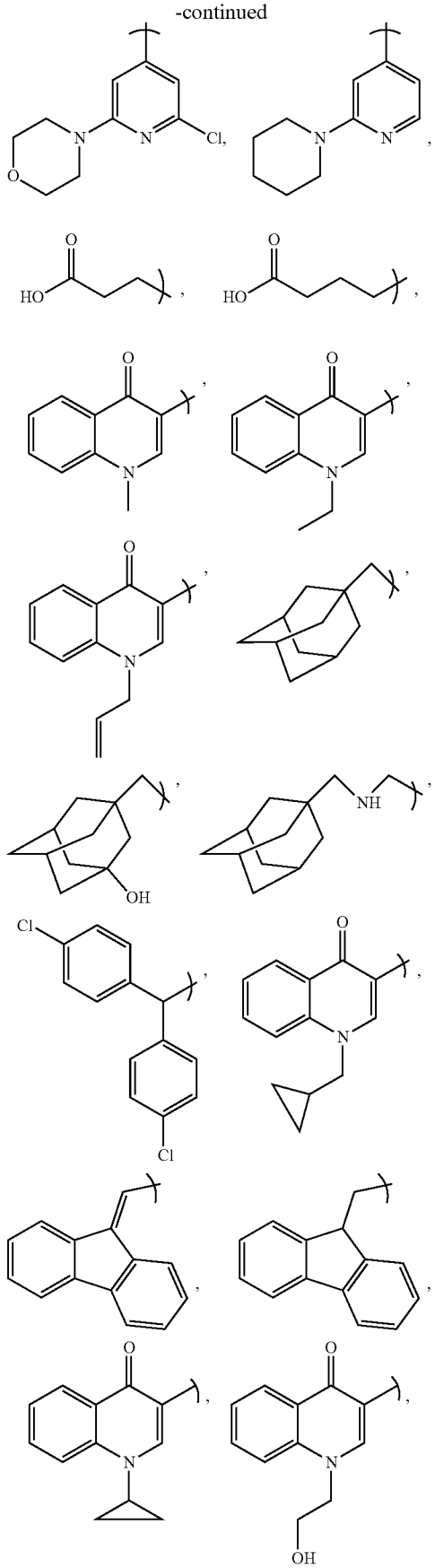
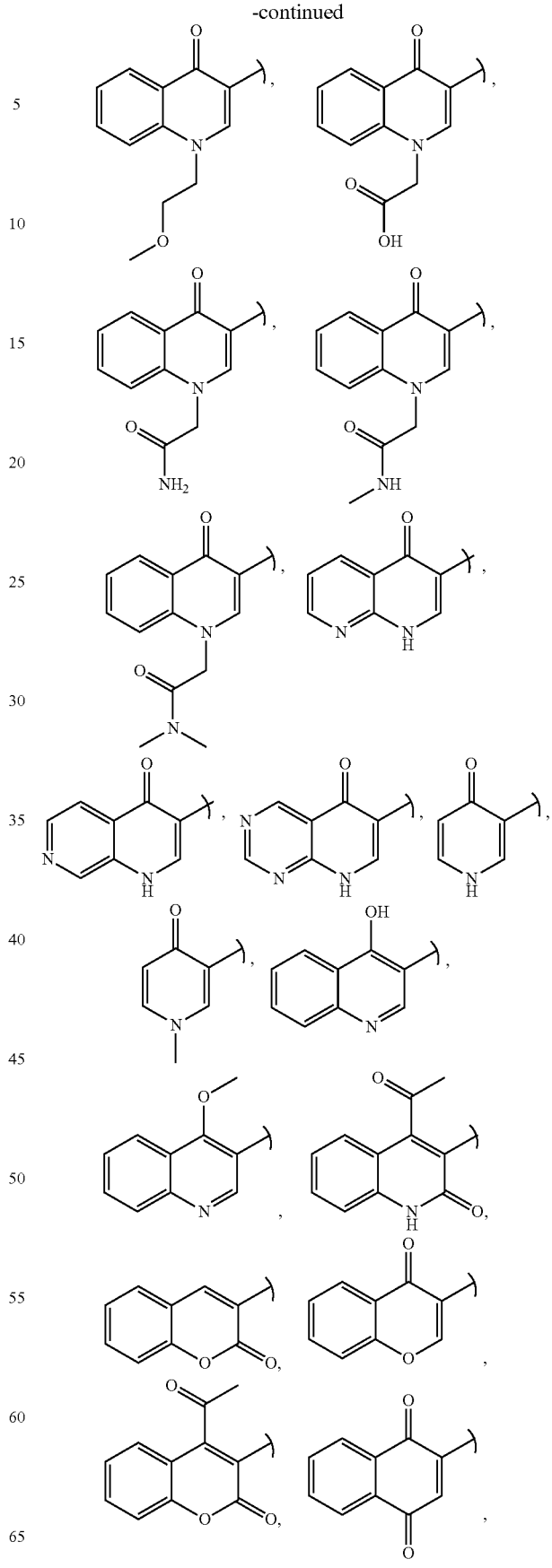

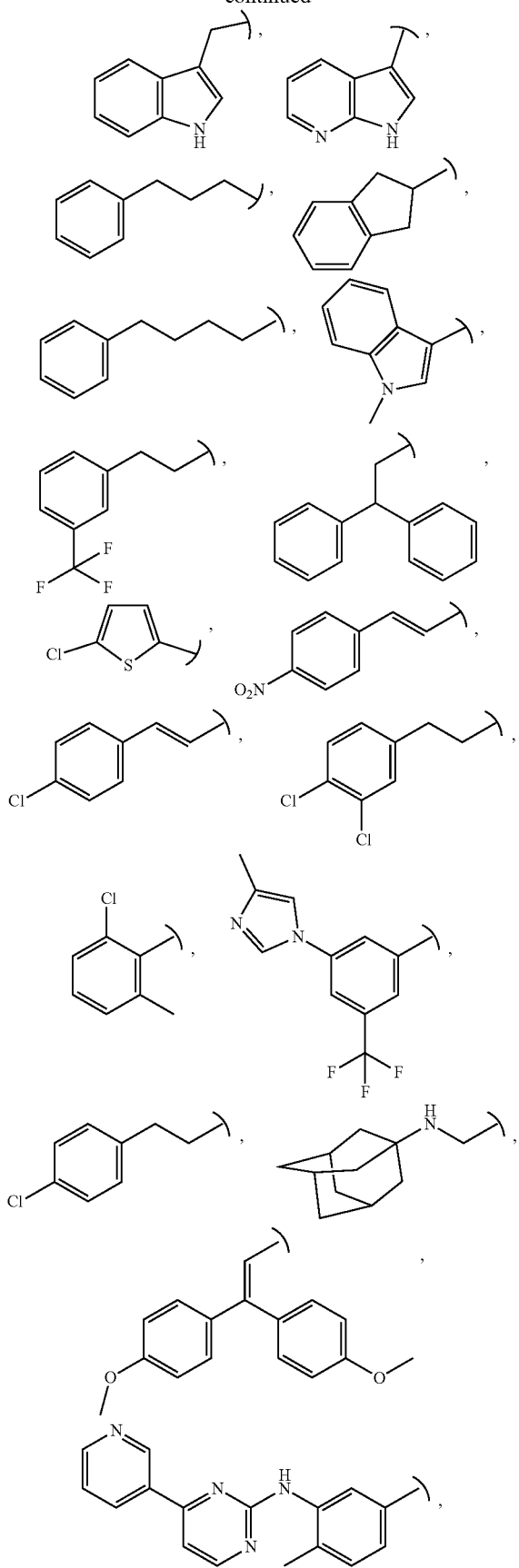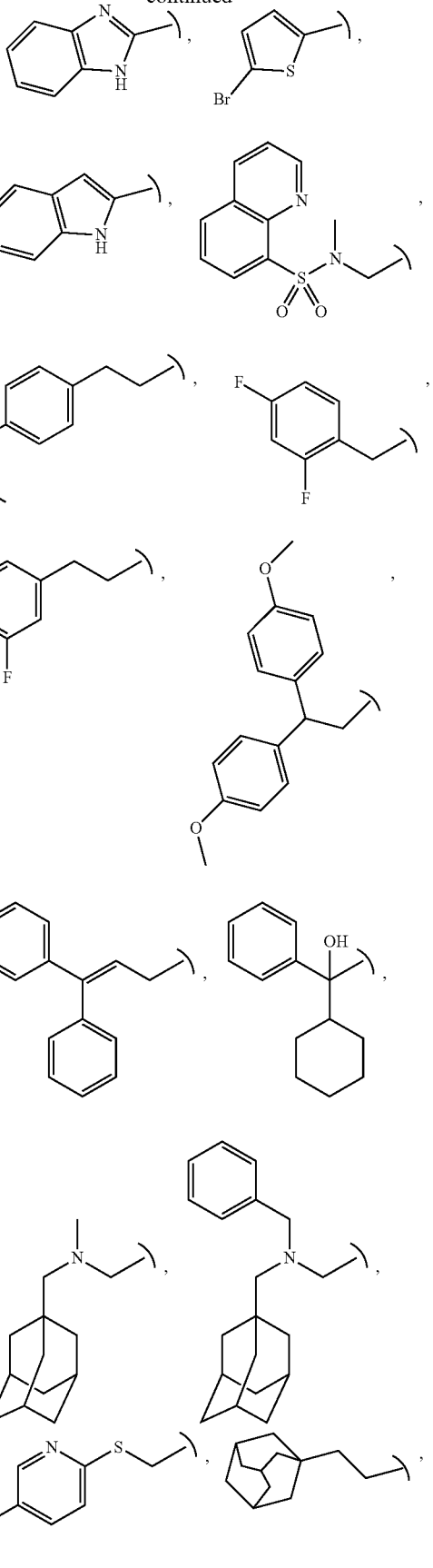

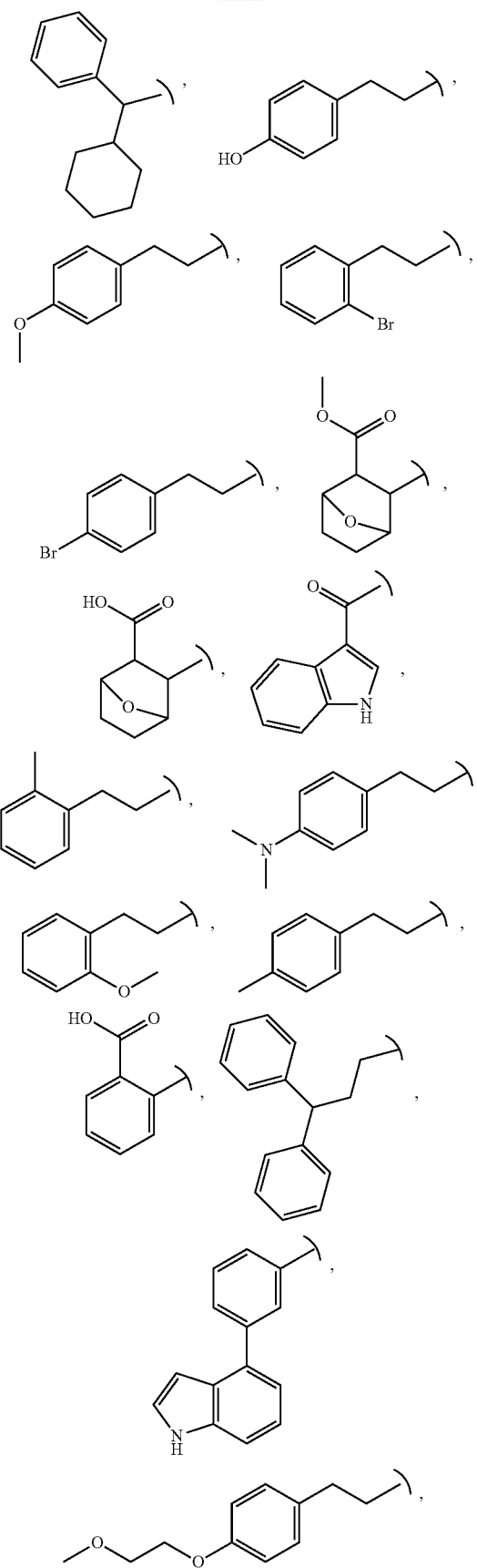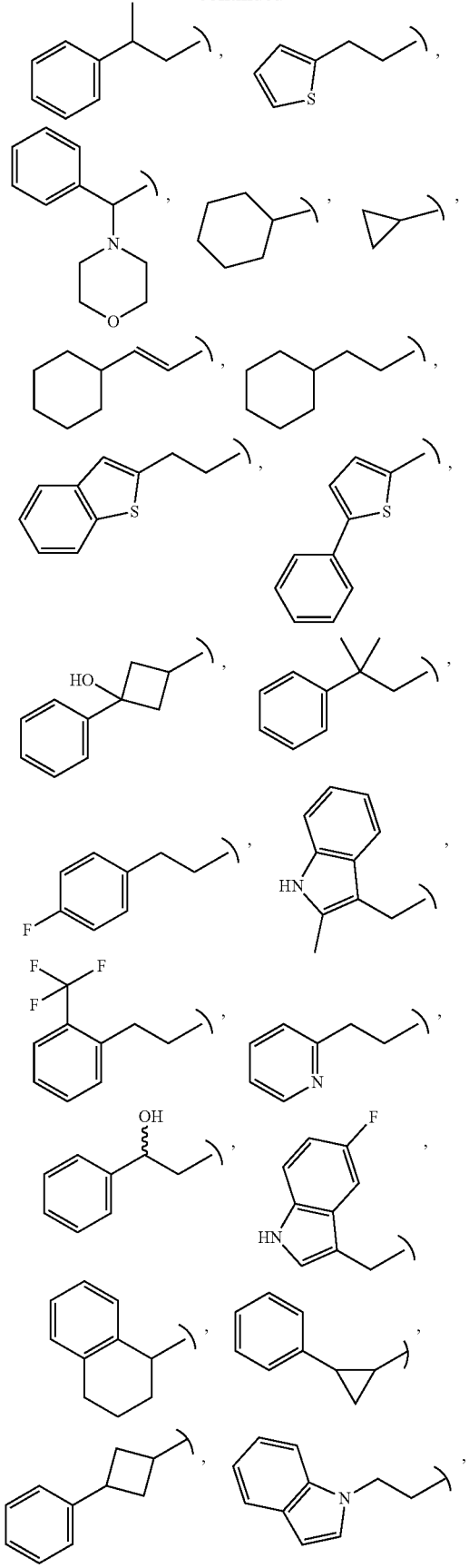

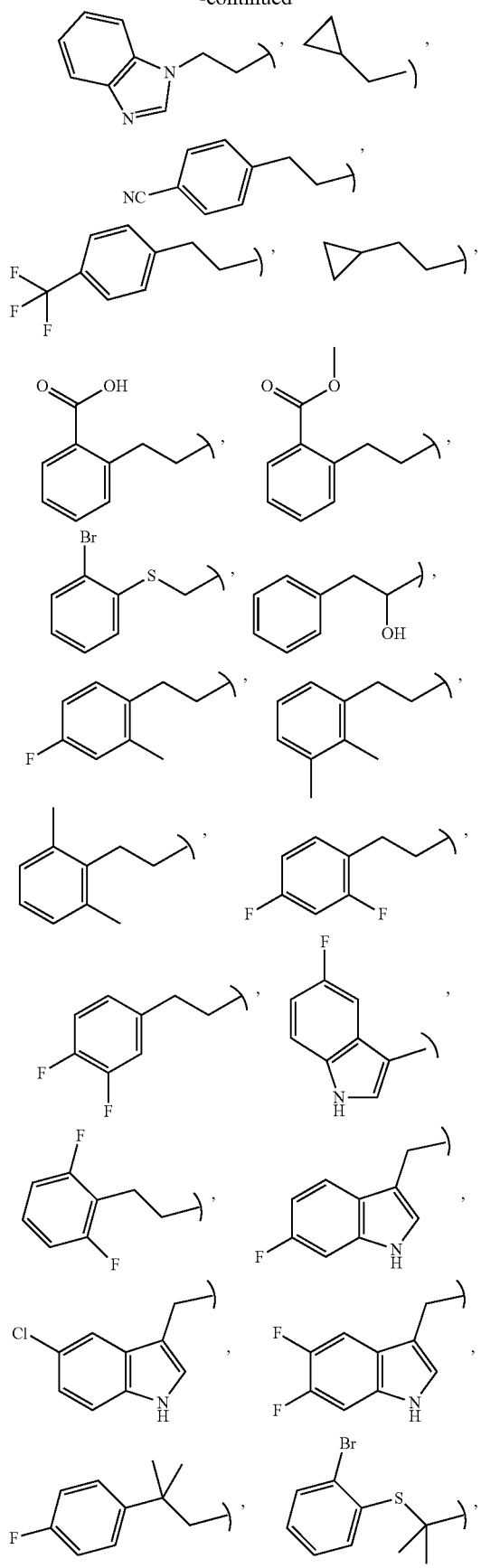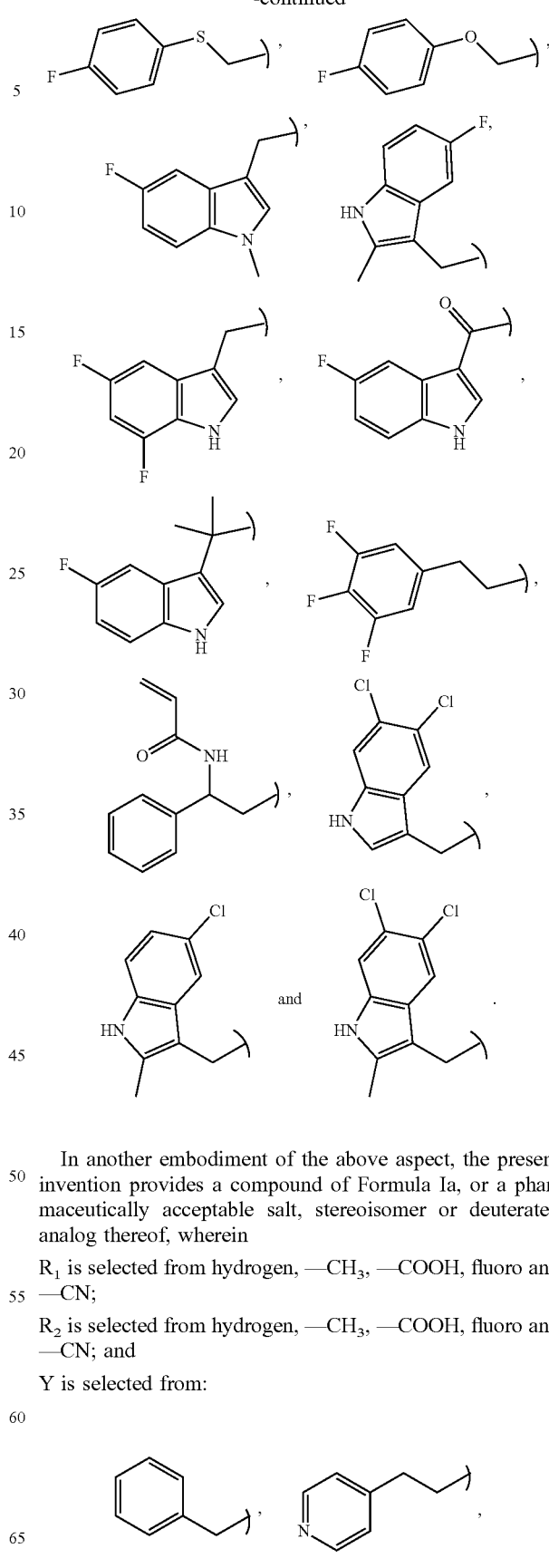
In another embodiment of the above aspect, the present invention provides a compound of Formula Ia, or a pharmaceutically acceptable salt, stereoisomer or deuterated analog thereof, wherein
$R_1$ is selected from hydrogen, —$CH_3$, —COOH, fluoro and —CN;
$R_2$ is selected from hydrogen, —$CH_3$, —COOH, fluoro and —CN; and
Y is selected from:
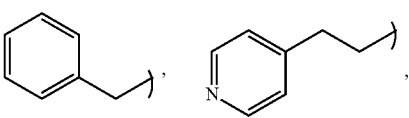

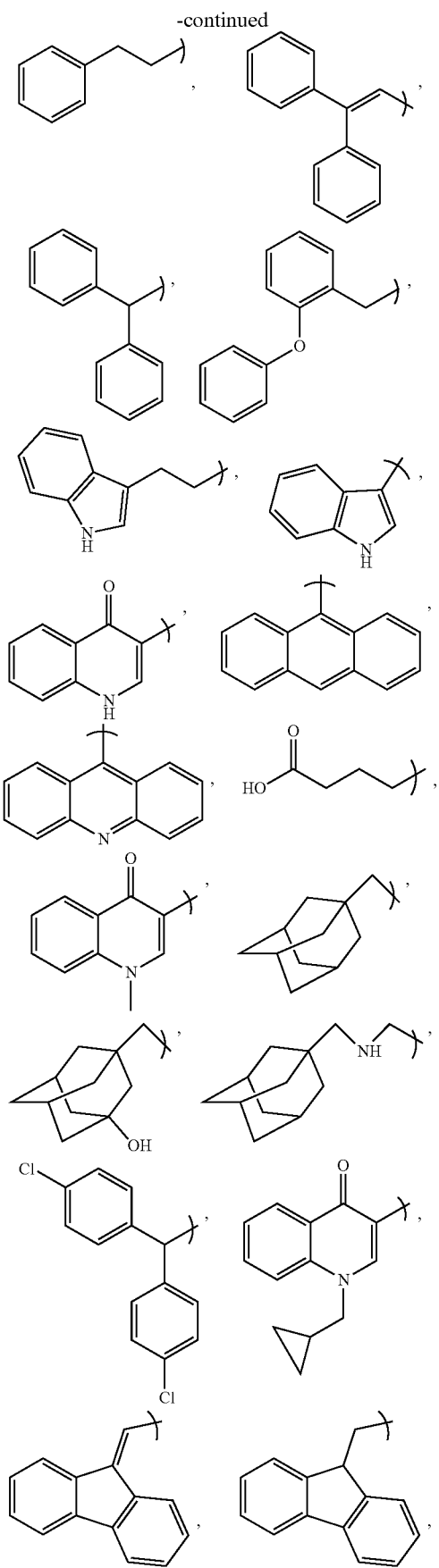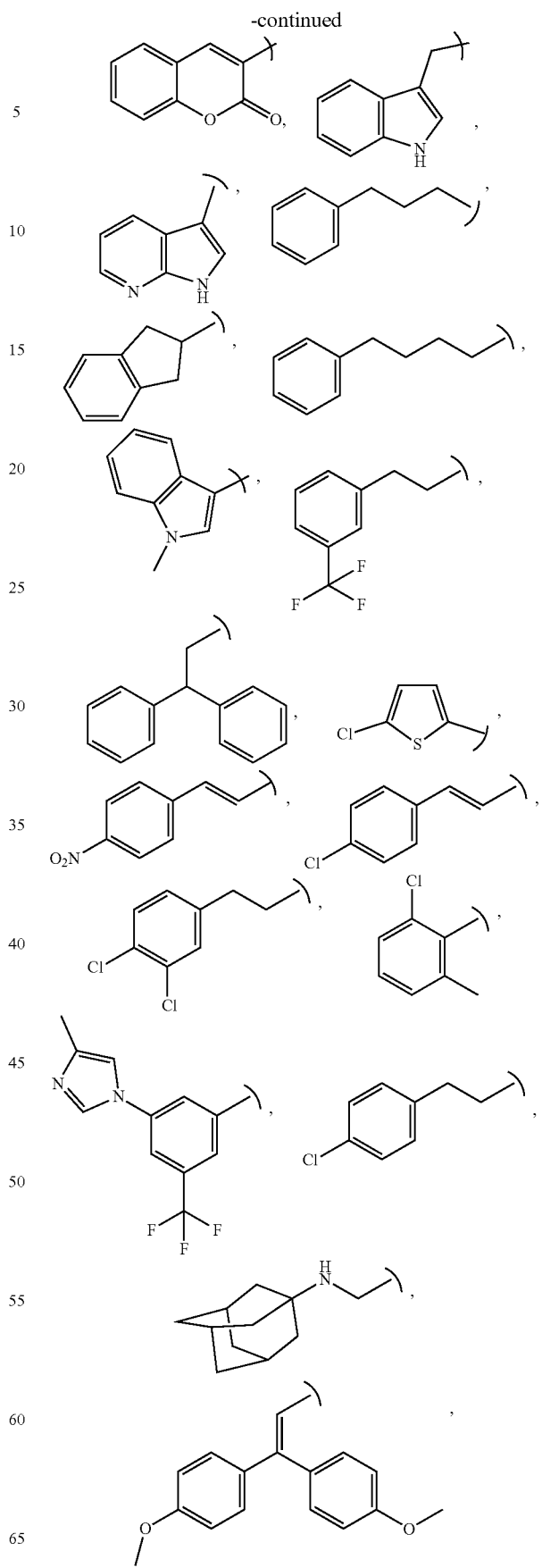

75
-continued
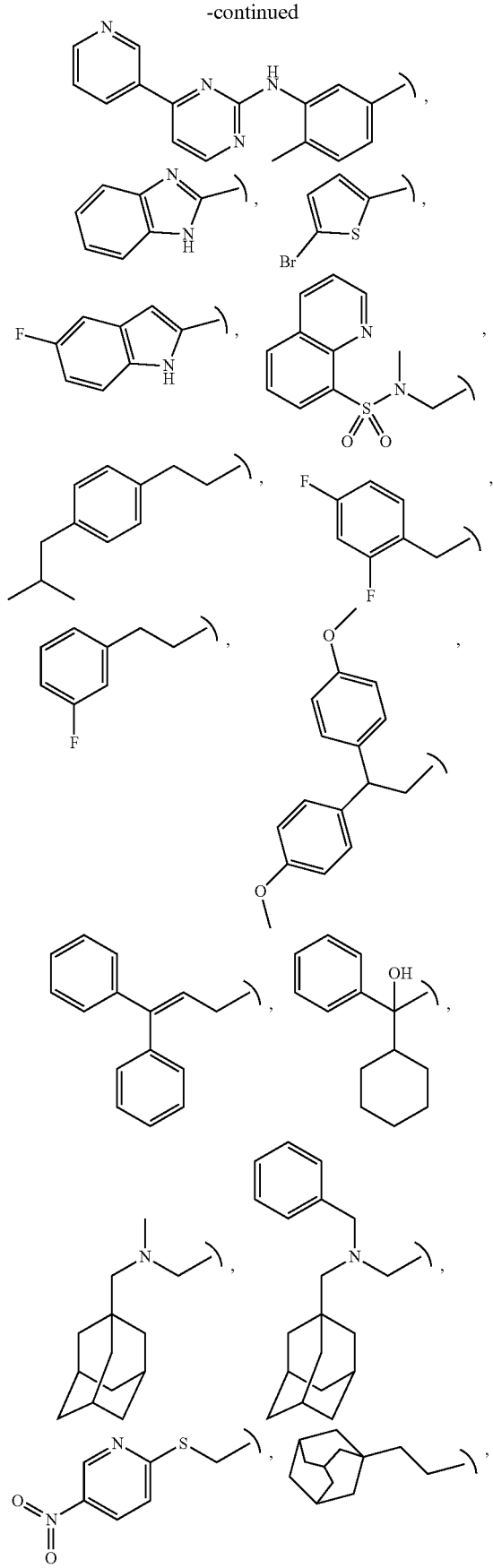
76
-continued
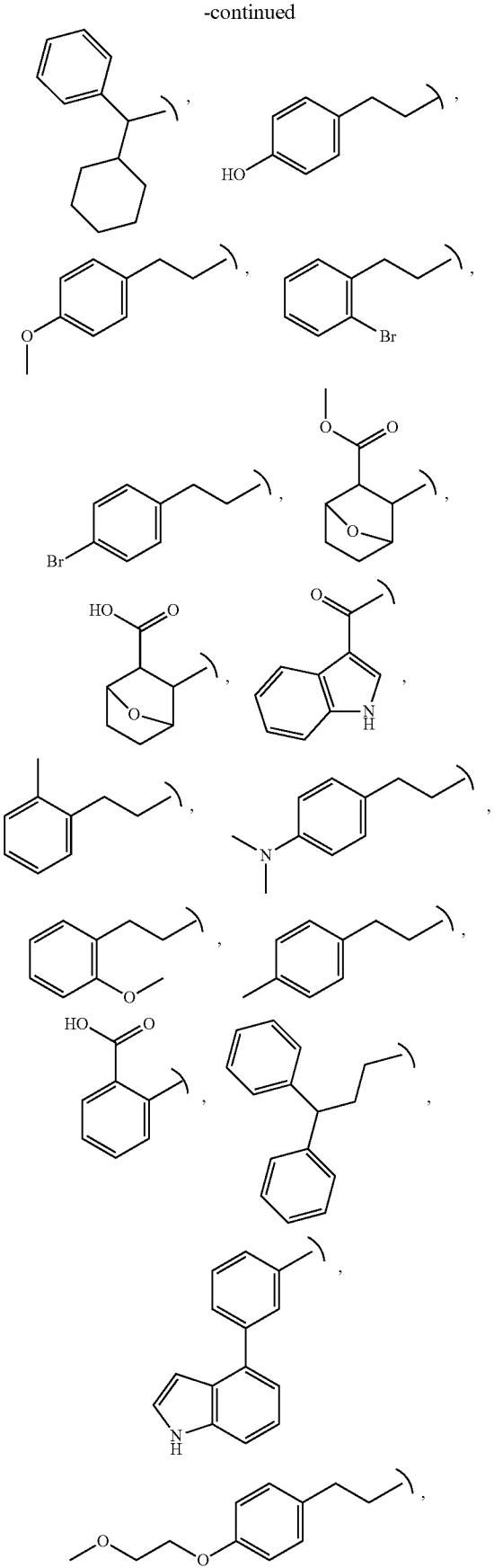

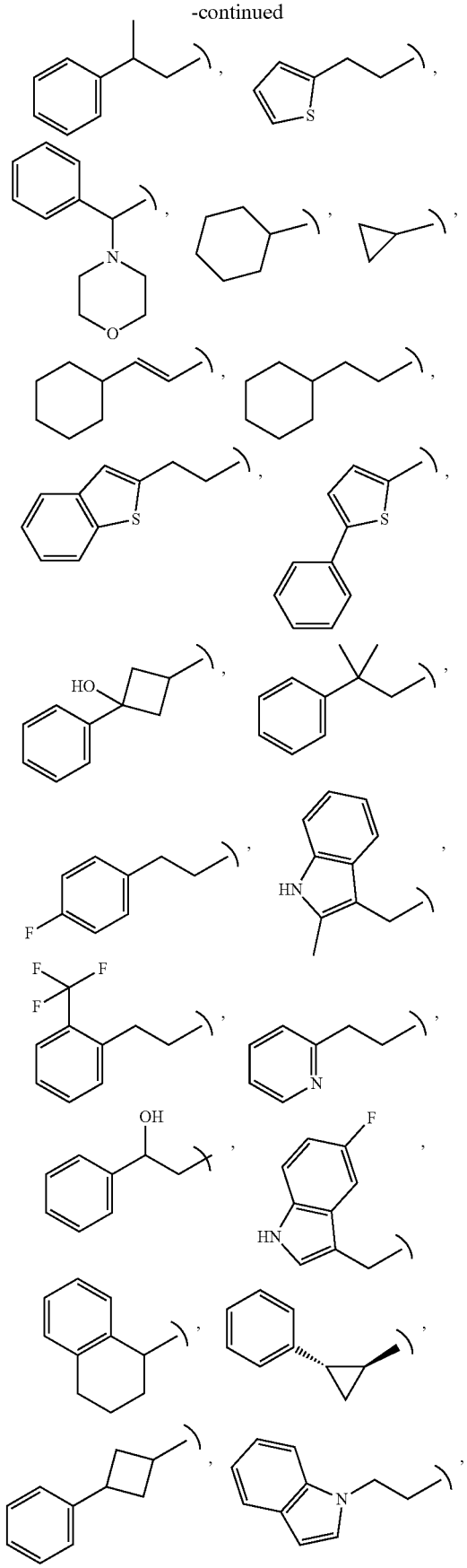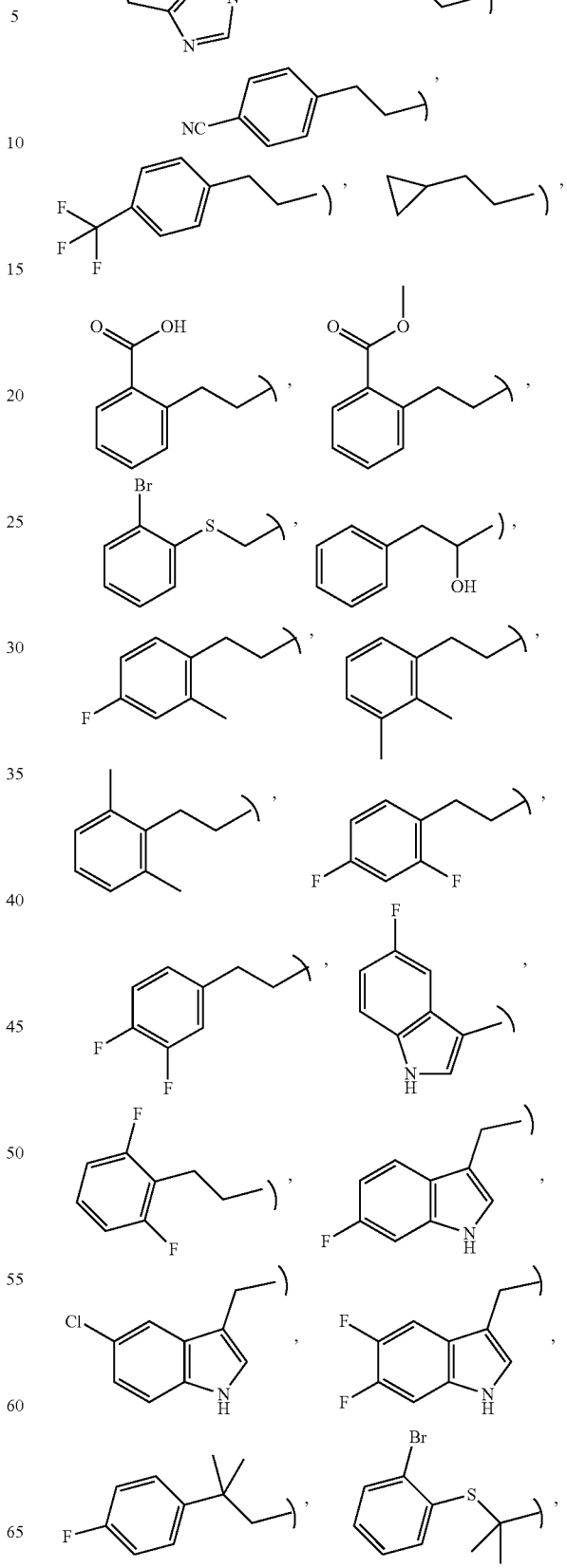

-continued

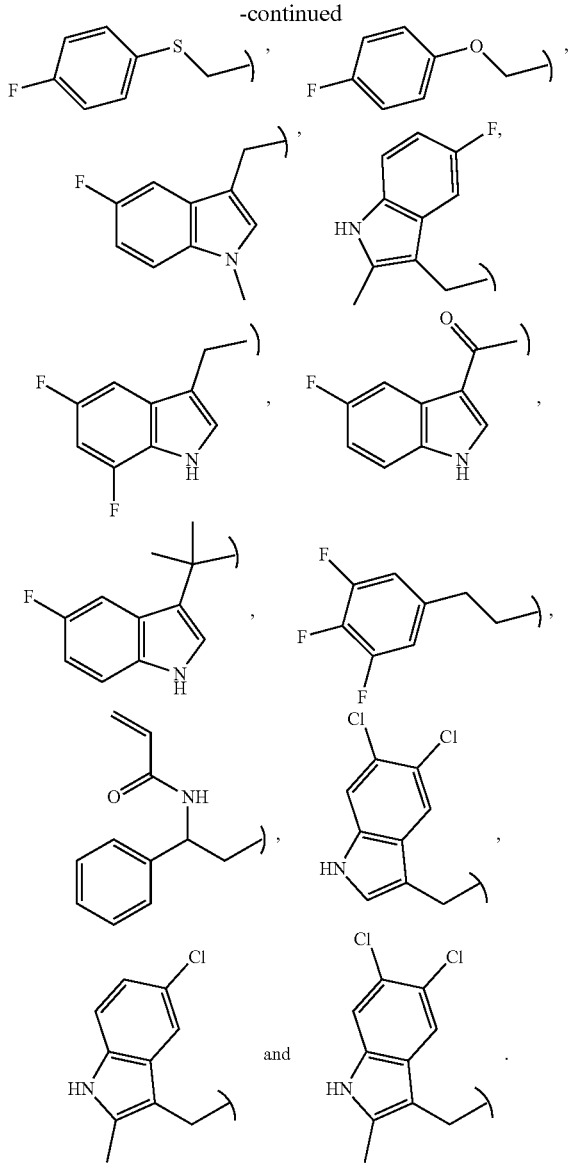

In another embodiment, the present invention provides a compound of Formula Ia, or a pharmaceutically acceptable salt, stereoisomer or deuterated analog thereof, wherein $R_1$ and $R_2$ are hydrogen.

In another embodiment, the present invention provides a compound of Formula Ia, or a pharmaceutically acceptable salt, stereoisomer or deuterated analog thereof, wherein $R_1$ and $R_2$ are hydrogen; and Y is selected from:

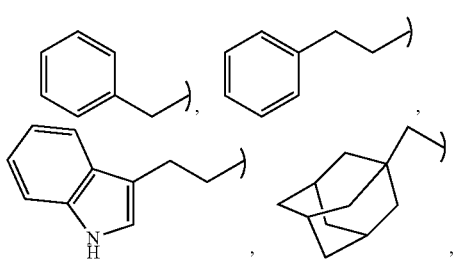

-continued

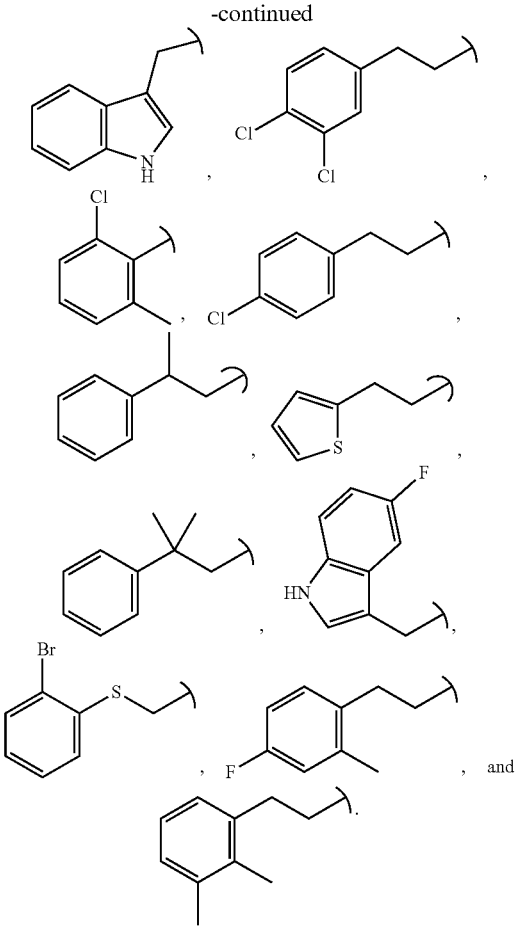

In another embodiment, the present invention provides a compound of Formula Ia, or a pharmaceutically acceptable salt, stereoisomer or deuterated analog thereof, wherein $R_1$ and $R_2$ are hydrogen; and Y is selected from:

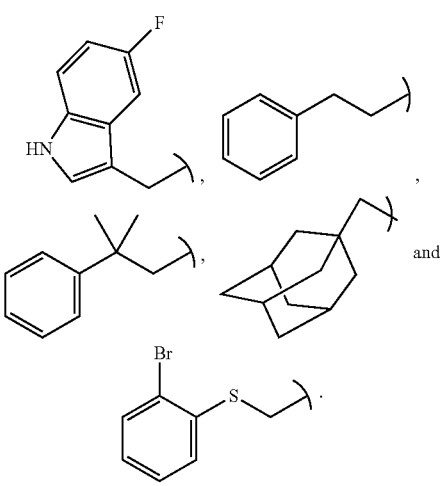

In another embodiment, the present invention provides a compound of Formula Ia, or a pharmaceutically acceptable salt, stereoisomer or deuterated analog thereof, wherein $R_1$ and $R_2$ are hydrogen, and Y is selected from:
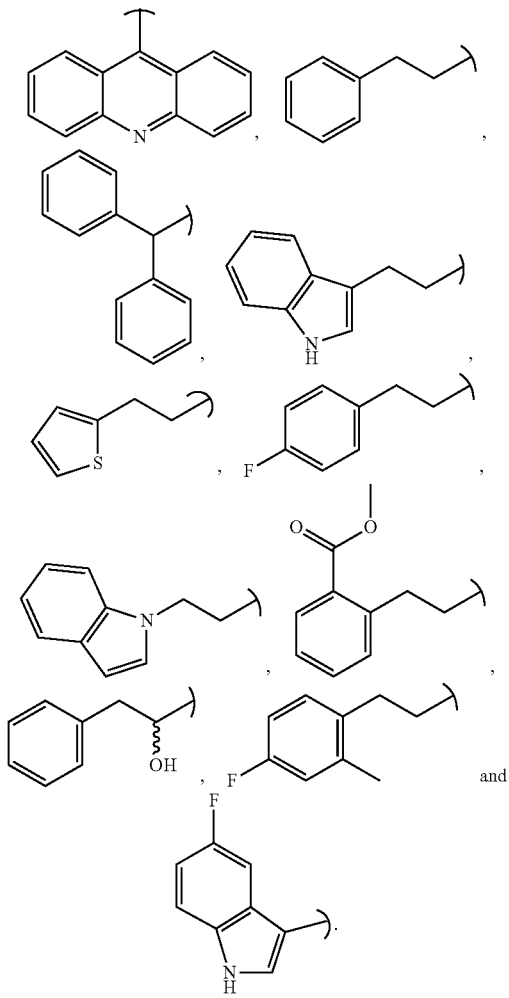
In another embodiment, the present invention provides a compound of Formula Ia, or a pharmaceutically acceptable salt, stereoisomer or deuterated analog thereof, wherein R₁ and R₂ are hydrogen, and
Y is selected from:
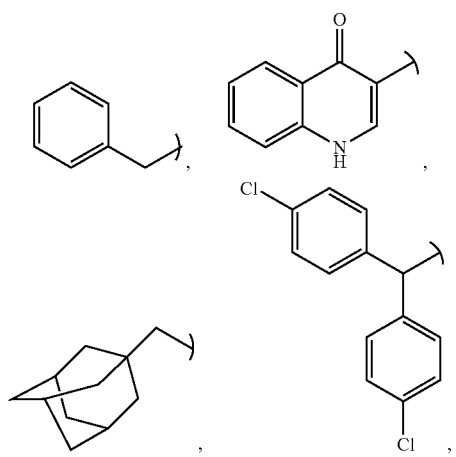
-continued
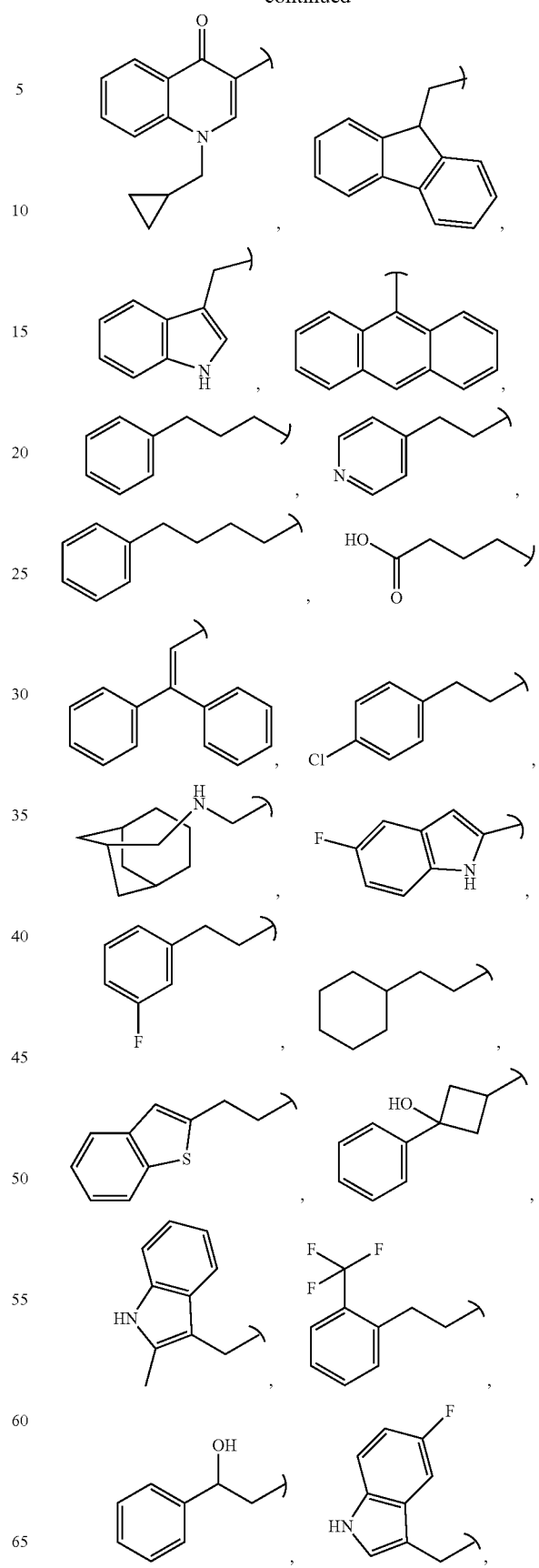

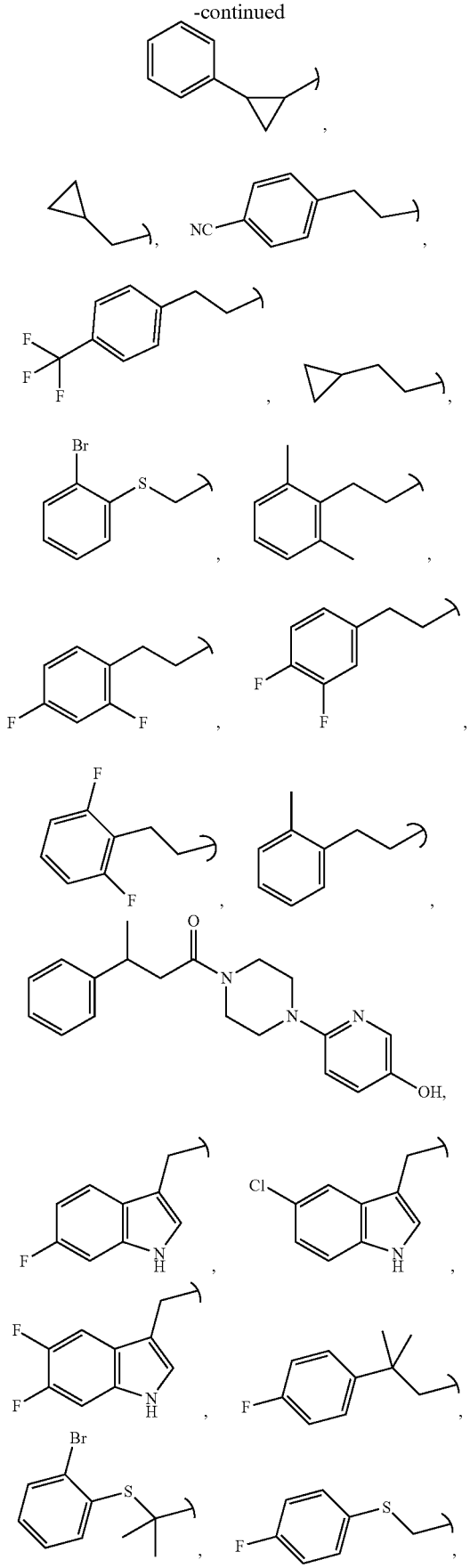
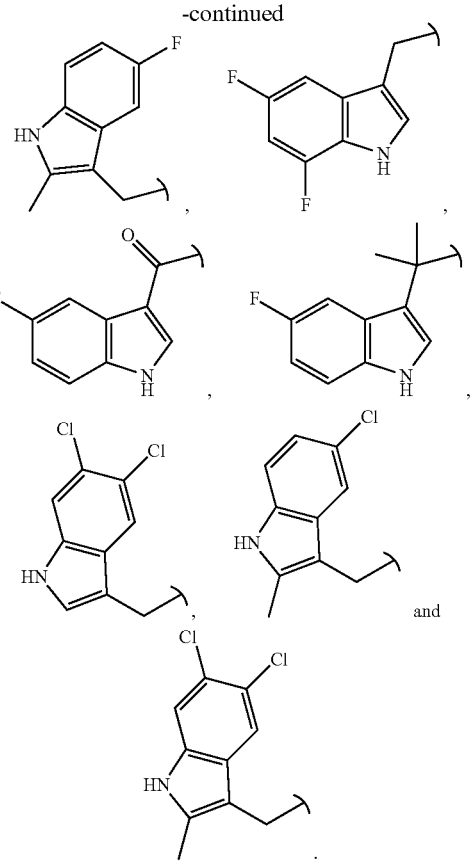
and
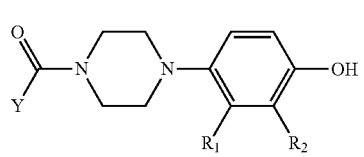
In another aspect, the present invention relates to a compound of Formula Ib
Formula Ib
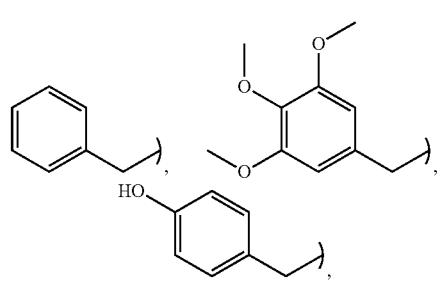
or a pharmaceutically acceptable salt, stereoisomer or deuterated analog thereof, wherein
R₁ is selected from hydrogen, —CH₃, —COOH, fluoro and —CN;
R₂ is selected from hydrogen, —CH₃, —COOH, fluoro and —CN;
Y is selected from:

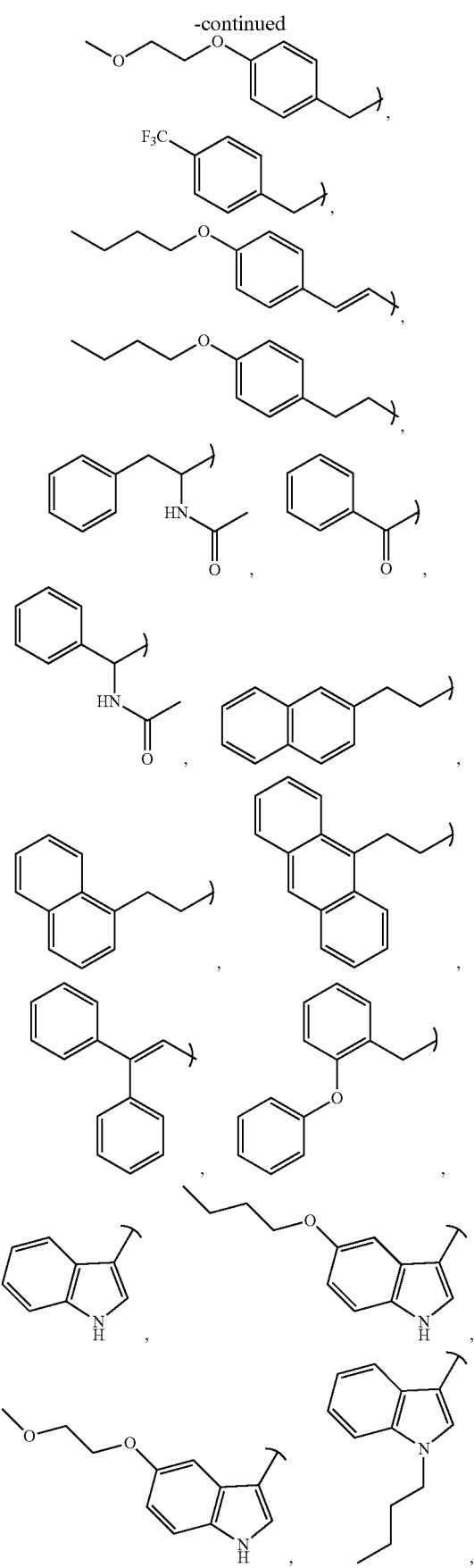
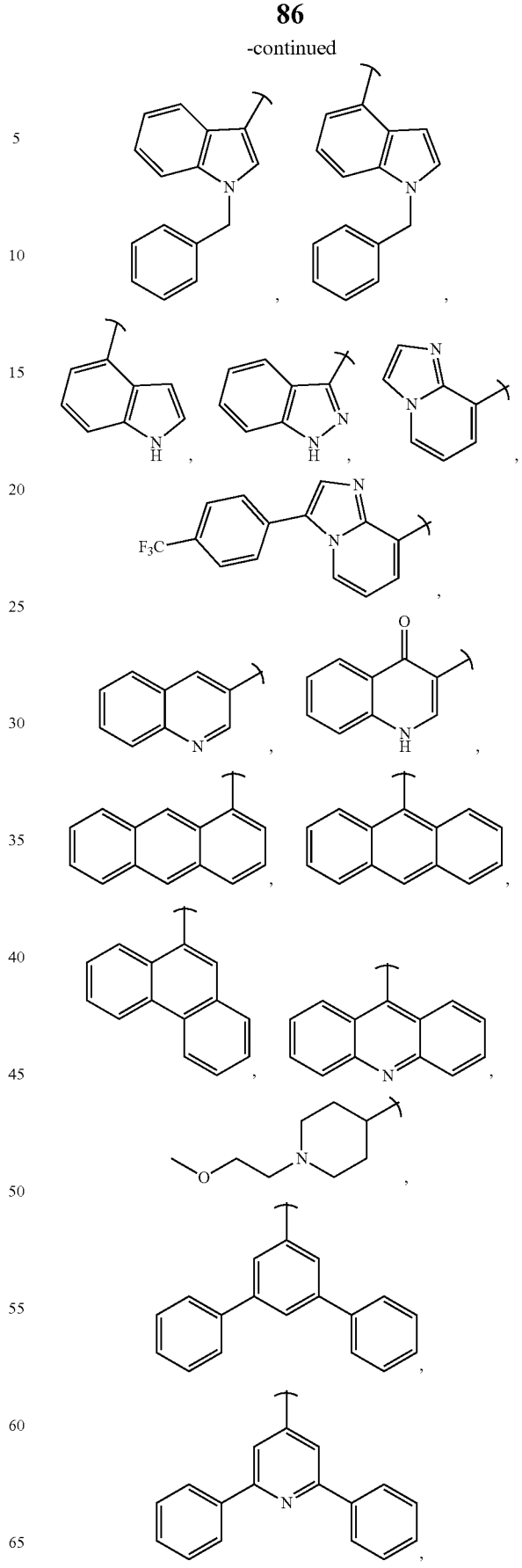

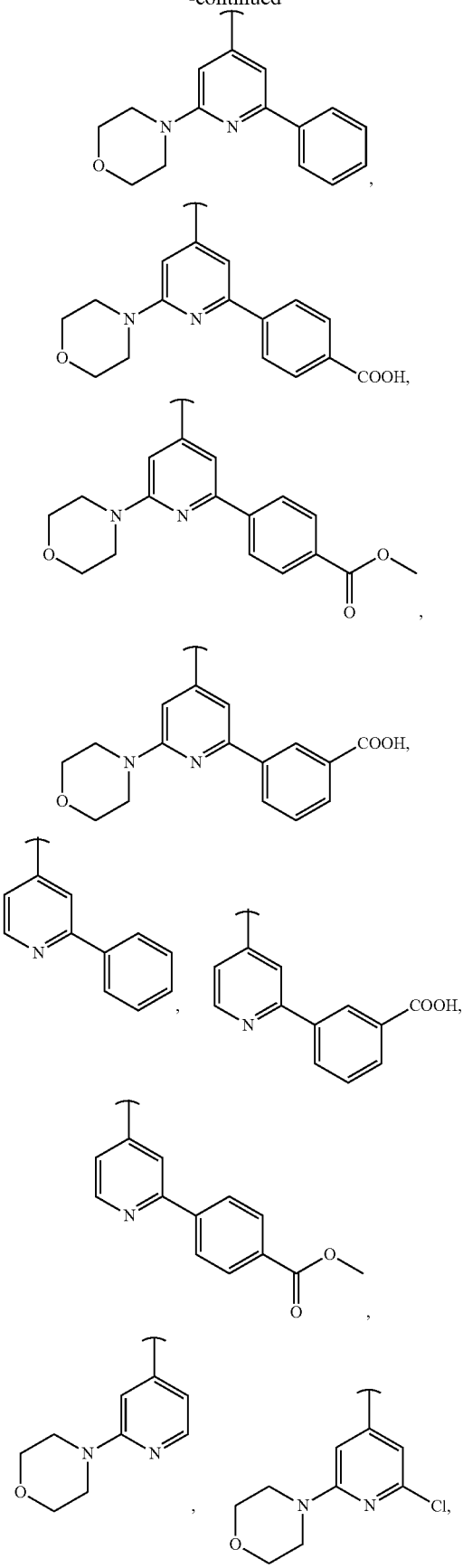
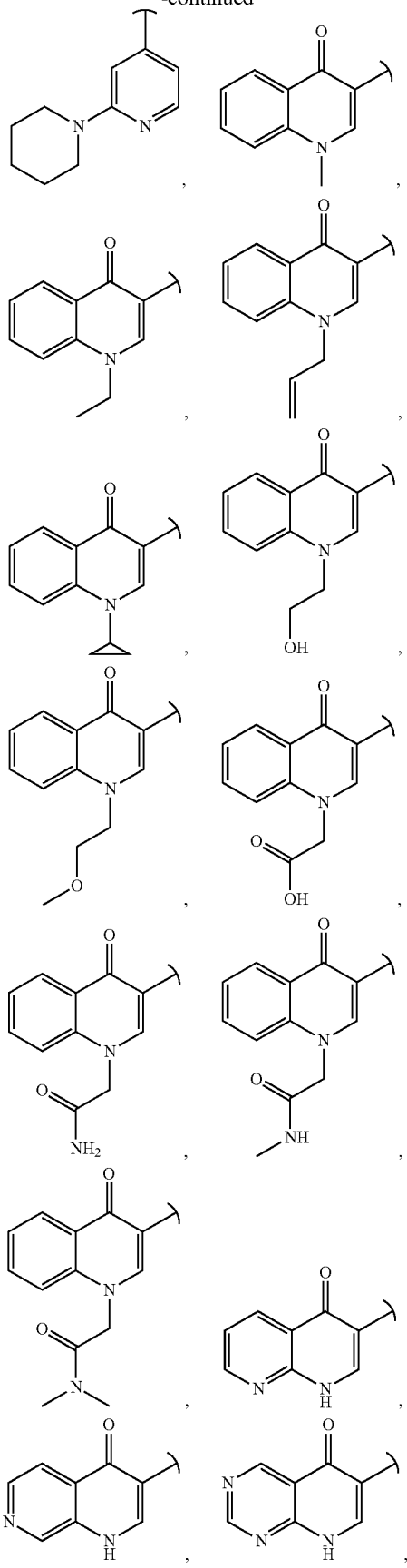

-continued
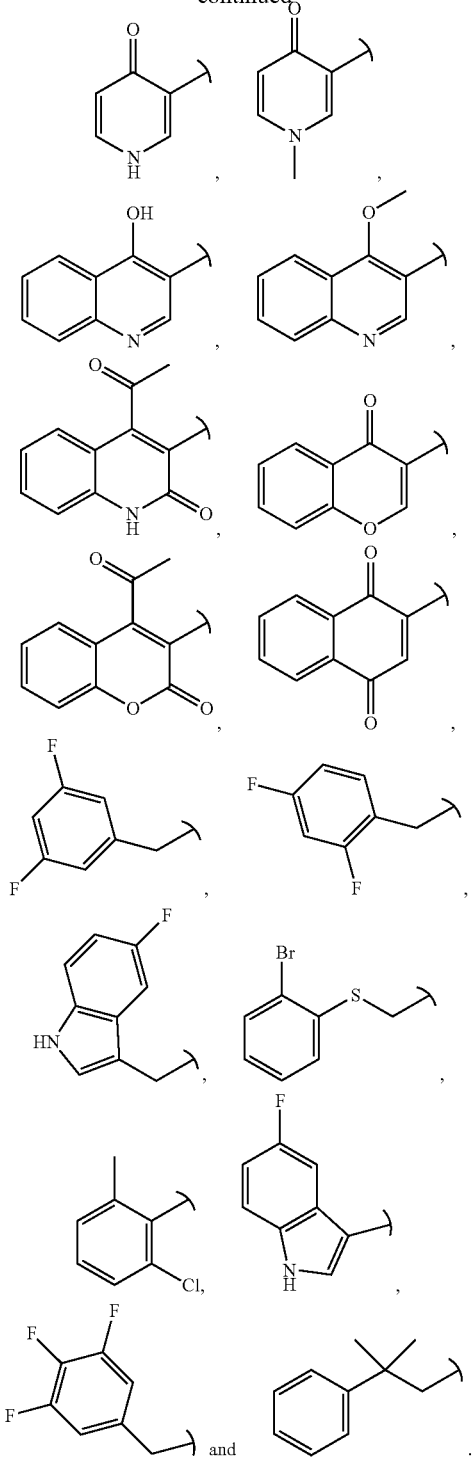
and
Y is selected from:
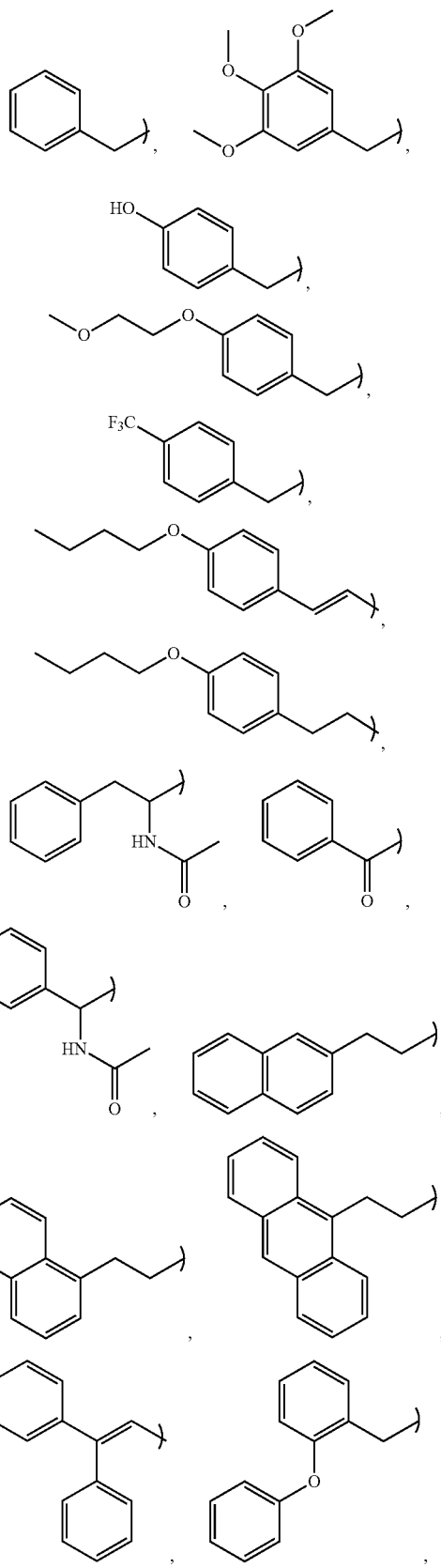
According to one embodiment, the present invention provides a compound of Formula Ib, or a pharmaceutically acceptable salt, stereoisomer or deuterated analog thereof, wherein
$R_1$ is selected from hydrogen, $CH_3$, —COOH, fluoro and CN;
$R_2$ is selected from hydrogen, $CH_3$, —COOH, fluoro and CN; and -continued
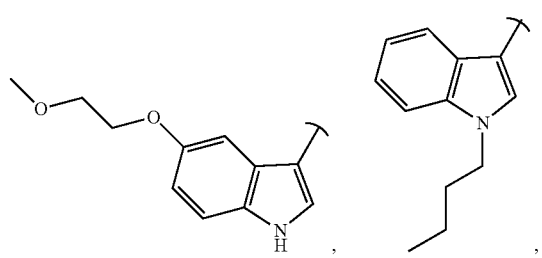
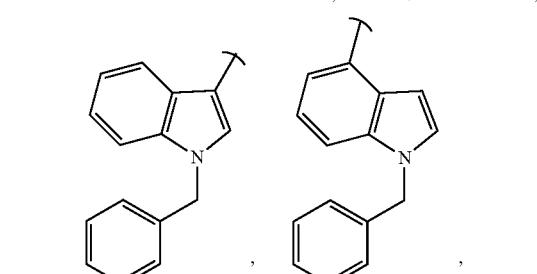
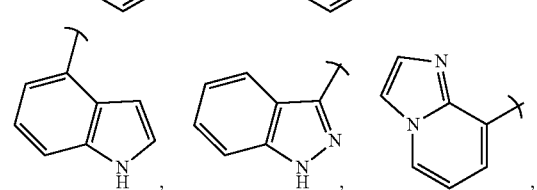
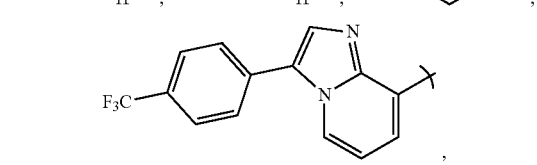
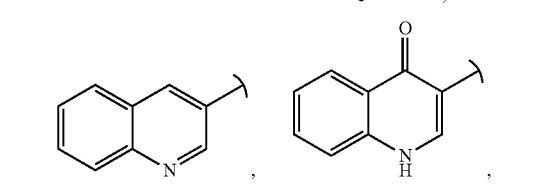
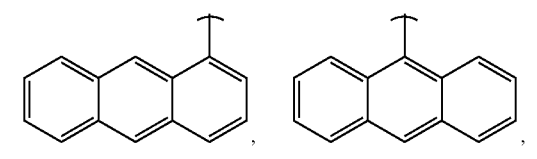
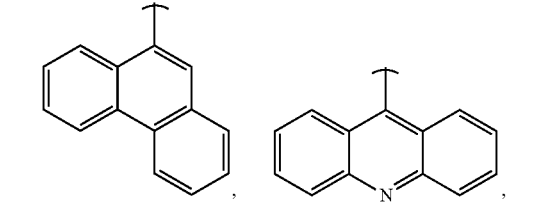
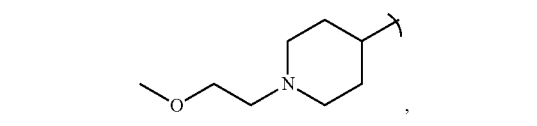
-continued
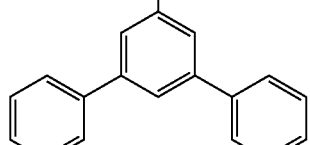
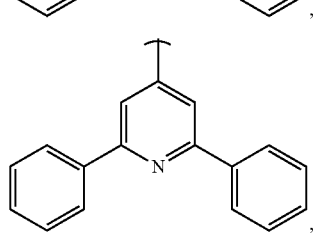
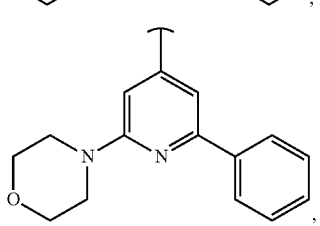
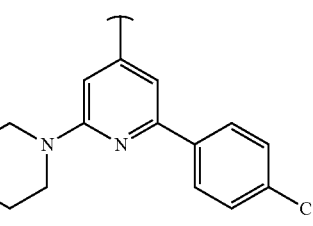
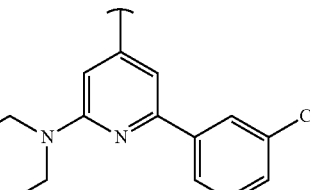
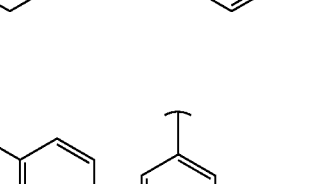
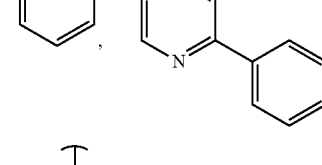
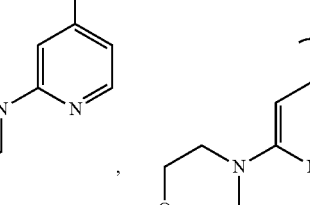
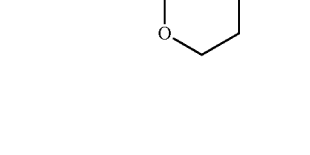

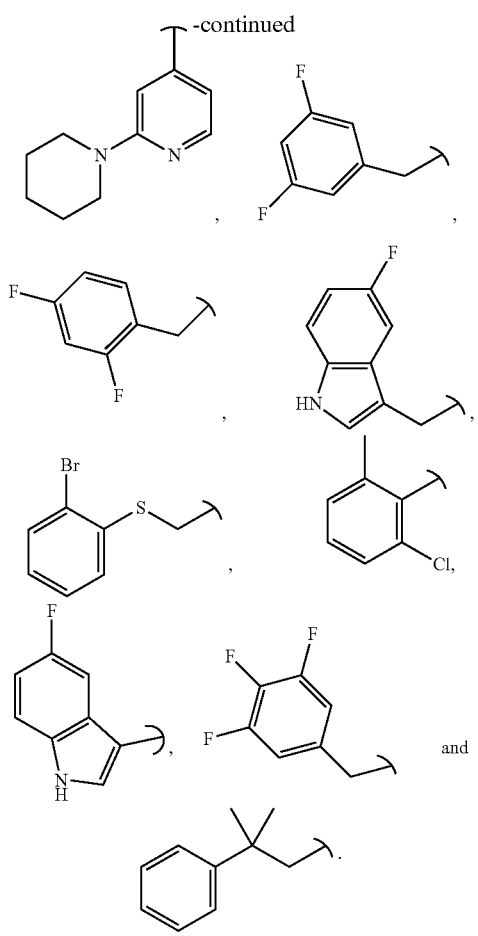

In another embodiment, the present invention provides a compound of Formula Ib, or a pharmaceutically acceptable salt, stereoisomer or deuterated analog thereof, wherein $R_1$ and $R_2$ both are hydrogen.

In another embodiment, the present invention provides a compound of Formula Ib, or a pharmaceutically acceptable salt, stereoisomer or deuterated analog thereof, wherein $R_1$ and $R_2$ both are hydrogen, and Y is selected from:

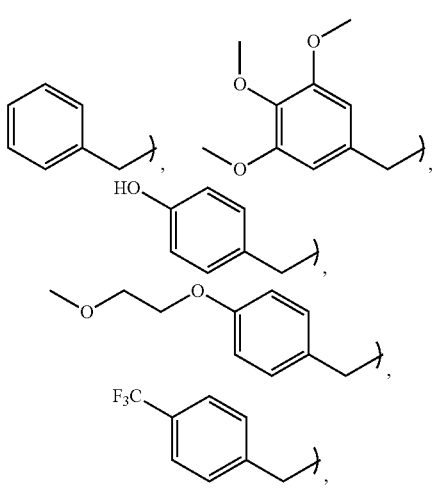

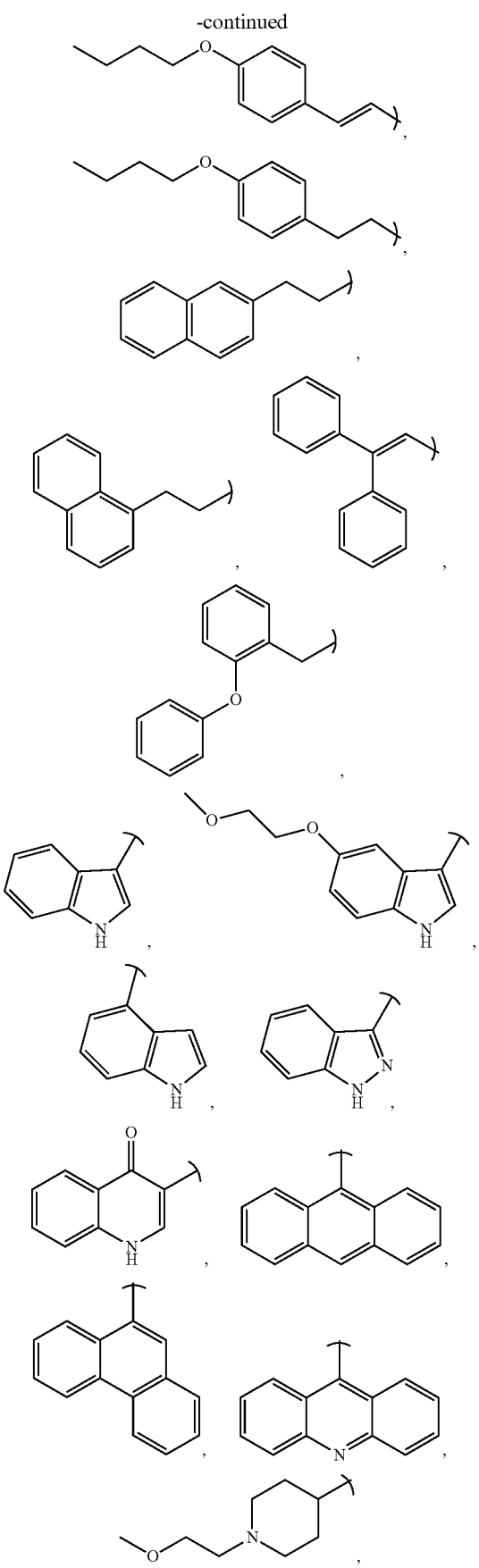

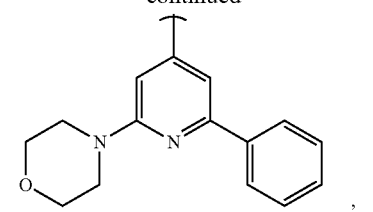
,
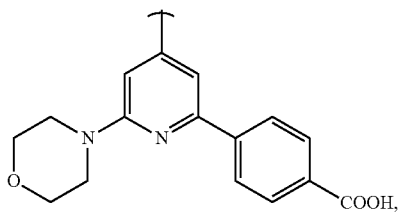
,
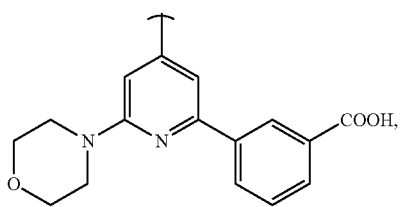
,
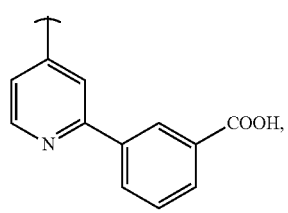
,
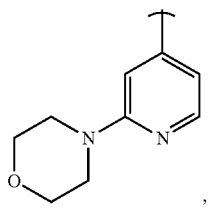
,
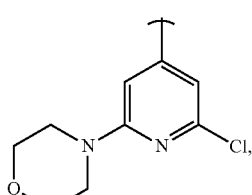
,
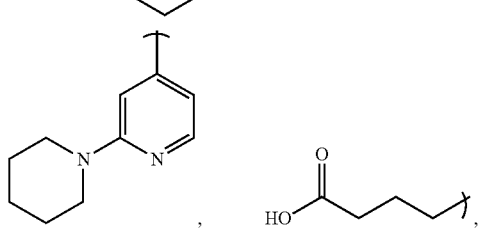
,
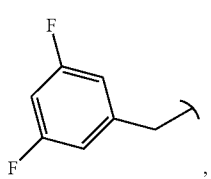
,

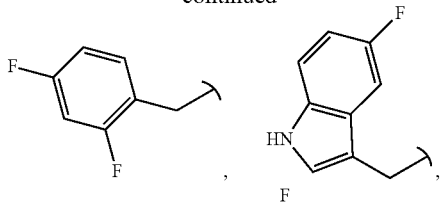
,
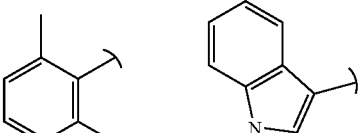
Cl, and
.

In another embodiment, the present invention provides a compound of Formula Ib, or a pharmaceutically acceptable salt, stereoisomer or deuterated analog thereof, wherein
$R_1$ and $R_2$ both are hydrogen, and
Y is selected from:

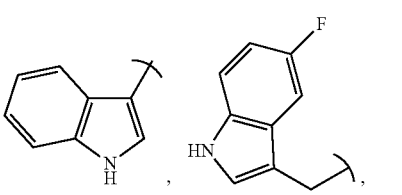
,
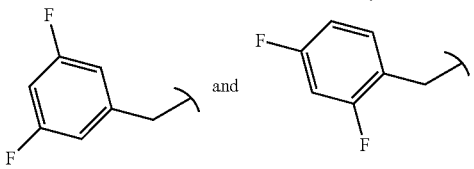
and
.

In another embodiment, the present invention provides a compound of Formula Ib, or a pharmaceutically acceptable salt, stereoisomer or deuterated analog thereof, wherein
$R_1$ is selected from hydrogen, $CH_3$, COOH, fluoro and CN;
$R_2$ is selected from hydrogen, $CH_3$, COOH, fluoro and CN; and
Y is selected from:

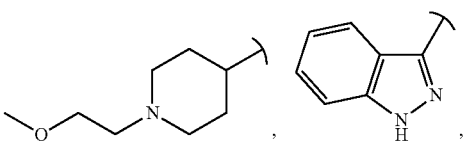
,
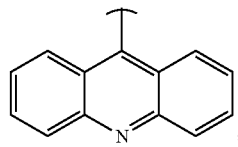
,
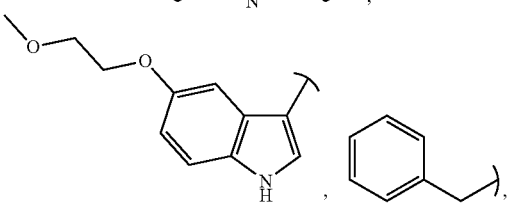
,

-continued
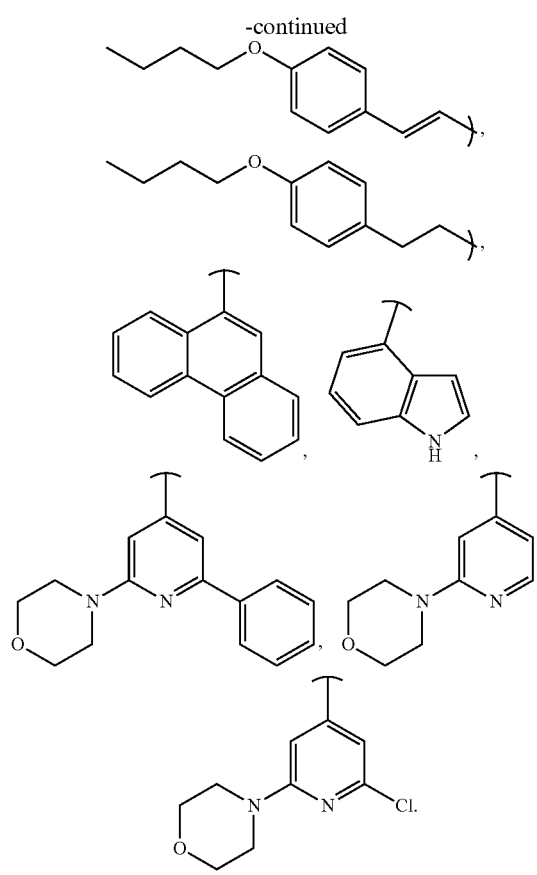
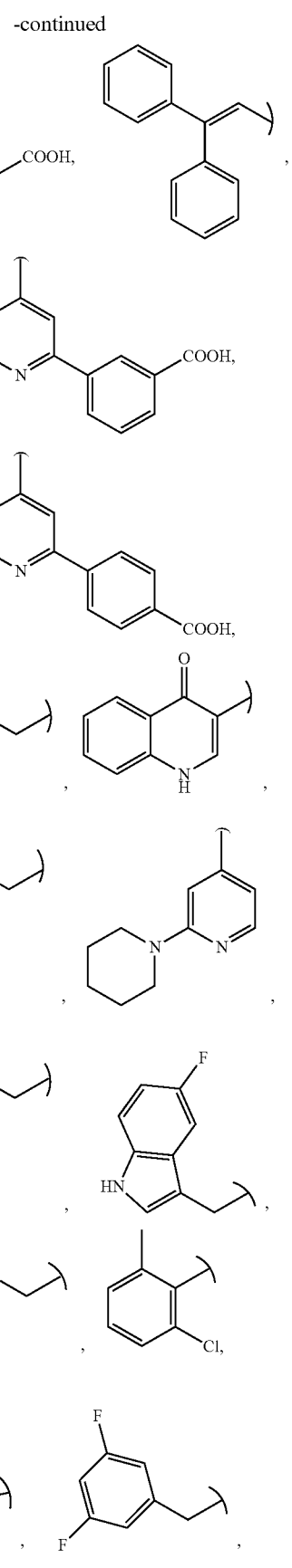
In another embodiment the present invention provides a compound of Formula Ib or a pharmaceutically acceptable salt, stereoisomer or deuterated analog thereof, wherein
$R_1$ is selected from hydrogen, —$CH_3$, —COOH, fluoro and —CN;
$R_2$ is selected from hydrogen, —$CH_3$, —COOH, fluoro and —CN; and
Y is selected from:
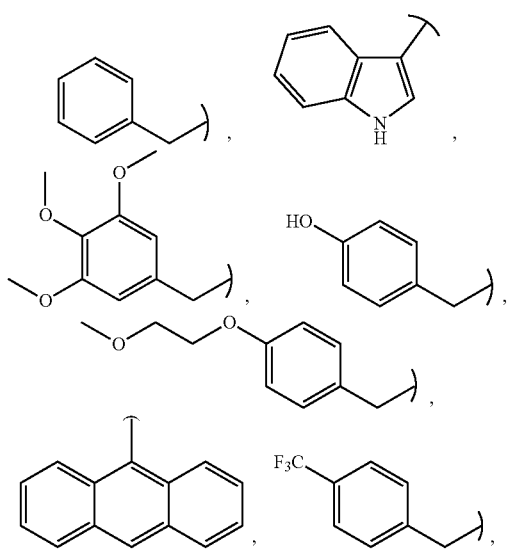

-continued

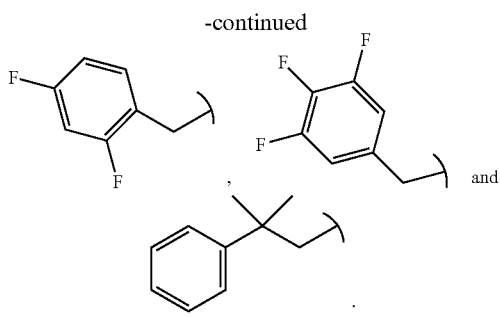

, and

In another embodiment, the present invention relates to a compound selected from:

1-[4-(4-Hydroxyphenyl)piperazin-1-yl]-2-phenylethanone,
4-(4-Hydroxyphenyl)piperazin-1-yl]-(1H-indol-3-yl)-methanone,
1-[4-(4-Hydroxyphenyl)-piperazin-1-yl]-2-(3,4,5-trimethoxyphenyl)-ethanone,
2-(4-Hydroxyphenyl)-1-[4-(4-hydroxyphenyl)-piperazin-1-yl]-ethanone,
1-[4-(4-Hydroxyphenyl)-piperazin-1-yl]-2-[4-(2-methoxyethoxy)-phenyl]-ethanone,
1-[4-(5-Hydroxypyridin-2-yl)-piperazin-1-yl]-2-phenylethanone,
[4-(4-Hydroxyphenyl)-piperazin-1-yl]-[1-(2-methoxyethyl)-piperidin-4-yl]-methanone,
[4-(4-Hydroxyphenyl)-piperazin-1-yl]-(1H-indazol-3-yl)-methanone,
Acridin-9-yl-[4-(4-hydroxy-phenyl)-piperazin-1-yl]-methanone,
[4-(4-Hydroxyphenyl)-piperazin-1-yl]-L[5-(2-methoxyethoxy)-1H-indol-3-yl]-methanone,
1-[4-(2-Fluoro-4-hydroxy-phenyl)-piperazin-1-yl]-2-phenylethanone,
3-(4-Butoxyphenyl)-1-[4-(4-hydroxyphenyl)-piperazin-1-yl]-propenone,
3-(4-Butoxyphenyl)-1-[4-(4-hydroxyphenyl)-piperazin-1-yl]-propan-1-one,
(5-Butoxy-1H-indol-3-yl)-[4-(4-hydroxyphenyl)-piperazin-1-yl]-methanone,
(1-Benzyl-1H-indol-3-yl)-[4-(4-hydroxyphenyl)-piperazin-1-yl]-methanone,
N-{(S)-1-Benzyl-2-[4-(4-hydroxyphenyl)-piperazin-1-yl]-2-oxoethyl}-acetamide,
1-[4-(4-Hydroxyphenyl)-piperazin-1-yl]-2-phenyl-ethane-1,2-dione,
(1-Butyl-1H-indol-3-yl)-[4-(4-hydroxyphenyl)-piperazin-1-yl]-methanone,
N-{(1R)-2-[4-(4-Hydroxyphenyl)piperazin-1-yl]-2-oxo-1-phenylethyl}acetamide,
(2,6-diphenyl-4-pyridyl)-[4-(4-hydroxyphenyl)piperazin-1-yl]methanone,
Anthracen-9-yl-[4-(4-hydroxyphenyl)-piperazin-1-yl]-methanone,
[4-(4-Hydroxyphenyl)-piperazin-1-yl]-phenanthren-9-yl-methanone,
1-[4-(4-Hydroxyphenyl)-piperazin-1-yl]-3-naphthalen-2-yl-propan-1-one,
[4-(4-Hydroxyphenyl)-piperazin-1-yl]-quinolin-3-yl-methanone,
Anthracen-1-yl-[4-(4-hydroxyphenyl)-piperazin-1-yl]-methanone,
(1-Benzylindol-4-yl)-[4-(4-hydroxyphenyl)piperazin-1-yl]methanone,
(3,5-Diphenylphenyl)-[4-(4-hydroxyphenyl)piperazin-1-yl]methanone,
1-[4-(4-Hydroxyphenyl)-piperazin-1-yl]-2-(4-trifluoromethylphenyl)-ethanone,
[4-(4-Hydroxyphenyl)-piperazin-1-yl]-imidazo[1,2-a]yridine-8-yl-methanone,
[4-(4-Hydroxyphenyl)-piperazin-1-yl]-(1H-indol-4-yl)-methanone,
[4-(4-Hydroxyphenyl)-piperazin-1-yl]-[3-(4-trifluoromethylphenyl)-imidazo[1,2-a]yridine-8-yl]-methanone,
2-Hydroxy-5-(4-phenylacetylpiperazin-1-yl)-benzoic acid,
[4-(4-Hydroxyphenyl)piperazin-1-yl]-(2-morpholino-6-phenyl-4-pyridyl)methanone,
[4-(4-Hydroxyphenyl)piperazin-1-yl]-(2-phenyl-4-pyridyl)methanone,
[4-(4-Hydroxyphenyl)piperazin-1-yl]-(2-morpholino-4-pyridyl)methanone,
(2-Chloro-6-morpholino-4-pyridyl)-[4-(4-hydroxyphenyl)piperazin-1-yl]methanone,
5-[4-(2,6-Diphenylpyridine-4-carbonyl)piperazin-1-yl]-2-hydroxy-benzonitrile,
5-[4-(2,6-Diphenylpyridine-4-carbonyl)piperazin-1-yl]-2-hydroxy-benzoic acid,
3-[4-[4-(4-Hydroxyphenyl)piperazine-1-carbonyl]-2-pyridyl]benzoic acid,
1-[4-(4-Hydroxyphenyl)piperazin-1-yl]-3,3-diphenyl-prop-2-en-1-one,
3-[4-[4-(4-Hydroxyphenyl)piperazine-1-carbonyl]-6-morpholino-2-pyridyl]benzoic acid,
4-[4-[4-(4-Hydroxyphenyl)piperazine-1-carbonyl]-6-morpholino-2-pyridyl]benzoic acid,
[4-(5-Hydroxypyridin-2-yl)-piperazin-1-yl]-(1H-indol-3-yl)-methanone,
Acridin-9-yl-[4-(5-hydroxy-pyridin-2-yl)-piperazin-1-yl]-methanone,
1-[4-(5-Hydroxypyridin-2-yl)-piperazin-1-yl]-3-phenyl-propan-1-one,
1-[4-(4-Hydroxyphenyl)-piperazin-1-yl]-3-naphthalen-1-yl-propan-1-one,
3-[4-(4-Hydroxyphenyl)piperazine-1-carbonyl]-1H-quinolin-4-one,
1-[4-(5-Hydroxy-2-pyridyl)piperazin-1-yl]-2,2-diphenyl-ethanone,
1-[4-(4-Hydroxyphenyl)-piperazin-1-yl]-2-(2-phenoxyphenyl)ethanone,
[4-(4-Hydroxyphenyl)piperazin-1-yl]-[2-(1-piperidyl)-4-pyridyl]methanone,
1-[4-(5-Hydroxypyridin-2-yl)-piperazin-1-yl]-3-(1H-indol-3-yl)-propan-1-one,
1-[4-(4-Hydroxy-3-methyl-phenyl)-piperazin-1-yl]-2-phenylethanone,
3-Anthracen-9-yl-1-[4-(4-hydroxyphenyl)-piperazin-1-yl]-propan-1-one,
3-[4-(5-Hydroxy-2-pyridyl)piperazine-1-carbonyl]-1H-quinolin-4-one,
2-(1-Adamantyl)-1-[4-(5-hydroxy-2-pyridyl)piperazin-1-yl]ethanone,
2-(3-Hydroxy-1-adamantyl)-1-[4-(5-hydroxy-2-pyridyl)piperazin-1-yl]ethanone,
2-(1-Adamantylmethylamino)-1-[4-(5-hydroxy-2-pyridyl)piperazin-1-yl]ethanone,
2,2-Bis(4-chlorophenyl)-1-[4-(5-hydroxy-2-pyridyl)piperazin-1-yl]ethanone,
1-(Cyclopropylmethyl)-3-[4-(5-hydroxy-2-pyridyl)piperazine-1-carbonyl]quinolin-4-one,
2-Fluoren-9-ylidene-1-[4-(5-hydroxy-2-pyridyl)piperazin-1-yl]ethanone, 2-(9H-Fluoren-9-yl)-1-[4-(5-hydroxy-2-pyridyl)piperazin-1-yl]ethanone,
1-[4-(5-Hydroxypyridin-2-yl)-piperazin-1-yl]-2-(1H-indol-3-yl)-ethanone,
[4-(5-Hydroxypyridin-2-yl)-piperazin-1-yl]-(1H-pyrrolo[2,3-b]pyridin-3-yl)-methanone,
Anthracen-9-yl-[4-(5-hydroxypyridin-2-yl)-piperazin-1-yl]-methanone,
1-[4-(5-Hydroxypyridin-2-yl)-piperazin-1-yl]-4-phenylbutan-1-one,
1-[4-(5-Hydroxypyridin-2-yl)-piperazin-1-yl]-3-pyridin-4-yl-propan-1-one,
[4-(5-Hydroxypyridin-2-yl)-piperazin-1-yl]-indan-2-yl-methanone,
1-[4-(5-Hydroxypyridin-2-yl)-piperazin-1-yl]-5-phenylpentan-1-one,
3-[4-(5-Hydroxy-2-pyridyl)piperazine-1-carbonyl]-1-methylquinolin-4-one,
5-[4-(5-Hydroxy-2-pyridyl)-piperazin-1-yl]-5-oxo-pentanoic acid,
[4-(5-Hydroxypyridin-2-yl)-piperazin-1-yl]-(1-methyl-1H-indol-3-yl)-methanone,
1-[4-(5-Hydroxypyridin-2-yl)-piperazin-1-yl]-3-(3-trifluoromethyl-phenyl)-propan-1-one,
3-[4-(5-Hydroxy-2-pyridyl)piperazine-1-carbonyl]chromen-2-one,
1-[4-(5-Hydroxy-2-pyridyl)piperazin-1-yl]-3,3-diphenyl-prop-2-en-1-one,
1-[4-(5-Hydroxy-2-pyridyl)piperazin-1-yl]-3,3-diphenyl-propan-1-one,
(5-Chlorothiophen-2-yl)-[4-(5-hydroxy-pyridin-2-yl)-piperazin-1-yl]-methanone,
(E)-1-[4-(5-Hydroxypyridin-2-yl)-piperazin-1-yl]-3-(4-nitrophenyl)-propenone,
(E)-3-(4-Chlorophenyl)-1-[4-(5-hydroxypyridin-2-yl)-piperazin-1-yl]-propenone,
3-(3,4-Dichlorophenyl)-1-[4-(5-hydroxypyridin-2-yl)-piperazin-1-yl]-propan-1-one,
(2-Chloro-6-methylphenyl)-[4-(5-hydroxypyridin-2-yl)-piperazin-1-yl]-methanone,
[4-(5-Hydroxypyridin-2-yl)-piperazin-1-yl]-[3-(4-methylimidazol-1-yl)-5-trifluoromethylphenyl]-methanone,
3-(4-Chlorophenyl)-1-[4-(5-hydroxy-pyridin-2-yl)-piperazin-1-yl]-propan-1-one,
2-(1-Adamantylamino)-1-[4-(5-hydroxy-2-pyridyl)piperazin-1-yl]ethanone,
1-[4-(5-Hydroxy-2-pyridyl)piperazin-1-yl]-3,3-bis(4-methoxyphenyl)prop-2-en-1-one,
[[4-(5-Hydroxypyridin-2-yl)-piperazin-1-yl]-[4-methyl-3-(4-pyridin-3-yl-pyrimidin-2-ylamino)phenyl]methanone,
(1H-Benzoimidazol-2-yl)-[4-(5-hydroxypyridin-2-yl)-piperazin-1-yl]-methanone,
(5-Bromothiophen-2-yl)-[4-(5-hydroxypyridin-2-yl)-piperazin-1-yl]-methanone,
[(5-Fluoro-1H-indol-2-yl)-[4-(5-hydroxypyridin-2-yl)-piperazin-1-yl]-methanone,
Quinoline-8-sulfonic acid {2-[4-(5-hydroxypyridin-2-yl)-piperazin-1-yl]-2-oxo-ethyl}-methylamide,
1-[4-(5-Hydroxypyridin-2-yl)-piperazin-1-yl]-3-(4-isobutylphenyl)-propan-1-one,
2-(2,4-Difluorophenyl)-1-[4-(5-hydroxypyridine-2-yl)-piperazin-1-yl]-ethanone,
3-(3-Fluorophenyl)-1-[4-(5-hydroxypyridin-2-yl)-piperazin-1-yl]-propan-1-one,
1-[4-(5-Hydroxy-2-pyridyl)piperazin-1-yl]-3,3-bis(4-methoxyphenyl)propan-1-one,
1-[4-(5-Hydroxy-2-pyridyl)piperazin-1-yl]-4,4-diphenyl-but-3-en-1-one,
2-Cyclohexyl-2-hydroxy-1-[4-(5-hydroxy-2-pyridyl)piperazin-1-yl]-2-phenyl-ethanone,
2-[1-Adamantylmethyl(methyl)amino]-1-[4-(5-hydroxy-2-pyridyl)piperazin-1-yl]ethanone,
1-[4-(5-Hydroxypyridin-2-yl)-piperazin-1-yl]-2-(5-nitropyridin-2-ylsulfanyl)-ethanone,
3-(1-Adamantyl)-1-[4-(5-hydroxy-2-pyridyl)piperazin-1-yl]propan-1-one,
2-Cyclohexyl-1-[4-(5-hydroxy-2-pyridyl)piperazin-1-yl]-2-phenyl-ethanone,
3-(4-Hydroxyphenyl)-1-[4-(5-hydroxypyridin-2-yl)-piperazin-1-yl]-propan-1-one,
3-(4-Methoxyphenyl)-1-[4-(5-hydroxypyridin-2-yl)-piperazin-1-yl]-propan-1-one,
3-(2-Bromophenyl)-1-[4-(5-hydroxypyridin-2-yl)-piperazin-1-yl]-propan-1-one,
3-(4-Bromophenyl)-1-[4-(5-hydroxypyridin-2-yl)-piperazin-1-yl]-propan-1-one,
3-[4-(5-Hydroxypyridin-2-yl)-piperazine-1-carbonyl]-7-oxa-bicyclo[2.2.1]heptane-2-carboxylic acid methyl ester,
3-[4-(5-Hydroxypyridin-2-yl)-piperazine-1-carbonyl]-7-oxa-bicyclo[2.2.1]heptane-2-carboxylic acid,
1-[4-(5-Hydroxypyridin-2-yl)-piperazin-1-yl]-2-(1H-indol-3-yl)-ethane-1,2-dione,
1-[4-(5-Hydroxypyridin-2-yl)-piperazin-1-yl]-3-o-tolyl-propan-1-one,
3-(4-Dimethylaminophenyl)-1-[4-(5-hydroxypyridin-2-yl)-piperazin-1-yl]-propan-1-one,
1-[4-(5-Hydroxypyridin-2-yl)-piperazin-1-yl]-3-(2-methoxyphenyl)-propan-1-one,
1-[4-(5-Hydroxypyridin-2-yl)-piperazin-1-yl]-3-p-tolyl-propan-1-one,
2-[4-(5-Hydroxypyridin-2-yl)-piperazine-1-carbonyl]benzoic acid,
1-[4-(5-Hydroxy-2-pyridyl)piperazin-1-yl]-4,4-diphenylbutan-1-one,
[4-(5-Hydroxypyridin-2-yl)-piperazin-1-yl]-[3-(1H-indol-4-yl)phenyl]methanone,
1-[4-(5-Hydroxypyridin-2-yl)-piperazin-1-yl]-3-[4-(2-methoxyethoxy)phenyl]-propan-1-one,
1-[4-(5-Hydroxypyridin-2-yl)-piperazin-1-yl]-3-phenylbutan-1-one,
1-[4-(5-Hydroxypyridin-2-yl)-piperazin-1-yl]-3-thiophen-2-yl-propan-1-one,
1-[4-(5-Hydroxy-2-pyridyl)piperazin-1-yl]-2-morpholino-2-phenylethanone,
Cyclohexyl-[4-(5-hydroxy-2-pyridyl)piperazin-1-yl]methanone,
Cyclopropyl-[4-(5-hydroxy-2-pyridyl)piperazin-1-yl]methanone,
(E)-3-Cyclohexyl-1-[4-(5-hydroxy-2-pyridyl)piperazin-1-yl]prop-2-en-1-one,
3-Cyclohexyl-1-[4-(5-hydroxy-2-pyridyl)piperazin-1-yl]propan-1-one,
3-Benzo[b]thiophen-2-yl-1-[4-(5-hydroxypyridin-2-yl)-piperazin-1-yl]-propan-1-one,
[4-(5-Hydroxypyridin-2-yl)-piperazin-1-yl]-(5-phenylthiophen-2-yl)-methanone,
(3-Hydroxy-3-phenylcyclobutyl)-[4-(5-hydroxypyridin-2-yl)-piperazin-1-yl]-methanone,
1-[4-(5-Hydroxypyridin-2-yl)-piperazin-1-yl]-3-methyl-3-phenylbutan-1-one,
3-(4-Fluorophenyl)-1-[4-(5-hydroxypyridin-2-yl)-piperazin-1-yl]-propan-1-one, 1-[4-(5-Hydroxypyridin-2-yl)-piperazin-1-yl]-2-(2-methyl-1H-indol-3-yl)-ethanone,
1-[4-(5-Hydroxypyridin-2-yl)-piperazin-1-yl]-3-(2-trifluoromethylphenyl)-propan-1-one,
1-[4-(5-Hydroxypyridin-2-yl)-piperazin-1-yl]-3-pyridin-2-yl-propan-1-one,
3-Hydroxy-1-[4-(5-hydroxypyridin-2-yl)-piperazin-1-yl]-3-phenylpropan-1-one,
2-(5-Fluoro-1H-indol-3-yl)-1-[4-(5-hydroxypyridin-2-yl)-piperazin-1-yl]-ethanone,
[4-(5-Hydroxypyridin-2-yl)-piperazin-1-yl]-(1,2,3,4-tetrahydronaphthalen-1-yl)-methanone,
[4-(5-Hydroxypyridin-2-yl)-piperazin-1-yl]-((1R,2R)-2-phenylcyclopropyl)-methanone,
[4-(5-Hydroxypyridin-2-yl)-piperazin-1-yl]-(3-phenylcyclobutyl)-methanone,
1-[4-(5-Hydroxypyridin-2-yl)-piperazin-1-yl]-3-indol-1-yl-propan-1-one,
3-Benzoimidazol-1-yl-1-[4-(5-hydroxypyridin-2-yl)-piperazin-1-yl]-propan-1-one,
2-Cyclopropyl-1-[4-(5-hydroxy-2-pyridyl)piperazin-1-yl]ethanone,
3-(4-Cyanophenyl)-1-[4-(5-hydroxypyridin-2-yl)-piperazin-1-yl]-propan-1-one,
3-(4-Trifluoromethylphenyl)-1-[4-(5-hydroxypyridin-2-yl)-piperazin-1-yl]-propan-1-one,
3-Cyclopropyl-1-[4-(5-hydroxy-2-pyridyl)piperazin-1-yl]propan-1-one,
2-{3-[4-(5-Hydroxypyridin-2-yl)-piperazin-1-yl]-3-oxopropyl}-benzoic acid,
2-{3-[4-(5-Hydroxypyridin-2-yl)-piperazin-1-yl]-3-oxopropyl}-benzoic acid methyl ester,
2-(2-Bromophenylsulfanyl)-1-[4-(5-hydroxypyridin-2-yl)-piperazin-1-yl]-ethanone,
2-Hydroxy-1-[4-(5-hydroxypyridin-2-yl)-piperazin-1-yl]-3-phenyl-propan-1-one,
3-(4-Fluoro-2-methylphenyl)-1-[4-(5-hydroxypyridin-2-yl)-piperazin-1-yl]-propan-1-one,
3-(2,3-Dimethylphenyl)-1-[4-(5-hydroxypyridin-2-yl)-piperazin-1-yl]-propan-1-one,
3-(2,6-Dimethylphenyl)-1-[4-(5-hydroxypyridin-2-yl)-piperazin-1-yl]-propan-1-one,
2-(3,5-Difluorophenyl)-1-[4-(4-hydroxyphenyl)-piperazin-1-yl]-ethanone,
2-(2,4-Difluorophenyl)-1-[4-(4-hydroxyphenyl)-piperazin-1-yl]-ethanone,
2-(5-Fluoro-1H-indol-3-yl)-1-[4-(4-hydroxyphenyl)-piperazin-1-yl]-ethanone,
2-(2-Bromophenylsulfanyl)-1-[4-(4-hydroxyphenyl)-piperazin-1-yl]-ethanone,
3-(2,4-Difluorophenyl)-1-[4-(5-hydroxypyridin-2-yl)-piperazin-1-yl]-propan-1-one,
3-(3,4-Difluorophenyl)-1-[4-(5-hydroxypyridin-2-yl)-piperazin-1-yl]-propan-1-one,
(2-Chloro-6-methylphenyl)-[4-(4-hydroxyphenyl)-piperazin-1-yl]-methanone,
(5-Fluoro-1H-indol-3-yl)-[4-(5-hydroxypyridin-2-yl)-piperazin-1-yl]-methanone,
(5-Fluoro-1H-indol-3-yl)-[4-(4-hydroxyphenyl)-piperazin-1-yl]-methanone,
3-(2,6-Difluorophenyl)-1-[4-(5-hydroxypyridin-2-yl)-piperazin-1-yl]-propan-1-one,
2-(6-Fluoro-1H-indol-3-yl)-1-[4-(5-hydroxy-pyridin-2-yl)-piperazin-1-yl]-ethanone,
2-(5-Chloro-1H-indol-3-yl)-1-[4-(5-hydroxy-pyridin-2-yl)-piperazin-1-yl]-ethanone,
2-(5,6-Difluoro-1H-indol-3-yl)-1-[4-(5-hydroxy-pyridin-2-yl)-piperazin-1-yl]-ethanone,
3-(4-Fluoro-phenyl)-1-[4-(5-hydroxy-pyridin-2-yl)-piperazin-1-yl]-3-methyl-butan-1-one,
2-(2-Bromo-phenylsulfanyl)-1-[4-(5-hydroxy-pyridin-2-yl)-piperazin-1-yl]-2-methyl-propan-1-one,
2-(4-Fluoro-phenylsulfanyl)-1-[4-(5-hydroxy-pyridin-2-yl)-piperazin-1-yl]-ethanone,
2-(4-Fluoro-phenoxy)-1-[4-(5-hydroxy-pyridin-2-yl)-piperazin-1-yl]-ethanone,
2-(5-Fluoro-1-methyl-indol-3-yl)-1-[4-(5-hydroxy-pyridin-2-yl)-piperazin-1-yl]-ethanone,
2-(5-Fluoro-2-methyl-1H-indol-3-yl)-1-[4-(5-hydroxy-pyridin-2-yl)-piperazin-1-yl]-ethanone,
2-(5,7-Difluoro-1H-indol-3-yl)-1-[4-(5-hydroxy-pyridin-2-yl)-piperazin-1-yl]-ethanone,
1-(5-Fluoro-1H-indol-3-yl)-2-[4-(5-hydroxy-pyridin-2-yl)-piperazin-1-yl]-ethane-1,2-dione,
2-(5-Fluoro-1H-indol-3-yl)-1-[4-(5-hydroxy-pyridin-2-yl)-piperazin-1-yl]-2-methyl-propan-1-one,
1-[4-(5-Hydroxy-pyridin-2-yl)-piperazin-1-yl]-3-(3,4,5-trifluoro-phenyl)-propan-1-one,
1-[4-(4-Hydroxy-phenyl)-piperazin-1-yl]-2-(3,4,5-trifluoro-phenyl)-ethanone,
N-{3-[4-(5-Hydroxy-pyridin-2-yl)-piperazin-1-yl]-3-oxo-1-phenyl-propyl}-acrylamide,
1-[4-(4-Hydroxy-phenyl)-piperazin-1-yl]-3-methyl-3-phenyl-butan-1-one,
2-(5,6-Dichloro-1H-indol-3-yl)-1-[4-(5-hydroxy-pyridin-2-yl)-piperazin-1-yl]-ethanone,
2-(5-Chloro-2-methyl-1H-indol-3-yl)-1-[4-(5-hydroxy-pyridin-2-yl)-piperazin-1-yl]-ethanone,
2-(5,6-Dichloro-2-methyl-1H-indol-3-yl)-1-[4-(5-hydroxy-pyridin-2-yl)-piperazin-1-yl]-ethanone,
and pharmaceutically acceptable salts, stereoisomers, and/or deuterated analogs thereof.

In another embodiment, the present invention relates to a compound selected from:
1-[4-(4-Hydroxyphenyl)piperazin-1-yl]-2-phenylethanone,
4-(4-Hydroxyphenyl)piperazin-1-yl]-(1H-indol-3-yl)-methanone,
1-[4-(4-Hydroxyphenyl)-piperazin-1-yl]-2-(3,4,5-trimethoxyphenyl)-ethanone,
2-(4-Hydroxyphenyl)-1-[4-(4-hydroxyphenyl)-piperazin-1-yl]-ethanone,
1-[4-(4-Hydroxyphenyl)-piperazin-1-yl]-2-[4-(2-methoxy-ethoxy)-phenyl]-ethanone,
[4-(4-Hydroxyphenyl)-piperazin-1-yl]-[1-(2-methoxy-ethyl)-piperidin-4-yl]-methanone,
[4-(4-Hydroxyphenyl)-piperazin-1-yl]-(1H-indazol-3-yl)-methanone,
Acridin-9-yl-[4-(4-hydroxy-phenyl)-piperazin-1-yl]-methanone,
[4-(4-Hydroxyphenyl)-piperazin-1-yl]-[5-(2-methoxy-ethoxy)-1H-indol-3-yl]-methanone,
1-[4-(2-Fluoro-4-hydroxy-phenyl)-piperazin-1-yl]-2-phenylethanone,
3-(4-Butoxyphenyl)-1-[4-(4-hydroxyphenyl)-piperazin-1-yl]-propenone,
3-(4-Butoxyphenyl)-1-[4-(4-hydroxyphenyl)-piperazin-1-yl]-propan-1-one,
(5-Butoxy-1H-indol-3-yl)-[4-(4-hydroxyphenyl)-piperazin-1-yl]-methanone,
(1-Benzyl-1H-indol-3-yl)-[4-(4-hydroxyphenyl)-piperazin-1-yl]-methanone,
N—{(S)-1-Benzyl-2-[4-(4-hydroxyphenyl)-piperazin-1-yl]-2-oxoethyl}-acetamide, 1-[4-(4-Hydroxyphenyl)-piperazin-1-yl]-2-phenyl-ethane-1,2-dione,
(1-Butyl-1H-indol-3-yl)-[4-(4-hydroxyphenyl)-piperazin-1-yl]-methanone,
N-{(1R)-2-[4-(4-Hydroxyphenyl)piperazin-1-yl]-2-oxo-1-phenylethyl}acetamide,
(2,6-diphenyl-4-pyridyl)-[4-(4-hydroxyphenyl)piperazin-1-yl]methanone,
Anthracen-9-yl-[4-(4-hydroxyphenyl)-piperazin-1-yl]-methanone,
[4-(4-Hydroxyphenyl)-piperazin-1-yl]-phenanthren-9-yl-methanone,
1-[4-(4-Hydroxyphenyl)-piperazin-1-yl]-3-naphthalen-2-yl-propan-1-one,
[4-(4-Hydroxyphenyl)-piperazin-1-yl]-quinolin-3-yl-methanone,
Anthracen-1-yl-[4-(4-hydroxyphenyl)-piperazin-1-yl]-methanone,
(1-Benzylindol-4-yl)-[4-(4-hydroxyphenyl)piperazin-1-yl]methanone,
(3,5-Diphenylphenyl)-[4-(4-hydroxyphenyl)piperazin-1-yl]methanone,
1-[4-(4-Hydroxyphenyl)-piperazin-1-yl]-2-(4-trifluoromethylphenyl)-ethanone,
[4-(4-Hydroxyphenyl)-piperazin-1-yl]-imidazo[1,2-a]yridine-8-yl-methanone,
[4-(4-Hydroxyphenyl)-piperazin-1-yl]-(1H-indol-4-yl)-methanone,
[4-(4-Hydroxyphenyl)-piperazin-1-yl]-[3-(4-trifluoromethylphenyl)-imidazo[1,2-a]yridine-8-yl]-methanone,
2-Hydroxy-5-(4-phenylacetylpiperazin-1-yl)-benzoic acid,
[4-(4-Hydroxyphenyl)piperazin-1-yl]-(2-morpholino-6-phenyl-4-pyridyl)methanone,
[4-(4-Hydroxyphenyl)piperazin-1-yl]-(2-phenyl-4-pyridyl)methanone,
[4-(4-Hydroxyphenyl)piperazin-1-yl]-(2-morpholino-4-pyridyl)methanone,
(2-Chloro-6-morpholino-4-pyridyl)-[4-(4-hydroxyphenyl)piperazin-1-yl]methanone,
5-[4-(2,6-Diphenylpyridine-4-carbonyl)piperazin-1-yl]-2-hydroxy-benzonitrile,
5-[4-(2,6-Diphenylpyridine-4-carbonyl)piperazin-1-yl]-2-hydroxy-benzoic acid,
3-[4-(4-Hydroxyphenyl)piperazine-1-carbonyl]-2-pyridyl]benzoic acid,
1-[4-(4-Hydroxyphenyl)piperazin-1-yl]-3,3-diphenyl-prop-2-en-1-one,
3-[4-[4-(4-Hydroxyphenyl)piperazine-1-carbonyl]-6-morpholino-2-pyridyl]benzoic acid,
4-[4-[4-(4-Hydroxyphenyl)piperazine-1-carbonyl]-6-morpholino-2-pyridyl]benzoic acid,
1-[4-(4-Hydroxyphenyl)-piperazin-1-yl]-3-naphthalen-1-yl-propan-1-one,
3-[4-(4-Hydroxyphenyl)piperazine-1-carbonyl]-1H-quinolin-4-one,
1-[4-(4-Hydroxyphenyl)piperazin-1-yl]-2-(2-phenoxyphenyl)ethanone,
[4-(4-Hydroxyphenyl)piperazin-1-yl]-[2-(1-piperidyl)-4-pyridyl]methanone,
1-[4-(4-Hydroxy-3-methyl-phenyl)-piperazin-1-yl]-2-phenylethanone,
3-Anthracen-9-yl-1-[4-(4-hydroxyphenyl)-piperazin-1-yl]-propan-1-one,
2-(3,5-Difluorophenyl)-1-[4-(4-hydroxyphenyl)-piperazin-1-yl]-ethanone,
2-(2,4-Difluorophenyl)-1-[4-(4-hydroxyphenyl)-piperazin-1-yl]-ethanone,
2-(5-Fluoro-1H-indol-3-yl)-1-[4-(4-hydroxyphenyl)-piperazin-1-yl]-ethanone,
2-(2-Bromophenylsulfanyl)-1-[4-(4-hydroxyphenyl)-piperazin-1-yl]-ethanone,
(2-Chloro-6-methylphenyl)-[4-(4-hydroxyphenyl)-piperazin-1-yl]-methanone,
(5-Fluoro-1H-indol-3-yl)-[4-(4-hydroxyphenyl)-piperazin-1-yl]-methanone,
1-[4-(4-Hydroxy-phenyl)-piperazin-1-yl]-2-(3,4,5-trifluoro-phenyl)-ethanone,
1-[4-(4-Hydroxy-phenyl)-piperazin-1-yl]-3-methyl-3-phenyl-butan-1-one,
and pharmaceutically acceptable salts, stereoisomers, and/or deuterated analogs thereof.

In another embodiment, the present invention relates to a compound selected from:
1-[4-(5-Hydroxypyridin-2-yl)-piperazin-1-yl]-2-phenylethanone,
[4-(5-Hydroxypyridin-2-yl)-piperazin-1-yl]-(1H-indol-3-yl)-methanone,
Acridin-9-yl-[4-(5-hydroxy-pyridin-2-yl)-piperazin-1-yl]-methanone,
1-[4-(5-Hydroxypyridin-2-yl)-piperazin-1-yl]-3-phenyl-propan-1-one,
1-[4-(5-Hydroxy-2-pyridyl)piperazin-1-yl]-2,2-diphenyl-ethanone,
1-[4-(5-Hydroxypyridin-2-yl)-piperazin-1-yl]-3-(1H-indol-3-yl)-propan-1-one,
3-[4-(5-Hydroxy-2-pyridyl)piperazine-1-carbonyl]-1H-quinolin-4-one,
2-(1-Adamantyl)-1-[4-(5-hydroxy-2-pyridyl)piperazin-1-yl]ethanone,
2-(3-Hydroxy-1-adamantyl)-1-[4-(5-hydroxy-2-pyridyl)piperazin-1-yl]ethanone,
2-(1-Adamantylmethylamino)-1-[4-(5-hydroxy-2-pyridyl)piperazin-1-yl]ethanone,
2,2-Bis(4-chlorophenyl)-1-[4-(5-hydroxy-2-pyridyl)piperazin-1-yl]ethanone,
1-(Cyclopropylmethyl)-3-[4-(5-hydroxy-2-pyridyl)piperazine-1-carbonyl]quinolin-4-one,
2-Fluoren-9-ylidene-1-[4-(5-hydroxy-2-pyridyl)piperazin-1-yl]ethanone,
2-(9H-Fluoren-9-yl)-1-[4-(5-hydroxy-2-pyridyl)piperazin-1-yl]ethanone,
1-[4-(5-Hydroxypyridin-2-yl)-piperazin-1-yl]-2-(1H-indol-3-yl)-ethanone,
[4-(5-Hydroxypyridin-2-yl)-piperazin-1-yl]-(1H-pyrrolo[2,3-b]pyridin-3-yl)-methanone,
Anthracen-9-yl-[4-(5-hydroxypyridin-2-yl)-piperazin-1-yl]-methanone,
1-[4-(5-Hydroxypyridin-2-yl)-piperazin-1-yl]-4-phenylbutan-1-one,
1-[4-(5-Hydroxypyridin-2-yl)-piperazin-1-yl]-3-pyridin-4-yl-propan-1-one,
[4-(5-Hydroxypyridin-2-yl)-piperazin-1-yl]-indan-2-yl-methanone,
1-[4-(5-Hydroxypyridin-2-yl)-piperazin-1-yl]-5-phenylpentan-1-one,
3-[4-(5-Hydroxy-2-pyridyl)piperazine-1-carbonyl]-1-methylquinolin-4-one,
5-[4-(5-Hydroxy-2-pyridyl)piperazin-1-yl]-5-oxo-pentanoic acid,
[4-(5-Hydroxypyridin-2-yl)-piperazin-1-yl]-(1-methyl-1H-indol-3-yl)-methanone,
1-[4-(5-Hydroxypyridin-2-yl)-piperazin-1-yl]-3-(3-trifluoromethyl-phenyl)-propan-1-one, 3-[4-(5-Hydroxy-2-pyridyl)piperazine-1-carbonyl] chromen-2-one,
1-[4-(5-Hydroxy-2-pyridyl)piperazin-1-yl]-3,3-diphenyl-prop-2-en-1-one,
1-[4-(5-Hydroxy-2-pyridyl)piperazin-1-yl]-3,3-diphenyl-propan-1-one,
(5-Chlorothiophen-2-yl)-[4-(5-hydroxy-pyridin-2-yl)-piperazin-1-yl]-methanone,
(E)-1-[4-(5-Hydroxypyridin-2-yl)-piperazin-1-yl]-3-(4-nitrophenyl)-propenone,
(E)-3-(4-Chlorophenyl)-1-[4-(5-hydroxypyridin-2-yl)-piperazin-1-yl]-propenone,
3-(3,4-Dichlorophenyl)-1-[4-(5-hydroxypyridin-2-yl)-piperazin-1-yl]-propan-1-one,
(2-Chloro-6-methylphenyl)-[4-(5-hydroxypyridin-2-yl)-piperazin-1-yl]-methanone,
[4-(5-Hydroxypyridin-2-yl)-piperazin-1-yl]-[3-(4-methylimidazol-1-yl)-5-trifluoromethylphenyl]-methanone,
3-(4-Chlorophenyl)-1-[4-(5-hydroxy-pyridin-2-yl)-piperazin-1-yl]-propan-1-one,
2-(1-Adamantylamino)-1-[4-(5-hydroxy-2-pyridyl)piperazin-1-yl]ethanone,
1-[4-(5-Hydroxy-2-pyridyl)piperazin-1-yl]-3,3-bis(4-methoxyphenyl)prop-2-en-1-one,
[[4-(5-Hydroxypyridin-2-yl)-piperazin-1-yl]-[4-methyl-3-(4-pyridin-3-yl-pyrimidin-2-ylamino)phenyl]methanone,
(1H-Benzoimidazol-2-yl)-[4-(5-hydroxypyridin-2-yl)-piperazin-1-yl]-methanone,
(5-Bromothiophen-2-yl)-[4-(5-hydroxypyridin-2-yl)-piperazin-1-yl]-methanone,
[(5-Fluoro-1H-indol-2-yl)-[4-(5-hydroxypyridin-2-yl)-piperazin-1-yl]-methanone,
Quinoline-8-sulfonic acid {2-[4-(5-hydroxypyridin-2-yl)-piperazin-1-yl]-2-oxo-ethyl}-methylamide,
1-[4-(5-Hydroxypyridin-2-yl)-piperazin-1-yl]-3-(4-isobutylphenyl)-propan-1-one,
2-(2,4-Difluorophenyl)-1-[4-(5-hydroxypyridine-2-yl)-piperazin-1-yl]-ethanone,
3-(3-Fluorophenyl)-1-[4-(5-hydroxypyridin-2-yl)-piperazin-1-yl]-propan-1-one,
1-[4-(5-Hydroxy-2-pyridyl)piperazin-1-yl]-3,3-bis(4-methoxyphenyl)propan-1-one,
1-[4-(5-Hydroxy-2-pyridyl)piperazin-1-yl]-4,4-diphenyl-but-3-en-1-one,
2-Cyclohexyl-2-hydroxy-1-[4-(5-hydroxy-2-pyridyl)piperazin-1-yl]-2-phenyl-ethanone,
2-[1-Adamantylmethyl(methyl)amino]-1-[4-(5-hydroxy-2-pyridyl)piperazin-1-yl]ethanone,
1-[4-(5-Hydroxypyridin-2-yl)-piperazin-1-yl]-2-(5-nitropyridin-2-ylsulfanyl)-ethanone,
3-(1-Adamantyl)-1-[4-(5-hydroxy-2-pyridyl)piperazin-1-yl] propan-1-one,
2-Cyclohexyl-1-[4-(5-hydroxy-2-pyridyl)piperazin-1-yl]-2-phenyl-ethanone,
3-(4-Hydroxyphenyl)-1-[4-(5-hydroxypyridin-2-yl)-piperazin-1-yl]-propan-1-one,
3-(4-Methoxyphenyl)-1-[4-(5-hydroxypyridin-2-yl)-piperazin-1-yl]-propan-1-one,
3-(2-Bromophenyl)-1-[4-(5-hydroxypyridin-2-yl)-piperazin-1-yl]-propan-1-one,
3-(4-Bromophenyl)-1-[4-(5-hydroxypyridin-2-yl)-piperazin-1-yl]-propan-1-one,
3-[4-(5-Hydroxypyridin-2-yl)-piperazine-1-carbonyl]-7-oxa-bicyclo[2.2.1]heptane-2-carboxylic acid methyl ester,
3-[4-(5-Hydroxypyridin-2-yl)-piperazine-1-carbonyl]-7-oxa-bicyclo[2.2.1]heptane-2-carboxylic acid,
1-[4-(5-Hydroxypyridin-2-yl)-piperazin-1-yl]-2-(1H-indol-3-yl)-ethane-1,2-dione,
1-[4-(5-Hydroxypyridin-2-yl)-piperazin-1-yl]-3-o-tolyl-propan-1-one,
3-(4-Dimethylaminophenyl)-1-[4-(5-hydroxypyridin-2-yl)-piperazin-1-yl]-propan-1-one,
1-[4-(5-Hydroxypyridin-2-yl)-piperazin-1-yl]-3-(2-methoxyphenyl)-propan-1-one,
1-[4-(5-Hydroxypyridin-2-yl)-piperazin-1-yl]-3-p-tolyl-propan-1-one,
2-[4-(5-Hydroxypyridin-2-yl)-piperazine-1-carbonyl]benzoic acid,
1-[4-(5-Hydroxy-2-pyridyl)piperazin-1-yl]-4,4-diphenylbutan-1-one,
[4-(5-Hydroxypyridin-2-yl)-piperazin-1-yl]-[3-(1H-indol-4-yl)phenyl]methanone,
1-[4-(5-Hydroxypyridin-2-yl)-piperazin-1-yl]-3-[4-(2-methoxyethoxy)phenyl]-propan-1-one,
1-[4-(5-Hydroxypyridin-2-yl)-piperazin-1-yl]-3-phenylbutan-1-one,
1-[4-(5-Hydroxypyridin-2-yl)-piperazin-1-yl]-3-thiophen-2-yl-propan-1-one,
1-[4-(5-Hydroxy-2-pyridyl)piperazin-1-yl]-2-morpholino-2-phenylethanone,
Cyclohexyl-[4-(5-hydroxy-2-pyridyl)piperazin-1-yl]methanone,
Cyclopropyl-[4-(5-hydroxy-2-pyridyl)piperazin-1-yl] methanone,
(E)-3-Cyclohexyl-1-[4-(5-hydroxy-2-pyridyl)piperazin-1-yl]prop-2-en-1-one,
3-Cyclohexyl-1-[4-(5-hydroxy-2-pyridyl)piperazin-1-yl] propan-1-one,
3-Benzo[b]thiophen-2-yl-1-[4-(5-hydroxypyridin-2-yl)-piperazin-1-yl]-propan-1-one,
[4-(5-Hydroxypyridin-2-yl)-piperazin-1-yl]-(5-phenylthiophen-2-yl)-methanone,
(3-Hydroxy-3-phenylcyclobutyl)-[4-(5-hydroxypyridin-2-yl)-piperazin-1-yl]-methanone,
1-[4-(5-Hydroxypyridin-2-yl)-piperazin-1-yl]-3-methyl-3-phenylbutan-1-one,
3-(4-Fluorophenyl)-1-[4-(5-hydroxypyridin-2-yl)-piperazin-1-yl]-propan-1-one,
1-[4-(5-Hydroxypyridin-2-yl)-piperazin-1-yl]-2-(2-methyl-1H-indol-3-yl)-ethanone,
1-[4-(5-Hydroxypyridin-2-yl)-piperazin-1-yl]-3-(2-trifluoromethylphenyl)-propan-1-one,
1-[4-(5-Hydroxypyridin-2-yl)-piperazin-1-yl]-3-pyridin-2-yl-propan-1-one,
3-Hydroxy-1-[4-(5-hydroxypyridin-2-yl)-piperazin-1-yl]-3-phenylpropan-1-one,
2-(5-Fluoro-1H-indol-3-yl)-1-[4-(5-hydroxypyridin-2-yl)-piperazin-1-yl]-ethanone,
[4-(5-Hydroxypyridin-2-yl)-piperazin-1-yl]-(1,2,3,4-tetrahydronaphthalen-1-yl)-methanone,
[4-(5-Hydroxypyridin-2-yl)-piperazin-1-yl]-((1R,2R)-2-phenylcyclopropyl)-methanone,
[4-(5-Hydroxypyridin-2-yl)-piperazin-1-yl]-(3-phenylcyclobutyl)-methanone,
1-[4-(5-Hydroxypyridin-2-yl)-piperazin-1-yl]-3-indol-1-yl-propan-1-one,
3-Benzoimidazol-1-yl-1-[4-(5-hydroxypyridin-2-yl)-piperazin-1-yl]-propan-1-one,
2-Cyclopropyl-1-[4-(5-hydroxy-2-pyridyl)piperazin-1-yl] ethanone,
3-(4-Cyanophenyl)-1-[4-(5-hydroxypyridin-2-yl)-piperazin-1-yl]-propan-1-one, 3-(4-Trifluoromethylphenyl)-1-[4-(5-hydroxypyridin-2-yl)-piperazin-1-yl]-propan-1-one,
3-Cyclopropyl-1-[4-(5-hydroxy-2-pyridyl)piperazin-1-yl] propan-1-one,
2-{3-[4-(5-Hydroxypyridin-2-yl)-piperazin-1-yl]-3-oxopropyl}-benzoic acid,
2-{3-[4-(5-Hydroxypyridin-2-yl)-piperazin-1-yl]-3-oxopropyl}-benzoic acid methyl ester,
2-(2-Bromophenylsulfanyl)-1-[4-(5-hydroxypyridin-2-yl)-piperazin-1-yl]-ethanone,
2-Hydroxy-1-[4-(5-hydroxypyridin-2-yl)-piperazin-1-yl]-3-phenyl-propan-1-one,
3-(4-Fluoro-2-methylphenyl)-1-[4-(5-hydroxypyridin-2-yl)-piperazin-1-yl]-propan-1-one,
3-(2,3-Dimethylphenyl)-1-[4-(5-hydroxypyridin-2-yl)-piperazin-1-yl]-propan-1-one,
3-(2,6-Dimethylphenyl)-1-[4-(5-hydroxypyridin-2-yl)-piperazin-1-yl]-propan-1-one,
3-(2,4-Difluorophenyl)-1-[4-(5-hydroxypyridin-2-yl)-piperazin-1-yl]-propan-1-one,
3-(3,4-Difluorophenyl)-1-[4-(5-hydroxypyridin-2-yl)-piperazin-1-yl]-propan-1-one,
(5-Fluoro-1H-indol-3-yl)-[4-(5-hydroxypyridin-2-yl)-piperazin-1-yl]-methanone,
3-(2,6-Difluorophenyl)-1-[4-(5-hydroxypyridin-2-yl)-piperazin-1-yl]-propan-1-one,
2-(6-Fluoro-1H-indol-3-yl)-1-[4-(5-hydroxy-pyridin-2-yl)-piperazin-1-yl]-ethanone,
2-(5-Chloro-1H-indol-3-yl)-1-[4-(5-hydroxy-pyridin-2-yl)-piperazin-1-yl]-ethanone,
2-(5,6-Difluoro-1H-indol-3-yl)-1-[4-(5-hydroxy-pyridin-2-yl)-piperazin-1-yl]-ethanone,
3-(4-Fluoro-phenyl)-1-[4-(5-hydroxy-pyridin-2-yl)-piperazin-1-yl]-3-methyl-butan-1-one,
2-(2-Bromo-phenylsulfanyl)-1-[4-(5-hydroxy-pyridin-2-yl)-piperazin-1-yl]-2-methyl-propan-1-one,
2-(4-Fluoro-phenylsulfanyl)-1-[4-(5-hydroxy-pyridin-2-yl)-piperazin-1-yl]-ethanone,
2-(4-Fluoro-phenoxy)-1-[4-(5-hydroxy-pyridin-2-yl)-piperazin-1-yl]-ethanone,
2-(5-Fluoro-1-methyl-indol-3-yl)-1-[4-(5-hydroxy-pyridin-2-yl)-piperazin-1-yl]-ethanone,
2-(5-Fluoro-2-methyl-1H-indol-3-yl)-1-[4-(5-hydroxy-pyridin-2-yl)-piperazin-1-yl]-ethanone,
2-(5,7-Difluoro-1H-indol-3-yl)-1-[4-(5-hydroxy-pyridin-2-yl)-piperazin-1-yl]-ethanone,
1-(5-Fluoro-1H-indol-3-yl)-2-[4-(5-hydroxy-pyridin-2-yl)-piperazin-1-yl]-ethane-1,2-dione,
2-(5-Fluoro-1H-indol-3-yl)-1-[4-(5-hydroxy-pyridin-2-yl)-piperazin-1-yl]-2-methyl-propan-1-one,
1-[4-(5-Hydroxy-pyridin-2-yl)-piperazin-1-yl]-3-(3,4,5-trifluoro-phenyl)-propan-1-one,
N-{3-[4-(5-Hydroxy-pyridin-2-yl)-piperazin-1-yl]-3-oxo-1-phenyl-propyl}-acrylamide,
2-(5,6-Dichloro-1H-indol-3-yl)-1-[4-(5-hydroxy-pyridin-2-yl)-piperazin-1-yl]-ethanone,
2-(5-Chloro-2-methyl-1H-indol-3-yl)-1-[4-(5-hydroxy-pyridin-2-yl)-piperazin-1-yl]-ethanone,
2-(5,6-Dichloro-2-methyl-1H-indol-3-yl)-1-[4-(5-hydroxy-pyridin-2-yl)-piperazin-1-yl]-ethanone,
and pharmaceutically acceptable salts, stereoisomers, and/or deuterated analogs thereof.

In another embodiment, the present invention relates to a compound selected from:
4-(4-Hydroxyphenyl)piperazin-1-yl]-(1H-indol-3-yl)-methanone,
2-(5-Fluoro-1H-indol-3-yl)-1-[4-(4-hydroxyphenyl)-piperazin-1-yl]-ethanone,
2-(3,5-Difluorophenyl)-1-[4-(4-hydroxyphenyl)-piperazin-1-yl]-ethanone,
2-(2,4-Difluorophenyl)-1-[4-(4-hydroxyphenyl)-piperazin-1-yl]-ethanone,
2-(5-Fluoro-1H-indol-3-yl)-1-[4-(5-hydroxypyridin-2-yl)-piperazin-1-yl]-ethanone,
1-[4-(5-Hydroxypyridin-2-yl)-piperazin-1-yl]-3-phenyl-propan-1-one,
1-[4-(5-Hydroxypyridin-2-yl)-piperazin-1-yl]-3-methyl-3-phenylbutan-1-one,
2-(1-Adamantyl)-1-[4-(5-hydroxy-2-pyridyl)piperazin-1-yl] ethanone,
2-(2-Bromophenylsulfanyl)-1-[4-(5-hydroxypyridin-2-yl)-piperazin-1-yl]-ethanone,
and pharmaceutically acceptable salts, stereoisomers, and/or deuterated analogs thereof.

In another embodiment, the present invention relates to a compound selected from:
[4-(4-Hydroxyphenyl)-piperazin-1-yl]-[1-(2-methoxy-ethyl)-piperidin-4-yl]-methanone,
[4-(4-Hydroxyphenyl)-piperazin-1-yl]-(1H-indazol-3-yl)-methanone,
Acridin-9-yl-[4-(4-hydroxy-phenyl)-piperazin-1-yl]-methanone,
[4-(4-Hydroxyphenyl)-piperazin-1-yl]-[5-(2-methoxy-ethoxy)-1H-indol-3-yl]-methanone,
1-[4-(2-Fluoro-4-hydroxy-phenyl)-piperazin-1-yl]-2-phenylethanone,
3-(4-Butoxyphenyl)-1-[4-(4-hydroxyphenyl)-piperazin-1-yl]-propenone,
3-(4-Butoxyphenyl)-1-[4-(4-hydroxyphenyl)-piperazin-1-yl]-propan-1-one,
[4-(4-Hydroxyphenyl)-piperazin-1-yl]-phenanthren-9-yl-methanone,
[4-(4-Hydroxyphenyl)-piperazin-1-yl]-(1H-indol-4-yl)-methanone,
[4-(4-Hydroxyphenyl)piperazin-1-yl]-(2-morpholino-6-phenyl-4-pyridyl)methanone,
[4-(4-Hydroxyphenyl)piperazin-1-yl]-(2-morpholino-4-pyridyl)methanone,
(2-Chloro-6-morpholino-4-pyridyl)-[4-(4-hydroxyphenyl) piperazin-1-yl]methanone,
and pharmaceutically acceptable salts, stereoisomers, and/or deuterated analogs thereof.

In another embodiment, the present invention relates to a compound selected from:
Acridin-9-yl-[4-(5-hydroxy-pyridin-2-yl)-piperazin-1-yl]-methanone,
1-[4-(5-Hydroxypyridin-2-yl)-piperazin-1-yl]-3-phenyl-propan-1-one,
1-[4-(5-Hydroxy-2-pyridyl)piperazin-1-yl]-2,2-diphenyl-ethanone,
1-[4-(5-Hydroxypyridin-2-yl)-piperazin-1-yl]-3-(1H-indol-3-yl)-propan-1-one,
1-[4-(5-Hydroxypyridin-2-yl)-piperazin-1-yl]-3-thiophen-2-yl-propan-1-one,
3-(4-Fluorophenyl)-1-[4-(5-hydroxypyridin-2-yl)-piperazin-1-yl]-propan-1-one,
1-[4-(5-Hydroxypyridin-2-yl)-piperazin-1-yl]-3-indol-1-yl-propan-1-one,
2-{3-[4-(5-Hydroxypyridin-2-yl)-piperazin-1-yl]-3-oxopropyl}-benzoic acid methyl ester,
2-Hydroxy-1-[4-(5-hydroxypyridin-2-yl)-piperazin-1-yl]-3-phenyl-propan-1-one, 3-(4-Fluoro-2-methylphenyl)-1-[4-(5-hydroxypyridin-2-yl)-piperazin-1-yl]-propan-1-one,
(5-Fluoro-1H-indol-3-yl)-[4-(5-hydroxypyridin-2-yl)-piperazin-1-yl]-methanone,
and pharmaceutically acceptable salts, stereoisomers, and/or deuterated analogs thereof.

In another embodiment, the present invention relates to a compound selected from:
1-[4-(5-Hydroxypyridin-2-yl)-piperazin-1-yl]-2-phenylethanone,
3-[4-(5-Hydroxy-2-pyridyl)piperazine-1-carbonyl]-1H-quinolin-4-one,
2-(1-Adamantyl)-1-[4-(5-hydroxy-2-pyridyl)piperazin-1-yl]ethanone,
2,2-Bis(4-chlorophenyl)-1-[4-(5-hydroxy-2-pyridyl)piperazin-1-yl]ethanone,
1-(Cyclopropylmethyl)-3-[4-(5-hydroxy-2-pyridyl)piperazine-1-carbonyl]quinolin-4-one,
2-(9H-Fluoren-9-yl)-1-[4-(5-hydroxy-2-pyridyl)piperazin-1-yl]ethanone,
1-[4-(5-Hydroxypyridin-2-yl)-piperazin-1-yl]-2-(1H-indol-3-yl)-ethanone,
Anthracen-9-yl-[4-(5-hydroxypyridin-2-yl)-piperazin-1-yl]-methanone,
1-[4-(5-Hydroxypyridin-2-yl)-piperazin-1-yl]-4-phenylbutan-1-one,
1-[4-(5-Hydroxypyridin-2-yl)-piperazin-1-yl]-3-pyridin-4-yl-propan-1-one,
1-[4-(5-Hydroxypyridin-2-yl)-piperazin-1-yl]-5-phenylpentan-1-one,
5-[4-(5-Hydroxy-2-pyridyl)piperazin-1-yl]-5-oxo-pentanoic acid,
1-[4-(5-Hydroxy-2-pyridyl)piperazin-1-yl]-3,3-diphenyl-prop-2-en-1-one,
3-(4-Chlorophenyl)-1-[4-(5-hydroxy-pyridin-2-yl)-piperazin-1-yl]-propan-1-one,
2-(1-Adamantylamino)-1-[4-(5-hydroxy-2-pyridyl)piperazin-1-yl]ethanone,
[(5-Fluoro-1H-indol-2-yl)-[4-(5-hydroxypyridin-2-yl)-piperazin-1-yl]-methanone,
3-(3-Fluorophenyl)-1-[4-(5-hydroxypyridin-2-yl)-piperazin-1-yl]-propan-1-one,
1-[4-(5-Hydroxypyridin-2-yl)-piperazin-1-yl]-3-o-tolyl-propan-1-one,
1-[4-(5-Hydroxypyridin-2-yl)-piperazin-1-yl]-3-phenylbutan-1-one,
3-Cyclohexyl-1-[4-(5-hydroxy-2-pyridyl)piperazin-1-yl]propan-1-one,
3-Benzo[b]thiophen-2-yl-1-[4-(5-hydroxypyridin-2-yl)-piperazin-1-yl]-propan-1-one,
(3-Hydroxy-3-phenylcyclobutyl)-[4-(5-hydroxypyridin-2-yl)-piperazin-1-yl]-methanone,
1-[4-(5-Hydroxypyridin-2-yl)-piperazin-1-yl]-2-(2-methyl-1H-indol-3-yl)-ethanone,
1-[4-(5-Hydroxypyridin-2-yl)-piperazin-1-yl]-3-(2-trifluoromethylphenyl)-propan-1-one,
3-Hydroxy-1-[4-(5-hydroxypyridin-2-yl)-piperazin-1-yl]-3-phenylpropan-1-one,
2-(5-Fluoro-1H-indol-3-yl)-1-[4-(5-hydroxypyridin-2-yl)-piperazin-1-yl]-ethanone,
[4-(5-Hydroxypyridin-2-yl)-piperazin-1-yl]-((1R,2R)-2-phenylcyclopropyl)-methanone,
2-Cyclopropyl-1-[4-(5-hydroxy-2-pyridyl)piperazin-1-yl]ethanone,
3-(4-Cyanophenyl)-1-[4-(5-hydroxypyridin-2-yl)-piperazin-1-yl]-propan-1-one,
3-(4-Trifluoromethylphenyl)-1-[4-(5-hydroxypyridin-2-yl)-piperazin-1-yl]-propan-1-one,
3-Cyclopropyl-1-[4-(5-hydroxy-2-pyridyl)piperazin-1-yl]propan-1-one,
2-(2-Bromophenylsulfanyl)-1-[4-(5-hydroxypyridin-2-yl)-piperazin-1-yl]-ethanone,
3-(2,6-Dimethylphenyl)-1-[4-(5-hydroxypyridin-2-yl)-piperazin-1-yl]-propan-1-one,
3-(2,4-Difluorophenyl)-1-[4-(5-hydroxypyridin-2-yl)-piperazin-1-yl]-propan-1-one,
3-(3,4-Difluorophenyl)-1-[4-(5-hydroxypyridin-2-yl)-piperazin-1-yl]-propan-1-one,
3-(2,6-Difluorophenyl)-1-[4-(5-hydroxypyridin-2-yl)-piperazin-1-yl]-propan-1-one,
2-(6-Fluoro-1H-indol-3-yl)-1-[4-(5-hydroxy-pyridin-2-yl)-piperazin-1-yl]-ethanone,
2-(5-Chloro-1H-indol-3-yl)-1-[4-(5-hydroxy-pyridin-2-yl)-piperazin-1-yl]-ethanone,
2-(5,6-Difluoro-1H-indol-3-yl)-1-[4-(5-hydroxy-pyridin-2-yl)-piperazin-1-yl]-ethanone,
3-(4-Fluoro-phenyl)-1-[4-(5-hydroxy-pyridin-2-yl)-piperazin-1-yl]-3-methyl-butan-1-one,
2-(2-Bromo-phenylsulfanyl)-1-[4-(5-hydroxy-pyridin-2-yl)-piperazin-1-yl]-2-methyl-propan-1-one,
2-(4-Fluoro-phenylsulfanyl)-1-[4-(5-hydroxy-pyridin-2-yl)-piperazin-1-yl]-ethanone,
2-(5-Fluoro-2-methyl-1H-indol-3-yl)-1-[4-(5-hydroxy-pyridin-2-yl)-piperazin-1-yl]-ethanone,
2-(5,7-Difluoro-1H-indol-3-yl)-1-[4-(5-hydroxy-pyridin-2-yl)-piperazin-1-yl]-ethanone,
1-(5-Fluoro-1H-indol-3-yl)-2-[4-(5-hydroxy-pyridin-2-yl)-piperazin-1-yl]-ethane-1,2-dione,
2-(5-Fluoro-1H-indol-3-yl)-1-[4-(5-hydroxy-pyridin-2-yl)-piperazin-1-yl]-2-methyl-propan-1-one,
2-(5,6-Dichloro-1H-indol-3-yl)-1-[4-(5-hydroxy-pyridin-2-yl)-piperazin-1-yl]-ethanone,
2-(5-Chloro-2-methyl-1H-indol-3-yl)-1-[4-(5-hydroxy-pyridin-2-yl)-piperazin-1-yl]-ethanone,
2-(5,6-Dichloro-2-methyl-1H-indol-3-yl)-1-[4-(5-hydroxy-pyridin-2-yl)-piperazin-1-yl]-ethanone,
and pharmaceutically acceptable salts, stereoisomers, and/or deuterated analogs thereof.

In another embodiment, the present invention relates to a compound selected from:
1-[4-(4-Hydroxyphenyl)piperazin-1-yl]-2-phenylethanone,
4-(4-Hydroxyphenyl)piperazin-1-yl]-(1H-indol-3-yl)-methanone,
2-(4-Hydroxyphenyl)-1-[4-(4-hydroxyphenyl)-piperazin-1-yl]-ethanone,
1-[4-(4-Hydroxyphenyl)-piperazin-1-yl]-2-[4-(2-methoxyethoxy)-phenyl]-ethanone,
Anthracen-9-yl-[4-(4-hydroxyphenyl)-piperazin-1-yl]-methanone,
1-[4-(4-Hydroxyphenyl)-piperazin-1-yl]-2-(4-trifluoromethylphenyl)-ethanone,
3-[4-[4-(4-Hydroxyphenyl)piperazine-1-carbonyl]-2-pyridyl]benzoic acid,
1-[4-(4-Hydroxyphenyl)piperazin-1-yl]-3,3-diphenyl-prop-2-en-1-one,
3-[4-[4-(4-Hydroxyphenyl)piperazine-1-carbonyl]-6-morpholino-2-pyridyl]benzoic acid,
4-[4-[4-(4-Hydroxyphenyl)piperazine-1-carbonyl]-6-morpholino-2-pyridyl]benzoic acid,
1-[4-(4-Hydroxyphenyl)-piperazin-1-yl]-3-naphthalen-1-yl-propan-1-one,
3-[4-(4-Hydroxyphenyl)piperazine-1-carbonyl]-1H-quinolin-4-one, 1-[4-(4-Hydroxyphenyl)piperazin-1-yl]-2-(2-phenoxyphenyl)ethanone,
[4-(4-Hydroxyphenyl)piperazin-1-yl]-[2-(1-piperidyl)-4-pyridyl]methanone,
1-[4-(4-Hydroxy-3-methyl-phenyl)-piperazin-1-yl]-2-phenylethanone,
3-Anthracen-9-yl-1-[4-(4-hydroxyphenyl)-piperazin-1-yl]-propan-1-one,
2-(3,5-Difluorophenyl)-1-[4-(4-hydroxyphenyl)-piperazin-1-yl]-ethanone,
2-(2,4-Difluorophenyl)-1-[4-(4-hydroxyphenyl)-piperazin-1-yl]-ethanone,
2-(5-Fluoro-1H-indol-3-yl)-1-[4-(4-hydroxyphenyl)-piperazin-1-yl]-ethanone,
2-(2-Bromophenylsulfanyl)-1-[4-(4-hydroxyphenyl)-piperazin-1-yl]-ethanone,
(2-Chloro-6-methylphenyl)-[4-(4-hydroxyphenyl)-piperazin-1-yl]-methanone,
(5-Fluoro-1H-indol-3-yl)-[4-(4-hydroxyphenyl)-piperazin-1-yl]-methanone,
1-[4-(4-Hydroxy-phenyl)-piperazin-1-yl]-2-(3,4,5-trifluoro-phenyl)-ethanone,
1-[4-(4-Hydroxy-phenyl)-piperazin-1-yl]-3-methyl-3-phenyl-butan-1-one,
and pharmaceutically acceptable salts, stereoisomers, and/or deuterated analogs thereof.

The compounds of the present invention can also include all isotopes of atoms occurring in the intermediates or final compounds. Isotopes include those atoms having the same atomic number but different mass numbers. For example, isotopes of hydrogen include tritium and deuterium.

In another embodiment, the present invention provides deuterated analogs of a compound of Formulae I, Ia or Ib, wherein one or more hydrogen atoms are replaced with deuterium. Such compounds can be synthesized by means well known in the art, for example by employing starting materials in which one or more hydrogen atoms have been replaced with deuterium. Deuterated analogs may have improved drug metabolism and pharmacokinetics properties, See, for example, Foster, "Deuterium Isotope Effects in Studies of Drug Metabolism," Trends Pharmacol. Sci., 5(12):524-527 (1984).

The compounds described herein are potent malic enzyme inhibitors and may be useful as medicaments, particularly for the treatment of diseases or disorders that benefit from the inhibition of malic enzyme. The compounds of the present invention may be useful in the treatment of a number of tumors and/or cancers including, but not limited to, leukemia, brain cancer, bladder cancer, breast cancer, cervical cancer, colorectal cancer, endometrial cancer, esophageal cancer, head and neck cancer, liver cancer, lung cancer, lymphoma, ovarian cancer, pancreatic cancer, prostate cancer, renal cancer, skin cancer, stomach cancer, testis cancer, thyroid cancer, and urothelial cancer.

According to one embodiment, the compounds of the present invention are inhibitors of malic enzyme 3 (ME3), malic enzyme 2 (ME2), and/or malic enzyme 1 (ME1).

In another embodiment, the compounds of the present invention are inhibitors of ME3.

Thus, in another aspect, the present invention provides a method of inhibiting a malic enzyme in a subject comprising administering to the subject a compound of Formulae I, Ia, Ib, or a pharmaceutically acceptable salt, stereoisomer or deuterated analog thereof.

In one embodiment, the present invention provides a method of inhibiting a malic enzyme in a subject comprising administering to the subject a compound of Formula I

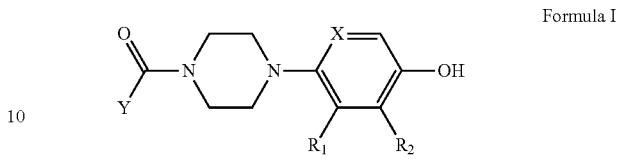

Formula I or a pharmaceutically acceptable salt, stereoisomer or deuterated analog thereof, wherein X is CH or nitrogen;

$R_1$ is selected from hydrogen, $CH_3$, —COOH, fluoro and CN;

$R_2$ is selected from hydrogen, $CH_3$, —COOH, fluoro and CN;

Y is selected from substituted or unsubstituted $C_{1-5}$ alkyl, substituted or unsubstituted $C_{2-4}$ alkenyl, substituted or unsubstituted 5 to 14 membered heteroaryl ring containing one, two or three heteroatoms each independently selected from nitrogen, oxygen, and sulfur, substituted or unsubstituted 5 to 14 membered heterocycloalkyl group containing one, two or three heteroatoms each independently selected from nitrogen and oxygen, substituted or unsubstituted $C_{3-15}$ cycloalkyl, substituted or unsubstituted $C_{3-15}$ cycloalkyl$C_{1-6}$alkyl, substituted or unsubstituted $C_{6-14}$ aryl, substituted or unsubstituted $C_{6-14}$aryl$C_{1-6}$alkyl, substituted or unsubstituted $C_{6-14}$aryl$C_{2-5}$alkenyl, substituted or unsubstituted 5 to 14 membered heteroaryl$C_{1-6}$alkyl, and substituted or unsubstituted 5 to 14 membered heterocycloalkyl$C_{1-6}$alkyl.

In another embodiment, the present invention provides a method of inhibiting a malic enzyme in a subject comprising administering to the subject a compound of Formula I, or a pharmaceutically acceptable salt, stereoisomer or deuterated analog thereof, wherein the malic enzyme is ME3, ME2, and/or ME1.

In another embodiment, the present invention provides a method of inhibiting a malic enzyme in a subject comprising administering to the subject a compound of Formula I, or a pharmaceutically acceptable salt, stereoisomer or deuterated analog thereof, wherein the malic enzyme is ME3.

In another embodiment, the present invention provides a method of inhibiting a malic enzyme in a subject comprising administering to the subject a compound of Formulae Ia or Ib, or a pharmaceutically acceptable salt, stereoisomer or deuterated analog thereof, wherein the malic enzyme is ME3, ME2, and/or ME1.

In another embodiment, the present invention provides a method of inhibiting a malic enzyme in a subject comprising administering to the subject a compound of Formulae Ia or Ib, or a pharmaceutically acceptable salt, stereoisomer or deuterated analog thereof, wherein the malic enzyme is ME3.

In another aspect, the present invention provides a method of inhibiting a malic enzyme in a subject comprising administering to the subject in need thereof, a compound of Formula I or a pharmaceutically acceptable salt, stereoisomer or deuterated analog thereof.

In one embodiment, the present invention provides a method of inhibiting a malic enzyme in a subject comprising administering to the subject in need thereof, a compound of Formula I

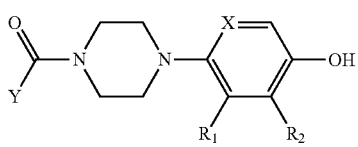

Formula I or a pharmaceutically acceptable salt, stereoisomer or deuterated analog thereof, wherein
X is CH or nitrogen;
R$_1$ is selected from hydrogen, CH$_3$, —COOH, fluoro and CN;
R$_2$ is selected from hydrogen, CH$_3$, —COOH, fluoro and CN;
Y is selected from substituted or unsubstituted C$_{1-5}$ alkyl, substituted or unsubstituted C$_{2-4}$ alkenyl, substituted or unsubstituted 5 to 14 membered heteroaryl ring containing one, two or three heteroatoms each independently selected from nitrogen, oxygen, and sulfur, substituted or unsubstituted 5 to 14 membered heterocycloalkyl group containing one, two or three heteroatoms each independently selected from nitrogen and oxygen, substituted or unsubstituted C$_{3-15}$ cycloalkyl, substituted or unsubstituted C$_{3-15}$ cycloalkylC$_{1-6}$alkyl, substituted or unsubstituted C$_{6-14}$ aryl, substituted or unsubstituted C$_{6-14}$arylC$_{1-6}$alkyl, substituted or unsubstituted C$_{6-14}$arylC$_{2-5}$alkenyl, substituted or unsubstituted 5 to 14 membered heteroarylC$_{1-6}$alkyl, and substituted or unsubstituted 5 to 14 membered heterocycloalkylC$_{1-6}$alkyl.

In another embodiment, the present invention provides a method of inhibiting a malic enzyme in a subject comprising administering to the subject in need thereof, a compound of Formula I, or a pharmaceutically acceptable salt, stereoisomer or deuterated analog thereof, wherein the malic enzyme is ME3, ME2, and/or ME1.

In another embodiment, the present invention provides a method of inhibiting a malic enzyme in a subject comprising administering to the subject in need thereof, a compound of Formula I, or a pharmaceutically acceptable salt, stereoisomer or deuterated analog thereof, wherein the malic enzyme is ME3.

In another aspect, the present invention provides a method of inhibiting a malic enzyme in a subject comprising administering to the subject in need thereof, a compound of Formulae Ia, or Ib, or a pharmaceutically acceptable salt, stereoisomer or deuterated analog thereof.

In one embodiment, the present invention provides a method of inhibiting a malic enzyme in a subject comprising administering to the subject in need thereof, a compound of Formulae Ia, or Ib, or a pharmaceutically acceptable salt, stereoisomer or deuterated analog thereof, wherein the malic enzyme is ME3, ME2, and/or ME1.

In one embodiment, the present invention provides a method of inhibiting a malic enzyme in a subject comprising administering to the subject in need thereof, a compound of Formulae Ia, or Ib, or a pharmaceutically acceptable salt, stereoisomer or deuterated analog thereof, wherein the malic enzyme is ME3, ME2, and/or ME1.

In another embodiment, the present invention provides a method of inhibiting a malic enzyme in a subject comprising administering to the subject in need thereof, a compound of Formula I, or a pharmaceutically acceptable salt, stereoisomer or deuterated analog thereof, wherein the subject has cancer.

In another embodiment, the present invention provides a method of inhibiting a malic enzyme in a subject comprising administering to the subject in need thereof, a compound of Formula Ia, or a pharmaceutically acceptable salt, stereoisomer or deuterated analog thereof, wherein the subject has cancer.

In another embodiment, the present invention provides a method of inhibiting a malic enzyme in a subject comprising administering to the subject in need thereof, a compound of Formula Ib, or a pharmaceutically acceptable salt, stereoisomer or deuterated analog thereof, wherein the subject has cancer.

In one embodiment, the cancer is selected from leukemia, brain cancer, bladder cancer, breast cancer, cervical cancer, colorectal cancer, endometrial cancer, esophageal cancer, head and neck cancer, liver cancer, lung cancer, lymphoma, ovarian cancer, pancreatic cancer, prostate cancer, renal cancer, skin cancer, stomach cancer, testis cancer, thyroid cancer, and urothelial cancer.

In another aspect, the present invention provides a method of treating a subject having cancer comprising administering to the subject a malic enzyme inhibitor, wherein the malic enzyme inhibitor is a compound of Formula I, or a pharmaceutically acceptable salt, stereoisomer or deuterated analog thereof.

In one embodiment, the present invention provides a method of treating a subject having cancer comprising administering to the subject a malic enzyme inhibitor, wherein the malic enzyme inhibitor is a compound of Formula I

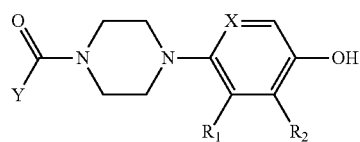

Formula I or a pharmaceutically acceptable salt, stereoisomer or deuterated analog thereof, wherein
X is CH or nitrogen;
R$_1$ is selected from hydrogen, CH$_3$, —COOH, fluoro and CN;
R$_2$ is selected from hydrogen, CH$_3$, —COOH, fluoro and CN;
Y is selected from substituted or unsubstituted C$_{1-5}$ alkyl, substituted or unsubstituted C$_{2-4}$ alkenyl, substituted or unsubstituted 5 to 14 membered heteroaryl ring containing one, two or three heteroatoms each independently selected from nitrogen, oxygen, and sulfur, substituted or unsubstituted 5 to 14 membered heterocycloalkyl group containing one, two or three heteroatoms each independently selected from nitrogen and oxygen, substituted or unsubstituted C$_{3-15}$ cycloalkyl, substituted or unsubstituted C$_{3-15}$ cycloalkylC$_{1-6}$alkyl, substituted or unsubstituted C$_{6-14}$ aryl, substituted or unsubstituted C$_{6-14}$arylC$_{1-6}$alkyl, substituted or unsubstituted C$_{6-14}$arylC$_{2-5}$alkenyl, substituted or unsubstituted 5 to 14 membered heteroarylC$_{1-6}$alkyl, and substituted or unsubstituted 5 to 14 membered heterocycloalkylC$_{1-6}$alkyl.

In another aspect, the present invention provides a method of treating a subject having cancer comprising administering to the subject a malic enzyme inhibitor, wherein the malic enzyme inhibitor is a compound of Formula Ia, or a pharmaceutically acceptable salt, stereoisomer or deuterated analog thereof.

In another aspect, the present invention provides a method of treating a subject having cancer comprising administering to the subject a malic enzyme inhibitor, wherein the malic enzyme inhibitor is a compound of Formula Ib, or a pharmaceutically acceptable salt, stereoisomer or deuterated analog thereof.

In one embodiment, the cancer in any of the methods and/or uses described herein is selected from leukemia, brain cancer, bladder cancer, breast cancer, cervical cancer, colorectal cancer, endometrial cancer, esophageal cancer, head and neck cancer, liver cancer, lung cancer, lymphoma, ovarian cancer, pancreatic cancer, prostate cancer, renal cancer, skin cancer, stomach cancer, testis cancer, thyroid cancer, and urothelial cancer.

In another embodiment, the malic enzyme inhibitor is an inhibitor of ME3, ME2, and/or ME1.

In another embodiment, the malic enzyme inhibitor is an inhibitor of ME3.

The compounds of the present invention can be used either alone or in combination with other malic enzyme inhibitors, or any appropriate drugs for the treatment of disease mediated by malic enzyme such as cancers, particularly in pancreatic ductal adenocarcinoma (PDAC) in humans.

Pharmaceutical Compositions

Any of the compounds disclosed herein may be formulated into a composition that additionally comprises one or more suitable pharmaceutically acceptable carriers, including excipients and other compounds that facilitate administration of the compound to a subject. The pharmaceutical compositions may be formulated in a conventional manner using one or more pharmaceutically acceptable excipients. Such pharmaceutical compositions and the processes for preparing the same are described, for example, in Remington: The Science and Practice of Pharmacy (D. B. Troy, Editor, 21st Edition, Lippincott, Williams & Wilkins, 2006), the contents of which are incorporated herein by reference in their entirety.

Thus, in one embodiment, the present invention provides a pharmaceutical composition comprising a compound of Formula I, or a pharmaceutically acceptable salt or deuterated analog thereof, and a pharmaceutically acceptable carrier, diluent, or excipient.

In another embodiment, the present invention provides a pharmaceutical composition comprising a compound of Formula Ia, or a pharmaceutically acceptable salt or deuterated analog thereof, and a pharmaceutically acceptable carrier, diluent, or excipient.

In another embodiment, the present invention provides a pharmaceutical composition comprising a compound of Formula Ib, or a pharmaceutically acceptable salt or deuterated analog thereof, and a pharmaceutically acceptable carrier, diluent, or excipient.

Suitable doses of the compounds for use in treating any of the diseases, disorders and/or conditions described herein can be determined by those skilled in the relevant art. Therapeutic doses are generally identified through a dose ranging study in humans based on preliminary evidence derived from animal studies. Doses must be sufficient to result in a desired therapeutic benefit without causing unwanted side effects. The mode of administration, dosage forms, and suitable pharmaceutical excipients can also be understood and adjusted by those skilled in the art.

General Synthetic Methods for the Preparation of Compounds of Formula I

In one embodiment, the compounds of Formula I can be prepared by following the process as shown in Scheme 1 below:

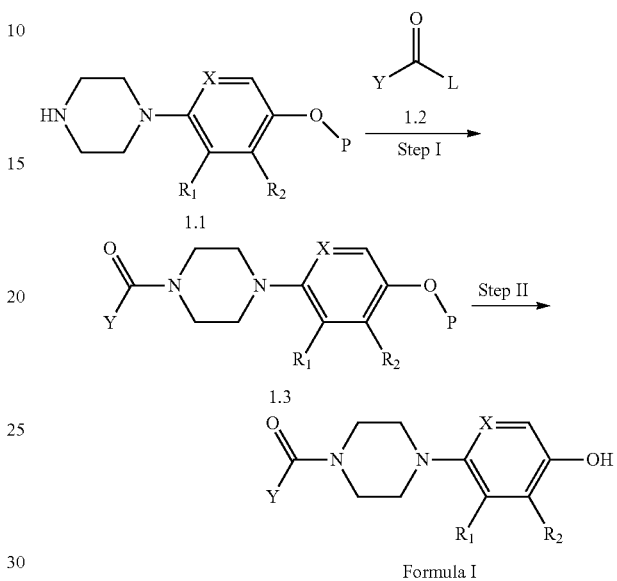

Variables $R_1$, $R_2$, X and Y in the compounds depicted in Scheme 1 are as defined in the any of the embodiments described herein. Step-I involves condensation of a suitably protected and substituted amine compound of Formula 1.1 (where P is a hydroxy protecting group such as benzyl, benzoyl, etc.) with a compound of Formula 1.2 (wherein L is a leaving group such as halogen) to obtain a suitably substituted and protected compound 1.3. Preferably, the condensation reaction is carried out in the presence of an inert base such as triethylamine or di-isopropylethylamine and/or a suitable catalyst in an inert solvent such as tetrahydrofuran, dichloromethane, N,N-dimethylformamide, dimethylacetamide, etc. The starting compound of Formula 1.1 can be obtained commercially or can be prepared by methods known in the art.

The compound of the Formula 1.2 which is in activated form (i.e. —C(O)-L) is preferably an acid halide, an ester, an anhydride or a cyclic imide and can be prepared from the corresponding acid (L is —OH) by general methods known to those skilled in the art. For example, a compound of the Formula 1.2 wherein L is a halide can be obtained by treatment of the corresponding acid (L is —OH) of Formula 1.2 with a halogenating agent such as thionyl chloride, phosphorus pentachloride or oxalyl chloride. The compound of Formula 1.2 in activated form can alternatively be generated in-situ from the corresponding acid (when L=OH), for example, reactive esters formed by using 1-ethyl-3-(3-dimethylaminopropyl)carbodiimide (EDC) or 1-[bis(dimethylamino)methylene]-1H-1,2,3-triazolo[4,5-b]pyridinium 3-oxide hexafluorophosphate (HATU); and then condensed with the compound of Formula 1.1 to generate the compound of Formula 1.3.

The compound of Formula 1.2 in activated form is preferably generated in situ from the corresponding acid (i.e. when L=OH). For example, N,N'-disubstituted amidino esters can be formed in situ by reacting a mixture of the acid of Formula 1.2 (i.e., when L=OH) and the compound of Formula 1.1 in the presence of a suitable condensation agent, such as, for example N,N'-dicyclohexylcarbodiimide. Reactive mixed anhydrides of the acid may also be generated with an organic phosphonic acid in situ by reaction with propylphosphonic anhydride or diethylcyanophosphonate in the presence of suitable base for e.g. triethylamine or 4-(N,N-dimethylamino)pyridine.

The reaction may be carried out in a manner known in the art, the reaction conditions being dependent on how the acid group of Formula 1.2 has been activated, usually in the presence of a suitable solvent or diluent or of a mixture thereof and, if necessary, in the presence of a condensation agent. Condensation agents include, for example, (i) carbodiimides such as N,N'-diethyl-, N,N'-diisopropyl, N,N'-dicyclohexyl- or N-ethyl-N'-(3-diethylaminopropyl)-carbodiimide, (ii) carbonyl compounds, for example, carbonyldiimidazole, (iii) 1,2-oxazolium compounds, for example, 2-ethyl-5-phenyl-1,2-oxazolium 3'-sulfonate and 2-tert-butyl-5-methyl-isoxazolium perchlorate, and (iv) an acylamino compound, for example, 2-ethoxy-1-ethoxycarbonyl-1,2-dihydroquinoline. The bases normally used for aiding the condensation are either inorganic bases such as sodium or potassium carbonate, or organic bases, such as pyridine, triethyamine, N,N-diisopropylethylamine or 4-(dimethylamino)pyridine.

The subsequent Step-II involves deprotection of the substituted amide 1.3 with suitable deprotecting agents known in art to obtain the desired compounds of Formula I.

Alternatively, the compounds of Formula I can also be prepared by reacting a compound of Formula 2.1 with a compound of Formula 1.2, using similar condensation methods as described above (for Scheme 1-Step I). The method is as shown in Scheme 2 below, wherein $R_1$, $R_2$, X, L and Y are as defined according to any of the embodiments herein. The starting compound of Formula 2.1 can be obtained commercially or can be prepared by methods known in the art.

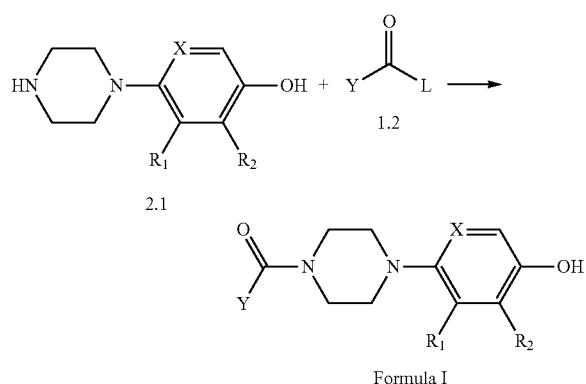

Scheme 2

The compounds of Formula I can be converted into salts thereof by methods known in the art, such as, for example, dissolving the compound of Formula I in a suitable solvent and treating it with an appropriate acid.

Alternatively, the starting materials, i.e. a compound of Formula 1.1 or a compound of Formula 2.1 used in Scheme 1 or Scheme 2, respectively, can be prepared as depicted in synthetic Scheme 3 below:

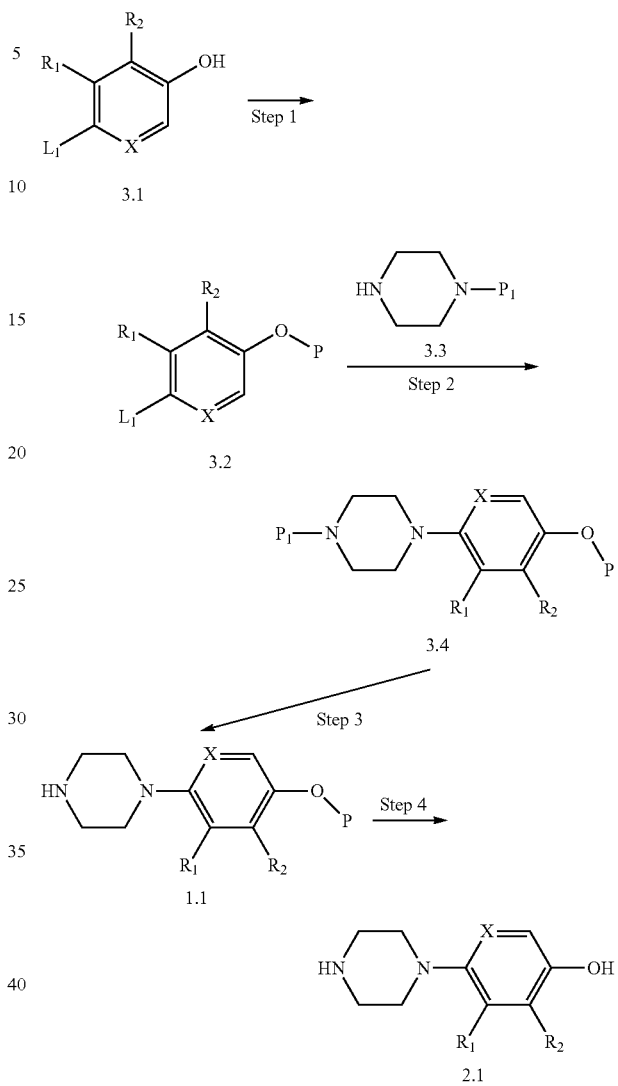

Variables $R_1$, $R_2$, and X in the compounds of Scheme 3 are as defined in any of the embodiments described herein. Step 1 in Scheme 3 involves protection of the hydroxyl group of compound 3.1 (wherein Li is leaving group such as a halide) to obtain compound 3.2 (wherein P is a hydroxy protecting group such as benzyl, benzoyl, etc.). Compound 3.2 can be coupled with compound 3.3, wherein $P_1$ is a nitrogen protecting group, such as tert-butyloxycarbonyl (Boc), fluorenylmethyloxycarbonyl (Fmoc), etc.; by known methods such as Buchwald coupling to obtain compound 3.4. The compound 3.4 on selective deprotection of $P_1$ group using an acid or base can give compound 1.1. Compound 1.1 on further deprotection of protecting group P by using known methods, such as debenzylation using catalytic hydrogenation, can give compound 2.1.

Similarly, the compounds of Formulae Ia or Ib, can be prepared by following the processes described above.

Similarly, the compounds of Formulae Ia, or Ib, can be converted into their pharmaceutically acceptable salts by treating them with an appropriate acid in a suitable solvent.

Representative compounds of Formula I are as shown in Table 1 below:

TABLE 1

Formula I

| Compound No. | Y | R$_1$ | R$_2$ | X |
|---|---|---|---|---|
| I.1 | benzyl | H | H | CH |
| I.2 | (1H-indol-3-yl)methyl | H | H | CH |
| I.3 | (3,4,5-trimethoxyphenyl)methyl | H | H | CH |
| I.4 | (4-hydroxyphenyl)methyl | H | H | CH |
| I.5 | [4-(2-methoxyethoxy)phenyl]methyl | H | H | CH |
| I.6 | benzyl | H | H | N |
| I.7 | [1-(2-methoxyethyl)piperidin-4-yl] | H | H | CH |
| I.8 | (1H-indazol-3-yl)methyl | H | H | CH |
| I.9 | acridin-9-ylmethyl | H | H | CH |
| I.10 | [5-(2-methoxyethoxy)-1H-indol-3-yl]methyl | H | H | CH |
| I.11 | benzyl | F | H | CH |
| I.12 | (E)-2-(4-butoxyphenyl)ethenyl | H | H | CH |
| I.13 | [4-butoxyphenyl]methyl | H | H | CH |
| I.14 | (5-butoxy-1H-indol-3-yl)methyl | H | H | CH |
| I.15 | (1-benzyl-1H-indol-3-yl)methyl | H | H | CH |
| I.16 | (S)-1-acetamido-2-phenylethyl | H | H | CH |
| I.17 | phenyl(oxo)methyl | H | H | CH |

TABLE 1-continued

Formula I

| Compound No. | Y | R₁ | R₂ | X |
|---|---|---|---|---|
| I.18 | 1-butyl-1H-indol-3-yl | H | H | CH |
| I.19 | (S)-α-acetamidobenzyl | H | H | CH |
| I.20 | 2,6-diphenylpyridin-4-yl | H | H | CH |
| I.21 | anthracen-9-yl | H | H | CH |
| I.22 | phenanthren-9-yl | H | H | CH |
| I.23 | 2-(naphthalen-2-yl)ethyl | H | H | CH |
| I.24 | quinolin-3-yl | H | H | CH |
| I.25 | anthracen-2-yl | H | H | CH |
| I.26 | 1-benzyl-1H-indol-4-yl | H | H | CH |
| I.27 | [1,1':3',1''-terphenyl]-5'-yl | H | H | CH |
| I.28 | 4-(trifluoromethyl)benzyl | H | H | CH |
| I.29 | imidazo[1,2-a]pyridin-8-yl | H | H | CH |
| I.30 | 1H-indol-4-yl | H | H | CH |
| I.31 | 3-(4-(trifluoromethyl)phenyl)imidazo[1,2-a]pyridin-8-yl | H | H | CH |
| I.32 | benzyl | H | COOH | CH |

TABLE 1-continued

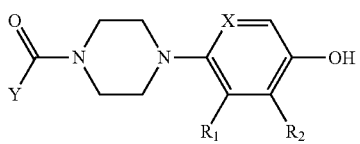

Formula I

| Compound No. | Y | R₁ | R₂ | X |
|---|---|---|---|---|
| I.33 | 4-(6-morpholinopyridin-2-yl)-phenyl (morpholine-pyridine-phenyl) | H | H | CH |
| I.34 | 2-phenylpyridin-4-yl | H | H | CH |
| I.35 | 2-morpholinopyridin-4-yl | H | H | CH |
| I.36 | 6-chloro-2-morpholinopyridin-4-yl | H | H | CH |
| I.37 | 2,6-diphenylpyridin-4-yl | H | CN | CH |
| I.38 | 2,6-diphenylpyridin-4-yl | H | —COOH | CH |

TABLE 1-continued

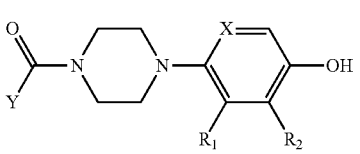

Formula I

| Compound No. | Y | R₁ | R₂ | X |
|---|---|---|---|---|
| I.39 | 3-(pyridin-2-yl)benzoic acid | H | H | CH |
| I.40 | 2,2-diphenylethenyl | H | H | CH |
| I.41 | 3-(6-morpholinopyridin-2-yl)benzoic acid | H | H | CH |
| I.42 | 4-(6-morpholinopyridin-2-yl)benzoic acid | H | H | CH |
| I.43 | 1H-indol-3-yl | H | H | N |
| I.44 | acridin-9-yl | H | H | N |
| I.45 | 2-phenylethyl | H | H | N |

TABLE 1-continued

Formula I

| Compound No. | Y | R₁ | R₂ | X |
|---|---|---|---|---|
| I.46 | naphthalen-1-yl-ethyl | H | H | CH |
| I.47 | (4-oxo-1H-quinolin-3-yl)methyl | H | H | CH |
| I.48 | diphenylmethyl | H | H | N |
| I.49 | (2-phenoxyphenyl)methyl | H | H | CH |
| I.50 | (2-piperidin-1-yl-pyridin-4-yl)methyl | H | H | CH |
| I.51 | 2-(1H-indol-3-yl)ethyl | H | H | N |
| I.52 | benzyl | H | CH₃ | CH |
| I.53 | 2-(anthracen-9-yl)ethyl | H | H | CH |
| I.54 | (4-oxo-1H-quinolin-3-yl)methyl | H | H | N |
| I.55 | adamantan-1-yl-methyl | H | H | N |
| I.56 | (3-hydroxyadamantan-1-yl)methyl | H | H | N |
| I.57 | (adamantan-1-yl-methylamino)methyl | H | H | N |
| I.58 | bis(4-chlorophenyl)methyl | H | H | N |

TABLE 1-continued

Formula I

| Compound No. | Y | R₁ | R₂ | X |
|---|---|---|---|---|
| I.59 | 1-(cyclopropylmethyl)-4-oxo-1,4-dihydroquinolin-3-yl | H | H | N |
| I.60 | 9H-fluoren-9-ylidenemethyl | H | H | N |
| I.61 | 9H-fluoren-9-ylmethyl | H | H | N |
| I.62 | (1H-indol-3-yl)methyl | H | H | N |
| I.63 | (1H-pyrrolo[2,3-b]pyridin-3-yl)methyl | H | H | N |
| I.64 | anthracen-9-ylmethyl | H | H | N |
| I.65 | 3-phenylpropyl | H | H | N |
| I.66 | 2-(pyridin-4-yl)ethyl | H | H | N |
| I.67 | 2,3-dihydro-1H-inden-2-yl | H | H | N |
| I.68 | 4-phenylbutyl | H | H | N |
| I.69 | 1-methyl-4-oxo-1,4-dihydroquinolin-3-yl | H | H | N |
| I.70 | 4-carboxybutyl | H | H | N |
| I.71 | (1-methyl-1H-indol-3-yl)methyl | H | H | N |
| I.72 | 2-(3-(trifluoromethyl)phenyl)ethyl | H | H | N |
| I.73 | 2-oxo-2H-chromen-3-yl | H | H | N |
| I.74 | 2,2-diphenylvinyl | H | H | N |

TABLE 1-continued

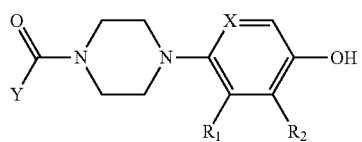

Formula I

| Compound No. | Y | R₁ | R₂ | X |
|---|---|---|---|---|
| I.75 | 2,2-diphenylethyl | H | H | N |
| I.76 | 5-chlorothiophen-2-yl | H | H | N |
| I.77 | (E)-2-(4-nitrophenyl)ethenyl | H | H | N |
| I.78 | (E)-2-(4-chlorophenyl)ethenyl | H | H | N |
| I.79 | 2-(3,4-dichlorophenyl)ethyl | H | H | N |
| I.80 | 3-chloro-2-methylphenyl | H | H | N |
| I.81 | 3-(4-methylimidazol-1-yl)-5-(trifluoromethyl)phenyl | H | H | N |
| I.82 | 2-(4-chlorophenyl)ethyl | H | H | N |

TABLE 1-continued

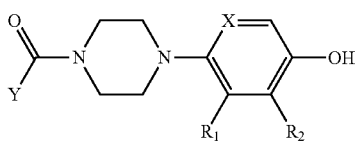

Formula I

| Compound No. | Y | R₁ | R₂ | X |
|---|---|---|---|---|
| I.83 | adamantan-1-ylaminomethyl | H | H | N |
| I.84 | 2,2-bis(4-methoxyphenyl)ethenyl | H | H | N |
| I.85 | 4-[(4-pyridin-3-ylpyrimidin-2-yl)amino]-3-methylphenyl | H | H | N |
| I.86 | 1H-benzimidazol-2-yl | H | H | N |
| I.87 | 5-bromothiophen-2-yl | H | H | N |
| I.88 | 5-fluoro-1H-indol-2-yl | H | H | N |
| I.89 | 2-[methyl(quinolin-8-ylsulfonyl)amino]ethyl | H | H | N |
| I.90 | 2-[4-(2-methylpropyl)phenyl]ethyl | H | H | N |

TABLE 1-continued

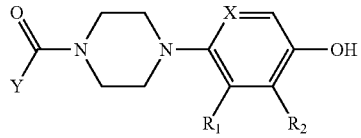

Formula I

| Compound No. | Y | R₁ | R₂ | X |
|---|---|---|---|---|
| I.91 | 2,4-difluorobenzyl | H | H | N |
| I.92 | 3-fluorophenethyl | H | H | N |
| I.93 | bis(4-methoxyphenyl)methyl-CH₂ | H | H | N |
| I.94 | 4,4-diphenyl-3-butenyl | H | H | N |
| I.95 | α-cyclohexyl-α-hydroxybenzyl | H | H | N |
| I.96 | (1-adamantylmethyl)(methyl)amino-ethyl | H | H | N |
| I.97 | 2-(5-nitropyridin-2-ylthio)ethyl | H | H | N |
| I.98 | 2-(1-adamantyl)ethyl | H | H | N |
| I.99 | α-cyclohexylbenzyl | H | H | N |
| I.100 | 2-(4-hydroxyphenyl)ethyl | H | H | N |
| I.101 | 2-(4-methoxyphenyl)ethyl | H | H | N |
| I.102 | 2-(2-bromophenyl)ethyl | H | H | N |
| I.103 | 2-(4-bromophenyl)ethyl | H | H | N |
| I.104 | methyl 8-oxabicyclo[3.2.1]octane-3-carboxylate | H | H | N |

TABLE 1-continued

Formula I: piperazine carbonyl-Y, linked to pyridine ring with X, OH, R₁, R₂ substituents.

| Compound No. | Y | R₁ | R₂ | X |
|---|---|---|---|---|
| I.105 | 7-oxabicyclic carboxylic acid group | H | H | N |
| I.106 | 1H-indol-3-yl carbonyl | H | H | N |
| I.107 | 2-(2-methylphenyl)ethyl | H | H | N |
| I.108 | 2-(4-dimethylaminophenyl)ethyl | H | H | N |
| I.109 | 2-(2-methoxyphenyl)ethyl | H | H | N |
| I.110 | 2-(4-methylphenyl)ethyl | H | H | N |
| I.111 | 2-carboxyphenyl | H | H | N |
| I.112 | 3,3-diphenylpropyl | H | H | N |
| I.113 | 4-(1H-indol-4-yl)phenyl | H | H | N |
| I.114 | 2-(4-(2-methoxyethoxy)phenyl)ethyl | H | H | N |
| I.115 | 2-phenylpropyl | H | H | N |
| I.116 | 2-(thiophen-2-yl)ethyl | H | H | N |
| I.117 | (morpholin-4-yl)(phenyl)methyl | H | H | N |
| I.118 | cyclohexyl | H | H | N |
| I.119 | cyclopropyl | H | H | N |
| I.120 | 2-cyclohexylvinyl | H | H | N |
| I.121 | 2-cyclohexylethyl | H | H | N |

TABLE 1-continued

Formula I

| Compound No. | Y | R₁ | R₂ | X |
|---|---|---|---|---|
| I.122 | benzothiophen-2-ylmethyl | H | H | N |
| I.123 | 5-phenylthiophen-2-yl | H | H | N |
| I.124 | (1-hydroxy-3-phenyl)cyclobutyl | H | H | N |
| I.125 | 2-methyl-2-phenylpropyl | H | H | N |
| I.126 | 4-fluorophenethyl | H | H | N |
| I.127 | (2-methyl-1H-indol-3-yl)methyl | H | H | N |
| I.128 | 2-(trifluoromethyl)phenethyl | H | H | N |
| I.129 | 2-(pyridin-2-yl)ethyl | H | H | N |
| I.130 | 2-hydroxy-2-phenylethyl | H | H | N |
| I.131 | (5-fluoro-1H-indol-3-yl)methyl | H | H | N |
| I.132 | 1,2,3,4-tetrahydronaphthalen-1-yl | H | H | N |
| I.133 | trans-2-phenylcyclopropyl | H | H | N |
| I.134 | 3-phenylcyclobutyl | H | H | N |
| I.135 | 2-(1H-indol-1-yl)ethyl | H | H | N |
| I.136 | 2-(1H-benzimidazol-1-yl)ethyl | H | H | N |
| I.137 | cyclopropylmethyl | H | H | N |
| I.138 | 4-cyanophenethyl | H | H | N |

TABLE 1-continued

Formula I: Structure with piperazine carbonyl-Y group, connected to pyridine/phenyl ring with X, OH, R₁, R₂ substituents.

| Compound No. | Y | R₁ | R₂ | X |
|---|---|---|---|---|
| I.139 | 4-(trifluoromethyl)phenethyl | H | H | N |
| I.140 | cyclopropylethyl | H | H | N |
| I.141 | 2-carboxyphenethyl | H | H | N |
| I.142 | 2-(methoxycarbonyl)phenethyl | H | H | N |
| I.143 | 2-(2-bromophenylthio)ethyl | H | H | N |
| I.144 | 2-hydroxy-2-phenylethyl | H | H | N |
| I.145 | 2-(4-fluoro-2-methylphenyl)ethyl | H | H | N |
| I.146 | 2-(2,3-dimethylphenyl)ethyl | H | H | N |
| I.147 | 2-(2,6-dimethylphenyl)ethyl | H | H | N |
| I.148 | 2-(3,5-difluorophenyl)ethyl | H | H | CH |
| I.149 | 2-(2,5-difluorophenyl)ethyl | H | H | CH |
| I.150 | 2-(5-fluoro-1H-indol-3-yl)ethyl | H | H | CH |
| I.151 | 2-(2-bromophenylthio)ethyl | H | H | CH |
| I.152 | 2-(2,4-difluorophenyl)ethyl | H | H | N |
| I.153 | 2-(3,4-difluorophenyl)ethyl | H | H | N |
| I.154 | 2-(2-chloro-6-methylphenyl)ethyl | H | H | CH |
| I.155 | 2-(5-fluoro-1H-indol-3-yl)ethyl | H | H | N |

TABLE 1-continued

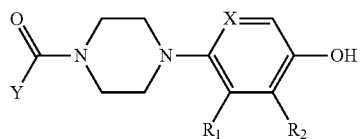

Formula I

| Compound No. | Y | R₁ | R₂ | X |
|---|---|---|---|---|
| I.156 | 5-fluoro-1H-indol-3-yl-methyl | H | H | CH |
| I.157 | 2,6-difluorobenzyl-ethyl | H | H | N |
| I.158 | 6-fluoro-1H-indol-3-yl-methyl | H | H | N |
| I.159 | 5-chloro-1H-indol-3-yl-methyl | H | H | N |
| I.160 | 5,6-difluoro-1H-indol-3-yl-methyl | H | H | N |
| I.161 | 2-(4-fluorophenyl)-2-methylpropyl | H | H | N |
| I.162 | 2-bromophenylthio-dimethyl | H | H | N |
| I.163 | 4-fluorophenylthio-ethyl | H | H | N |
| I.164 | 2-(4-fluorophenoxy)ethyl | H | H | N |
| I.165 | 5-fluoro-1-methyl-1H-indol-3-yl-methyl | H | H | N |
| I.166 | 5-fluoro-2-methyl-1H-indol-3-yl-methyl | H | H | N |
| I.167 | 5,7-difluoro-1H-indol-3-yl-methyl | H | H | N |
| I.168 | (5-fluoro-1H-indol-3-yl)carbonyl | H | H | N |
| I.169 | 2-(5-fluoro-1H-indol-3-yl)-2-methylpropyl | H | H | N |
| I.170 | 3,4,5-trifluorophenyl-ethyl | H | H | N |

TABLE 1-continued

Formula I

| Compound No. | Y | R₁ | R₂ | X |
|---|---|---|---|---|
| I.171 | (2,3,4-trifluorobenzyl) | H | H | CH |
| I.172 | (N-(1-phenyl-ethyl)acrylamide group) | H | H | N |
| I.173 | (2-methyl-2-phenylpropyl) | H | H | CH |
| I.174 | (5,6-dichloro-1H-indol-3-yl)methyl | H | H | N |
| I.175 | (5-chloro-2-methyl-1H-indol-3-yl)methyl | H | H | N |
| I.176 | (5,6-dichloro-2-methyl-1H-indol-3-yl)methyl | H | H | N |

The present invention is further illustrated in detail with reference to the following examples. It is desired that the examples be considered in all respect as illustrative and are not intended to limit the scope of the claimed invention.

EXAMPLES

The compounds of Formulae I, Ia and Ib may be prepared as described below. All solvents and reagents were used as obtained from commercial sources unless otherwise indicated. $^1$H-NMR spectra were recorded with a Bruker® spectrometer operating at 500 MHz in deuterated DMSO.

List of Abbreviations

EDC.HCl: N-Ethyl-N'-(3-dimethylaminopropyl)carbodiimide hydrochloride.
HATU: 1-[Bis(dimethylamino)methylene]-1H-1,2,3-triazolo[4,5-b]pyridinium 3-oxide hexafluorophosphate.
NBS: N-Bromosuccinimide.
AIBN: Azobisisobutyronitrile.
THF: Tetrahydrofuran.

Preparation of Intermediate: 4-piperazin-1-yl-phenol (1D)

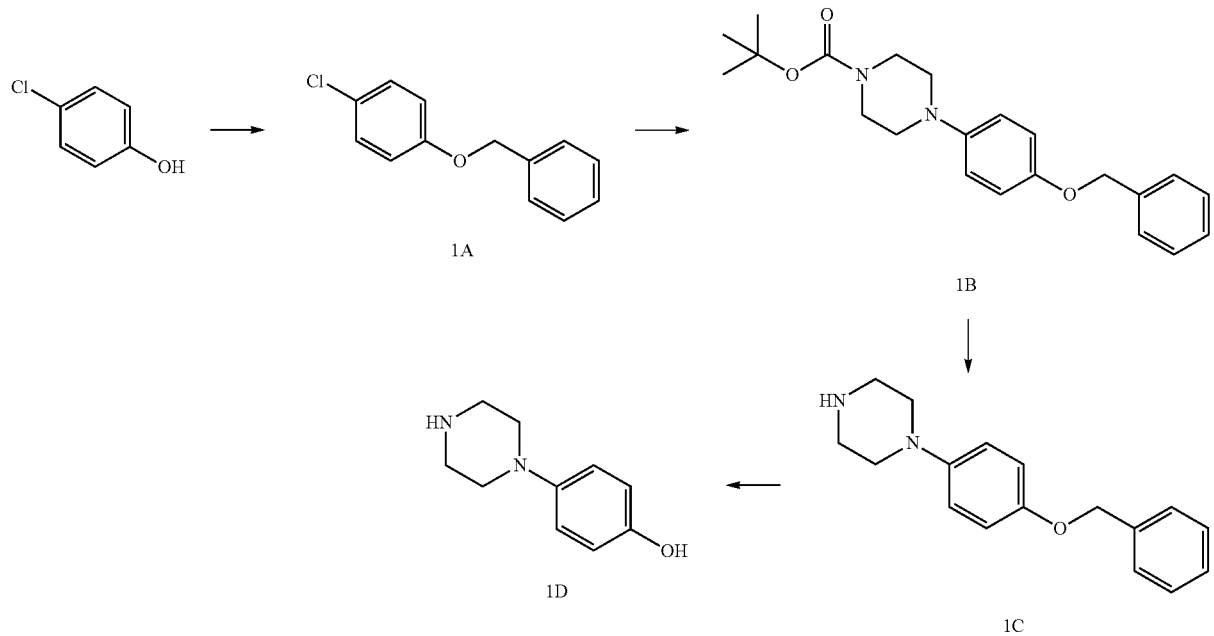

Step-I: To a solution of 4-chlorophenol (2 g, 1 eq) in N,N-dimethylformamide (10 ml) was added potassium carbonate (3.2 g, 1.5 eq) and benzyl bromide (1.9 ml, 1.05 eq). The resultant reaction mixture was heated to 40° C. for 18 hours. The reaction was monitored by thin layer chromatography (TLC). On completion of reaction, the reaction mixture was quenched with water and extracted with ethyl acetate. The combined organic layers were washed with saturated sodium chloride solution, dried over anhydrous sodium sulfate and concentrated under reduced pressure. The resultant residue was purified using column chromatography on silica gel (230-400 mesh) using an ethyl acetate-hexane mixture as eluent to afford pure compound 1A.

Step-II: To a solution of t-butyl piperazine-1-carboxylate (1.7 g, 1.0 eq) in toluene (40 ml) was added compound 1A (2.0 g, 1.0 eq), Pd$_2$(dba)$_3$ (0.42 g, 0.05 eq) and S-Phos (0.37 g, 0.1 eq) at room temperature and heated to 50° C. for 15 minutes under nitrogen atmosphere. Sodium t-butoxide (2.6 g, 3.0 eq) was added to the reaction mixture and the reaction mixture was heated at 100° C. for 6 hours. On completion of reaction, the reaction mixture was filtered through celite bed and washed with ethyl acetate. The combined organic layers were washed with water, dried over anhydrous sodium sulfate and concentrated under reduced pressure. The resultant residue was purified using column chromatography on silica gel (230-400 mesh) using an ethyl acetate-hexane mixture as eluent to afford the pure compound 1B.

Step-III: A solution of compound 1B (1.0 g) in dichloromethane (10 ml) was treated with trifluoroacetic acid (5 ml) and stirred for 2 hours. On completion of reaction, the residual solvents were evaporated under reduced pressure. The resultant residue was dissolved in water, basified with saturated sodium bicarbonate solution and extracted with ethyl acetate. The combined organic layers were dried over anhydrous sodium sulfate and concentrated under reduced pressure to afford compound 1C.

Step-IV: To a solution of compound 1C (1.0 g) in methanol-tetrahydrofuran (1:1) (30 ml) was added 10% Palladium on activated carbon (0.1 g) and the suspension was stirred under hydrogen atmosphere for 2 hours at room temperature. On completion of reaction, the reaction mixture was filtered off from the catalyst and the solution was evaporated under reduced pressure to afford compound 1D which was used in the next step without further purification.

Example 1: Preparation of 1-[4-(4-hydroxyphenyl)piperazin-1-yl]-2-phenylethanone (I.1)

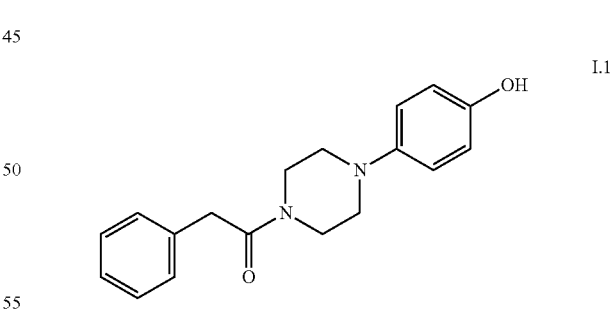

To a solution of phenyl acetic acid (1 g, 1.0 eq) in N,N-dimethylacetamide (10 ml) was added HATU (3.07 g, 1.2 eq) and triethylamine (1.88 ml, 2.0 eq). The reaction mixture was stirred for 10 minutes and then compound 1D (1.2 g, 1.0 eq) was added and further stirred at room temperature for 3 hours. On completion of reaction, the reaction mixture was quenched with water and extracted with ethyl acetate. The combined organic layer was washed with saturated sodium chloride solution, dried over anhydrous sodium sulfate and concentrated under reduced pressure. The resultant residue was purified using column chromatography on silica gel (230-400 mesh) using an ethyl acetate-hexane mixture as eluent to afford pure compound I.1.

Example 2: Preparation of 2-hydroxy-5-(4-phenylacetyl-piperazin-1-yl)-benzoic acid (I.32)

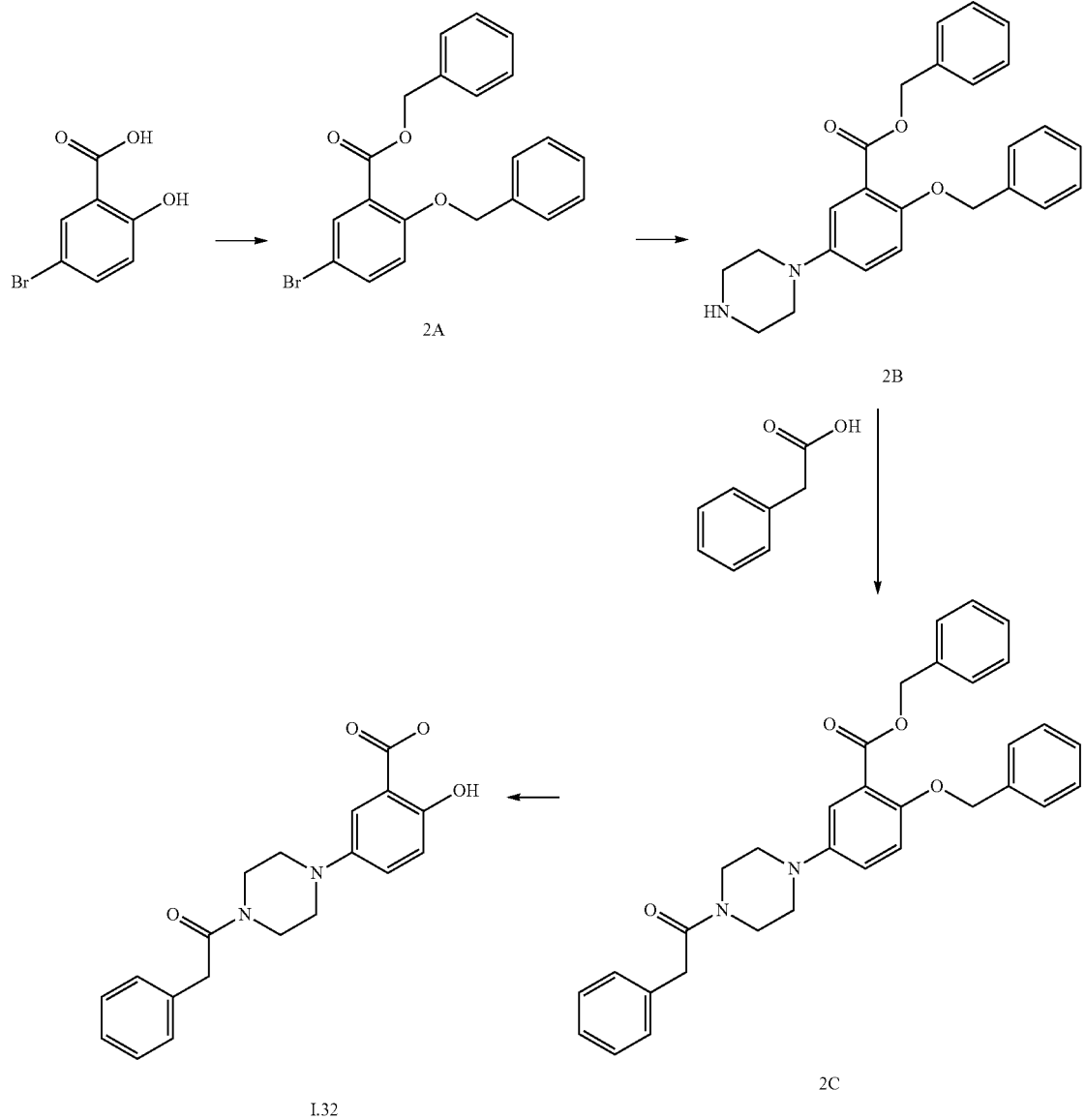 [SMILES: O=C(O)c1cc(Br)ccc1O ; O=C(OCc1ccccc1)c1cc(Br)ccc1OCc1ccccc1 ; O=C(OCc1ccccc1)c1cc(N2CCNCC2)ccc1OCc1ccccc1 ; O=C(O)Cc1ccccc1 ; O=C(O)c1cc(N2CCN(C(=O)Cc3ccccc3)CC2)ccc1O ; O=C(OCc1ccccc1)c1cc(N2CCN(C(=O)Cc3ccccc3)CC2)ccc1OCc1ccccc1]

Step-I: A solution of 5-bromo-2-hydroxybenzoic acid (2.0 g, 1.0 eq) in N,N-dimethylformamide (10 ml) was added $K_2CO_3$ (2.8 g, 2.2 eq) and benzyl bromide (3.1 g, 2.0 eq) and the resultant reaction mixture was stirred at room temperature for 2 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure to afford compound 2A.

Step-II: To a solution of tert-butyl piperazine-1-carboxylate (0.63 g, 1.3 eq) in toluene (40 ml) was added compound 2A (1.0 g, 1.0 eq), cesium carbonate (2.5 g, 3.0 eq) and S-Phos (0.10 g, 0.1 eq) at room temperature and purged with nitrogen for 5 min. $Pd_2(dba)_3$ (0.12 g, 0.05 eq) was then added and the resultant reaction mixture was heated at 100° C. for 6 hours. On completion of reaction, the reaction mixture was filtered through celite bed and washed with ethyl acetate. The combined organic layers were washed with water, dried over anhydrous sodium sulfate and concentrated under reduced pressure. The resultant residue was purified using column chromatography on silica gel (230-400 mesh) using an ethyl acetate-hexane mixture as eluent to afford protected piperazine intermediate.

The protected piperazine intermediate (0.9 g) was dissolved in dichloromethane (9 ml), treated with trifluoroacetic acid (4.5 ml) and the resultant solution was stirred for 2 hours. On completion of reaction, the solvents were evaporated under reduced pressure and the resultant residue was dissolved in water. The above solution was basified with saturated sodium bicarbonate solution and extracted with ethyl acetate. The combined organic layers were dried over anhydrous sodium sulfate and concentrated under reduced pressure to afford compound 2B.

Step-III: To a cooled solution (0-5° C.) of phenylacetic acid (0.25 g, 1.0 eq) in N,N-dimethylformamide (5 ml) was added HATU (0.90 gm, 1.3 eq) followed by diisopropylethylamine (0.37 ml, 1.3 eq). After stirring the reaction mixture for 10 minutes, compound 2B (0.67 g, 0.9 eq) was added and stirring was continued for 1 hour at 0-5° C. On completion of reaction, the reaction mixture was quenched with water and extracted with ethyl acetate. The combined organic layers were washed with saturated sodium chloride solution, dried over anhydrous sodium sulfate and concentrated under reduced pressure. The resultant residue was purified using column chromatography on silica gel (230-400 mesh) using an ethyl acetate-hexane mixture as eluent to afford pure compound 2C.

Step-IV: A solution of compound 2C (0.2 g) in methanol:tetrahydrofuran (1:1) (20 ml) was added 10% Palladium on activated carbon (0.2 g) and the resultant suspension was stirred under hydrogen atmosphere for 6 hours at room temperature. On completion of reaction, the reaction mixture was filtered off from the catalyst and the filtrate was evaporated under reduced pressure to obtain a residue. The residue was stirred with diethyl ether (5 ml) for 30 minutes. The resultant suspension was filtered, washed with diethyl ether (1 ml) and dried to afford pure Compound 1.32.

Example 3: Preparation of 1-[4-(4-hydroxyphenyl)piperazin-1-yl]-3,3-diphenylprop-2-en-1-one (I.40)

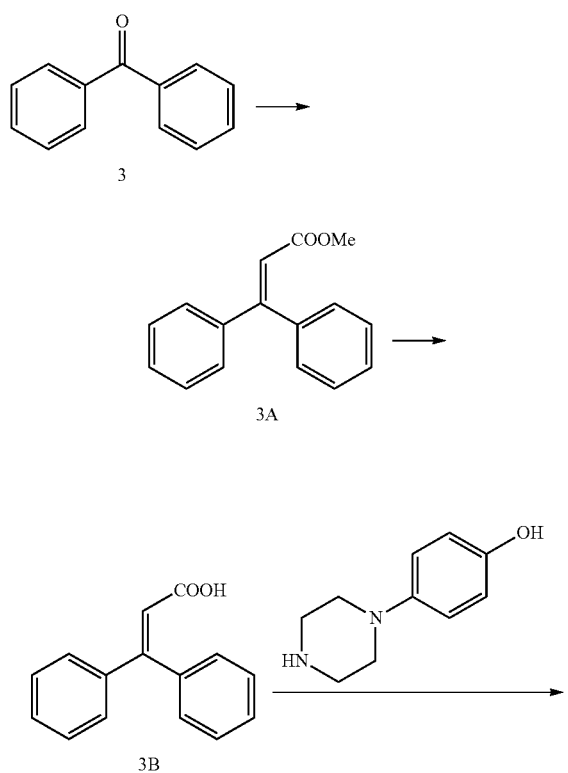

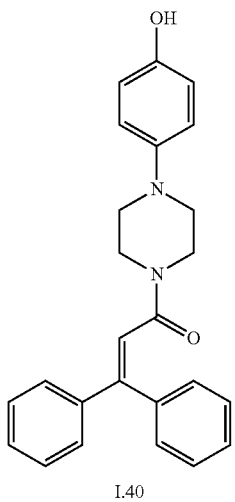

Step-I: Sodium hydride (0.24 g, 1.1 eq) was charged to tetrahydrofuran (10 ml) under stirring and cooled to −20° C. under argon atmosphere. Trimethylphosphonoacetate (1.0 g, 1 eq) dissolved in tetrahydrofuran (2 ml) was added dropwise and the resultant reaction mixture was stirred at ambient temperature for 30 minutes. The reaction mixture was again cooled to −20° C. and a tetrahydrofuran (3 ml) solution of compound 3 (1 g, 1 eq) was added dropwise and then heated to 65° C. for 18 hours. Then the reaction mixture was cooled to ambient temperature, quenched with water and extracted with ethyl acetate. The organic layer was separated, washed with brine, dried over anhydrous $Na_2SO_4$ and the solvent was removed under reduced pressure. The resultant crude residue was purified by flash column chromatography with hexane and ethylacetate as gradient eluent to obtain compound 3A.

Step-II: Compound 3A (1 gm, 1 eq) was dissolved in dioxane:water (1:2) (5 ml) and potassium hydroxide (0.6 g, 2 eq) was then added. The resultant reaction mixture was then heated to 65° C. for 2 hours until TLC analysis showed completion of the reaction. The reaction mixture was then acidified to pH 5 using sulphuric acid (10N) and the resultant white solid precipitate was filtered and washed with water and hexanes to get pure compound 3B.

Step-III: Synthesis of compound 1.40: Compound 3B (0.05 g, 1.0 eq) was dissolved in N,N-dimethylformamide (3 ml) and to this solution was added EDC.HCl (0.07 g, 1.5 eq) and HOBt (0.05 g, 1.5 eq). The resultant reaction mixture was stirred for 30 minutes at room temperature under nitrogen atmosphere. A solution of compound 1D (0.04 gm, 1.0 eq) in N,N-dimethylformamide (1 ml) was then added drop wise to the above reaction mixture and the resultant reaction mixture was stirred at room temperature for 3 hours. After completion of reaction, the reaction mixture was quenched with water (20 ml). Precipitated solids were filtered and washed with water (10 ml) followed by diethylether (5 ml) to obtain compound 1.40.

Example 4: Preparation of 1-[4-(4-hydroxyphenyl)piperazin-1-yl]-2-(2-phenoxy phenyl)ethanone (I.49)

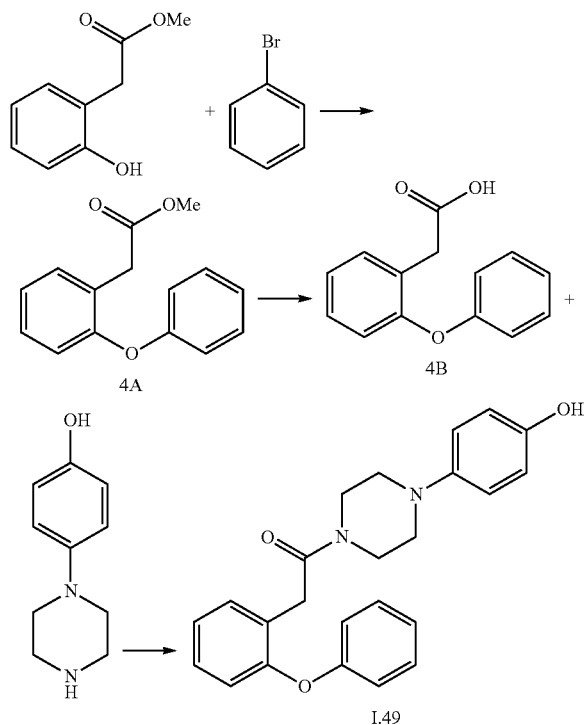

Step-I: Methyl 2-(2-hydroxyphenyl)acetate (0.25 g, 1.0 eq) was dissolved in N,N-dimethylformamide (5 ml) at ambient temperature and to this solution was added potassium carbonate (0.7 g, 3 eq), bromobenzene (0.17 ml, 1.1 eq), copper (I) iodide (0.06 g, 0.2 eq), and N,N-dimethylglycine hydrochloride (0.09 g, 0.4 eq) under stirring and nitrogen atmosphere. The resultant reaction mixture was heated to 120° C. for 3 hours until the reaction was completed. The reaction was quenched with water, extracted with ethyl acetate and washed with brine. The organic layer was separated, dried over anhydrous sodium sulfate, and concentrated under reduced pressure to obtain a crude material which was purified by column chromatography to obtain compound 4A.

Step-II: To a solution of compound 4A (0.5 g, 1.0 eq) in methanol:water (4:1) (5 ml) was added sodium hydroxide (0.24 g, 3 eq) and the resultant reaction mixture was stirred for 3 hours. After completion of reaction, the solvent was removed under reduced pressure, acidified with 1N HCl and extracted with ethyl acetate. The organic layer was washed with brine. The organic layer was separated, dried over anhydrous Na$_2$SO$_4$ and concentrated under reduced pressure to obtain almost pure compound 4B in quantitative yields which was used without further purification in the next step.

Step-III: Synthesis of compound 1.50: Compound 4B (0.250 g, 1.0 eq) was dissolved in N,N-dimethylformamide (3 ml) and to this solution was added EDC.HCl (0.32 g, 1.5 eq) and HOBt (0.22 g, 1.5 eq). The resultant reaction mixture was stirred for 30 minutes at room temperature under nitrogen atmosphere. A solution of compound 1D (0.22 g, 1.1 eq) in N,N-dimethylformamide (1 ml) was added dropwise to the above reaction mixture and the resultant reaction mixture was then stirred for 3 hours till reaction was completed. The reaction was quenched with water, extracted with ethyl acetate and washed with brine. The organic layer was dried over anhydrous Na$_2$SO$_4$, concentrated under reduced pressure and purified by flash column chromatography using hexane and ethyl acetate as gradient eluent to obtain compound 1.49.

Example 5: Preparation of 4-(4-hydroxyphenyl)piperazin-1-yl]-(1H-indol-3-yl)-methanone (I.2)

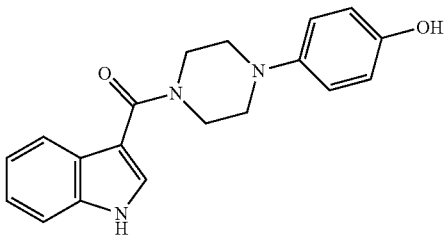 [SMILES: O=C(c1c[nH]c2ccccc12)N1CCN(c2ccc(O)cc2)CC1]

To a solution of indole-3-carboxylic acid (1 g, 1.0 eq) in N,N-dimethylacetamide (5 ml) was added EDC.HCl (1.78 g, 1.5 eq). The reaction mixture was stirred for 15 minutes and then compound 1D (1.10 g, 1.0 eq) was added and the reaction mixture was further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford the pure compound as a pale pink solid.

Example 6: Preparation of 1-[4-(4-hydroxyphenyl)-piperazin-1-yl]-2-phenyl-ethane-1,2-dione (I.17)

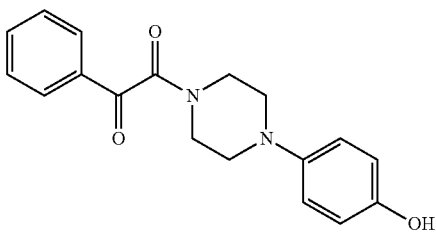 [SMILES: O=C(C(=O)N1CCN(c2ccc(O)cc2)CC1)c1ccccc1]

To a solution of phenylglyoxylic acid (1 g, 1.0 eq) in N,N-dimethylacetamide (5 ml) was added EDC.HCl (1.91 g, 1.5 eq). The reaction mixture was stirred for 15 minutes and then compound 1D (1.18 g, 1.0 eq) was added. The resultant reaction mixture was further stirred at room temperature for 3 hours. On completion of reaction, the reaction mixture was quenched with water and extracted with ethyl acetate. The combined organic layer was washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford the pure compound as an off white solid.

Example 7: Preparation of 2-(3,5-difluoro-phenyl)-1-[4-(4-hydroxy-phenyl)-piperazin-1-yl]-ethanone (I.148)

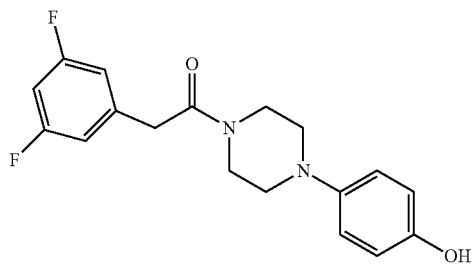 [SMILES: O=C(Cc1cc(F)cc(F)c1)N1CCN(c2ccc(O)cc2)CC1]

To a solution of 3,5-difluorophenylacetic acid (1 g, 1.0 eq) in N,N-dimethylacetamide (5 ml) was added EDC.HCl (1.67 g, 1.5 eq). The reaction mixture was stirred for 15 minutes and then compound 1D (1.03 g, 1.0 eq) was added. The resultant reaction mixture was then further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford pure compound 1.148 as an off white solid

Example 8: Preparation of 2-(2,4-difluoro-phenyl)-1-[4-(4-hydroxy-phenyl)-piperazin-1-yl]-ethanone (I.149)

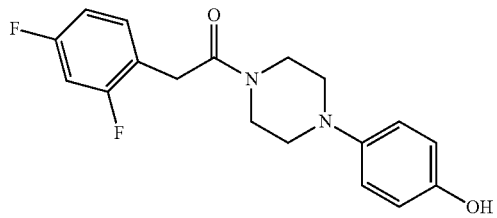 [SMILES: O=C(Cc1ccc(F)cc1F)N1CCN(c2ccc(O)cc2)CC1]

To a solution of 2,4-difluorophenylacetic acid (1 g, 1.0 eq) in N,N-dimethylacetamide (5 ml) was added EDC.HCl (1.67 gm, 1.5 eq). The reaction mixture was stirred for 15 minutes and then compound 1D (1.03 g, 1.0 eq) was added. The resultant reaction mixture was then further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford pure compound 1.149 as an off white solid.

Example 9: Preparation of 2-(5-fluoro-1H-indol-3-yl)-1-[4-(4-hydroxy-phenyl)-piperazin-1-yl]-ethanone (I.150)

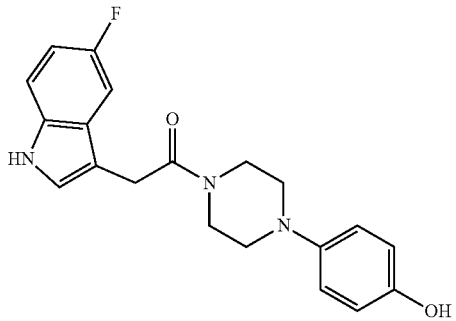 [SMILES: O=C(Cc1c[nH]c2ccc(F)cc12)N1CCN(c2ccc(O)cc2)CC1]

To a solution of 5-fluoroindole-3-acetic acid (1 g, 1.0 eq) in N,N-dimethylacetamide (5 ml) was added EDC.HCl (1.48 g, 1.5 eq). The reaction mixture was stirred for 15 minutes and then compound 1D (0.92 g, 1.0 eq) was added and the reaction mixture was further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford the pure compound as an off white solid.

Example 10: Preparation of 2-(2-bromo-phenylsulfanyl)-1-[4-(4-hydroxy-phenyl)-piperazin-1-yl]-ethanone (I.151)

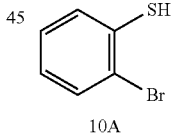

10A

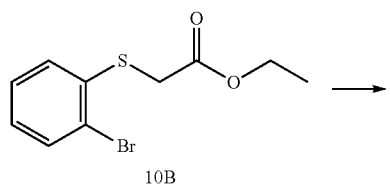

10B

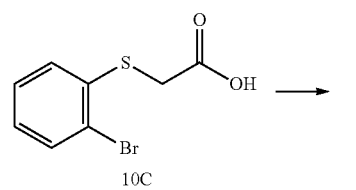

10C

-continued

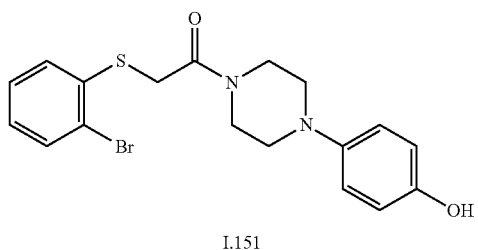

I.151

Step-I: Synthesis of compound 10B: To a solution of 2-bromo thiophenol (10A) (2.0 g, 1.0 eq) in acetone (40 ml) was added cesium carbonate (5.17 g, 1.5 eq) and ethyl bromoacetate (2.12 g, 1.0 eq). The resultant reaction mixture was stirred at room temperature for 3 hours. On completion of reaction, the reaction mixture was quenched with water (50 ml) and extracted with ethyl acetate (2×30 ml). The combined organic layers were washed with saturated aq. sodium chloride solution (10 ml), dried over anhydrous sodium sulfate and concentrated under reduced pressure. The resultant residue was purified using column chromatography on silica gel (230-400 mesh) using an ethyl acetate-hexane mixture as eluent to afford pure compound 10B (2.72 g, yield: 93%) as an off white solid.

Step-II: Synthesis of compound 10C: To a solution of compound 10B (2.72 g, 1.0 eq) in methanol:tetrahydrofuran (1:1) (30 ml) was added a solution of sodium hydroxide (0.79 g, 2.0 eq) in water (5 ml) and the resultant suspension was stirred for 2 hours at 90° C. On completion of reaction, reaction mixture was evaporated under reduced pressure at 50° C. Aqueous layer washed with diethyl ether (50 ml). The aqueous layer was acidified with hydrochloric acid (1N). Precipitated solid was filtered and dried under reduced pressure at 55° C. for 5 hours to afford compound 10C (1.3 g, yield: 53%) as an off white solid.

Step-III: Synthesis of 2-(2-bromo-phenylsulfanyl)-1-[4-(4-hydroxy-phenyl)-piperazin-1-yl]-ethanone (0.151)

To a cooled solution (0-5° C.) of compound 10C (0.3 g, 1.0 eq) in N,N-dimethylacetamide (5 ml) was added HATU (0.6 g, 1.3 eq) followed by triethylamine (0.260 ml, 1.5 eq). After stirring the reaction mixture for 10 minutes, compound 1D (0.194 g, 0.9 eq) was added and stirring was continued for 2 hours at 0 to 5° C. On completion of reaction, the reaction mixture was quenched with water (50 ml) and extracted with ethyl acetate (2×30 ml). The combined organic layers were washed with saturated aq. sodium chloride solution (10 ml), dried over anhydrous sodium sulfate and concentrated under reduced pressure. The resultant residue was purified using column chromatography on silica gel (230-400 mesh) using a dichloromethane:methanol mixture as eluent to afford pure compound (0.125 g, yield: 25%) as an off white solid.

Example 11: Preparation of [4-(4-hydroxy-phenyl)-piperazin-1-yl]-[3-(4-trifluoromethyl-phenyl)-imidazo[1,2-a]pyridin-8-yl]-methanone (I.31)

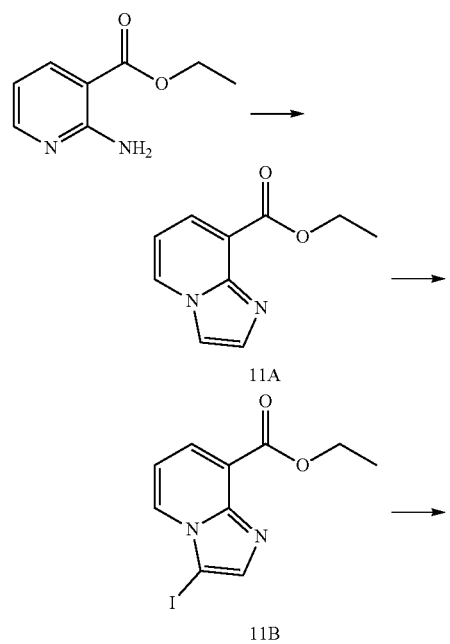

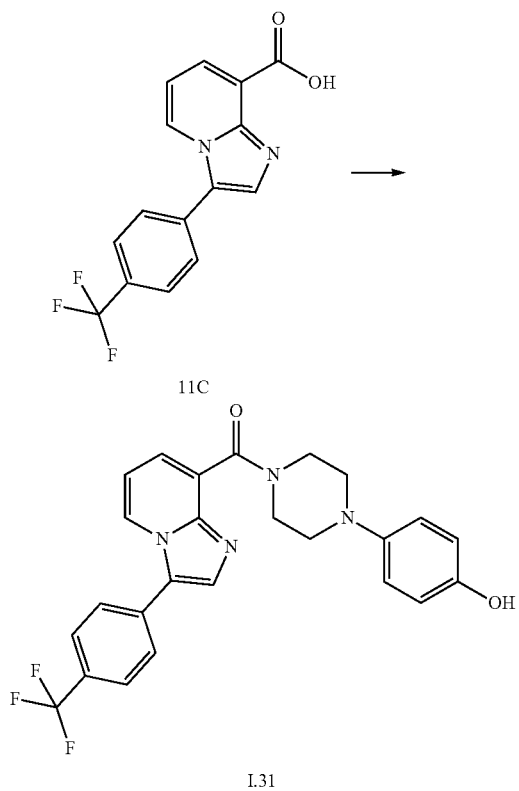

I.31

Step-I: Synthesis of compound 11A (imidazo[1,2-a]pyridine-8-carboxylic acid ethyl ester): Bromoacetaldehyde dimethyl acetal (1.3 ml, 2.1 eq) was added in 40% HBr in water (5 ml) and the resultant reaction mixture was stirred for 30 min. The reaction mixture was then diluted with ethanol (30 ml) and basified with sodium bicarbonate (3 g)

under vigorous stirring. Ethyl 2-aminonicotinate (0.9 g, 1.0 eq) was then added and the resultant reaction mixture was then heated at 70° C. for 16 hrs. On completion of reaction, the reaction mixture was concentrated, quenched with water (50 ml) and extracted with dichloromethane (2×30 ml). The combined organic layers were dried over anhydrous sodium sulfate and concentrated under reduced pressure. The resultant residue was crystalized with diethyl ether, filtered and dried to obtain compound 11A (0.6 g, yield: 58%) as an off white solid.

Step-II: Synthesis of compound 11B (3-iodo-imidazo[1,2-a]pyridine-8-carboxylic acid ethyl ester): To a solution of compound 11A (0.6 g, 1.0 eq) in acetonitrile (20 ml) was added N-iodo succinimide (0.7 g, 1.0 eq) and the resultant reaction mixture was stirred under nitrogen atmosphere for 2 hours at room temperature. On completion of reaction, the reaction mixture was quenched with 10% sodium thiosulfate solution (50 ml) and extracted with ethyl acetate (2×30 ml). The combined organic layers were dried over anhydrous sodium sulfate and concentrated under reduced pressure. The resultant residue was purified using column chromatography on silica gel (230-400 mesh) using a dichloromethane: methanol mixture as eluent to afford pure compound 11B (0.70 g, yield: 70.7%) as a pale yellow solid.

Step-III: Synthesis of Compound 11C (3-(4-trifluoromethyl-phenyl)-imidazo[1,2-a]pyridine-8-carboxylic acid): A mixture of compound 11B (0.9 g, 1.0 eq), 4-(trifluoromethyl) phenyl boronic acid (0.39 g, 1.3 eq) and sodium carbonate (0.5 g, 3.0 eq) in ethanol (20 ml), toluene (20 ml) and water (5 ml) was degassed at room temperature for 10 minutes then added tetrakis(triphenylphosphine) palladium (0.09 g, 0.05 eq). The resultant reaction mixture was heated at 90° C. for 18 hours. On completion of reaction, the reaction mixture was cooled to room temperature, diluted with ethyl acetate (30 ml) and quenched with cold water (20 ml). The suspension was filtered over a pad of celite. The aqueous layer was acidified with hydrochloric acid (6N) (5 ml) and extracted with ethyl acetate (2×30 ml). The combined organic layers were dried over anhydrous sodium sulfate and concentrated under reduced pressure to afford compound 11C (0.15 g, yield: 29%) as a brown solid.

Step-IV: Synthesis of 4-(4-hydroxy-phenyl)-piperazin-1-yl]-[3-(4-trifluoromethyl-phenyl)-imidazo[1,2-a]pyridin-8-yl]-methanone (1.31)

To a cooled solution (0-5° C.) of compound 11C (0.15 g, 1.0 eq) in N,N-dimethylformamide (5 ml) was added HATU (0.24 gm, 1.3 eq) followed by N,N-diisopropylethylamine (0.260 ml, 1.5 eq). After stirring the reaction mixture for 10 minutes, compound 1D (0.096 g, 1.1 eq) was added and stirring continued for 2 hours at 0-5° C. On completion of reaction, the reaction mixture was quenched with aqueous sodium bicarbonate solution (30 ml) and extracted with dichloromethane (2×30 ml). The combined organic layers were dried over anhydrous sodium sulfate and concentrated under reduced pressure. The resultant residue was purified using column chromatography on silica gel (230-400 mesh) using a dichloromethane:methanol mixture as eluent to obtain pure compound (0.070 g, yield: 30%) as an off white solid.

Example 12: Preparation of (2,6-diphenyl-4-pyridyl)-[4-(4-hydroxyphenyl)piperazin-1-yl]methanone (I.20)

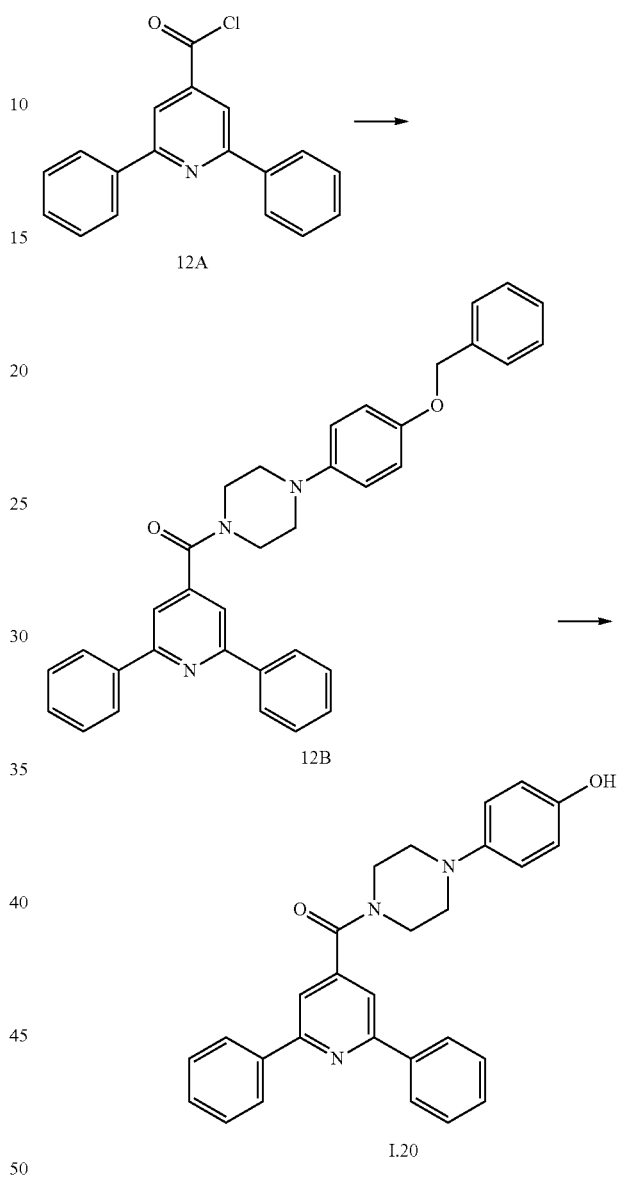

Step-I: To a solution of compound 1C (0.294 g, 1.1 eq) in methylene chloride (2 ml) was added triethylamine (0.3 mL, 2.7 eq). The resultant reaction mixture was stirred at 0° C. under nitrogen atmosphere for 15 minutes and then compound 12A (0.2 g, 1.0 eq) was added in portions. The resultant reaction mixture was stirred at ambient temperature for 2 hours. After completion of reaction, the reaction mixture was quenched with aqueous saturated sodium bicarbonate solution and extracted with methylene chloride (2×10 ml). The combined organic layers were dried over anhydrous sodium sulfate and concentrated under reduced pressure. The resultant residue was purified by silica gel column chromatography to afford pure compound 12B (0.15 g).

Step-II: Compound 12B (0.15 g) was dissolved in methanol (10 ml) and 10% by weight of palladium on carbon (0.05 g) was added to it. The resultant reaction mixture was stirred under hydrogen atmosphere created using hydrogen balloon at ambient temperature for 3 hours. After completion of reaction, the reaction mixture was filtered on celite and washed with methanol (2×10 ml). The organic layer was concentrated under reduced pressure and the resultant crude product was purified by silica gel column chromatography to get pure title compound (0.07 g) as an off white solid.

Example 13: Preparation of (1-benzylindol-4-yl)-[4-(4-hydroxyphenyl)piperazin-1-yl]methanone (I.26)

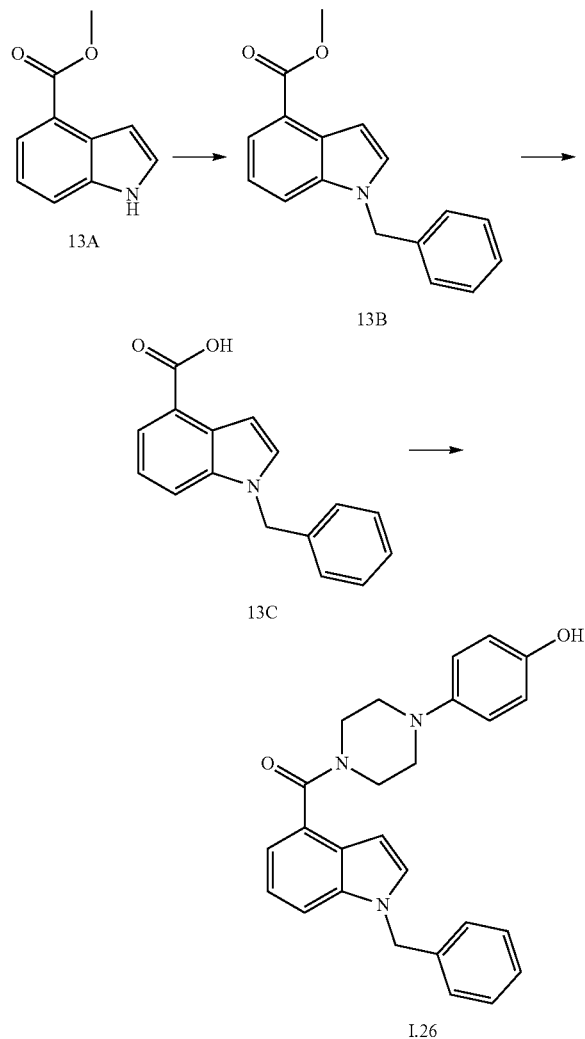

Step-I: To a solution of compound 13A (2.0 g, 1.0 eq) in N,N-dimethylformamide (20 ml), was added sodium hydride (0.36 g, 1.3 eq) at ambient temperature. Benzyl bromide (2.53 g, 1.3 eq) was then added drop wise to the above reaction mixture. The resultant reaction mixture was stirred for 1 h and then quenched with water (10 ml) and extracted with ethyl acetate (3×15 ml). The combined organic layers were dried over anhydrous sodium sulfate and concentrated under reduced pressure to afford the crude product. The crude product was then purified with silica gel column chromatography to afford compound 13B.

Step-II: To a solution of compound 13B (2.9 g, 1.0 eq) in tetrahydrofuran:water (4:1) (20 ml) was added lithium hydroxide (0.87 g, 2.0 eq). The resultant reaction mixture was heated to 90° C. for 15 hours. On completion of reaction, it was quenched with hydrochloric acid (1N) (20 ml) and extracted with ethyl acetate (3×20 ml). The organic layer was dried over anhydrous sodium sulfate and the crude product was purified by silica gel column chromatography to get pure compound 13C (0.9 g).

Step-III: To a cooled (0° C.) solution of compound 13C (0.4 g, 1.0 eq) in N,N-dimethylformamide (5 ml) was added HATU (0.78 g, 1.2 eq) and N,N-diisopropylethylamine (0.80 ml, 3.0 eq). The resultant reaction mixture was allowed to attain room temperature, and then compound 1D (0.07 g, 1.0 eq) was added into it. The resultant reaction mixture was further stirred for 2 hours. On completion of reaction, the reaction mixture was quenched with water (10 ml) and extracted with ethyl acetate (3×10 ml). The combined organic layers were dried over sodium sulfate and concentrated under reduced pressure. The crude residue was purified by flash column chromatography using hexane and ethyl acetate as gradient eluent to afford pure compound as an off white solid.

Example 14: Preparation 2-chloro-6-morpholino-4-pyridyl)-[4-(4-hydroxyphenyl)piperazin-1-yl]methanone (I.36)

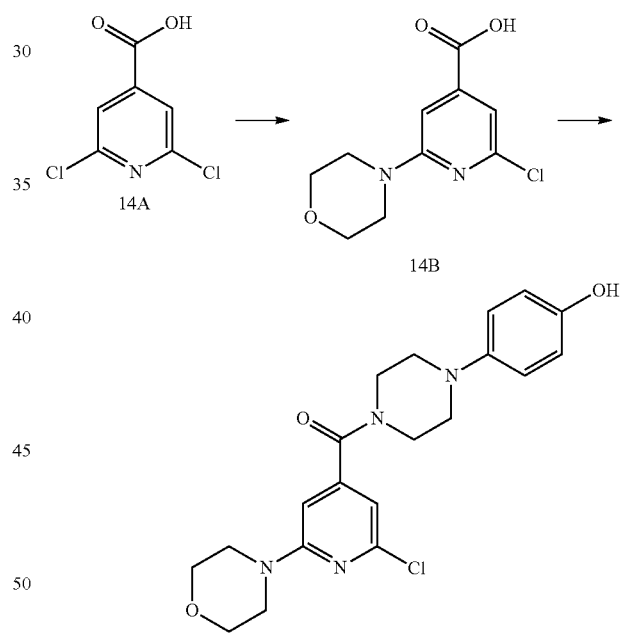

Step-I: To a solution of 2,6-dichloroisonicotinic acid (1.0 gm, 1.0 eq) in N,N-dimethylacetamide (5 ml) was added N,N-diisopropylethylamine (1.8 ml, 2 eq) and morpholine (0.49 g, 1.1 eq). The resultant reaction mixture was heated to 120° C. for 20 hours. On completion of reaction, reaction mixture was neutralised using hydrochloric acid to pH 6. Precipitated brown solid was filtered and washed with diethyl ether to afford pure compound 14B (0.650 g)

Step-II: To a solution of compound 14B (0.4 g, 1.0 eq) in N,N-dimethylformamide (5 ml), was added EDC.HCl (0.36 g 1.5 eq) and HOBt (0.25 g, 1.8 mmol, 1.5 eq). The resultant reaction mixture was stirred at room temperature for 30 minutes under nitrogen atmosphere. To the reaction mixture was then added compound 1D (0.23 g, 1.0 eq) and the mixture was stirred for 3 hours. On completion, the reaction mixture was quenched with water (10 ml) and extracted with ethyl acetate (3×20 ml). The combined organic layers were dried over anhydrous sodium sulfate and concentrated under reduced pressure. The crude residue was purified by flash column chromatography using hexane and ethyl acetate as gradient eluent to afford pure title compound (0.4 g) as an off white solid Example 15: Preparation of 5-[4-(2,6-diphenylpyridine-4-carbonyl)piperazin-1-yl]-2-hydroxy-benzonitrile (I.37)

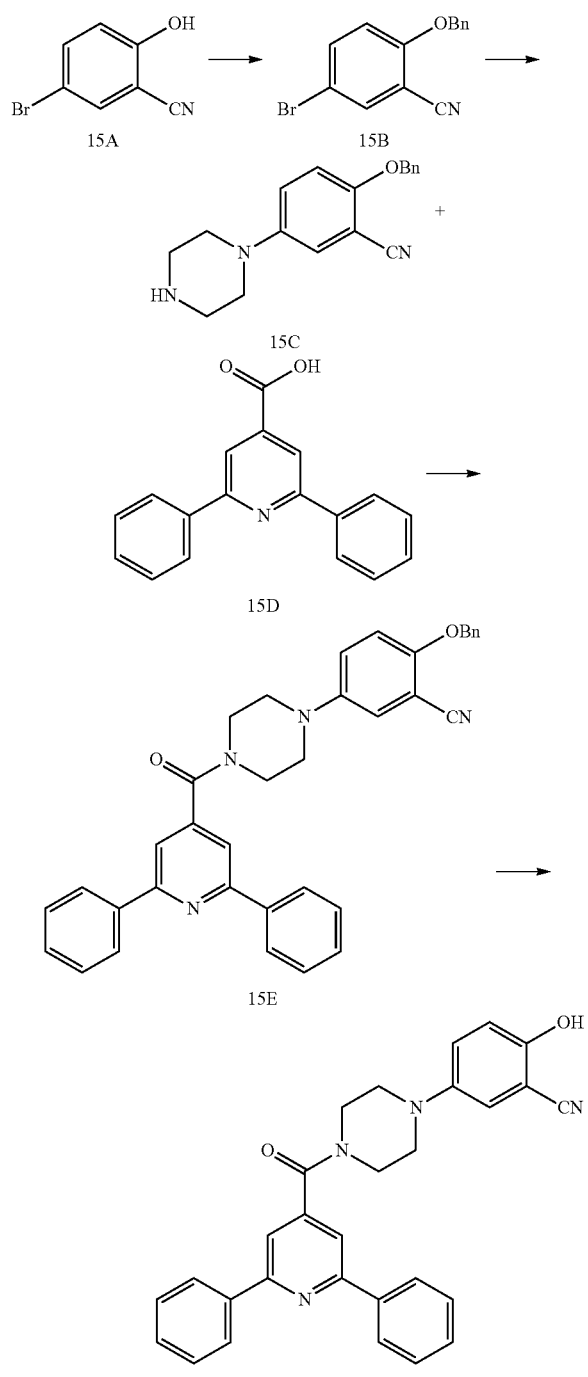

Step-I: Compound 15A (2 g, 1.0 eq) was dissolved in N,N-dimethylformamide (20 ml) and to it was added potassium carbonate (2.1 g, 1.5 eq) followed by benzyl bromide (1.3 ml, 1.1 eq). The resultant reaction mixture was stirred at ambient temperature under nitrogen atmosphere for 1 hour. On completion of reaction, the reaction mixture was quenched with water. Precipitated solid was filtered, dried and purified by flash column chromatography using hexane and ethyl acetate as gradient eluent to afford pure compound 15B (2.6 g) as a white solid.

Step-II: Compound 15B (2.5 g, 1.0 eq) was dissolved in 1,4-dioxane (20 ml) and to it was added 1-Boc-piperazine (1.62 g, 1.0 eq), Xantphos (0.37 g, 0.0065 mol, 0.75 eq), tris(dibenzylideneacetone)dipalladium(0) (0.39 g, 0.05 eq) and sodium tert-butoxide (3.6 g, 6.0 eq). The resultant reaction mixture was refluxed for 2 hours. On completion of the reaction, reaction mixture was quenched with water (20 ml) and extracted with ethyl acetate (3×20 ml). The combined organic layers were washed with water, dried over anhydrous sodium sulfate and concentrated under reduced pressure. The resultant crude product was purified by silica gel column chromatography to get Boc-protected intermediate (0.91 g) as yellow solid. The obtained Boc-protected intermediate was then dissolved in 1,4-dioxane (10 ml) and hydrochloric acid (4M in dioxane) (20 ml) was added to it. The resultant reaction mixture was then stirred at room temperature. On completion of reaction, solvent was removed on rotavapour and co-distilled with methanol. The crude product was triturated with diethyl ether (25 ml) to obtain pure product compound 15C (0.5 g) as a brown solid in the form of a hydrochloride salt.

Step-III: Compound 15D (0.4 g, 1.0 eq) was dissolved in N,N-dimethylformamide (20 ml) and was added triethylamine (0.36 ml, 2.0 eq), EDC.HCl (0.37 g, 1.5 eq) and HOBt (0.26 g, 1.5 eq). The resultant reaction mixture was stirred under nitrogen atmosphere for 10 minutes and then added compound 15C (0.46 g, 1.0 eq) and the reaction was further stirred for 1 hour. On completion of reaction, reaction mixture was quenched with sodium bicarbonate (20 ml) and extracted with ethyl acetate (3×20 ml). The combined organic layers were washed with water, dried over sodium sulfate and concentrated under reduced pressure to get crude product, which was triturated with diethyl ether (25 ml) to afford pure compound 15E (0.258 g) as a brown solid.

Step-IV: Compound 15E (0.258 g, 1.0 eq) was dissolved in THF (10 ml) and added palladium on carbon (0.0025 g, 10% by weight, 50% wet) and stirred under hydrogen atmosphere created using balloon for 5 hours. On completion of reaction, the reaction mixture was filtered through celite bed and washed with tetrahydrofuran (3×10 ml). The combined organic layers were concentrated under reduced pressure to get a brown solid. The obtained brown solid was triturated with diethyl ether (25 ml) and filtered to get the pure title product (0.038 g) as a brown solid.

Preparation of Intermediate:
6-Piperazin-1-yl-pyridin-3-ol (5D)

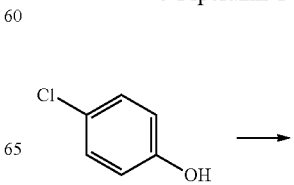

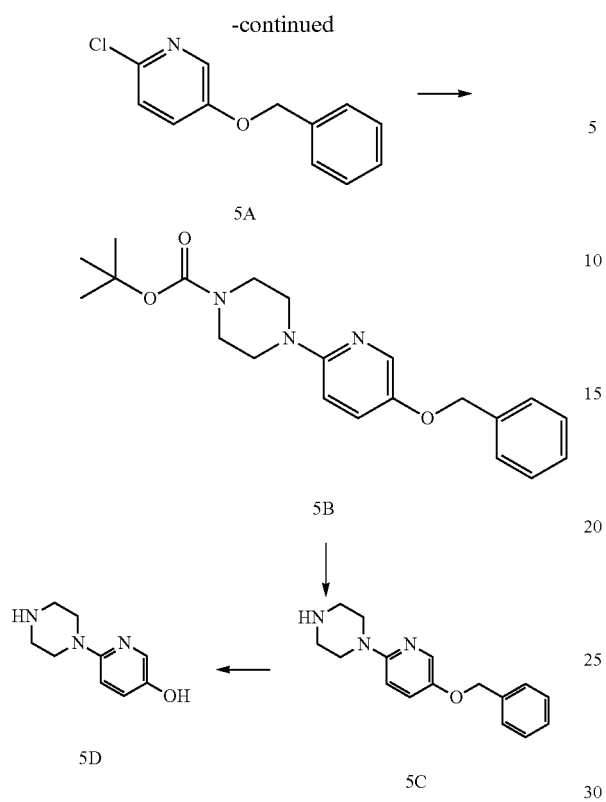

Step-I: To a solution of 2-chloro-5-hydroxypyridine (100 g) in N,N-dimethylformamide (500 ml) was added potassium carbonate (159.7 g, 1.5 eq) and benzyl bromide (96.3 ml, 1.05 eq) drop wise and stirred at room temperature for 4 hours. On completion of reaction, the reaction mixture was quenched with water (2000 ml) and extracted with ethyl acetate (2×100 ml). The combined organic layers were dried over anhydrous sodium sulfate and concentrated under reduced pressure. The resultant residue was purified using column chromatography on silica gel using an ethyl acetate-hexane mixture as eluent to afford compound 5A.

Step-II: To a solution of compound 5A (100 g, 1 eq) in toluene (500 ml) was added 1-Boc-piperazine (84.8 g, 1 eq), tris(dibenzylideneacetone)dipalladium(0) (20.84 g, 0.05 eq) and S-phos (18.6 g, 0.1 eq) at room temperature. The resultant reaction mixture was heated to 50° C. for 10 minutes and then added sodium tert-butoxide (131.2 g, 3 eq) portion wise and further heated at 110° C. for 3 hours. On completion of reaction, water (200 ml) and ethyl acetate (100 ml) was added to the reaction mixture and mixture was stirred. The resulting mixture was passed through celite bed and washed with ethyl acetate (2×200 ml). To filtrate was added brine solution (300 ml) and stirred for 15 minutes. The aqueous layer was separated and extracted in ethyl acetate (500 ml). The combined organic layers were dried over anhydrous sodium sulphate and concentrated under reduced pressure. The resultant residue was purified using column chromatography on silica gel using an ethyl acetate-hexane mixture as eluent to afford 5B.

Step-III: To a solution of compound 5B (100 g) in 1,4-dioxane (200 ml) was added hydrochloric acid (200 ml) drop wise and the resultant reaction mixture was stirred for 3 hours after completion of addition. After completion of reaction, the reaction mixture was quenched in saturated aqueous sodium bicarbonate solution (1.5 liter). Precipitated solid was filtered, washed with water (2×100 ml) and dried to afford compound 5C.

Step-IV: To a solution of compound 5C (100 g) in methanol:tetrahydrofuran (1:1) (1000 ml) was added palladium on activated carbon (5.0 g, 10% by weight, 50% wet). The suspension was stirred under hydrogen atmosphere created using hydrogen balloon for 8 hours at room temperature. On completion of reaction, the reaction mixture was filtered off from the catalyst and the solution was evaporated under reduced pressure to afford compound 5D, which was used in the next step without any further purification.

Example 16: Preparation of 1-[4-(5-hydroxy-pyridin-2-yl)-piperazin-1-yl]-3-phenyl-propan-1-one (I.45)

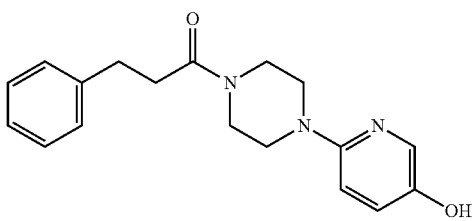 [SMILES: O=C(CCc1ccccc1)N1CCN(c2ccc(O)cn2)CC1]

To a solution of 3-phenylpropanoic acid (1 g, 1.0 eq) in N,N-dimethylacetamide (5 ml) was added EDC.HCl (1.91 g, 1.5 eq). The reaction mixture was stirred for 15 minutes, then added compound 5D (1.19 g, 1.0 eq). The reaction mixture was further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford the compound 1.45 as an off white solid.

Example 17: Preparation of 1-[4-(5-Hydroxy-pyridin-2-yl)-piperazin-1-yl]-3-methyl-3-phenyl-butan-1-one (I. 125)

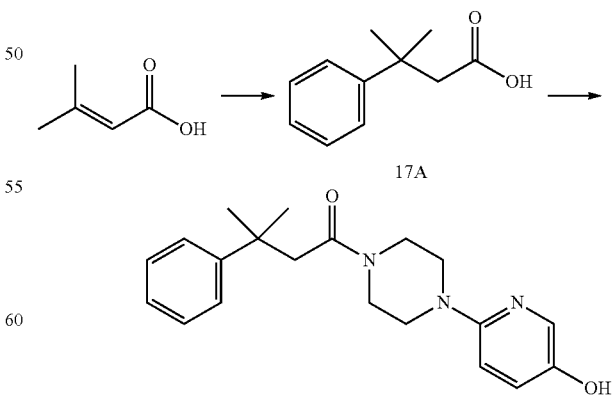

Step-I: To a cooled (0-5° C.) solution of 3,3-dimethylacrylic acid (10 g, 1.0 eq) in dry benzene (50 ml) was added anhydrous aluminum chloride (16 g, 1.2 eq) in small portions and the temperature was kept below 5° C. The reaction mixture was stirred for 20 minutes and then allowed to attain to room temperature. After completion of reaction, diethyl ether (50 ml) was added to reaction mixture and it was then cooled to 0° C. Hydrochloric acid (1N) was added to the reaction mixture until all of the solid dissolved and pH was less than 2. The aqueous layer was extracted with diethyl ether (3×50 ml). The organic layer was concentrated to reduce the volume to 50 ml and then extracted with saturated aq. sodium bicarbonate solution (6×30 ml). The combined aqueous layers were acidified with hydrochloric acid until the pH was less than 2. The aqueous layer was extracted with diethyl ether (3×50 ml). The combined organic layers were dried over anhydrous sodium sulfate and distilled to afford compound 17A (17.5 g, yield: 98%) as a low melting off white solid.

Step-II: To a solution of 3-methyl-3-phenyl-butyric acid (1 g, 1.0 eq) in N,N dimethylacetamide (5 ml) was added EDC.HCl (1.61 g, 1.5 eq). The resultant reaction mixture was stirred for 15 minutes, then added compound 5D (1 g, 1.0 eq) and further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford compound I.125 as an off white solid.

Example 18: Preparation of [4-(5-hydroxy-pyridin-2-yl)-piperazin-1-yl]-[4-methyl-3-(4-pyridin-3-yl-pyrimidin-2-ylamino)-phenyl]-methanone (I.85)

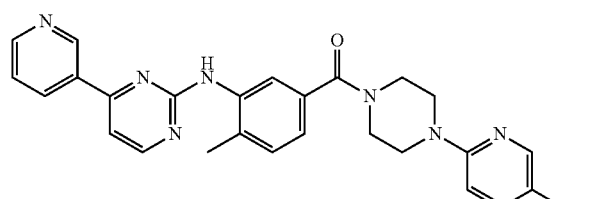

To a cooled solution (0-5° C.) of 4-methyl-3-(4-pyridin-3-yl-pyrimidin-2-ylamino)-benzoic acid (0.312 g, 1.1 eq) in N,N-dimethylformamide (5 ml) was added HATU (0.423 g, 1.2 eq) followed by triethylamine (0.17 ml, 1.2 eq). After stirring the reaction mixture for 10 minutes, compound 5D (0.2 g, 1.0 eq) was added and stirring was continued for 1 hour at 0-5° C. On completion of reaction, the reaction mixture was quenched with water (50 ml) and extracted with ethyl acetate (2×30 ml). The combined organic layers were washed with saturated aq. sodium chloride solution (10 ml), dried over anhydrous sodium sulfate and concentrated under reduced pressure. The resultant residue was purified using column chromatography over silica gel (230-400 mesh) using a dichloromethane:methanol mixture as eluent to afford pure compound I.85 (0.10 g, yield: 20%) as an off white solid.

Example 19: Preparation of 1-[4-(5-hydroxy-pyridin-2-yl)-piperazin-1-yl]-2-(5-nitro-pyridin-2-ylsulfanyl)-ethanone (I.97)

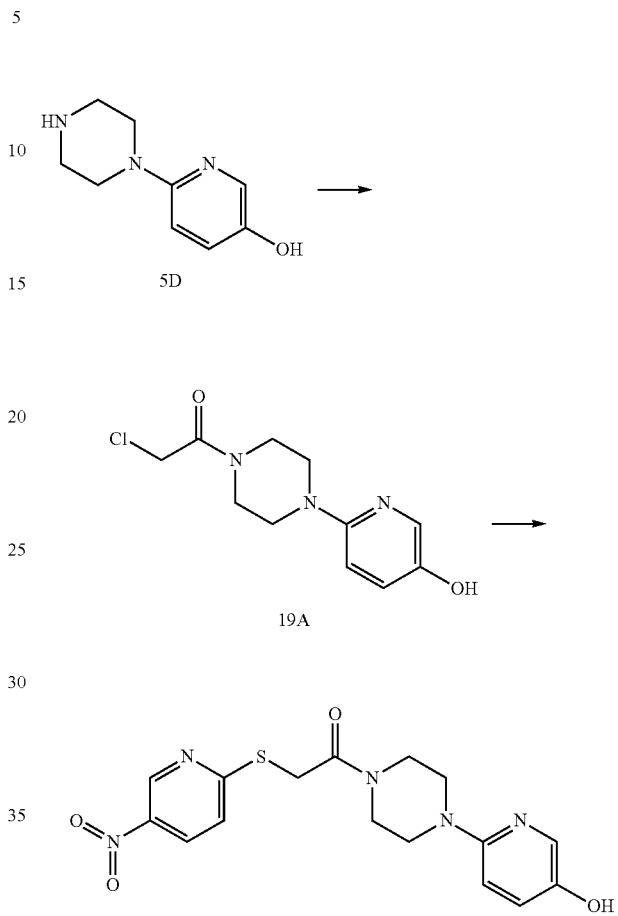

Step-I: To a cooled solution (0-5° C.) of compound 5D (0.7 g, 1.0 eq) in dichloromethane (10 ml) was added N,N-diisopropylethylamine (0.926 g, 3.0 eq). The resultant reaction mixture was stirred 10 minutes, then added chloroacetylchloride (0.206 ml, 1.1 eq). After addition, the reaction mixture was allowed to attain room temperature and then further stirred for 2 hours. On completion of reaction, the reaction mixture was quenched with saturated aq. sodium bicarbonate solution (20 ml) and extracted with dichloromethane (2×20 ml). The combined organic layers were washed with saturated aq. sodium chloride solution (10 ml), dried over anhydrous sodium sulfate and concentrated under reduced pressure to afford pure compound 19A (0.380 g, yield: 40%) as an off white solid.

Step-II: A solution of compound 19A (0.38 g, 1.0 eq) in ethanol (25 ml) was added to 5-nitropyridine-2-thiol (0.232 g, 1.0 eq) at room temperature and the resultant reaction mixture was heated to 95° C. for 15 hours. On completion of reaction, the reaction mixture was cooled to 0-5° C. Precipitated solid was filtered and washed with diethyl ether (2×10 ml). The solid obtained was dried under reduced pressure at 55° C. for 3 hours to afford pure compound (I.97) (0.35 g, yield: 66%) as a red brown colored solid.

Example 20: Preparation of 2-(2-Bromo-phenylsulfanyl)-1-[4-(5-hydroxy-pyridin-2-yl)-piperazin-1-yl]-ethanone (I.143)

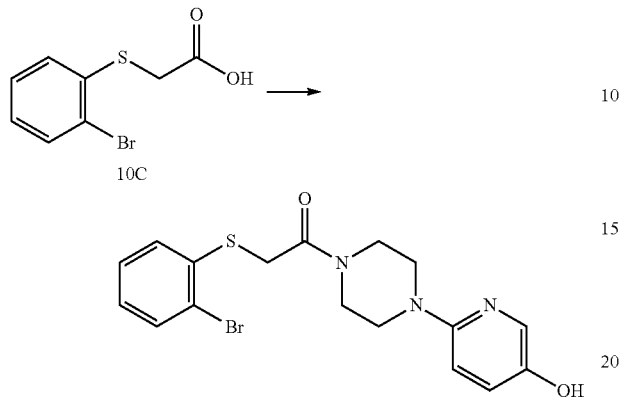

To a cooled solution (0-5° C.) of compound 10C (0.25 g, 1.0 eq) in N,N-dimethylformamide (5 ml) was added HATU (0.5 g, 1.3 eq) followed by triethylamine (0.21 ml, 1.5 eq). After stirring the reaction mixture for 10 minutes, compound 5D (0.199 g, 1.1 eq) was added and stirring was continued for 2 hours at 0-5° C. On completion of reaction, the reaction mixture was quenched with water (50 ml) and extracted with ethyl acetate (2×30 ml). The combined organic layers were washed with saturated aq. sodium chloride solution (10 ml), dried over anhydrous sodium sulfate and concentrated under reduced pressure. The resultant residue was purified using column chromatography on silica gel (230-400 mesh) using a dichloromethane:methanol mixture as eluent to afford the pure compound (1.143) (0.15 g, yield: 45%) as a yellow solid.

Example 21: Preparation of 2-(5-fluoro-1H-indol-3-yl)-1-[4-(5-hydroxypyridin-2-yl)-piperazin-1-yl]-ethanone (I.131)

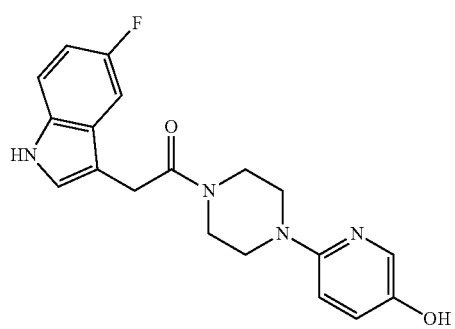 [SMILES: O=C(Cc1c[nH]c2ccc(F)cc12)N1CCN(c2ccc(O)cn2)CC1]

To a solution of 5-fluoroindole-3-acetic acid (1 g, 1.0 eq) in N,N-dimethylacetamide (5 ml) was added EDC.HCl (1.49 g, 1.5 eq). The resultant reaction mixture was stirred for 15 minutes, and added compound 5D (0.93 g, 1.0 eq) and then further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford the pure compound (0.131) as an off white solid.

Example 22: Preparation of [4-(5-hydroxypyridin-2-yl)-piperazin-1-yl]-((1R,2R)-2-phenylcyclopropyl)-methanone (I.133)

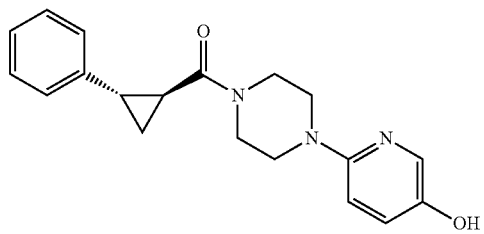 [SMILES: O=C([C@H]1C[C@@H]1c1ccccc1)N1CCN(c2ccc(O)cn2)CC1]

A solution of (1R,2R)-2-phenyl-cyclopropanecarboxylic acid (0.207 g, 1.0 eq) in N,N-dimethylacetamide (10 ml) was added EDC.HCl (0.363 g, 1.7 eq). After stirring the reaction mixture for 10 minutes, compound 5D (0.2 g, 1.1 eq) was added and stirring continued for 2 hours at room temperature. On completion of reaction, the reaction mixture was quenched with water (50 ml) and extracted with ethyl acetate (2×30 ml). The combined organic layers were washed with saturated aq. sodium chloride solution (10 ml) and concentrated. The resultant residue was purified using column chromatography on silica gel (230-400 mesh) using a dichloromethane:methanol (9:1) mixture as eluent to afford the pure compound (1.133) (0.100 g, yield: 27%) as a white solid.

Example 23: Preparation of quinoline-8-sulfonic acid {2-[4-(5-hydroxypyridin-2-yl)-piperazin-1-yl]-2-oxo-ethyl}-methylamide (I.89)

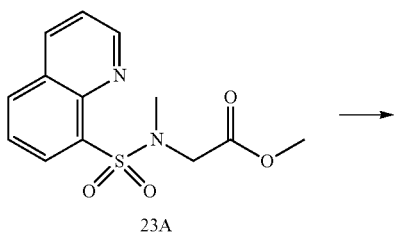

Example 24: Preparation of [4-(5-hydroxypyridin-2-yl)-piperazin-1-yl]-[3-(1H-indol-4-yl) phenyl]methanone (I.113)

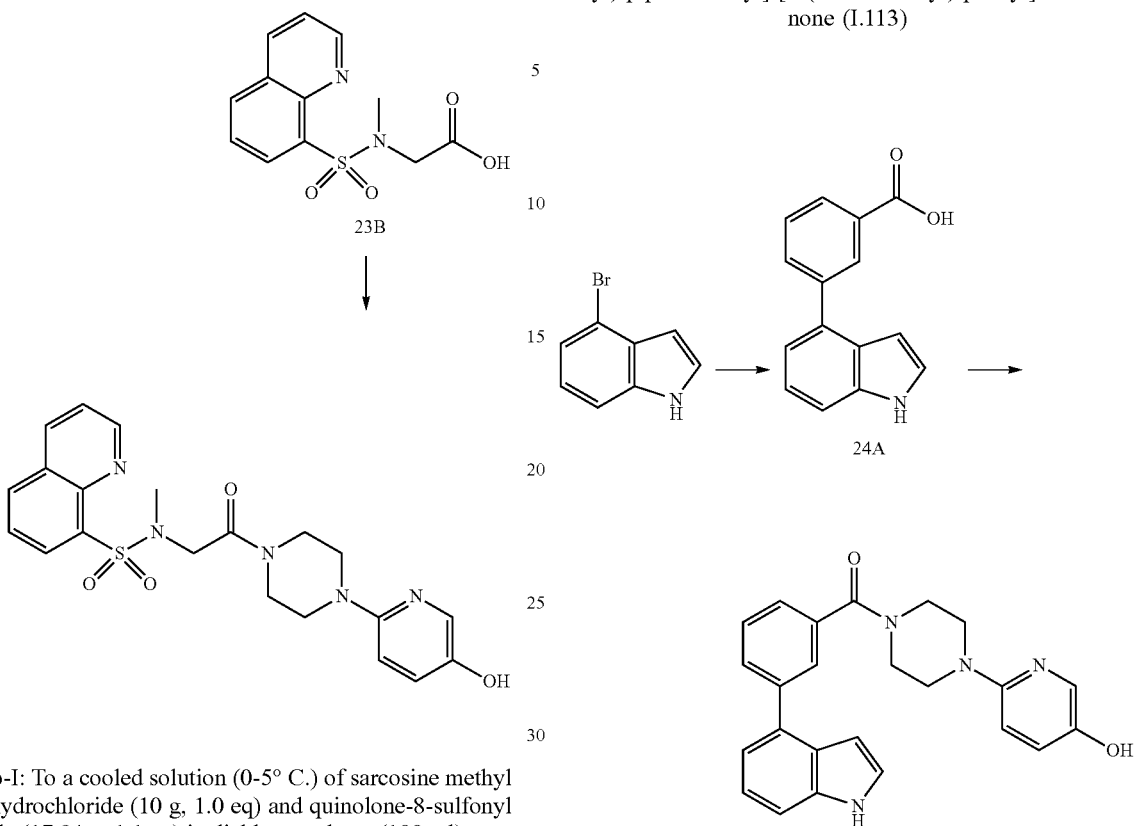

Step-I: To a cooled solution (0-5° C.) of sarcosine methyl ester hydrochloride (10 g, 1.0 eq) and quinolone-8-sulfonyl chloride (17.94 g, 1.1 eq) in dichloromethane (100 ml), was added N,N-diisopropylethylamine (37.43 ml, 3.0 eq) drop wise over 10 min. The resultant reaction mixture was stirred at room temperature for 16 hours. After completion of reaction, the reaction mixture was quenched with saturated aq. sodium bicarbonate solution (300 ml) under stirring. The organic layer was separated, dried on anhydrous sodium sulfate and concentrated in vacuum. The resultant residue was purified by column chromatography, eluting with ethyl acetate:hexane (7:3) to afford pure compound 23A as an orange solid.

Step-II: Compound 23A (12 g) was dissolved in methanol (120 ml) and added aqueous sodium hydroxide solution (2N) (120 ml). The resultant reaction mixture was stirred at room temperature for 2 hours. After completion of reaction, the reaction mixture was acidified with hydrochloric acid (1N) and extracted with ethyl acetate (120 ml). The organic layer was dried over anhydrous sodium sulfate and concentrated in vacuum to afford compound 23B as an off yellow solid, which was taken forward without further purification.

Step-III: To a solution of compound 23B (1 g, 1.0 eq) in N,N-dimethylacetamide (10 ml) was added EDC.HCl (1.02 g, 1.5 eq). The resultant reaction mixture was stirred for 15 minutes, then added compound 5D (0.693 g, 1.0 eq) and further stirred the reaction at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified using column chromatography on silica gel (230-400 mesh) using dichloromethane:methanol (9:1) as eluent to afford the pure compound (1.89) as an off white solid.

Step-I: To a mixture of 4-bromoindole (11.81 g, 1.0 eq) and 3-carboxyphenylboronic acid (10.0 g, 1.0 eq) in acetonitrile (100 ml) and N,N-dimethylformamide (100 ml) were added palladium catalyst Pd(PPh$_3$)$_4$ (2.09 g, 0.03 eq) and freshly prepared sodium hydroxide (9.64 g, 4.0 eq) solution in 80 ml water. The resultant reaction mixture was stirred under nitrogen at 100° C. for 4 hours. After completion of coupling reaction, the reaction mixture was cooled to room temperature and filtered through celite bed. The filtrate was diluted with ethyl acetate and separated from the water layer. The organic layer was washed with brine, dried over anhydrous sodium sulfate and concentrated under reduced pressure. The resultant crude product was purified by a silica gel column eluting with dichloromethane:methanol to afford compound 24A.

Step-II: To a solution of compound 24A (1 g, 1.0 eq) in N,N-dimethylacetamide (10 ml) was added EDC.HCl (1.21 g, 1.5 eq). The reaction mixture was stirred for 15 minutes and then added compound 5D (0.755 g, 1.0 eq) and further stirred at room temperature for 3 hours. On completion of reaction, the reaction mixture was quenched with water and extracted with ethyl acetate. The combined organic layers were washed with saturated aq. sodium chloride solution, dried over anhydrous sodium sulfate and concentrated under reduced pressure. The resultant residue was purified by column chromatography on silica gel (230-400 mesh) using dichloromethane:methanol (9:1) as eluent to afford the pure compound (1.113) as an off white solid.

Example 25: Preparation of 2-(1-adamantyl)-1-[4-(5-hydroxy-2-pyridyl)piperazin-1-yl]ethanone (I.55)

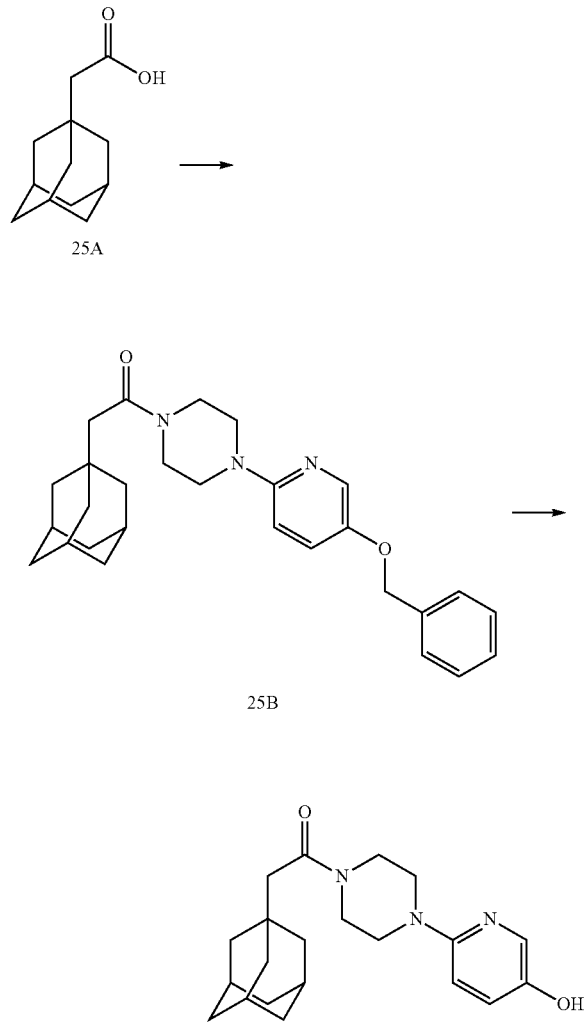

Step-I: To a solution of compound 25A (0.30 g, 1.0 eq) in N,N-dimethylformamide (5 ml), was added EDC.HCl (0.44 g, 1.5 eq) and HOBt (0.31 g, 1.5 eq). The resultant reaction mixture was stirred for 30 minutes at room temperature, then added compound 5C (0.42 g, 1.0 eq) and further stirred at room temperature for 3 hours. On completion of reaction, the reaction mixture was quenched with water (25 ml) under vigorous stirring. Precipitated yellow solid was filtered, washed with diethyl ether and dried under vacuum to afford pure compound 25B in quantitative yield.

Step-II: To a solution of compound 25B (0.56 g) in methanol:dichloromethane (4:1) (10 ml), was added palladium on carbon (0.18 g, 10% by weight, 50% wet) and stirred under hydrogen atmosphere created using balloon for 3 hours at room temperature. After completion of reaction mixture, the reaction mixture was filtered through celite bed and the filtrate was concentrated under reduced pressure. The obtained yellow solid was leached with diethyl ether and filtered to afford pure product (1.55) in quantitative yield.

Example 26: Preparation of 2-(1-adamantylmethylamino)-1-[4-(5-hydroxy-2-pyridyl)piperazin-1-yl]ethanone (I.57)

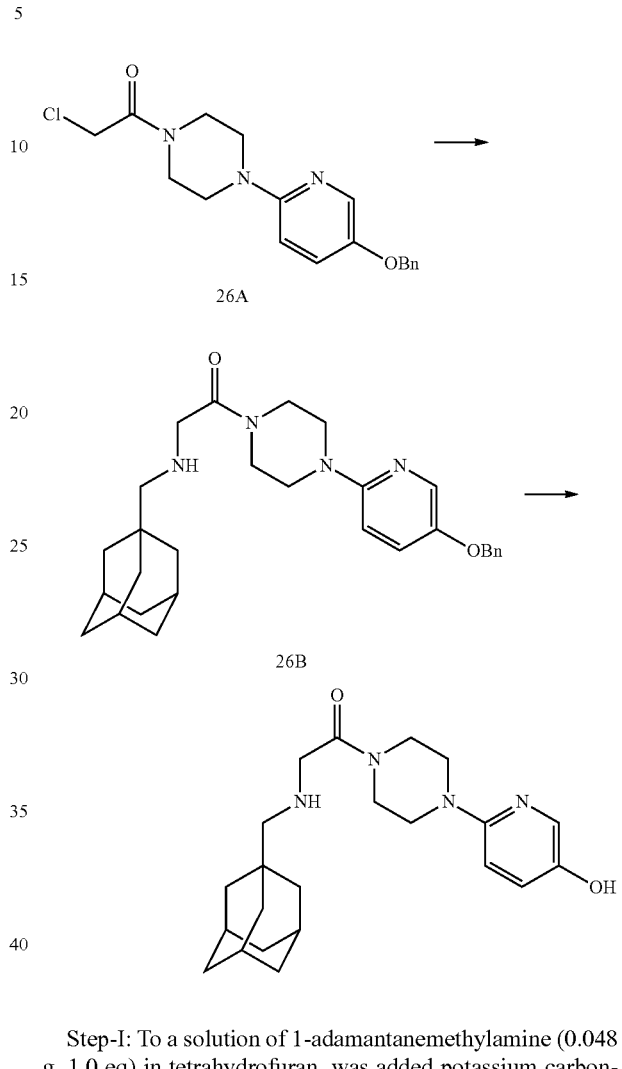

Step-I: To a solution of 1-adamantanemethylamine (0.048 g, 1.0 eq) in tetrahydrofuran, was added potassium carbonate (0.04 g, 1.0 eq). The resultant reaction mixture was stirred at room temperature for 10 minutes, then added compound 26A (0.1 g, 1.0 eq) and further stirred under nitrogen atmosphere for 3 hours. After completion of reaction, the reaction mixture was quenched with water and extracted with ethyl acetate (3×20 ml). The combined organic layers were washed with water, dried over anhydrous sodium sulfate and concentrated under reduced pressure. The resultant residue was purified by column chromatography on silica gel (230-400 mesh) to afford pure compound 26B (0.1 g).

Step-II: Compound 26B (0.1 g) was dissolved in methanol (5 ml) and palladium on carbon (0.01 g, 10% by weight, 50% wet) was added to it. The resultant reaction mixture was stirred under hydrogen atmosphere created using hydrogen balloon for 3 hours at room temperature. On completion of reaction, the reaction mixture was filtered through celite bed and the filtrate was concentrated under reduced pressure. The resultant crude product was purified by column chromatography on silica gel (230-400 mesh) to afford pure product (1.57) (0.04 g).

Example 27: Preparation of 5-[4-(5-hydroxy-2-pyridyl)piperazin-1-yl]-5-oxo-pentanoic acid (I.70)

Example 28: Preparation of 2-cyclohexyl-2-hydroxy-1-[4-(5-hydroxy-2-pyridyl)piperazin-1-yl]-2-phenyl-ethanone (I.95)

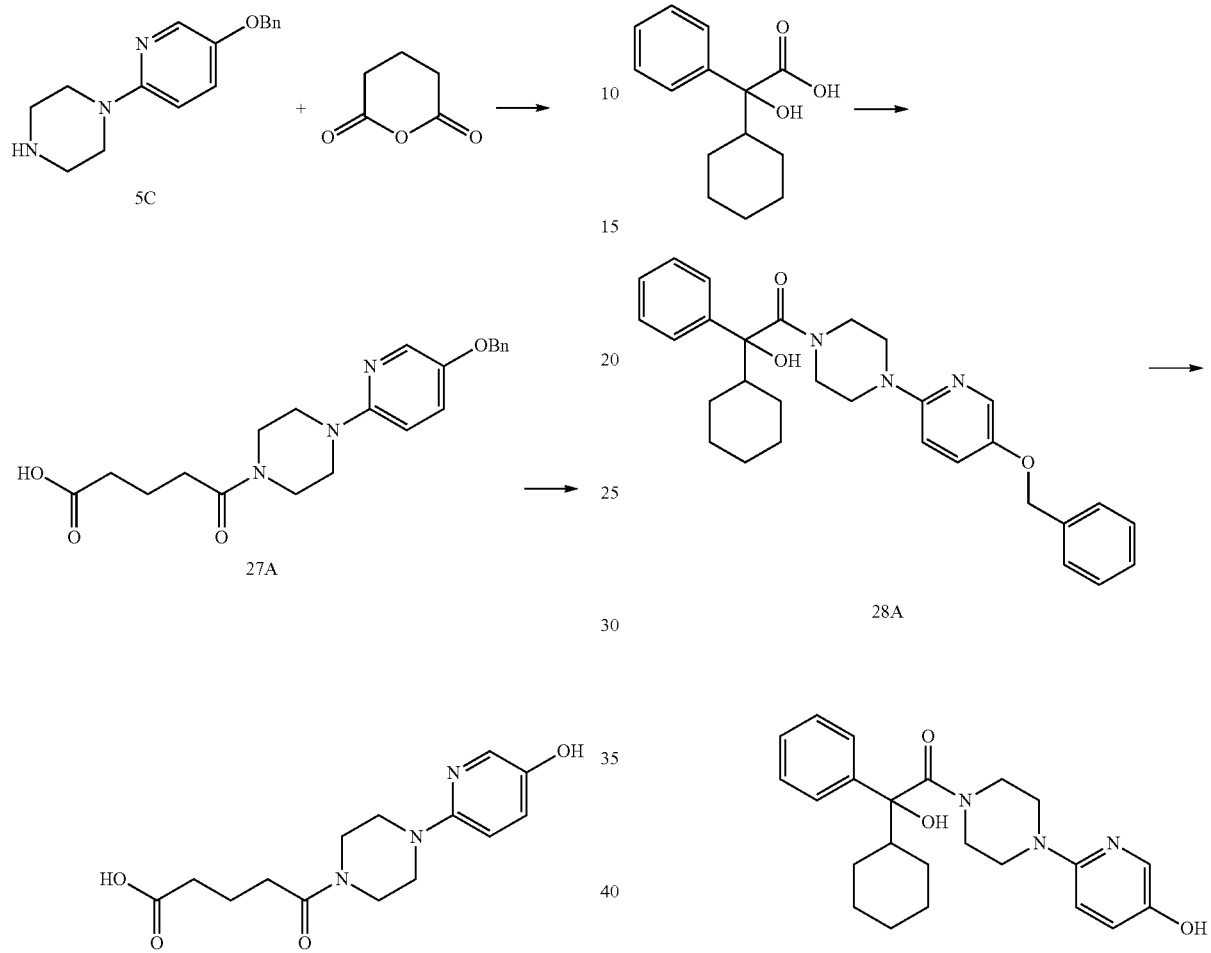

Step-I: To a solution of compound 5C (1 g, 1.0 eq) in tetrahydrofuran (10 ml), was added glutaric anhydride (0.71 g, 1.7 eq) and the resultant reaction mixture was heated to 65° C. for 16 hours. On completion of reaction, the reaction mixture was concentrated under reduced pressure. The resultant residue was triturated with diethyl ether (5 ml) and filtered to afford compound 27A (0.9 g) as an off white solid.

Step-II: Compound 27A (0.9 g) was dissolved in methanol (10 ml) and palladium on carbon (0.05 g, 10% by weight, 50% wet) was added to it. The resultant reaction mixture was stirred under hydrogen atmosphere created using hydrogen balloon for 3 hours at room temperature. On completion of reaction, the reaction mixture was filtered through celite bed and concentrated under reduced pressure. The resultant crude product was purified by column chromatography on silica gel (230-400 mesh) to afford pure product (I.70) (0.58 g) in quantitative yield.

Step-I: To a solution of 2-cyclohexyl-2-phenylglycolic acid (0.3 g, 1.0 eq) in N,N-dimethylformamide (5 ml), was added EDC.HCl (0.36 g, 1.5 eq) and HOBt (0.26 g, 1.5 eq). The resultant reaction mixture was stirred for 15 minutes at room temperature and then added compound 5C (0.34 g, 1.0 eq) and further stirred for 2 hours. After completion of reaction, the reaction mixture was quenched with a saturated aq. sodium bicarbonate solution (5 ml) and extracted with ethyl acetate (3×20 ml). The organic layer was dried over anhydrous sodium sulfate and concentrated under reduced pressure to afford crude product. The crude product was purified by column chromatography on silica gel (230-400 mesh) to get compound 28A as a white solid (0.314 g).

Step-II: To a solution of compound 28A (0.314 g) in methanol:dichloromethane (1:1) (10 ml), was added 10% by weight palladium on carbon (0.15 g) and stirred under hydrogen atmosphere created by hydrogen balloon for 2 hours. After completion of reaction, the reaction mixture was filtered through celite bed and the filtrate was concentrated under reduced pressure. The crude product was triturated with diethyl ether (5 ml) and filtered to afford pure product (I.95) as a white solid (0.19 g).

Example 29: Preparation of 1-[4-(5-hydroxy-2-pyridyl)piperazin-1-yl]-2-morpholino-2-phenyl-ethanone (I.117)

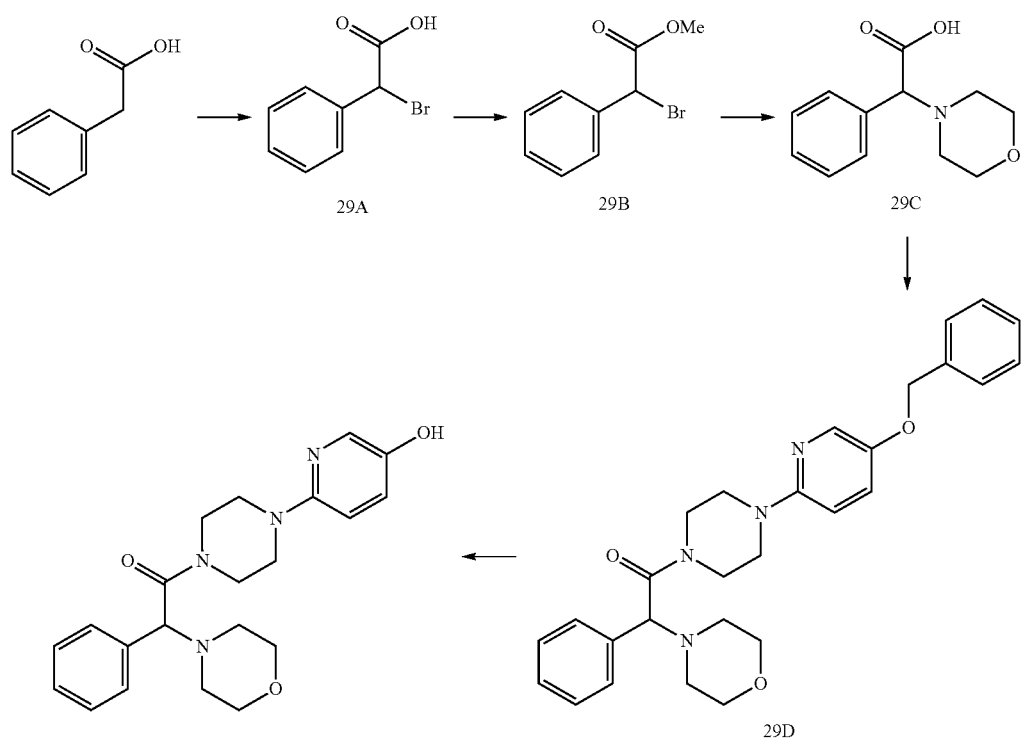 [SMILES: O=C(O)Cc1ccccc1 ; O=C(O)C(Br)c1ccccc1 ; COC(=O)C(Br)c1ccccc1 ; O=C(O)C(c1ccccc1)N1CCOCC1 ; O=C(C(c1ccccc1)N1CCOCC1)N1CCN(c2ccc(O)cn2)CC1 ; O=C(C(c1ccccc1)N1CCOCC1)N1CCN(c2ccc(OCc3ccccc3)cn2)CC1]

Step-I: To a solution of phenylacetic acid (5 g, 1.0 eq) in carbon tetrachloride (50 ml), was added NBS (7.18 g, 1.1 eq) and AIBN (0.3 g, 0.05 eq). The resultant reaction mixture was heated to reflux and stirred for 19 hours under nitrogen atmosphere. After completion of the reaction, the reaction mixture was cooled to room temperature, diluted with n-hexane (50 ml) and filtered through celite bed. The filtrate was concentrated under reduced pressure and the residue was purified by column chromatography on silica gel (230-400 mesh) to afford compound 29A (8.0 g) as a light yellow liquid.

Step-II: To a solution of compound 29A (7.5 g, 1.0 eq) in methanol (70 ml), was added sulfuric acid (0.1 ml, 0.05 eq) slowly under stirring. The resultant reaction mixture was refluxed for 24 hours. After completion of the reaction, the reaction mixture was cooled to room temperature, quenched with water (30 ml) and extracted with ethyl acetate (4×20 ml). The combined organic layers were washed with water, dried over anhydrous sodium sulfate and concentrated under reduced pressure to afford compound 29B (6.65 g) as a light brown liquid, which was used directly in next step without further purification.

Step-III: To a solution of compound 29B (5.65 g, 1 eq) in acetonitrile (30 ml), was added N,N-diisopropylethylamine (4.3 ml, 1 eq) and morpholine (2.55 ml, 1.2 eq). The resultant reaction mixture was stirred at room temperature for 4 hours. On completion of reaction, the reaction mixture was quenched with water and extracted with ethyl acetate (3×20 ml). The combined organic layers were washed with water, dried over anhydrous sodium sulfate and concentrated under reduced pressure. The resultant crude product was purified by column chromatography on silica gel (230-400 mesh) to obtain pure ester intermediate (4.0 g) as a light brown liquid. The ester intermediate (4.0 g, 1 eq) was dissolved in 1,4-dioxane (40 ml) and to it was added hydrochloric acid (14.88 ml, 10.0 eq). The resultant reaction mixture was heated at 110° C. for 24 hours. On completion of reaction, the reaction mixture was concentrated under reduced pressure and the resulting residue was triturated with diethyl ether (50 ml). Precipitated solid was filtered to afford compound 29C (4.1 g) as an off white solid in the form of a hydrochloride salt.

Step-IV: To a solution of compound 29C (0.43 g, 1.0 eq) in N,N-dimethylformamide (10 ml), was added triethylamine (0.23 ml, 1.0 eq), EDC.HCl (0.48 g, 1.5 eq) and HOBt (0.34 g, 1.5 eq). The resultant reaction mixture was stirred at room temperature for 15 minutes, then added compound 5C (0.45 g, 1.0 eq) and further stirred for 2 hours. On completion of reaction, the reaction mixture was quenched with saturated aq. sodium bicarbonate solution (20 ml) and extracted with ethyl acetate (3×20 ml). The combined organic layers were washed with water, dried over sodium sulfate and concentrated under reduced pressure to get the crude product. The crude obtained was triturated with diethyl ether (5 ml). The resultant solid was filtered to afford compound 29D (0.55 g) as an off white solid.

Step-V: To a solution of compound 29D (0.5 g) in methanol:dichloromethane (1:1) (10 ml), was added 10% by weight palladium on carbon (0.15 g) and the resultant reaction mixture was stirred under hydrogen atmosphere created by hydrogen balloon for 2 hours. After completion of reaction, the reaction mixture was filtered through celite bed and the filtrate was concentrated under reduced pressure to afford the crude product. The crude product was purified by column chromatography on silica gel (230-400 mesh) to afford pure compound (1.117) (0.160 g) as a light brown solid.

Table 2 set forth below provides characterizing data (¹H NMR spectral data) for the compounds of the instant invention. The compounds for which data is provided below but for which a description of the synthesis is not explicitly provided above were made in an analogous manner to the synthetic procedures provided above.

TABLE 2

Chemical Name and ¹H NMR Data for Compound of Formula I

| Compound No. | Structure | IUPAC Name | ¹H NMR (δ ppm) in DMSO-$d_6$ as solvent, 500 MHz |
|---|---|---|---|
| I.1 | 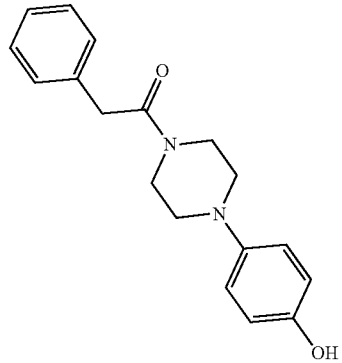 [SMILES: O=C(Cc1ccccc1)N1CCN(c2ccc(O)cc2)CC1] | 1-[4-(4-Hydroxy-phenyl)-piperazin-1-yl]-2-phenyl-ethanone | 2.88 (t, 2H, J = 4.47 Hz), 2.93 (t, 2H, J = 4.68 Hz), 3.65 (t, 4H, J = 4.91 Hz), 6.69 (d, 2H, J = 8.77 Hz), 6.82 (d, 2H, J = 8.78 Hz), 7.26-7.30 (m, 3H), 7.36 (t, 2H, J = 7.51 Hz), 8.93 (s, 1H) |
| I.2 | 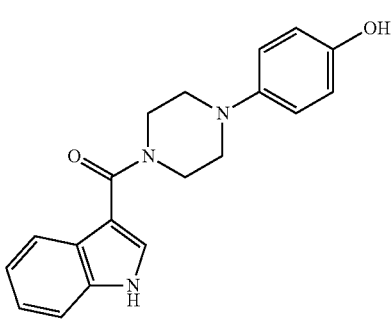 [SMILES: O=C(c1c[nH]c2ccccc12)N1CCN(c2ccc(O)cc2)CC1] | 4-(4-Hydroxy-phenyl)-piperazin-1-yl]-(1H-indol-3-yl)-methanone | 2.99 (t, 4H, J = 4.67 Hz), 3.74 (t, 4H, J = 4.73 Hz), 6.66 (d, 2H, J = 8.82 Hz), 6.82 (d, 2H, J = 8.85 Hz), 7.10 (t, 1H, J = 7.40 Hz), 7.16 (t, 1H, J = 7.41 Hz), 7.44 (d, 1H, J = 8.03 Hz), 7.69 (d, 1H, J = 7.86 Hz), 7.72 (d, 1H, J = 2.63 Hz), 8.89 (s, 1H), 11.61 (s, 1H) |
| I.3 | 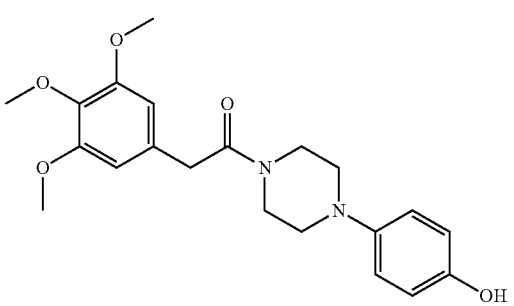 [SMILES: COc1cc(CC(=O)N2CCN(c3ccc(O)cc3)CC2)cc(OC)c1OC] | 1-[4-(4-Hydroxy-phenyl)-piperazin-1-yl]-2-(3,4,5-trimethoxy-phenyl)-ethanone | 2.90-2.95 (m, 4H), 3.65-3.66 (m, 4H), 3.68 (s, 3H), 3.73 (s, 2H), 3.79 (s, 6H), 6.59 (s, 2H), 6.70 (d, 2H, J = 8.85 Hz), 6.83 (d, 2H, J = 8.86 Hz), 8.94 (s, 1H) |
| I.4 | 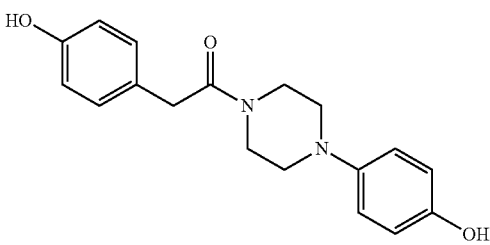 [SMILES: O=C(Cc1ccc(O)cc1)N1CCN(c2ccc(O)cc2)CC1] | 2-(4-Hydroxy-phenyl)-1-[4-(4-hydroxy-phenyl)-piperazin-1-yl]-ethanone | 2.86 (t, 2H, J = 4.38 Hz), 2.91 (t, 2H, J = 4.68 Hz), 3.62 (t, 4H, J = 4.68 Hz), 3.66 (s, 2H), 6.69 (d, 2H, J = 8.81 Hz), 6.73 (d, 2H, J = 8.34 Hz), 6.82 (d, 2H, J = 8.82 Hz), 7.08 (d, 2H, J = 8.31 Hz), 8.93 (s, 1H), 9.30 (s, 1H) |

TABLE 2-continued

Chemical Name and ¹H NMR Data for Compound of Formula I

| Compound No. | IUPAC Name | ¹H NMR (δ ppm) in DMSO-d$_6$ as solvent, 500 MHz |
|---|---|---|
| I.5 | 1-[4-(4-Hydroxyphenyl)-piperazin-1-yl]-2-[4-(2-methoxyethoxy)-phenyl]-ethanone | 2.88 (t, 2H, J = 4.38 Hz), 2.92 (t, 2H, J = 4.68 Hz), 3.35 (s, 3H), 3.63 (t, 4H, J = 4.68 Hz), 3.69 (t, 2H, J = 4.53 Hz), 3.72 (s, 2H), 4.10 (t, 2H, J = 4.54 Hz), 6.69 (d, 2H, J = 8.83 Hz), 6.82 (d, 2H, J = 8.86 Hz), 6.92 (d, 2H, J = 8.56 Hz), 7.19 (d, 2H, J = 8.52 Hz), 8.93 (s, 1H) |
| I.6 | 1-[4-(5-Hydroxypyridin-2-yl)-piperazin-1-yl]-2-phenyl-ethanone | 3.25 (m, 2H), 3.30 (m, 2H), 3.62-3.63 (m, 4H), 3.81 (s, 2H), 6.78 (d, 1H, J = 8.98 Hz), 7.10-7.13 (m, 1H), 7.26-7.30 (m, 3H), 7.34-7.37 (m, 2H), 7.78 (d, 1H, J = 2.74 Hz), 9.09 (s, 1H) |
| I.7 | [4-(4-Hydroxyphenyl)-piperazin-1-yl]-[1-(2-methoxyethyl)-piperidin-4-yl]-methanone | 1.66 (br-s, 4H), 2.42 (m, 2H), 2.93 (m, 3H), 2.98 (m, 4H), 3.29 (m, 4H), 3.50 (br-s, 2H), 3.62 (s, 3H), 3.64 (br-s, 2H), 6.70-6.71 (d, 2H, J = 5.96 Hz), 6.84 (d, 2H), 8.94 (s, 1H) |
| I.8 | [4-(4-Hydroxyphenyl)-piperazin-1-yl]-(1H-indazol-3-yl)-methanone | 3.07 (m, 4H), 3.90 (m, 2H), 4.19 (m, 2H), 6.72 (d, 2H, J = 8.81 Hz), 6.89 (d, 2H, J = 8.84 Hz), 7.28 (t, 1H, J = 7.51 Hz), 7.47 (t, 1H, J = 7.61 Hz), 7.67 (d, 1H, J = 8.40 Hz), 8.04 (d, 1H, J = 8.15 Hz), 8.93 (s, 1H), 13.59 (s, 1H) |
| I.9 | Acridin-9-yl-[4-(4-hydroxyphenyl)-piperazin-1-yl]-methanone | 2.94 (s, 2H), 3.12 (s, 2H), 3.53 (s, 2H), 4.16 (s, 2H), 6.69 (d, 2H, J = 8.81 Hz), 6.83 (d, 2H, J = 8.85 Hz), 7.76 (t, 2H, J = 7.69 Hz), 7.97 (d, 2H, J = 7.76 Hz), 8.01 (d, 2H, J = 7.90 Hz), 8.27 (d, 2H, J = 6.72 Hz), 8.95 (s, 1H). |
| I.10 | [4-(4-Hydroxyphenyl)-piperazin-1-yl]-[5-(2-methoxyethoxy)-1H-indol-3-yl]-methanone | 3.05 (s, 4H), 3.37 (s, 3H), 3.71-3.73 (m, 2H), 3.80 (s, 4H), 4.13 (t, 2H, J = 4.66 Hz), 6.72 (d, 2H, J = 9.06 Hz), 6.85 (d, 1H, J = 2.35 Hz), 6.88 (d, 2H, J = 8.38 Hz), 7.21 (d, 1H, J = 1.98 Hz), 7.38 (d, 1H, J = 8.78 Hz), 7.73 (d, 1H, J = 2.63 Hz), 8.94 (s, 1H), 11.55 (s, 1H). |

TABLE 2-continued

Chemical Name and $^1$H NMR Data for Compound of Formula I

| Compound No. | IUPAC Name | $^1$H NMR (δ ppm) in DMSO-d$_6$ as solvent, 500 MHz |
|---|---|---|
| I.11 | 1-[4-(2-Fluoro-4-hydroxyphenyl)-piperazin-1-yl]-2-phenyl-ethanone | 2.81 (t, 2H, J = 4.58 Hz), 2.85 (t, 2H, J = 4.82 Hz), 3.65-3.67 (m, 4H), 3.80 (s, 2H), 6.56 (dd, 1H, J$_1$ = 8.52 Hz, J$_2$ = 2.7 Hz), 6.60 (dd, 1H, J$_1$ = 13.7 Hz, J$_2$ = 2.59 Hz), 6.89 (t, 1H, J = 9.39 Hz), 7.26-7.30 (m, 3H), 7.35-7.38 (t, 2H, J = 7.44 Hz), 9.52 (s, 1H) |
| I.12 | 3-(4-Butoxyphenyl)-1-[4-(4-hydroxyphenyl)-piperazin-1-yl]-propenone | 1.00 (t, 3H, J = 7.38 Hz), 1.45-1.53 (m, 2H), 1.72-1.78 (m, 2H), 3.01 (m, 4H), 3.74 (m, 2H), 3.88 (m, 2H), 4.06 (t, 2H, J = 6.47 Hz), 6.72 (d, 2H, J = 8.84 Hz), 6.88 (d, 2H, J = 8.81 Hz), 7.00 (d, 2H, J = 8.64 Hz), 7.20 (d, 1H, J = 15.33 Hz), 6.52 (d, 1H, J = 15.22 Hz), 7.72 (d, 2H, J = 8.62 Hz), 8.94 (s, 1H) |
| I.13 | 3-(4-Butoxyphenyl)-1-[4-(4-hydroxyphenyl)-piperazin-1-yl]-propan-1-one | 0.97 (t, 3H, J = 7.39 Hz), 1.42-1.50 (m, 2H), 1.68-1.74 (m, 2H), 2.65 (t, 2H, J = 7.59 Hz), 2.80 (t, 2H, J = 7.60 Hz), 2.86 (t, 2H, J = 4.81 Hz), 2.90 (t, 2H, J = 4.99 Hz), 3.56 (t, 2H, J = 4.81 Hz), 3.61 (t, 2H, J = 4.94 Hz), 3.94 (t, 2H, J = 6.49 Hz), 6.70 (d, 2H, J = 8.93 Hz), 6.83 (d, 2H, J = 8.94 Hz), 6.87 (d, 2H, J = 8.60 Hz), 7.18 (d, 2H, J = 8.61 Hz), 8.93 (s, 1H) |
| I.14 | (5-Butoxy-1H-indol-3-yl)-[4-(4-hydroxyphenyl)-piperazin-1-yl]-methanone | 0.99 (t, 3H, J = 7.40 Hz), 1.46-1.54 (m, 2H), 1.73-1.79 (m, 2H), 3.05 (s, 4H), 3.80 (s, 4H), 4.00 (t, 2H, J = 6.46 Hz), 6.72 (d, 2H, J = 8.83 Hz), 6.83-6.85 (m, 1H), 6.86 (d, 2H, J = 8.79 Hz), 7.21 (d, 1H, J = 2.12 Hz), 7.37 (d, 1H, J = 8.78 Hz), 7.72 (d, 1H, J = 2.7 Hz), 8.94 (s, 1H), 11.55 (s, 1H). |
| I.15 | (1-Benzyl-1H-indol-3-yl)-[4-(4-hydroxyphenyl)-piperazin-1-yl]-methanone | 3.05 (s, 4H), 3.80 (s, 4H), 5.53 (s, 2H), 6.72 (d, 2H, J = 8.85 Hz), 6.88 (d, 2H, J = 8.87 Hz), 7.17-7.24 (m, 2H), 7.32 (d, 3H, J = 7.37 Hz), 7.38 (d, 2H, J = 7.17 Hz), 7.56 (d, 1H, J = 7.38 Hz), 7.78 (d, 1H, J = 7.58 Hz), 8.02 (s, 1H), 8.94 (s, 1H). |

TABLE 2-continued

Chemical Name and ¹H NMR Data for Compound of Formula I

| Compound No. | Structure | IUPAC Name | ¹H NMR (δ ppm) in DMSO-d₆ as solvent, 500 MHz |
|---|---|---|---|
| I.16 | | N-{(1S)-1-Benzyl-2-[4-(4-hydroxyphenyl)-piperazin-1-yl]-2-oxoethyl}-acetamide | 1.98 (s, 3H), 2.56 (m, 1H), 2.65-2.70 (m, 1H), 2.71-2.82 (m, 3H), 2.95-3.15 (m, 1H), 3.49-3.52 (m, 1H), 3.52-3.65 (m, 3H), 5.02 (q, 1H, J₁ = 8.08 Hz, J₂ = 7.60 Hz), 6.69 (d, 2H, J = 8.87 Hz), 6.78 (d, 2H, J = 8.92 Hz), 7.20-7.25 (m, 1H), 7.27-7.34 (m, 4H), 8.41 (d, 1H), J = 8.34 Hz), 8.94 (s, 1H). |
| I.17 | | 1-[4-(4-Hydroxyphenyl)-piperazin-1-yl]-2-phenylethane-1,2-dione | 2.95 (t, 2H, J = 5.04 Hz), 3.13 (t, 2H, J = 5.14 Hz), 3.45 (t, 2H, J = 5.01 Hz), 3.82 (t, 2H, J = 5.14 Hz), 6.72 (d, 2H, J = 8.92 Hz), 6.86 (d, 2H, J = 8.93 Hz), 7.69 (t, 2H, J = 7.80 Hz), 7.82-7.85 (m, 1H), 7.98 (dd, 2H, J₁ = 8.32 Hz, J₂ = 1.19 Hz), 8.98 (s, 1H) |
| I.18 | | (1-Butyl-1H-indol-3-yl)-[4-(4-hydroxyphenyl)-piperazin-1-yl]-methanone | 0.95 (t, 3H, J = 7.32 Hz), 1.29-1.34 (m, 2H), 1.80-1.83 (m, 2H), 3.00-3.08 (m, 4H), 3.80 (m, 4H), 4.28 (t, 2H, J = 6.89 Hz), 6.71 (d, 2H, J = 8.60 Hz), 6.88 (d, 2H, J = 8.52 Hz), 7.18 (t, 1H, J = 7.27 Hz), 7.26 (t, 1H, J = 7.49 Hz), 7.60 (d, 1H, J = 8.11 Hz), 7.77 (d, 1H, J = 7.92 Hz), 7.85 (s, 1H), 8.94 (s, 1H) |
| I.19 | | N-{(1R)-2-[4-(4-Hydroxyphenyl)-piperazin-1-yl]-2-oxo-1-phenylethyl}acetamide | 1.92 (s, 3H), 2.81-2.97 (m, 4H), 3.43-3.64 (m, 4H), 5.96 (d, 1H, J = 7.90 Hz), 6.68 (d, 2H, J = 8.89 Hz), 6.78 (d, 2H, J = 8.93 Hz), 7.35-7.37 (m, 1H), 7.40-7.44 (m, 4H), 8.57 (d, 1H, J = 7.87 Hz), 8.92 (s, 1H) |
| I.20 | | (2,6-Diphenyl-4-pyridyl)-[4-(4-hydroxyphenyl)-piperazin-1-yl]methanone | 3.03 (m, 2H), 3.15 (m, 2H), 3.54 (m, 2H), 3.88 (m, 2H), 6.71 (d, J = 8.75 Hz, 2H), 6.87 (d, J = 8.68 Hz, 2H), 7.54-7.56 (m, 2H), 7.59-7.62 (m, 4H), 8.01 (s, 2H), 8.33 (d, J = 7.45 Hz, 4H), 8.95 (s, 1H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.21 | Anthracen-9-yl-[4-(4-hydroxyphenyl)-piperazin-1-yl]-methanone | 2.77 (t, 2H, J = 4.56 Hz), 3.11 (t, 2H, J = 4.73 Hz), 3.27 (t, 2H, J = 4.78 Hz), 4.15 (t, 2H, J = 4.75 Hz), 6.69 (d, 2H, J = 8.75 Hz), 6.82 (d, 2H, J = 8.80 Hz), 7.61-7.68 (m, 4H), 7.94 (d, 2H, J = 8.39 Hz), 8.22 (d, 2H, J = 8.17 Hz), 8.75 (s, 1H), 8.94 (s, 1H) |
| I.22 | [4-(4-Hydroxyphenyl)-piperazin-1-yl]-phenanthren-9-yl-methanone | 2.81-2.82 (m, 1H), 2.95 (m, 1H), 3.19 (m, 2H), 3.33 (m, 2H), 3.93-3.95 (m, 1H), 4.05-4.07 (m, 1H), 6.70 (d, 2H, J = 8.68 Hz), 6.84 (d, 2H, J = 8.72 Hz), 7.74-7.78 (m, 2H), 7.81 (t, 2H, J = 7.49 Hz), 7.91 (d, 1H, J = 7.67 Hz), 7.92 (s, 1H), 8.11 (d, 1H, J = 7.83 Hz), 8.93 (d, 1H, J = 8.26 Hz), 8.97 (s, 1H), 8.98 (d, 1H, J = 8.43 Hz) |
| I.23 | 1-[4-(4-Hydroxyphenyl)-piperazin-1-yl]-3-naphthalen-2-yl-propan-1-one | 2.81 (t, 2H, J = 7.69 Hz), 2.87 (t, 2H, J = 4.61 Hz), 2.90 (t, 2H, J = 4.84 Hz), 3.06 (t, 2H, J = 7.65 Hz), 3.60 (t, 2H, J = 4.58 Hz), 3.62 (t, 2H, J = 5.00 Hz), 6.69 (d, 2H, J = 8.82 Hz), 6.79 (d, 2H, J = 8.85 Hz), 7.48-7.54 (m, 3H), 7.79 (s, 1H), 7.87-7.92 (m, 3H), 8.93 (s, 1H) |
| I.24 | [4-(4-Hydroxyphenyl)-piperazin-1-yl]-quinolin-3-yl-methanone | 3.03-3.13 (m, 4H), 3.61 (s, 2H), 3.88 (s, 2H), 6.67 (d, 2H, J = 8.78 Hz), 6.87 (d, 2H, J = 8.82 Hz), 7.57 (t, 1H, J = 7.79 Hz), 7.91 (t, 1H, J = 7.70 Hz), 8.13 (d, 2H, J = 8.61 Hz), 8.56 (s, 1H), 8.96 (s, 1H), 9.00 (d, 1H, J = 1.54 Hz). |
| I.25 | Anthracen-1-yl-[4-(4-hydroxyphenyl)-piperazin-1-yl]-methanone | 2.80 (m, 1H), 2.91 (m, 1H), 3.22-3.33 (m, 4H), 3.98 (m, 1H), 4.10 (m, 1H), 6.69 (d, 2H, J = 8.79 Hz), 6.84 (d, 2H, J = 8.78 Hz), 7.54 (d, 1H, J = 6.59 Hz), 7.58-7.63 (m, 3H), 8.17 (d, 1H, J = 7.83 Hz), 8.22-8.23 (m, 2H), 8.50 (s, 1H), 8.73 (s, 1H), 8.94 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.26 | (1-Benzyl-indol-4-yl)-[4-(4-hydroxy-phenyl)-piperazin-1-yl]methanone | 7.20-7.50 (m, 6H), 7.13-7.25 (m, 1H), 7.11 (d, J = 7.08 Hz, 2H), 6.84 (d, J = 8.86 Hz, 2H), 6.76 (d, J = 8.85 Hz, 2H), 6.57 (d, J = 3.09 Hz, 1H), 5.35 (s, 2H), 4.58-4.49 (bs, 1H), 3.90-4.10 (m, 2H), 3.40-3.60 (m, 2H), 3.10-3.20 (m, 2H), 2.90-3.00 (m, 2H). |
| I.27 | (3,5-Diphenyl-phenyl)-[4-(4-hydroxy-phenyl)-piperazin-1-yl]methanone | 2.98-3.05 (m, 2H), 3.07-3.15 (m, 2H), 3.61 (s, 2H), 3.86 (s, 2H), 6.71 (d, J = 8.76 Hz, 2H), 6.87 (d, J = 8.81 Hz, 2H), 7.46-7.49 (m, 2H), 7.56 (t, J = 7.65 Hz, 4H), 7.73 (s, 2H), 7.87 (d, J = 7.52 Hz, 4H), 8.05 (s, 1H), 8.95 (s, 1H). |
| I.28 | 1-[4-(4-Hydroxy-phenyl)-piperazin-1-yl]-2-(4-trifluoro-methyl-phenyl)-ethanone | 2.95 (m, 4H), 3.65-3.68 (m, 4H), 3.94 (s, 2H), 6.70 (d, 2H, J = 8.79 Hz), 6.84 (d, 2H, J = 8.81 Hz), 7.51 (d, 2H, J = 7.97 Hz), 7.72 (d, 2H, J = 8.01 Hz), 8.94 (s, 1H) |
| I.29 | [4-(4-Hydroxy-phenyl)-piperazin-1-yl]-imidazo[1,2-a]124yridine-8-yl-methanone | 2.95 (s, 2H), 2.99-3.12 (m, 2H), 3.32-3.33 (m, 2H), 3.87 (s, 2H), 6.71 (d, 2H, J = 8.80 Hz), 6.85 (d, 2H, J = 8.82 Hz), 7.03 (t, 1H, J = 6.81 Hz), 7.32 (d, 1H, J = 7.42 Hz), 7.68 (s, 1H), 8.10 (s, 1H), 8.68 (d, 1H, J = 6.74 Hz), 8.94 (s, 1H). |
| I.30 | [4-(4-Hydroxy-phenyl)-piperazin-1-yl]-(1H-indol-4-yl)-methanone | 2.92-3.09 (m, 4H), 3.87 (m, 4H), 6.44 (s, 1H), 6.70 (d, 2H, J = 8.79 Hz), 6.84 (d, 2H, J = 8.83 Hz), 7.06 (d, 1H, J = 7.11 Hz), 7.20 (t, 1H, J = 7.65 Hz), 7.48 (t, 1H, J = 2.56 Hz), 7.53 (d, 1H, J = 8.13 Hz), 8.93 (s, 1H), 11.38 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.31 | [4-(4-Hydroxy-phenyl)-piperazin-1-yl]-[3-(4-trifluoro-methyl-phenyl)-imidazo[1,2-a]1,2,4yridine-8-yl]-methanone | 2.95 (s, 2H), 2.99-3.12 (m, 2H), 3.32-3.33 (m, 2H), 3.87 (s, 2H), 6.71 (d, 2H, J = 8.80 Hz), 6.85 (d, 2H, J = 8.82 Hz), 7.03 (m, 1H), 7.32 (m, 1H), 8.13-8.25 (m, 5H), 8.68 (d, 1H, J = 6.74 Hz), 8.94 (s, 1H). |
| I.32 | 2-Hydroxy-5-(4-phenylacetyl-piperazin-1-yl)-benzoic acid | 2.95 (s, 2H), 3.00 (s, 2H), 3.66 (m, 4H), 3.67 (s, 2H), 6.90-6.92 (m, 1H), 7.26-7.30 (m, 5H), 7.35-7.38 (m, 2H). |
| I.33 | [4-(4-Hydroxy-phenyl)-piperazin-1-yl]-(2-morpholino-6-phenyl-4-pyridyl)-methanone | 2.99-3.03 (m, 2H), 3.08-3.12 (m, 2H), 3.47-3.52 (m, 2H), 3.63-3.67 (m, 4H), 3.77-3.84 (m, 6H), 6.71 (d, J = 8.76 Hz, 2H), 6.84-6.87 (m, 3H), 7.30 (s, 1H), 7.46-7.53 (m, 3H), 8.14 (d, J = 7.39 Hz, 2H), 8.94 (s, 1H). |
| I.34 | [4-(4-Hydroxy-phenyl)-piperazin-1-yl]-(2-phenyl-4-pyridyl)-methanone | 2.94-3.00 (m, 2H), 3.12-3.19 (m, 2H), 3.42-3.48 (m, 2H), 3.84-3.94 (m, 2H), 6.70-6.74 (m, 2H), 6.85-6.90 (m, 2H), 7.40-7.44 (s, 1H), 7.50-7.70 (m, 3H), 8.04 (s, 1H), 8.19-8.21 (m, 2H), 8.81-8.82 (m, 1H), 8.95 (s, 1H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.35 | [4-(4-Hydroxy-phenyl)-piperazin-1-yl]-(2-morpholino-4-pyridyl)-methanone | 2.97-2.98 (m, 2H), 3.07-3.10 (m, 2H), 3.43-3.46 (m, 2H), 3.53 (t, J = 4.80 Hz, 4H), 3.74 (t, J = 4.80 Hz, 4H), 3.77-3.82 (m, 2H), 6.70-6.74 (m, 3H), 6.86-6.90 (m, 3H), 8.24 (d, J = 4.85 Hz, 1H), 8.97 (s, 1H). |
| I.36 | (2-Chloro-6-morpholino-4-pyridyl)-[4-(4-hydroxy-phenyl)-piperazin-1-yl]methanone | 2.95-3.01 (m, 2H), 3.05-3.09 (m, 2H), 3.43-3.48 (m, 2H), 3.53-3.57 (m, 4H), 3.70-3.75 (m, 4H), 3.75-3.78 (m, 2H), 6.70-6.72 (m, 2H), 6.76 (s, 1H), 6.84 (s, 1H), 6.85-6.87 (m, 2H), 8.95 (s, 1H). |
| I.37 | 5-[4-(2,6-Diphenyl-pyridine-4-carbonyl)-piperazin-1-yl]-2-hydroxy-benzonitrile | 3.10-3.14 (m, 2H), 3.22-3.25 (m, 2H), 3.52-3.57 (m, 2H), 3.86-3.90 (m, 2H), 6.96-6.70 (m, 1H), 7.18-7.29 (m, 2H), 7.52-7.64 (m, 6H), 8.02 (s, 1H), 8.29-8.36 (m, 4H) 10.54 (s, 1H). |
| I.38 | 5-[4-(2,6-Diphenyl-pyridine-4-carbonyl)-piperazin-1-yl]-2-hydroxy-benzoic acid | 3.09-3.14 (m, 2H), 3.20-3.24 (m, 2H), 3.54-3.53 (m, 2H), 3.87-3.93 (m, 2H), 6.94 (d, J = 8.90 Hz, 1H), 7.31-7.36 (m, 2H), 7.54-7.56 (m, 2H), 7.59-7.62 (m, 4H), 8.02 (s, 2H), 8.33 (d, J = 7.30 Hz, 4H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.39 | 3-[4-[4-(4-Hydroxy-phenyl)-piperazine-1-carbonyl]-2-pyridyl]-benzoic acid | 2.98-3.01 (m, 2H), 3.11-3.15 (m, 2H), 3.47-3.51 (m, 2H), 3.83-3.87 (m, 2H), 6.71 (d, J = 8.90 Hz, 2H), 6.86 (d, J = 8.95 Hz, 2H), 7.47 (dd, J₁ = 1.15 Hz, J₂ = 4.85 Hz, 1H), 7.66 (t, J = 7.72 Hz, 1H), 8.08 (d, J = 7.65 Hz, 1H), 8.10 (s, 1H), 8.39 (d, J = 7.65 Hz, 1H), 8.77 (s, 1H), 8.84 (d, J = 4.85 Hz, 1H), 8.98 br s, 1H). |
| I.40 | 1-[4-(4-Hydroxy-phenyl)-piperazin-1-yl]-3,3-diphenyl-prop-2-en-1-one | 2.51 (t, J = 4.72 Hz, 2H), 2.78 (t, J = 4.55 Hz, 2H), 3.44 (t, J = 4.80 Hz, 2H), 3.53 (t, J = 4.58 Hz, 2H), 6.55 (s, 1H), 6.67 (d, J = 8.95 Hz, 2H), 6.73 (d, J = 9.00 Hz, 2H), 7.22-7.24 (m, 2H), 7.35-7.38 (m, 2H), 7.40-7.46 (m, 6H), 8.93 (s, 1H). |
| I.41 | 3-[4-[4-(4-Hydroxy-phenyl)-piperazine-1-carbonyl]-6-morpholino-2-pyridyl]-benzoic acid | 2.99-3.01 (m, 2H), 3.09-3.13 (m, 2H), 3.49-3.52 (m, 2H), 3.64-3.68 (m, 4H), 3.79-3.85 (m, 6H), 6.71 (d, J = 8.90 Hz, 2H), 6.89 (d, J = 8.90 Hz, 2H), 6.89 (s, 1H), 7.35 (s, 1H), 7.65 (t, J = 7.75 Hz, 1H), 8.04 (d, J = 7.60 Hz, 1H), 8.37 (d, J = 7.95 Hz, 1H), 8.65 (s, 1H), 8.95 (s, 1H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.42 | 4-[4-[4-(4-Hydroxy-phenyl)-piperazine-1-carbonyl]-6-morpholino-2-pyridyl]-benzoic acid | 3.00 (m, 1H), 3.10 (m, 1H), 3.43-3.47 (m, 1H), 3.49 (m, 1H), 3.66-3.70 (m, 5.5H), 3.80-3.90 (m, 6.5H), 6.71 (d, J = 8.88, 1H), 6.87 (d, J = 8.90, 1H), 6.91, 7.39 (s, 1H), 7.31 (s, 1H), 7.68-7.78 (m, 1H), 8.05-8.10 (m, 3H), 8.23-8.29 (m, 3H), 8.95 (s, 1H). |
| I.43 | [4-(5-Hydroxy-pyridin-2-yl)-piperazin-1-yl]-(1H-indol-3-yl)-methanone | 3.42 (t, 4H, J = 4.84 Hz), 3.78 (t, 4H, J = 4.89 Hz), 6.81 (d, 1H, J = 8.97 Hz), 7.13-7.17 (m, 2H), 7.21 (t, 1H, J = 7.50 Hz), 7.49 (d, 1H, J = 8.06 Hz), 7.75 (d, 1H, J = 7.89 Hz), 7.80 (dd, 2H, J₁ = 14.37 Hz, J₂ = 2.66 Hz), 9.10 (s, 1H), 11.66 (s, 1H) |
| I.44 | Acridin-9-yl-[4-(5-hydroxy-pyridin-2-yl)-piperazin-1-yl]-methanone | 3.14-3.17 (m, 4H), 3.67 (t, 2H, J = 4.9 Hz), 4.12 (t, 2H, J = 4.95 Hz), 6.78 (d, 1H, J = 8.99 Hz), 7.12 (dd, 1H, J₁ = 8.95 Hz, J₂ = 2.87 Hz), 7.75 (t, 2H, J = 7.55 Hz), 7.78 (d, 1H, J = 2.81 Hz), 7.96 (t, 2H, J = 7.60 Hz), 8.02 (d, 2H, J = 8.6 Hz), 8.28 (d, 2H, J = 8.77 Hz), 9.13 (s, 1H) |
| I.45 | 1-[4-(5-Hydroxy-pyridin-2-yl)-piperazin-1-yl]-3-phenyl-propan-1-one | 2.71 (t, 2H, J = 7.75 Hz), 2.88 (t, 2H, J = 7.70 Hz), 3.29 (m, 4H), 3.55-3.60 (m, 4H), 6.78 (d, 1H, J = 8.98 Hz), 7.12 (dd, 1H, J₁ = 8.93 Hz, J₂ = 2.86 Hz), 7.22 (t, 1H, J = 6.63 Hz), 7.29-7.34 (m, 4H), 7.79 (d, 1H, J = 2.75 Hz), 9.08 (s, 1H) |
| I.46 | 1-[4-(4-Hydroxy-phenyl)-piperazin-1-yl]-3-naphthalen-1-yl-propan-1-one | 2.80-2.83 (m, 4H), 2.90 (t, 2H, J = 4.82 Hz), 3.36 (t, 2H, J = 7.77 Hz), 3.51-3.64 (m, 4H), 6.70 (d, 2H, J = 8.82 Hz), 6.81 (d, 2H, J = 8.86 Hz), 7.46-7.50 (m, 2H), 7.57 (t, 1H, J = 7.36 Hz), 7.62 (t, 1H, J = 7.45 Hz), 7.82-7.84 (m, 1H), 7.98 (d, 1H, J = 7.95 Hz), 8.12 (d, 1H, J = 8.35 Hz), 8.96 (s, 1H) |

TABLE 2-continued

Chemical Name and ¹H NMR Data for Compound of Formula I

| Compound No. | | IUPAC Name | ¹H NMR (δ ppm) in DMSO-d₆ as solvent, 500 MHz |
|---|---|---|---|
| I.47 | | 3-[4-(4-Hydroxyphenyl)-piperazine-1-carbonyl]-1H-quinolin-4-one | 2.98-3.08 (m, 4H), 3.44-3.48 (br s, 2H), 3.76-3.82 (br s, 2H), 6.71 (d, J = 8.85 Hz, 2H), 6.86 (d, J = 8.45 Hz, 2H), 7.42-7.45 (m, 1H), 7.66 (d, J = 8.20 Hz, 1H), 7.73-7.77 (m, 1H), 8.20-8.21 (m, 2H), 8.13 (s, 1H), 12.29 (d, J = 6.10 Hz, 1H). |
| I.48 | | 1-[4-(5-Hydroxy-2-pyridyl)-piperazin-1-yl]-2,2-diphenyl-ethanone | 3.03-3.08 (m, 2H), 3.28-3.32 (m, 2H), 3.62-3.70 (m, 4H), 5.64 (s, 1H), 6.75 (d, J = 8.85 Hz, 1H), 7.10 (dd, J₁ = 2.72 Hz, J₂ = 8.95 Hz, 1H), 7.26-7.38 (m, 10H), 7.76 (d, J = 2.70 Hz, 1H), H 9.10 (s, 1H). |
| I.49 | | 1-[4-(4-Hydroxyphenyl)-piperazin-1-yl]-2-(2-phenoxyphenyl)-ethanone | 2.69 (m, 1H), 2.85-2.90 (m, 3H), 3.58-3.62 (m, 4H), 3.76 (s, 2H), 6.69 (d, J = 8.83 Hz, 2H), 6.80 (d, J = 8.87 Hz, 2H), 6.89 (d, J = 7.58 Hz, 1H), 6.98 (d, J = 7.77 Hz, 2H), 7.13-7.19 (m, 2H), 7.29-7.32 (m, 1H), 7.36-7.41 (m, 3H), 8.93 (s, 1H). |
| I.50 | | [4-(4-Hydroxyphenyl)-piperazin-1-yl]-[2-(1-piperidyl)-4-pyridyl]-methanone | 1.50-1.60 (m, 4H), 1.63-1.68 (m, 2H), 2.95-3.00 (m, 2H), 3.05-3.10 (m, 2H), 3.40-3.45 (m, 2H), 3.58-3.60 (m, 4H), 3.75-3.80 (m, 2H), 6.58-6.60 (m, 1H), 6.71 (d, J = 7.58 Hz, 2H), 6.80 (s, 1H), 6.68 (d, J = 8.90 Hz, 2H), 8.19 (d, J = 4.97 Hz, 1H), 8.95 (s, 1H). |

TABLE 2-continued

Chemical Name and ¹H NMR Data for Compound of Formula I

| Compound No. | IUPAC Name | ¹H NMR (δ ppm) in DMSO-d$_6$ as solvent, 500 MHz |
|---|---|---|
| I.51 | 1-[4-(5-Hydroxy-pyridin-2-yl)-piperazin-1-yl]-3-(1H-indol-3-yl)-propan-1-one | 2.76 (t, 2H, J = 7.74 Hz), 2.94-3.00 (m, 2H), 3.22-3.29 (m, 4H), 3.55 (t, 2H, J = 4.88 Hz), 3.61 (t, 2H, J = 4.97 Hz), 6.77 (d, 1H, J = 9.00 Hz), 7.02 (t, 1H, J = 7.04 Hz), 7.09-7.13 (m, 2H), 7.20 (d, 1H, J = 2.06 Hz), 7.37 (d, 1H, J = 8.04 Hz), 7.57 (d, 1H, J = 7.81 Hz), 7.79 (d, 1H, J = 2.89 Hz), 9.10 (s, 1H), 10.84 (s, 1H) |
| I.52 | 1-[4-(4-Hydroxy-3-methyl-phenyl)-piperazin-1-yl]-2-phenyl-ethanone | 2.12 (s, 3H), 2.87-2.92 (m, 4H), 3.64 (m, 4H), 3.80 (s, 2H), 6.62 (d, 1H, J = 8.29 Hz), 6.68 (d, 1H, J = 8.52 Hz), 6.74 (s, 1H), 7.28-7.30 (m, 3H), 7.35-7.37 (m, 2H), 8.78 (s, 1H) |
| I.53 | 3-Anthracen-9-yl-1-[4-(4-hydroxy-phenyl)-piperazin-1-yl]-propan-1-one | 2.65 (t, 2H, J = 4.80 Hz), 2.81-2.86 (m, 4H), 3.37 (t, 2H, J = 4.89 Hz), 3.63 (t, 2H, J = 5.03 Hz) 3.92 (t, 2H, J = 7.93 Hz), 6.68 (d, 2H, J = 8.95 Hz), 6.77 (d, 2H, J = 9.00 Hz), 7.55-7.58 (m, 2H), 7.61-7.64 (m, 2H), 8.14 (d, 2H, J = 8.28 Hz), 8.35 (d, 2H, J = 8.87 Hz), 8.56 (s, 1H), 8.94 (s, 1H) |
| I.54 | 3-[4-(5-Hydroxy-2-pyridyl)-piperazine-1-carbonyl]-1H-quinolin-4-one | 3.35-3.44 (m, 6H), 3.74-3.78 (br s, 2H), 6.82 (d, J = 9.00 Hz, 1H), 7.15 (dd, J1 = 2.85 Hz, J2 = 8.95 Hz, 1H), 7.44 (t, J = 7.50 Hz, 1H), 7.67 (d, J = 8.20 Hz, 1H), H 7.73-7.77 (m, 1H), 7.80 (d, J = 2.80 Hz, 1H), 8.20-8.22 (m, 2H), 9.15 (s, 1H), 12.32 (d, J = 6.05 Hz, 1H). |
| I.55 | 2-(1-Adamantyl)-1-[4-(5-hydroxy-2-pyridyl)-piperazin-1-yl]-ethanone | 1.63-1.71 (m, 12H), 1.96 (s, 3H), 2.19 (s, 2H), 3.28-3.31 (m, 2H), 3.33-3.36 (m, 2H), 3.61-3.67 (m, 4H), 6.80 (d, J = 8.95 Hz, 1H), 7.13 (dd, J$_1$ = 2.97 Hz, J$_2$ = 9.00 Hz, 1H), 7.80 (d, J = 2.85 Hz, 1H), 9.11 (s, 1H). |

TABLE 2-continued

Chemical Name and ¹H NMR Data for Compound of Formula I

| Compound No. | | IUPAC Name | ¹H NMR (δ ppm) in DMSO-d₆ as solvent, 500 MHz |
|---|---|---|---|
| I.56 | 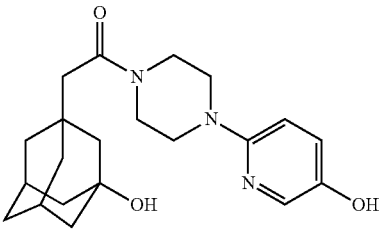 [SMILES: CC1(O)CC2CCCC(CC(=O)N3CCN(c4ccc(O)cn4)CC3)(C2)C1] | 2-(3-Hydroxy-1-adamantyl)-1-[4-(5-hydroxy-2-pyridyl)-piperazin-1-yl]ethanone | 1.48-1.62 (m, 12H), 2.09-2.15 (bs, 2H), 2.24 (s, 2H), 3.27-3.33 (m, 2H), 3.59-3.68 (m, 4H), 4.41 (s, 1H), 6.80 (d, J = 8.99 Hz, 1H), 7.10 (dd, $J_1$ = 8.98 Hz, $J_2$ = 2.99 Hz, 1H), 7.80 (d, J = 2.90 Hz, 1H), 9.11 (s, 1H). |
| I.57 | 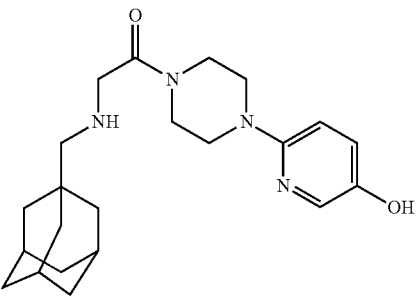 [SMILES: CC1CC2CCCC(CNCC(=O)N3CCN(c4ccc(O)cn4)CC3)(C1)C2] | 2-(1-Adamantyl-methylamino)-1-[4-(5-hydroxy-2-pyridyl)-piperazin-1-yl]-ethanone | 1.39 (m, 1H), 1.54 (m, 6H), 1.65 (d, J = 11.68 Hz, 3H), 1.72 (d, J = 11.96 Hz, 3H), 1.96-1.98 (m, 3H), 2.23 (m, 2H), 3.32-3.33 (m, 2H), 3.45 (m, 2H), 3.55-3.60 (m, 6H), 6.80 (d, J = 8.92 Hz, 1H), 7.13 (dd, $J_1$ = 8.92 Hz, $J_2$ = 2.90 Hz, 1H), 7.79 (d, J = 2.75 Hz, 1H), 9.10 (s, 1H). |
| I.58 | 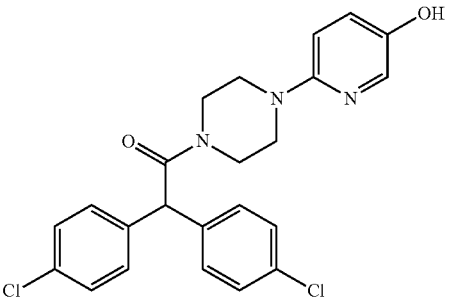 [SMILES: O=C(C(c1ccc(Cl)cc1)c1ccc(Cl)cc1)N1CCN(c2ccc(O)cn2)CC1] | 2,2-bis(4-Chloro-phenyl)-1-[4-(5-hydroxy-2-pyridyl)-piperazin-1-yl]ethanone | 3.07-3.13 (m, 2H), 3.28-3.34 (m, 2H), 3.60-3.64 (m, 2H), 3.65-3.70 (m, 2H), 5.73 (s, 1H), 6.76 (d, J = 9 Hz, 1H), 7.10 (dd, $J_1$ = 8.97 Hz, $J_2$ = 2.96 Hz, 1H), 7.30-7.35 (m, 4H), 7.42-7.47 (m, 4H), 7.77 (d, J = 2.88 Hz, 1H), 9.09 (s, 1H). |
| I.59 | 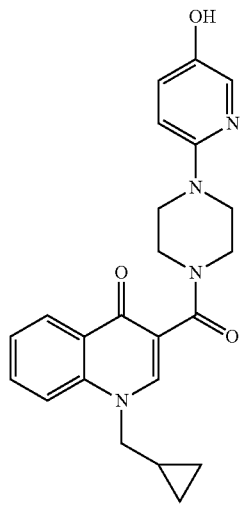 [SMILES: O=C(c1cn(CC2CC2)c2ccccc2c1=O)N1CCN(c2ccc(O)cn2)CC1] | 1-(Cyclo-propyl-methyl)-3-[4-(5-hydroxy-2-pyridyl)-piperazine-1-carbonyl]-quinolin-4-one | 0.50-0.51 (m, 2H), 0.58-0.60 (m, 2H), 1.30-1.60 (m, 1H), 3.30-3.40 (m, 2H), 3.41-3.55 (m, 4H), 3.70-3.90 (m, 2H), 4.27 (d, J = 7.08 Hz, 2H), 6.80 (d, J = 8.99 Hz, 1H), 7.14 (dd, $J_1$ = 2.94 Hz, $J_2$ = 8.96 Hz, 1H), 7.51-7.54 (m, 1H), 7.78-7.82 (m, 1H), 7.83-7.89 (m, 1H), 7.96-8.01 (m, 1H), 8.29-8.34 (m, 1H), 8.36 (s, 1H), 9.10 (s, 1H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.60 | 2-Fluoren-9-ylidene-1-[4-(5-hydroxy-2-pyridyl)-piperazin-1-yl]ethanone | 9.11 (s, 1H), 7.99-8.05 (m, 1H), 7.88-7.94 (m, 2H), 7.78-7.84 (m, 2H), 7.32-7.53 (m, 5H), 7.11-7.16 (m, 1H), 6.75-6.85 (m, 1H), 3.85-3.90 (m, 2H), 3.64-3.70 (m, 2H), 3.45-3.55 (m, 2H), 3.27-3.35 (m, 2H). |
| I.61 | 2-(9H-Fluoren-9-yl)-1-[4-(5-hydroxy-2-pyridyl)-piperazin-1-yl]ethanone | 9.10 (s, 1H), 7.90-7.95 (m, 2H), 7.78-7.82 (m, 1H), 7.65-7.69 (m, 2H), 7.40-7.46 (m, 2H), 7.32-7.38 (m, 2H), 7.11-7.16 (m, 1H), 6.57-6.58 (m, 1H), 4.51 (t, J = 6.96 HZ, 1H), 3.75-3.85 (m, 2H), 3.40-3.60 (m, 4H), 3.25-3.35 (m, 2H), 2.90 (d, J = 7.06 Hz, 2H). |
| I.62 | 1-[4-(5-Hydroxy-pyridin-2-yl)-piperazin-1-yl]-2-(1H-indol-3-yl)-ethanone | 3.20 (t, 2H, J = 4.94 Hz), 3.27 (t, 2H, J = 5.12 Hz), 3.62 (t, 2H, J = 5.05 Hz), 3.66 (t, 2H, J = 4.93 Hz), 3.86 (s, 2H), 6.76 (d, 1H, J = 8.90 Hz), 7.00-7.03 (m, 1H), 7.09-7.13 (m, 2H), 7.27 (d, 1H, J = 2.27 Hz), 7.38 (d, 1H, J = 8.08 Hz), 7.62 (d, 1H, J = 7.90 Hz), 7.77 (d, 1H, J = 2.84 Hz), 9.08 (s, 1H), 10.95 (s, 1H) |
| I.63 | [4-(5-Hydroxy-pyridin-2-yl)-piperazin-1-yl]-(1H-pyrrolo[2,3-b]pyridin-3-yl)-methanone | 3.43 (t, 4H, J = 4.83 Hz), 3.80 (t, 4H, J = 5.05 Hz), 6.81 (d, 1H, J = 8.99 Hz), 7.14 (dd, 1H, J₁ = 8.95 Hz, J₂ = 2.98 Hz), 7.22 (dd, 1H, J₁ = 7.91 Hz, J₂ = 4.64 Hz), 7.81 (d, 1H, J = 2.90 Hz), 7.93 (s, 1H), 8.16 (dd, 1H, J₁ = 7.91 Hz, J₂ = 1.48 Hz), 8.34 (dd, 1H, J₁ = 4.62 Hz, J₂ = 1.47 Hz), 9.11 (s, 1H), 12.25 (s, 1H) |

TABLE 2-continued

Chemical Name and $^1$H NMR Data for Compound of Formula I

| Compound No. | IUPAC Name | $^1$H NMR (δ ppm) in DMSO-$d_6$ as solvent, 500 MHz |
|---|---|---|
| I.64 | Anthracen-9-yl-[4-(5-hydroxy-pyridin-2-yl)-piperazin-1-yl]-methanone | 3.09-3.13 (m, 4H), 3.65 (t, 2H, J = 5.02 Hz), 4.12 (t, 2H, J = 5.06 Hz), 6.77 (d, 1H, J = 9.01 Hz), 7.12 (dd, 1H, J$_1$ = 8.98 Hz, J$_2$ = 2.95 Hz), 7.61-7.66 (m, 4H), 7.77 (d, 1H, J = 2.87 Hz), 7.94 (d, 2H, J = 8.09 Hz), 8.22 (d, 2H, J = 7.43 Hz), 8.75 (s, 1H), 9.12 (s, 1H) |
| I.65 | 1-[4-(5-Hydroxy-pyridin-2-yl)-piperazin-1-yl]-4-phenylbutan-1-one | 1.83-1.89 (m, 2H), 2.41 (t, 2H, J = 7.39 Hz), 2.65 (t, 2H, J = 7.70 Hz), 3.30 (t, 2H, J = 4.96 Hz), 3.35 (t, 2H, J = 5.07 Hz), 3.55 (t, 2H, J = 5.21 Hz), 3.60 (t, 2H, J = 4.94 Hz), 6.80 (d, 1H, J = 8.98 Hz), 7.12 (dd, 1H, J$_1$ = 8.93 Hz, J$_2$ = 2.98 Hz), 7.21-7.26 (m, 3H), 7.33 (t, 2H, J = 7.50 Hz), 7.79 (d, 1H, J = 2.91 Hz), 9.10 (s, 1H) |
| I.66 | 1-[4-(5-Hydroxy-pyridin-2-yl)-piperazin-1-yl]-3-pyridin-4-yl-propan-1-one | 2.78 (t, 2H, J = 7.5 Hz), 2.89 (t, 2H, J = 7.5 Hz), 3.30 (t, 2H, J = 4.9 Hz, 3.33 (t, 2H, J = 4.75 Hz), 3.57-3.61 (m, 4H), 6.79 (d, 1H, J = 8.9 Hz), 7.12 (dd, 1H, J$_1$ = 8.93 Hz, J$_2$ = 2.86 Hz), 7.34 (d, 2H, J = 5.39 Hz), 7.79 (d, 1H, J = 2.84 Hz), 8.49 (d, 2H, J = 5.48 Hz), 9.1 (s, 1H) |
| I.67 | [4-(5-Hydroxy-pyridin-2-yl)-piperazin-1-yl]-indan-2-yl-methanone | 3.18 (d, 4H, J = 8.32 Hz), 3.34 (t, 2H, J = 5.00 Hz), 3.42 (t, 2H, J = 4.98 Hz), 3.65 (t, 2H, J = 5.00 Hz), 3.69-3.78 (m, 3H), 6.83 (d, 1H, J = 8.96 Hz), 7.13-7.20 (m, 3H), 7.23-7.26 (m, 2H), 7.81 (d, 1H, J = 2.92 Hz), 9.16 (s, 1H) |
| I.68 | 1-[4-(5-Hydroxy-pyridin-2-yl)-piperazin-1-yl]-5-phenylpentan-1-one hydrochloride | 1.55-1.60 (m, 2H), 1.62-1.68 (m, 2H), 2.43 (t, 2H, J = 7.3 Hz), 2.65 (t, 2H, J = 7.4 Hz), 3.65 (m, 8H), 7.20-7.28 (m, 3H), 7.31-7.34 (m, 3H), 7.65 (m, 2H), 10.20 (br-s, 1H) |

TABLE 2-continued

Chemical Name and $^1$H NMR Data for Compound of Formula I

| Compound No. | IUPAC Name | $^1$H NMR ($\delta$ ppm) in DMSO-$d_6$ as solvent, 500 MHz |
|---|---|---|
| I.69 | 3-[4-(5-Hydroxy-2-pyridyl)-piperazine-1-carbonyl]-1-methyl-quinolin-4-one | 3.35-3.39 br s, 2H), 3.41-3.45 (br s, 4H), 3.76-3.79 (br s, 2H), 3.95 (s, 3H), 6.82 (d, J = 5.00 Hz, 1H), 7.16 (dd, J$_1$ = 2.45 Hz, J$_2$ = 8.87 Hz, 1H), 7.53 (t, J = 7.40 Hz, 1H), 7.77-7.81 (m, 2H), 7.85-7.89 (m, 1H), 8.30 (dd, J$_1$ = 1.15 Hz, J$_2$ = 8.00 Hz, 1H), 8.35 (s, 1H), 9.15 (s, 1H). |
| I.70 | 5-[4-(5-hHydroxy-2-pyridyl)-piperazin-1-yl]-5-oxo-pentanoic acid | 12.10 (bs, 1H), 9.10 (bs, 1H), 7.80 (d, J = 2.92 Hz, 1H), 7.13 (dd, J$_1$ = 5.90 Hz, J$_2$ = 2.98 Hz, 1H), 6.80 (d, J = 8.99 Hz, 1H), 3.55-3.65 (m, 4H), 3.25-3.45 (m, 4H), 2.42 (t, J = 7.42 Hz, 2H), 2.31 (m, 2H), 1.77 (m, 2H). |
| I.71 | [4-(5-Hydroxy-pyridin-2-yl)-piperazin-1-yl]-(1-methyl-1H-indol-3-yl)-methanone | 3.42 (t, 4H, J = 5.09 Hz), 3.78 (t, 4H, J = 5.11 Hz), 3.89 (s, 3H), 6.82 (d, 1H, J = 8.98 Hz), 7.14 (dd, 1H, J$_1$ = 8.96 Hz, J$_2$ = 3.00 Hz), 7.19-7.22 (m, 1H), 7.27-7.30 (m, 1H), 7.55 (d, 1H, J = 8.22 Hz), 7.78 (d, 1H, J = 7.91 Hz), 7.81 (d, 1H, J = 2.9 Hz), 7.82 (s, 1H), 9.10 (s, 1H) |
| I.72 | 1-[4-(5-Hydroxy-pyridin-2-yl)-piperazin-1-yl]-3-(3-trifluoromethylphenyl)-propan-1-one | 2.78 (t, 2H, J = 7.65 Hz), 2.98 (t, 2H, J = 7.61 Hz), 3.28-3.31 (m, 4H), 3.56-3.61 (m, 4H), 6.78 (d, 1H, J = 8.99 Hz), 7.12 (dd, 1H, J$_1$ = 8.96 Hz, J$_2$ = 2.99 Hz), 7.54-7.59 (m, 2H), 7.63 (d, 1H, J = 7.10 Hz), 7.68 (s, 1H), 7.79 (d, 1H, J = 2.90 Hz), 9.09 (s, 1H) |
| I.73 | 3-[4-(5-Hydroxy-2-pyridyl)-piperazine-1-carbonyl]-chromen-2-one | 3.34-3.38 (m, 2H), 3.44-3.47 (m, 2H), 3.53-3.56 (m, 2H), 3.75-3.77 (m, 2H), 6.82 (d, J = 9.00 Hz, 1H), 7.14 (dd, J$_1$ = 3.00 Hz, J$_2$ = 9.00 Hz, 1H), 7.45-7.48 (m, 1H), 7.52 (d, J = 8.25 Hz, 1H), 7.74 (td, J$_1$ = 1.55 Hz, J$_2$ = 7.86 Hz, 1H), 7.80 (d, J = 2.90 Hz, 1H), 7.83 (dd, J$_1$ = 1.55 Hz, J$_2$ = 7.86 Hz, 1H), 8.29 (s, 1H), 9.13 (s, 1H). |

TABLE 2-continued

Chemical Name and ¹H NMR Data for Compound of Formula I

| Compound No. | IUPAC Name | ¹H NMR (δ ppm) in DMSO-$d_6$ as solvent, 500 MHz |
|---|---|---|
| I.74 | 1-[4-(5-Hydroxy-2-pyridyl)-piperazin-1-yl]-3,3-diphenyl-prop-2-en-1-one | 2.91-2.93 (m, 2H), 3.15-3.17 (m, 2H), 3.40-3.42 (m, 2H), 3.49-3.51 (m, 2H), 6.56 (s, 1H), 6.70 (d, J = 9.05 Hz, 1H), 7.11 (dd, $J_1$ = 3.00 Hz, $J_2$ = 8.95 Hz, 1H), 7.22-7.24 (m, 2H), 7.35-7.39 (m, 3H), 7.41-7.46 (m, 5H), 7.76 (d, J = 2.85 Hz, 1H), 9.07 (s, 1H). |
| I.75 | 1-[4-(5-Hydroxy-2-pyridyl)-piperazin-1-yl]-3,3-diphenyl-propan-1-one | 3.18-3.20 (m, 3H), 3.22-3.24 (m, 3H), 3.50-3.52 (m, 2H), 3.62-3.65 (m, 2H), 4.56 (t, J = 7.45 Hz, 1H), 6.76 (d, J = 9.00 Hz, 1H), 7.12 (dd, $J_1$ = 2.95 Hz, $J_2$ = 9.00 Hz, 1H), 7.17-7.20 (m, 2H), 7.30 (t, J = 7.62 Hz, 4H), 7.37-7.39 (m, 4H), 7.79 (d, J = 2.90 Hz, 1H), 9.08 (s, 1H). |
| I.76 | (5-Chloro-thiophen-2-yl)-[4-(5-hydroxy-pyridin-2-yl)-piperazin-1-yl]-methanone | 3.44 (t, 4H, J = 5.22 Hz), 3.79 (m, 4H), 6.81 (d, 1H, J = 8.86 Hz), 7.15 (dd, 1H, $J_1$ = 8.95 Hz, $J_2$ = 3.00 Hz), 7.23 (d, 1H, J = 3.99 Hz), 7.42 (d, 1H, J = 3.99 Hz), 7.80 (s, 1H), 7.81 (s, 1H), 9.11 (s, 1H) |
| I.77 | (E)-1-[4-(5-Hydroxy-pyridin-2-yl)-piperazin-1-yl]-3-(4-nitro-phenyl)-propenone | 3.36 (m, 4H), 3.69 (m, 2H), 3.83 (m, 2H), 6.78 (d, 1H, J = 8.94 Hz), 7.09 (dd, 1H, $J_1$ = 8.93 Hz, $J_2$ = 2.99 Hz), 7.55 (d, 1H, J = 15.48 Hz), 7.60 (d, 1H, J = 15.47 Hz), 7.75 (d, 1H, J = 2.7 Hz), 8.03 (d, 2H, J = 8.85 Hz), 8.25 (d, 2H, J = 8.84 Hz), 9.05 (s, 1H) |
| I.78 | (E)-3-(4-Chlorophenyl)-1-[4-(5-hydroxy-pyridin-2-yl)-piperazin-1-yl]-propenone | 3.39 (m, 4H), 3.72 (m, 2H), 3.86 (m, 2H), 6.83 (d, 1H, J = 8.99 Hz), 7.14 (dd, 1H, $J_1$ = 8.96 Hz, $J_2$ = 2.99 Hz), 7.40 (d, 1H, J = 15.40 Hz), 7.52 (d, 2H, J = 8.52 Hz), 7.56 (d, 1H, J = 15.5 Hz), 7.82 (d, 1H, J = 2.9 Hz), 7.84 (d, 2H, J = 8.49 Hz), 9.10 (s, 1H) |

TABLE 2-continued

Chemical Name and ¹H NMR Data for Compound of Formula I

| Compound No. | | IUPAC Name | ¹H NMR (δ ppm) in DMSO-d₆ as solvent, 500 MHz |
|---|---|---|---|
| I.79 | 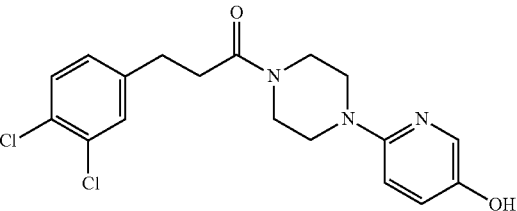 [SMILES: O=C(CCc1ccc(Cl)c(Cl)c1)N1CCN(c2ccc(O)cn2)CC1] | 3-(3,4-Dichlorophenyl)-1-[4-(5-hydroxy-pyridin-2-yl)-piperazin-1-yl]-propan-1-one | 2.74 (t, 2H, J = 7.76 Hz), 2.88 (t, 2H, J = 7.42 Hz), 3.28-3.34 (m, 4H), 3.56-3.59 (m, 4H), 6.79 (d, 1H, J = 8.99 Hz), 7.12 (dd, 1H, J₁ = 8.95 Hz, J₂ = 2.96 Hz), 7.31 (d, 1H, J = 7.53 Hz), 7.57 (d, 1H, J = 8.23 Hz), 7.61 (d, 1H, J = 1.9 Hz), 7.79 (d, 1H, J = 2.74 Hz), 9.09 (s, 1H) |
| I.80 | 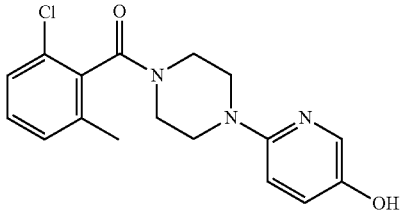 [SMILES: Cc1cccc(Cl)c1C(=O)N1CCN(c2ccc(O)cn2)CC1] | (2-Chloro-6-methylphenyl)-[4-(5-hydroxy-pyridin-2-yl)-piperazin-1-yl]-methanone | 2.28 (s, 3H), 3.26-3.31 (m, 4H), 3.46 (m, 2H), 3.82 (m, 2H), 6.80 (d, 1H, J = 8.05 Hz), 7.14 (d, 1H, J = 7.60 Hz), 7.34-7.40 (m, 3H), 7.80 (s, 1H), 9.13 (s, 1H) |
| I.81 | 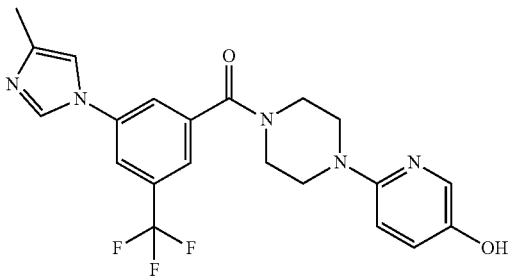 [SMILES: Cc1cn(-c2cc(C(=O)N3CCN(c4ccc(O)cn4)CC3)cc(C(F)(F)F)c2)cn1] | [4-(5-Hydroxy-pyridin-2-yl)-piperazin-1-yl]-[3-(4-methyl-imidazol-1-yl)-5-trifluoro-methylphenyl]-methanone | 2.22 (s, 3H), 3.49 (m, 6H), 3.81 (m, 2H), 6.80-6.82 (d, 1H, J = 8.90 Hz), 7.13-7.15 (m, 1H, J = 8.71 Hz), 7.75-7.76 (d, 2H, J = 2.40 Hz), 7.80-7.81 (d, 1H, J = 1.97 Hz), 8.08 (m, 1H), 8.17 (m, 1H), 8.44 (s, 1H), 9.12 (s, 1H) |
| I.82 | 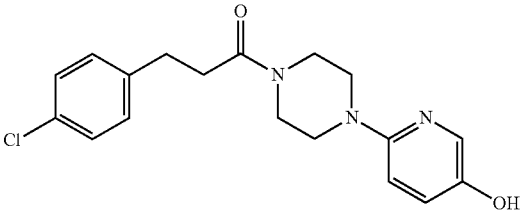 [SMILES: O=C(CCc1ccc(Cl)cc1)N1CCN(c2ccc(O)cn2)CC1] | 3-(4-Chloro-phenyl)-1-[4-(5-hydroxy-pyridin-2-yl)-piperazin-1-yl]-propan-1-one | 2.71 (t, 2H, J = 7.64 Hz), 2.87 (t, 2H, J = 7.61 Hz), 3.28-3.34 (m, 4H), 3.56 (t, 2H, J = 5.01 Hz), 3.59 (t, 2H, J = 5.1 Hz), 6.79 (d, 1H, J = 8.83 Hz), 7.12 (dd, 1H, J₁ = 8.96 Hz, J₂ = 3.00 Hz), 7.31-7.34 (m, 2H), 7.36-7.38 (m, 2H), 7.79 (d, 1H, J = 2.55 Hz), 9.08 (s, 1H) |
| I.83 | 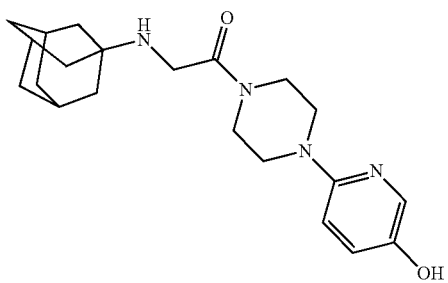 [SMILES: CC1(NCC(=O)N2CCN(c3ccc(O)cn3)CC2)CC2CCCC(C2)C1] | 2-(1-Adamantyl-amino)-1-[4-(5-hydroxy-2-pyridyl)-piperazin-1-yl]ethanone | 1.28-1.35 (m, 6H), 1.39 (s, 1H), 1.62-1.76 (m, 3H), 1.76-1.84 (m, 3H), 2.08-2.15 (m, 2H), 3.29 (m, 2H), 3.42-3.44 (m, 2H), 3.53-3.55 (m, 4H), 3.71 (m, 2H), 6.78 (d, J = 8.90 Hz, 1H), 7.12 (dd, J₁ = 8.86 Hz, J₂ = 2.90 Hz, 1H), 7.79 (d, J = 2.83 Hz, 1H), 9.09 (s, 1H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.84 | 1-[4-(5-Hydroxy-2-pyridyl)-piperazin-1-yl]-3,3-bis(4-methoxyphenyl)-prop-2-en-1-one | 2.92-2.97 (m, 2H), 3.18-3.22 (m, 2H), 3.5-3.38 (m, 2H), 3.49-3.53 (m, 2H), 3.77 (s, 3H), 3.83 (s, 3H), 6.34 (s, 1H), 6.71 (d, J = 8.95 Hz, 1H), 6.98-6.99 (m, 4H), 7.09 (dd, $J_1$ = 2.80 Hz, $J_2$ = 9.00 Hz, 1H), 7.14 (d, J = 8.45 Hz, 2H), 7.29 (d, J = 8.55 Hz, 2H), 7.76 (d, J = 2.65 Hz, 1H), 9.08 (s, 1H). |
| I.85 | [[4-(5-Hydroxy-pyridin-2-yl)-piperazin-1-yl]-[4-methyl-3-(4-pyridin-3-yl-pyrimidin-2-ylamino)-phenyl]-methanone | 2.37 (s, 3H), 3.51-3.72 (m, 8H), 6.76 (d, 1H, J = 8.96 Hz), 7.12-7.14 (m, 2H), 7.19 (d, 1H, J = 7.60 Hz), 7.37-7.59 (m, 2H), 7.75-7.80 (m, 2H), 8.46 (d, 1H, J = 7.88 Hz), 8.59 (d, 1H, J = 5.05 Hz), 8.74 (d, 1H, J = 3.99 Hz), 9.11 (s, 1H), 9.22 (s, 1H), 9.31 (s, 1H) |
| I.86 | (1H-Benzoimidazol-2-yl)-[4-(5-hydroxy-pyridin-2-yl)-piperazin-1-yl]-methanone | 3.5 (m, 4H), 3.8 (t, 2H, J = 4.8 Hz), 4.6 (t, 2H, J = 4.5 Hz), 6.8 (d, 1H, J = 8.9 Hz), 7.15 (dd, 1H, $J_1$ = 8.92 Hz, $J_2$ = 2.79 Hz), 7.35 (m, 2H), 7.59 (s, 1H), 7.8 (m, 2H), 9.11 (s, 1H), 13.21 (s, 1H) |
| I.87 | (5-Bromo-thiophen-2-yl)-[4-(5-hydroxy-pyridin-2-yl)-piperazin-1-yl]-methanone | 3.38-3.39 (m, 4H), 3.73 (m, 4H), 6.76 (d, 1H, J = 8.96 Hz), 7.08 (dd, 1H, $J_1$ = 8.92 Hz, $J_2$ = 2.89 Hz), 7.3 (d, 1H, J = 3.89 Hz), 7.2 (d, 1H, J = 3.89 Hz), 7.75 (d, 1H, J = 2.83 Hz), 9.05 (s, 1H) |

TABLE 2-continued

Chemical Name and ¹H NMR Data for Compound of Formula I

| Compound No. | Structure | IUPAC Name | ¹H NMR (δ ppm) in DMSO-d₆ as solvent, 500 MHz |
|---|---|---|---|
| I.88 | 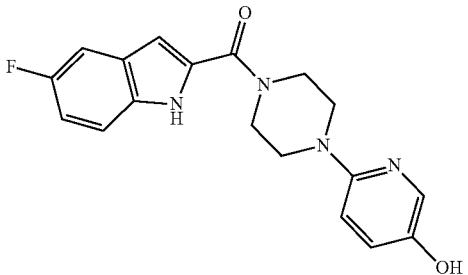 [SMILES: O=C(c1cc2cc(F)ccc2[nH]1)N1CCN(c2ccc(O)cn2)CC1] | [(5-Fluoro-1H-indol-2-yl)-[4-(5-hydroxy-pyridin-2-yl)-piperazin-1-yl]-methanone | 3.45-3.47 (m, 4H), 3.90 (m, 4H), 6.83 (d, 1H, J = 8.93 Hz), 6.88 (s, 1H), 7.16-7.10 (m, 2H), 7.42-7.44 (m, 1H), 7.46-7.49 (m, 1H), 7.81 (d, 1H, J = 2.88 Hz), 9.12 (s, 1H) |
| I.89 | 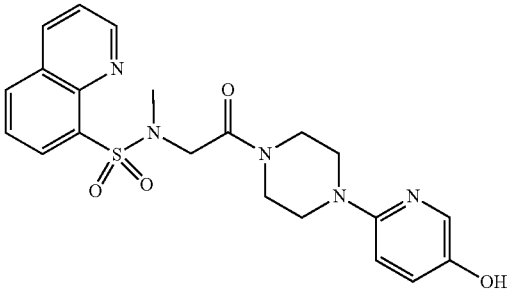 [SMILES: CN(CC(=O)N1CCN(c2ccc(O)cn2)CC1)S(=O)(=O)c1cccc2cccnc12] | Quinoline-8-sulfonic acid {2-[4-(5-hydroxy-pyridin-2-yl)-piperazin-1-yl]-2-oxo-ethyl}-methylamide | 2.90 (s, 3H), 3.32-3.34 (m, 2H), 3.45 (t, 2H, J = 5.35 Hz), 3.51-3.52 (m, 2H), 3.63 (m, 2H), 4.5 (s, 2H), 6.82 (d, 1H, J = 8.9 Hz), 7.15 (dd, 1H, J₁ = 8.96 Hz, J₂ = 3.0 Hz), 7.73-7.75 (m, 1H), 7.81-7.82 (m, 2H), 8.36 (dd, 1H, J₁ = 8.23 Hz, J₂ = 1.34 Hz), 8.45 (dd, 1H, J₁ = 7.34 Hz, J₂ = 1.41 Hz), 8.58 (dd, 1H, J₁ = 8.4 Hz, J₂ = 1.75 Hz), 9.10 (s, 1H), 9.14 (dd, 1H, J₁ = 4.18 Hz, J₂ = 1.78 Hz) |
| I.90 | 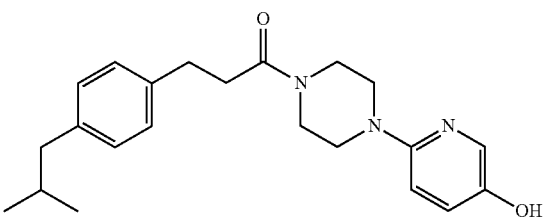 [SMILES: CC(C)Cc1ccc(CCC(=O)N2CCN(c3ccc(O)cn3)CC2)cc1] | 1-[4-(5-Hydroxy-pyridin-2-yl)-piperazin-1-yl]-3-(4-isobutyl-phenyl)-propan-1-one | 0.82 (m, 6H), 1.27 (d, 3H, J = 6.72 Hz) 1.78 (m, 1H), 2.38 (m, 2H), 2.60 (m, 1H), 3.00 (m, 1H), 3.22 (m, 1H), 3.43 (m, 2H), 3.49-3.50 (m, 1H), 3.69-3.70 (m, 1H), 4.08-4.09 (m, 1H), 6.64 (d, 1H, J = 8.98 Hz), 7.02 (dd, 1H, J₁ = 8.93 Hz, J₂ = 2.74 Hz), 7.08 (d, 2H, J = 7.83 Hz), 7.16 (d, 2H, J = 7.83 Hz), 7.69 (d, 1H, J = 2.81 Hz), 9.0 (s, 1H) |
| I.91 | 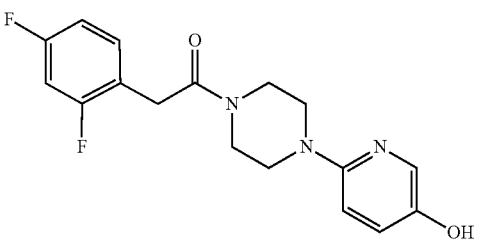 [SMILES: O=C(Cc1ccc(F)cc1F)N1CCN(c2ccc(O)cn2)CC1] | 2-(2,4-Difluoro-phenyl)-1-[4-(5-hydroxy-pyridine-2-yl)-piperazin-1-yl]-ethanone | 3.33 (t, 2H, J = 4.77 Hz), 3.40-3.41 (m, 2H), 3.62 (t, 2H, J = 4.78 Hz), 3.68-3.69 (m, 2H), 3.82 (s, 2H), 6.82 (d, 1H, J = 8.98 Hz), 7.06-7.10 (m, 1H), 7.13 (dd, 1H, J₁ = 8.90 Hz, J₂ = 2.86 Hz), 7.21-7.24 (m, 1H), 7.37 (q, 1H, J₁ = 15.53 Hz, J₂ = 8.40 Hz), 7.81 (d, 1H), J = 2.84 Hz), 9.10 (s, 1H) |
| I.92 | 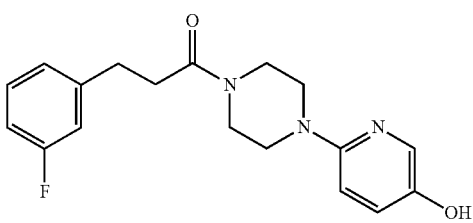 [SMILES: O=C(CCc1cccc(F)c1)N1CCN(c2ccc(O)cn2)CC1] | 3-(3-Fluoro-phenyl)-1-[4-(5-hydroxy-pyridin-2-yl)-piperazin-1-yl]-propan-1-one | 2.74 (t, 2H, J = 7.7 Hz), 2.90 (t, 2H, J = 7.7 Hz), 3.30 (m, 4H), 3.59 (m, 4H), 6.79 (d, 1H, J = 8.98 Hz), 7.05 (t, 1H, J = 7.54 Hz), 7.14 (m, 3H), 7.36 (q, 1H, J₁ = 14.54 Hz, J₂ = 7.52 Hz), 7.8 (d, 1H, J = 2.84 Hz), 9.09 (s, 1H) |

TABLE 2-continued

Chemical Name and $^1$H NMR Data for Compound of Formula I

| Compound No. | | IUPAC Name | $^1$H NMR (δ ppm) in DMSO-$d_6$ as solvent, 500 MHz |
|---|---|---|---|
| I.93 | 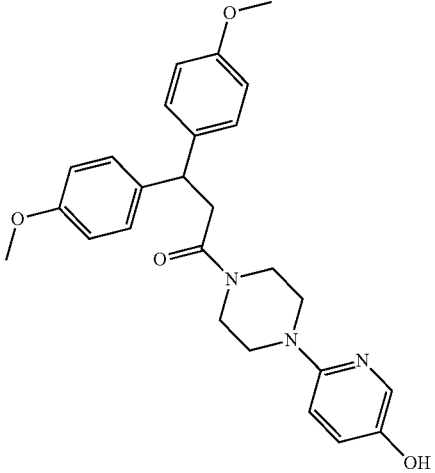 [SMILES: COc1ccc(C(CC(=O)N2CCN(c3ccc(O)cn3)CC2)c2ccc(OC)cc2)cc1] | 1-[4-(5-Hydroxy-2-pyridyl)-piperazin-1-yl]-3,3-bis(4-methoxy-phenyl)-propan-1-one | 3.12 (br d, J = 7.45 Hz, 2H), 3.20 (br s, 4H), 3.50-3.53 (m, 2H), 3.60-3.63 (m, 2H), 3.72 (s, 6H), 4.44 (t, J = 7.37 Hz, 1H), 6.76 (d, J = 9.00 Hz, 1H), 6.86 (d, J = 8.30 Hz, 4H), 7.12 (dd, J$_1$ = 2.55 Hz, J$_2$ = 8.92 Hz, 1H), 7.25 (d, J = 8.35 Hz, 4H), 7.79 (d, J = 2.45 Hz, 1H), 9.09 (s, 1H). |
| I.94 | 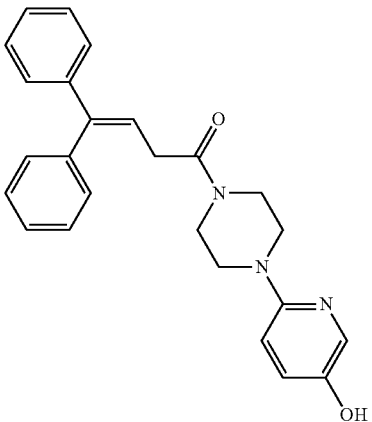 [SMILES: O=C(CC=C(c1ccccc1)c1ccccc1)N1CCN(c2ccc(O)cn2)CC1] | 1-[4-(5-Hydroxy-2-pyridyl)-piperazin-1-yl]-4,4-diphenyl-but-3-en-1-one | 2.27-2.37 (m, 4H), 3.23-3.32 (m, 4H), 3.57-3.62 (m, 2H), 4.20 (t, J = 7.20 Hz, 1H), 6.78 (d, J = 9.00 Hz, 1H), 7.13-7.16 (m, 1H), 7.20-7.24 (m, 2H), 7.32-7.38 (m, 8H), 7.73 (d, J = 2.60 Hz, 1H), 9.09 (s, 1H). |
| I.95 | 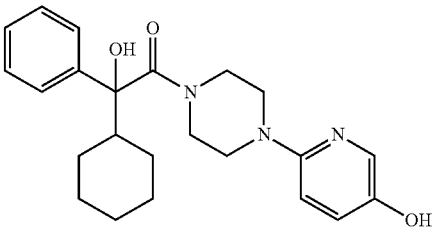 [SMILES: O=C(N1CCN(c2ccc(O)cn2)CC1)C(O)(c1ccccc1)C1CCCCC1] | 2-Cyclohexyl-2-hydroxy-1-[4-(5-hydroxy-2-pyridyl)-piperazin-1-yl]-2-phenyl-ethanone | 0.9-1.3 (m, 6H), 1.58-1.64 (m, 2H), 1.70-1.80 (m, 1H), 1.90-2.00 (m, 1H), 2.20-2.30 (m, 1H), 2.90-3.20 (m, 2H), 3.40-3.60 (m, 4H), 3.70-3.90 (m, 2H), 5.85 (s, 1H), 6.65 (d, J = 2.90 Hz, 1H), 7.04-7.08 (m, 1H), 7.24-7.29 (m, 1H), 7.36-7.41 (m, 4H), 7.72 (d, J = 2.80 Hz, 1H), 9.04 (s, 1H). |
| I.96 | 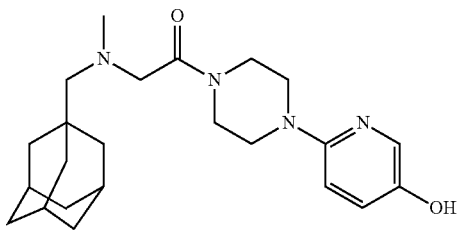 [SMILES: CC1CC2CCCC(CN(C)CC(=O)N3CCN(c4ccc(O)cn4)CC3)(C1)C2] | 2-[1-Adamantyl-methyl-(methyl)-amino]-1-[4-(5-hydroxy-2-pyridyl)-piperazin-1-yl]ethanone | 1.40-1.58 (m, 6H), 1.55-1.67 (m, 3H), 1.67-1.80-2.10 (m, 3H), 2.10-2.25 (m, 2H), 2.36 (s, 3H), 3.25-3.44 (m, 6H), 3.52-3.62 (m, 2H), 3.63 = 3.80 (m, 2H), 6.81 (d, J = 8.96 Hz, 1H), 7.13 (dd, J$_1$ = 8.87 Hz, J$_2$ = 2.58 Hz, 1H), 7.79 (d, J = 2.67 Hz, 1H), 9.10 (s, 1H). |

TABLE 2-continued

Chemical Name and ¹H NMR Data for Compound of Formula I

| Compound No. | IUPAC Name | ¹H NMR (δ ppm) in DMSO-$d_6$ as solvent, 500 MHz |
|---|---|---|
| I.97 | 1-[4-(5-Hydroxy-pyridin-2-yl)-piperazin-1-yl]-2-(5-nitropyridin-2-ylsulfanyl)-ethanone | 3.34-3.36 (m, 2H), 3.45-3.74 (m, 2H), 3.62-3.64 (m, 2H), 3.75-3.78 (m, 2H), 4.44 (s, 2H), 6.83 (d, 1H, J = 8.97 Hz), 7.14 (dd, 1H, $J_1$ = 8.95 Hz, $J_2$ = 3.00 Hz), 7.69 (dd, 1H, $J_1$ = 8.94 Hz, $J_2$ = 0.49 Hz), 7.81 (d, 1H, J = 2.79 Hz), 8.45 (dd, 1H, $J_1$ = 8.93 Hz, $J_2$ = 2.72 Hz), 9.12 (s, 1H), 9.24 (dd, 1H, $J_1$ = 2.68 Hz, $J_2$ = 0.5 Hz) |
| I.98 | 3-(1-Adamantyl)-1-[4-(5-hydroxy-2-pyridyl)-piperazin-1-yl]propan-1-one | 1.32-1.37 (m, 2H), 1.51 (s, 6H), 1.65 (d, J = 11.80 Hz, 3H), 1.72 (d, J = 11.80 Hz, 3H), 1.98 (s, 3H), 2.30-2.34 (m, 2H), 3.28-3.32 (m, 2H), 3.35-3.37 (m, 2H), 3.57-3.60 (m, 4H), 6.80 (d, J = 8.95 Hz, 1H), 7.14 (dd, $J_1$ = 2.25 Hz, $J_2$ = 8.80 Hz, 1H), 7.80 (d, J = 2.15 Hz, 1H), 9.24 (s, 1H). |
| I.99 | 2-Cyclohexyl-1-[4-(5-hydroxy-2-pyridyl)-piperazin-1-yl]-2-phenyl-ethanone | 0.81-0.88 (m, 1H), 0.97-1.05 (m, 1H), 1.07-1.18 (m, 3H), 1.22-1.31 (m, 1H), 1.62 (s, 2H), 1.70-1.72 (m, 1H), 1.82-1.84 (m, 1H), 2.02-2.09 (m, 1H), 2.89-2.94 (m, 1H), 3.12-3.18 (m, 1H), 3.21-3.26 (m, 2H), 3.54-3.67 (m, 3H), 3.78 (d, J = 10.10 Hz, 1H), 3.80-3.86 (m, 1H), 6.73 (d, J = 9.00 Hz, 1H), 7.10 (dd, $J_1$ = 2.70 Hz, $J_2$ = 8.90 Hz, 1H), 7.25 (t, J = 7.12 Hz, 1H), 7.34 (t, J = 7.52 Hz, 2H), 7.39 (d, J = 7.70 Hz, 2H), 7.76 (d, J = 2.70 Hz, 1H), 9.09 (s, 1H). |
| I.100 | 3-(4-Hydroxyphenyl)-1-[4-(5-hydroxy-pyridin-2-yl)-piperazin-1-yl]-propan-1-one | 2.63 (t, 2H, J = 7.35 Hz), 2.76 (t, 2H, J = 7.53 Hz), 3.29 (m, 4H), 3.54-3.59 (m, 4H), 6.70 (d, 2H, J = 8.00 Hz), 6.78 (d, 1H, J = 8.97 Hz), 7.07 (d, 2H, J = 7.90 Hz), 7.13 (d, 1H, J = 8.90 Hz), 7.79 (s, 1H), 9.19 (s, 1H) |
| I.101 | 3-(4-Methoxyphenyl)-1-[4-(5-hydroxy-pyridin-2-yl)-piperazin-1-yl]-propan-1-one hydrochloride | 2.68 (t, 2H, J = 7.62 Hz), 2.81 (t, 2H, J = 7.58 Hz), 3.59 (m, 4H), 3.65 (m, 4H), 3.75 (s, 3H), 6.87 (d, 2H, J = 8.27 Hz), 7.19 (d, 2H, J = 8.3 Hz), 7.34 (d, 1H, J = 9.63 Hz), 7.63 (d, 1H, J = 2.38 Hz), 7.75 (d, 1H, J = 8.95 Hz), 10.37 (s, 1H) |
| I.102 | 3-(2-Bromophenyl)-1-[4-(5-hydroxy-pyridin-2-yl)-piperazin-1-yl]-propan-1-one | 2.70-2.72 (m, 2H), 2.99 (m, 2H), 3.31 (m, 4H), 3.58-3.61 (m, 4H), 6.79 (d, 1H, J = 8.28 Hz), 7.12 (d, 1H, J = 7.12 Hz), 7.20-7.22 (m, 1H), 7.37-7.56 (m, 2H), 7.64 (d, 1H, J = 7.68), 7.79 (s, 1H), 9.09 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.103 | 3-(4-Bromophenyl)-1-[4-(5-hydroxy-pyridin-2-yl)-piperazin-1-yl]-propan-1-one | 2.72 (m, 2H), 2.85 (m, 2H), 3.30 (m, 4H), 3.58 (m, 4H), 6.79 (d, 1H, J = 8.96 Hz), 7.12 (d, 1H, J = 6.88 Hz), 7.28 (d, 2H, J = 7.16 Hz), 7.50 (d, 2H, J = 7.60 Hz), 7.79 (s, 1H), 9.09 (s, 1H) |
| I.104 | 3-[4-(5-Hydroxy-pyridin-2-yl)-piperazine-1-carbonyl]-7-oxa-bicyclo-[2.2.1]heptane-2-carboxylic acid methyl ester | 1.66 (s, 4H), 3.15 (br-s, 4H), 3.39 (s, 2H), 3.63 (s, 3H), 3.71 (br-s, 3H), 4.82 (s, 1H), 4.93 (s, 1H), 7.00 (d, 1H, J = 9.05 Hz), 7.41 (d, 1H, J = 8.05 Hz), 7.95 (s, 1H) |
| I.105 | 3-[4-(5-Hydroxy-pyridin-2-yl)-piperazine-1-carbonyl]-7-oxa-bicyclo-[2.2.1]heptane-2-carboxylic acid | 1.49-1.57 (m, 4H), 2.81-2.87 (m, 2H), 3.21 (m, 4H), 3.61-3.66 (m, 4H), 4.63 (d, 1H, J = 11.11 Hz), 4.74 (d, 1H, J = 11.85 Hz), 6.69-6.79 (m, 1H), 7.12 (d, 1H, J = 8.02 Hz), 7.77 (s, 1H), 9.42 (br-s, 1H) |
| I.106 | 1-[4-(5-Hydroxy-pyridin-2-yl)-piperazin-1-yl]-2-(1H-indol-3-yl)-ethane-1,2-dione | 3.28 (d, 2H, J = 4.68 Hz), 3.70-3.72 (m, 4H), 4.10 (d, 2H, J = 4.20 Hz), 6.75 (d, 1H, J = 8.98 Hz), 7.06-7.09 (m, 1H), 7.24-7.30 (m, 2H), 7.53 (d, 1H, J = 7.80 Hz), 7.75 (d, 1H, J = 2.65 Hz), 8.13 (d, 1H, J = 7.30 Hz), 8.20 (s, 1H), 9.06 (s, 1H), 12.13 (s, 1H) |
| I.107 | 1-[4-(5-Hydroxy-pyridin-2-yl)-piperazin-1-yl]-3-o-tolyl-propan-1-one | 2.28 (s, 3H), 2.59 (t, 2H, J = 7.86 Hz), 2.80 (t, 2H, J = 7.81 Hz), 3.24 (m, 4H), 3.49-3.55 (m, 4H), 6.73 (d, 1H, J = 8.98 Hz), 7.05-7.13 (m, 4H), 7.16 (d, 1H, J = 7.21 Hz), 7.73 (d, 1H, J = 2.37 Hz), 9.03 (s, 1H) |
| I.108 | 3-(4-Dimethyl-aminophenyl)-[4-(5-hydroxy-pyridin-2-yl)-piperazin-1-yl]-propan-1-one | 2.57 (t, 2H, J = 7.66 Hz), 2.70 (t, 2H, J = 7.63 Hz), 3.21-3.22 (m, 4H), 3.48-3.53 (m, 4H), 6.63 (d, 2H, J = 8.24 Hz), 6.71 (d, 1H, J = 8.97 Hz), 7.04 (d, 2H, J = 8.45 Hz), 7.07 (d, 1H, J = 2.63 Hz), 7.73 (d, 1H, J = 2.59 Hz), 9.02 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.109 | 1-[4-(5-Hydroxy-pyridin-2-yl)-piperazin-1-yl]-3-(2-methoxy-phenyl)-propan-1-one | 2.56 (t, 2H, J = 7.88 Hz), 2.77 (t, 2H, J = 7.82 Hz), 3.24 (m, 4H), 3.50-3.54 (m, 4H), 3.79 (s, 3H), 6.73 (d, 1H, J = 8.98 Hz), 6.85 (t, 1H, J = 7.35 Hz), 6.94 (d, 1H, J = 8.06 Hz), 7.06 (dd, 1H, J₁ = 8.89 Hz, J₂ = 2.61 Hz), 7.15-7.19 (m, 2H), 7.73 (d, 1H, J = 2.55 Hz), 9.03 (s, 1H) |
| I.110 | 1-[4-(5-Hydroxy-pyridin-2-yl)-piperazin-1-yl]-3-p-tolyl-propan-1-one | 2.23 (s, 3H), 2.61 (t, 2H, J = 7.71 Hz), 2.77 (t, 2H, J = 7.68 Hz), 3.22-3.23 (m, 4H), 3.49-3.54 (m, 4H), 6.72 (d, 1H, J = 8.98 Hz), 7.05-7.07 (m, 3H), 7.12 (d, 2H, J = 7.77 Hz), 7.73 (d, 1H, J = 2.76 Hz), 9.03 (s, 1H) |
| I.111 | 2-[4-(5-Hydroxy-pyridin-2-yl)-piperazine-1-carbonyl]-benzoic acid | 3.15-3.23 (m, 4H), 3.38 (m, 2H), 3.68 (m, 2H), 6.73 (d, 1H, J = 8.98 Hz), 7.07 (dd, 1H, J₁ = 8.90 Hz, J₂ = 2.66 Hz), 7.32 (d, 1H, J = 7.52 Hz), 7.53 (t, 1H, J = 7.60 Hz), 7.65 (t, 1H, J = 7.48 Hz), 7.73 (d, 1H, J = 2.66 Hz), 7.93 (d, 1H, J = 7.79 Hz), 9.05 (s, 1H) |
| I.112 | 1-[4-(5-Hydroxy-2-pyridyl)-piperazin-1-yl]-4,4-diphenyl-butan-1-one | 2.26-2.36 (m, 4H), 3.23-3.29 (m, 4H), 3.38-3.43 (m, 2H), 3.54-3.60 (m, 2H), 4.02 (t, J = 7.25 Hz, 1H), 6.77 (d, J = 9.00 Hz, 1H), 7.12 (dd, J₁ = 2.70 Hz, J₂ = 8.90 Hz, 1H), 7.21 (t, J = 6.70 Hz, 2H), 7.31-7.36 (m, 8H), 7.79 (d, J = 2.70 Hz, 1H), 9.08 (s, 1H). |
| I.113 | [4-(5-Hydroxy-pyridin-2-yl)-piperazin-1-yl]-[3-(1H-indol-4-yl)phenyl]-methanone | 3.43-3.46 (m, 4H), 3.60 (m, 2H), 3.80 (m, 2H), 6.60 (s, 1H), 6.81 (d, 1H, J = 9.01 Hz), 7.13 (dd, 1H, J₁ = 8.96 Hz, J₂ = 2.98 Hz), 7.17 (d, 1H, J = 7.21 Hz), 7.25 (t, 1H, J = 7.66 Hz), 7.47-7.50 (m, 3H), 7.64 (t, 1H, J = 7.65 Hz), 7.72 (s, 1H), 7.80 (d, 1H, J = 2.96 Hz), 7.82 (d, 1H, J = 8.03 Hz), 9.12 (s, 1H), 11.37 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.114 | 1-[4-(5-Hydroxy-pyridin-2-yl)-piperazin-1-yl]-3-[4-(2-methoxy-ethoxy)-phenyl]-propan-1-one dihydrochloride | 2.63 (t, 2H, J = 7.58 Hz), 2.76 (t, 2H, J = 7.55 Hz), 3.29 (s, 3H), 3.54-3.60 (m, 4H), 3.61-3.63 (m, 6H), 4.02 (t, 2H, J = 4.47 Hz), 6.84 (d, 2H, J = 8.32 Hz), 7.15 (d, 2H, J = 8.32 Hz), 7.29 (d, 1H, J = 9.66 Hz), 7.59 (d, 1H, J = 2.44 Hz), 7.70 (d, 1H, J = 9.04 Hz), 10.36 (s, 1H) |
| I.115 | 1-[4-(5-Hydroxy-pyridin-2-yl)-piperazin-1-yl]-3-phenyl-butan-1-one dihydrochloride | 1.27 (d, 3H, J = 6.88 Hz), 2.66-2.76 (m, 2H), 3.22-3.29 (m, 1H), 3.43-3.49 (m, 2H), 3.57-3.70 (m, 6H), 7.20-7.23 (m, 1H), 7.30-7.33 (m, 5H), 7.66 (s, 1H), 7.72 (d, 1H, J = 8.96 Hz), 10.35 (s, 1H) |
| I.116 | 1-[4-(5-Hydroxy-pyridin-2-yl)-piperazin-1-yl]-3-thiophen-2-yl-propan-1-one | 2.70 (t, 2H, J = 6.99 Hz), 3.04 (t, 2H, J = 6.81 Hz), 3.25-3.27 (m, 4H), 3.25-3.27 (m, 4H), 6.74 (d, 1H, J = 8.78 Hz), 6.89-6.92 (m, 2H), 7.07 (d, 1H, J = 7.95 Hz), 7.29 (d, 1H, J = 4.33 Hz), 7.74 (s, 1H), 9.03 (s, 1H) |
| I.117 | 1-[4-(5-Hydroxy-2-pyridyl)-piperazin-1-yl]-2-morpholino-2-phenyl-ethanone | 2.46-2.50 (m, 4H), 2.94-2.97 (m, 1H), 3.17-3.28 (m, 3H), 3.59-3.64 (m, 7H), 3.79-3.83 (m, 1H), 4.62 (s, 1H), 6.74 (d, J = 9.00 Hz, 1H), 7.10 (dd, J₁ = 2.60 Hz, J₂ = 8.95 Hz, 1H), 7.34 (t, J = 7.20 Hz, 1H), 7.40 (t, J = 7.40 Hz, 2H), 7.48 (d, J = 7.50 Hz, 2H), 7.76 (d, J = 2.60 Hz, 1H), 9.09 (s, 1H). |
| I.118 | Cyclohexyl-[4-(5-hydroxy-2-pyridyl)-piperazin-1-yl]methanone | 1.07-1.237 (m, 1H), 1.25-1.45 (m, 4H), 1.63-1.70 (m, 3H), 1.70-1.75 (m, 2H), 2.58-2.62 (m, 1H), 3.23-3.30 (m, 4H), 3.53-3.57 (m, 4H), 6.74 (d, J = 8.96 Hz, 1H), 7.07 (dd, J₁ = 8.93 Hz, J₂ = 2.82 Hz, 1H), 7.74 (d, J = 2.77 Hz, 1H), 9.04 (s, 1H). |
| I.119 | Cyclopropyl-[4-(5-hydroxy-2-pyridyl)-piperazin-1-yl]methanone | 0.69-0.76 (m, 4H), 2.00-2.03 (m, 1H), 3.25 (m, 2H), 3.35 (m, 2H), 3.55 (m, 2H), 3.76 (m, 2H), 6.75 (d, J = 8.95 Hz, 1H), 7.07 (dd, J₁ = 8.92 Hz, J₂ = 2.83 Hz, 1H), 7.74 (d, J = 2.71 Hz, 1H), 9.04 (s, 1H). |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.120 | (E)-3-Cyclohexyl-1-[4-(5-hydroxy-2-pyridyl)-piperazin-1-yl]prop-2-en-1-one | 1.14-1.27 (m, 3H), 1.29-1.38 (m, 2H), 1.67-1.72 (m, 1H), 1.74-1.78 (m, 4H), 2.17-2.26 (m, 1H), 3.34-3.38 (m, 4H), 3.65-3.72 (m, 4H), 6.48 (dd, J₁ = 1.20 Hz, J₂ = 15.12 Hz, 1H), 6.71 (dd, J₁ = 7.00 Hz, J₂ = 15.10 Hz, 1H), 6.80 (d, J = 8.95 Hz, 1H), 7.13 (dd, J₁ = 3.00 Hz, J₂ = 8.95 Hz, 1H), 7.80 (d, J = 2.70 Hz, 1H), 9.09 (s, 1H). |
| I.121 | 3-Cyclohexyl-1-[4-(5-hydroxy-2-pyridyl)-piperazin-1-yl]propan-1-one | 0.88-0.95 (m, 2H), 1.13-1.29 (m, 4H), 1.45 (q, J = 7.48 Hz, 1H), 1.65-1.73 (m, 5H), 2.38 (t, J = 7.87 Hz, 2H), 3.28-3.30 (m, 2H), 3.35-3.37 (m, 2H), 3.57-3.59 (m, 4H), 6.80 (d, J = 8.95 Hz, 1H), 7.13 (dd, J₁ = 3.00 Hz, J₂ = 8.95 Hz, 1H), 7.80 (d, J = 2.75 Hz, 1H), 9.15 (s, 1H). |
| I.122 | 3-Benzo[b]-thiophen-2-yl-1-[4-(5-hydroxy-pyridin-2-yl)-piperazin-1-yl]-propan-1-one | 2.87 (t, 2H, J = 7.22 Hz), 3.20 (t, 2H, J = 7.12 Hz), 3.32-3.35 (m, 4H), 3.62-3.63 (m, 4H), 6.79 (d, 1H, J = 8.96 Hz), 7.11-7.13 (m, 1H), 7.26 (s, 1H), 7.32 (t, 1H, J = 7.40 Hz), 7.37 (t, 1H, J = 7.35 Hz), 7.77 (d, 1H, J = 9.89 Hz), 7.79 (d, 1H, J = 2.06 Hz), 7.91 (d, 1H, J = 7.83 Hz), 9.10 (s, 1H) |
| I.123 | [4-(5-Hydroxy-pyridin-2-yl)-piperazin-1-yl]-(5-phenyl-thiophen-2-yl)-methanone | 3.46-3.47 (m, 4H), 3.83 (m, 4H), 6.82 (d, 1H, J = 8.95 Hz), 7.14-7.16 (m, 1H), 7.42 (t, 1H, J = 7.30 Hz), 7.49-7.53 (m, 3H), 7.58 (d, 1H, J = 3.62 Hz), 7.77 (d, 2H, J = 7.66 Hz), 7.83 (d, 1H, J = 2.29 Hz), 9.12 (s, 1H) |
| I.124 | (3-Hydroxy-3-phenylcyclobutyl)-[4-(5-hydroxy-pyridin-2-yl)-piperazin-1-yl]-methanone | 2.54-2.58 (m, 2H), 2.60-2.62 (m, 2H), 2.95-2.98 (m, 1H), 3.26 (t, 4H, J = 4.75 Hz), 3.56 (m, 2H), 3.57 (m, 2H), 5.61 (s, 1H), 6.73 (d, 1H, J = 8.98 Hz), 7.06-7.08 (m, 1H), 7.25 (t, 1H, J = 7.24 Hz), 7.36 (t, 2H, J = 7.52 Hz), 7.56 (d, 2H, J = 4.87 Hz), 7.74 (d, 1H, J = 2.69 Hz), 9.04 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.125 | 1-[4-(5-Hydroxy-pyridin-2-yl)-piperazin-1-yl]-3-methyl-3-phenyl-butan-1-one | 9.08 (s, 1H), 7.77 (d, 1H, J = 2.59 Hz), 7.43 (d, 2H, J = 7.94 Hz), 7.32 (t, 2H, J = 7.4 Hz), 7.19 (t, 1H, J = 7.21 Hz), 7.10 (dd, 1H, , J₁ = 8.9 Hz, J₂ = 2.6 Hz), 6.73 (d, 1H, J = 8.9 Hz), 3.48 (m, 2H), 3.36 (m, 2H), 3.18 (m, 2H), 3.09 (m, 2H), 2.73 (m, 2H), 1.46 (s, 6H) |
| I.126 | 3-(4-Fluoro-phenyl)-1-[4-(5-hydroxy-pyridin-2-yl)-piperazin-1-yl]-propan-1-one | 9.04 (s, 1H), 7.73 (d, 1H, J = 2.64 Hz), 7.28 (m, 2H), 7.06 (m, 3H), 6.73 (d, 1H, J = 8.9 Hz), 3.53 (m, 4H), 3.23 (m, 4H), 2.81 (t, 2H, J = 7.57 Hz), 2.65 (t, 2H, J = 7.61 Hz) |
| I.127 | 1-[4-(5-Hydroxy-pyridin-2-yl)-piperazin-1-yl]-2-(2-methyl-1H-indol-3-yl)-ethanone | 2.38 (s, 3H), 3.13 (m, 2H), 3.24 (m, 2H), 3.60 (m, 4H), 3.79 (s, 2H), 6.74 (d, 1H, J = 8.91 Hz), 6.94-6.95 (m, 1H), 7.00-7.03 (m, 1H), 7.09 (d, 1H, J = 6.95 Hz), 7.27 (d, 1H, J = 7.79 Hz), 7.47 (d, 1H, J = 7.58 Hz), 7.76 (s, 1H), 9.08 (s, 1H), 10.85 (s, 1H) |
| I.128 | 1-[4-(5-Hydroxy-pyridin-2-yl)-piperazin-1-yl]-3-(2-trifluoro-methylphenyl)-propan-1-one | 9.1 (s, 1H), 7.79 (d, 1H, J = 2.62 Hz), 7.73 (d, 1H, J = 7.88 Hz), 7.67 (t, 1H, J = 7.52 Hz), 7.60 (d, 1H, J = 7.69 Hz), 7.47 (t, 1H, J = 7.57 Hz), 7.13 (dd, 1H, J₁ = 8.92 Hz, J₂ = 2.69 Hz), 6.8 (d, 1H, J = 8.9 Hz), 3.62 (t, 2H, J = 4.71 Hz), 3.56 (t, 2H, J = 4.47 Hz), 3.32-3.33 (m, 4H), 3.05 (t, 2H, J = 7.93 Hz), 2.73 (t, 2H, J = 7.98 Hz) |
| I.129 | 1-[4-(5-Hydroxy-pyridin-2-yl)-piperazin-1-yl]-3-pyridin-2-yl-propan-1-one | 2.84 (t, 2H, J = 7.46 Hz), 3.03 (t, 2H, J = 7.61 Hz), 3.21-3.36 (m, 4H), 3.56-3.59 (m, 4H), 6.79 (d, 1H, J = 8.71 Hz), 7.15 (dd, 1H, J₁ = 8.85 Hz, J₂ = 2.42 Hz), 7.24 (t, 1H, J = 5.94 Hz), 7.34 (d, 1H, J = 8.03 Hz), 7.73 (t, 1H, J = 7.20 Hz), 7.80 (d, 1H, J = 2.16 Hz), 8.51 (d, 1H, J = 4.56 Hz), 9.22 (s, 1H) |
| I.130 | 3-Hydroxy-1-[4-(5-hydroxy-pyridin-2-yl)-piperazin-1-yl]-3-phenyl-propan-1-one | 2.63 (dd, 1H, J₁ = 14.88 Hz, J₂ = 4.68 Hz), 2.83 (dd, 1H, J₁ = 14.81 Hz, J₂ = 8.48 Hz), 3.20 (m, 1H), 3.26-3.30 (m, 3H), 3.43-3.53 (m, 1H), 3.59-3.60 (m, 3H), 5.02-5.04 (m, 1H), 5.40 (d, 1H, J = 4.2 Hz), 6.77 (d, 1H, J = 8.9 Hz), 7.12 (dd, 1H, J₁ = 8.9 Hz, J₂ = 3 Hz), 7.27 (t, 1H, J = 7.2 Hz), 7.37 (t, 2H, J = 7.5 Hz), 7.43 (d, 2H, J = 7.08 Hz), 7.78 (d, 1H, J = 2.8 Hz), 9.08 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.131 | 2-(5-Fluoro-1H-indol-3-yl)-1-[4-(5-hydroxy-pyridin-2-yl)-piperazin-1-yl]-ethanone | 3.22 (t, 2H, J = 4.6 Hz), 3.27 (t, 2H, J = 5.16 Hz), 3.62-3.66 (m, 4H), 3.84 (s, 2H), 6.76 (d, 1H, J = 9.0 Hz), 6.95 (td, 1H, J₁ = 15.8 Hz, J₂ = 4.6 Hz), 7.11 (dd, 1H, J₁ = 8.9 Hz, J₂ = 3 Hz), 7.37 (m, 3H), 7.77 (d, 1H, J = 2.8 Hz), 9.08 (s, 1H), 11.05 (s, 1H) |
| I.132 | [4-(5-Hydroxy-pyridin-2-yl)-piperazin-1-yl]-(1,2,3,4-tetrahydro-naphthalen-1-yl)-methanone | 1.85 (m, 1H), 1.87 (m, 1H), 1.93 (m, 1H), 1.98 (m, 1H), 3.69 (m, 2H), 3.76 (m, 2H), 3.80 (m, 2H), 3.87 (m, 1H), 4.16 (m, 1H), 4.30 (t, 1H, J = 6.66 Hz), 6.83 (d, 2H, J = 8.96 Hz), 6.95 (d, 1H, J = 7.0 Hz), 7.14 (m, 4H), 7.81 (s, 1H), 9.11 (s, 1H) |
| I.133 | [4-(5-Hydroxy-pyridin-2-yl)-piperazin-1-yl]-((1R,2R)-2-phenyl-cyclopropyl)-methanone | 1.27 (br-s, 1H), 1.48 (br-s, 1H), 2.38 (d, 2H, J = 5.04 Hz), 3.65 (s, 4H), 3.76 (br-s, 2H), 3.80 (br-s, 2H), 6.80 (d, 1H, J = 8.92 Hz), 7.12 (d, 1H, J = 6.05 Hz), 7.24 (d, 3H, J = 7.24 Hz), 7.31-7.34 (m, 2H), 7.80 (s, 1H), 9.09 (s, 1H) |
| I.134 | [4-(5-Hydroxy-pyridin-2-yl)-piperazin-1-yl]-(3-phenyl-cyclobutyl)-methanone | 2.27-2.35 (m, 2H), 2.58 (br-s, 1H), 3.31-3.38 (m, 1H), 3.41-3.45 (m, 2H), 3.46-3.48 (m, 1H), 3.50-3.52 (m, 3H), 3.55-3.60 (m, 4H), 6.80 (d, 1H, J = 8.92 Hz), 7.13 (d, 1H, J = 6.90 Hz), 7.23-7.27 (m, 2H), 7.33-7.37 (m, 3H), 7.80 (s, 1H), 9.13 (s, 1H) |
| I.135 | 1-[4-(5-Hydroxy-pyridin-2-yl)-piperazin-1-yl]-3-indol-1-yl-propan-1-one | 2.93 (t, 2H, J = 6.92 Hz), 3.20-3.26 (m, 4H), 3.43-3.57 (m, 4H), 4.48 (t, 2H, J = 6.90 Hz), 6.45 (d, 1H, J = 3.13 Hz), 6.75 (d, 1H, J = 9.00 Hz), 7.05 (t, 1H, J = 7.46 Hz), 7.11 (dd, 1H, J₁ = 8.96 Hz, J₂ = 3.00 Hz), 7.18 (t, 1H, J = 7.12 Hz), 7.43 (d, 1H, J = 3.12 Hz), 7.55 (dd, 2H, J₁ = 15.66 Hz, J₂ = 8.02 Hz), 7.78 (d, 1H, J = 2.8 Hz), 9.07 (s, 1H) |
| I.136 | 3-Benzo-imidazol-1-yl-1-[4-(5-hydroxy-pyridin-2-yl)-piperazin-1-yl]-propan-1-one | 3.02 (t, 2H, J = 6.78 Hz), 3.22-3.27 (m, 4H), 3.47-3.58 (m, 4H), 4.54 (t, 2H, J = 6.78 Hz), 6.76 (d, 1H, J = 9.01 Hz), 7.12 (dd, 1H, J₁ = 8.96 Hz, J₂ = 3.00 Hz), 7.24 (t, 1H, J = 7.02 Hz), 7.30 (t, 1H, J = 7.08 Hz), 7.68 (dd, 2H, J₁ = 7.88 Hz, J₂ = 2.92 Hz), 7.78 (d, 1H, J = 2.84 Hz), 8.27 (s, 1H), 9.08 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.137 | 2-Cyclopropyl-1-[4-(5-hydroxy-2-pyridyl)-piperazin-1-yl]ethanone | 0.17-0.18 (m, 2H), 0.49-0.51 (m, 2H), 1.01 (m, 1H), 2.34 (d, J = 6.72 Hz, 2H), 3.30-3.55 (m, 4H), 3.56-3.58 (m, 4H), 6.80 (d, J = 8.92 Hz, 1H), 7.12 ((d, J₁ = 8.92 Hz, J₂ = 2.80 Hz, 1H), 7.79 (d, J = 2.64 Hz, 1H), 9.09 (s, 1H). |
| I.138 | 3-(4-Cyanophenyl)-1-[4-(5-hydroxy-pyridin-2-yl)-piperazin-1-yl]-propan-1-one | 2.77 (t, 2H, J = 7.60 Hz), 2.97 (t, 2H, J = 7.55 Hz), 3.29-3.31 (m, 4H), 3.57-3.59 (m, 4H), 6.79 (d, 1H, J = 9.00 Hz), 7.13 (dd, 1H, J₁ = 9.0 Hz, J₂ = 3.0 Hz), 7.53 (d, 2H, J = 8.31 Hz), 7.79 (d, 2H, J = 7.65 Hz), 7.79 (s, 1H), 9.09 (s, 1H) |
| I.139 | 3-(4-Trifluoromethylphenyl)-1-[4-(5-hydroxy-pyridin-2-yl)-piperazin-1-yl]-propan-1-one | 2.77 (t, 2H, J = 7.40 Hz), 2.97 (t, 2H, J = 7.42 Hz), 3.30 (m, 4H), 3.58 (m, 4H), 6.79 (d, 1H, J = 9.00 Hz), 7.12 (d, 1H, J = 8.96 Hz), 7.54 (d, 2H, J = 7.85 Hz), 7.69 (d, 2H, J = 7.45 Hz), 7.79 (s, 1H), 9.08 (s, 1H) |
| I.140 | 3-Cyclopropyl-1-[4-(5-hydroxy-2-pyridyl)-piperazin-1-yl]propan-1-one | 0.07-0.11 (m, 2H), 0.40-0.45 (m, 2H), 0.76-0.80 (m, 1H), 1.43-1.50 (m, 2H), 2.47 (t, J = 7.64 Hz, 2H), 3.28-3.32 (m, 2H), 3.33-3.36 (m, 2H), 3.55-3.65 (m, 4H), 6.80 (d, J = 8.96 Hz, 1H), 7.12 ((d, J₁ = 8.96 Hz, J₂ = 3.00 Hz, 1H), 7.79 (d, J = 2.84 Hz, 1H), 9.09 (s, 1H). |
| I.141 | 2-{3-[4-(5-Hydroxy-pyridin-2-yl)-piperazin-1-yl]-3-oxo-propyl}-benzoic acid | 2.68 (t, 2H, J = 7.94 Hz), 3.18 (t, 2H, J = 7.92 Hz), 3.28-3.30 (m, 4H), 3.56-3.60 (m, 4H), 6.78 (d, 1H, J = 8.92 Hz), 7.12 (dd, 1H, J₁ = 8.96 Hz, J₂ = 3.0 Hz), 7.35 (t, 1H, J = 7.52 Hz), 7.40 (d, 1H, J = 6.96 Hz), 7.52 (t, 1H, J = 6.82 Hz), 7.79 (d, 1H, J = 2.84 Hz), 7.84 (d, 1H, J = 6.56 Hz), 9.09 (s, 1H), 13.0 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.142 | 2-{3-[4-(5-Hydroxy-pyridin-2-yl)-piperazin-1-yl]-3-oxo-propyl}-benzoic acid methyl ester | 2.68 (t, 2H, J = 7.84 Hz), 3.16 (t, 2H, J = 7.78 Hz), 3.29 (m, 4H), 3.54 (m, 2H), 3.59-3.60 (m, 2H), 3.88 (s, 3H), 6.78 (d, 1H, J = 8.96 Hz), 7.12 (dd, 1H, $J_1$ = 8.92 Hz, $J_2$ = 2.92 Hz), 7.37 (t, 1H, J = 7.5 Hz), 7.44 (d, 1H, J = 7.56 Hz), 7.55 (d, 1H, J = 7.5 Hz), 7.8 (d, 1H, J = 2.29 Hz), 7.84 (d, 1H, J = 7.76 Hz), 9.09 (s, 1H) |
| I.143 | 2-(2-Bromo-phenyl-sulfanyl)-1-[4-(5-hydroxy-pyridin-2-yl)-piperazin-1-yl]-ethanone | 3.34 (t, 2H, J = 5.00 Hz), 3.43 (t, 2H, J = 4.84 Hz), 3.62 (t, 2H, J = 4.96 Hz), 3.71 (t, 2H, J = 4.90 Hz), 4.18 (s, 2H), 6.83 (d, 1H, J = 8.96 Hz), 7.12-7.18 (m, 2H), 7.40-7.44 (m, 1H), 7.52 (dd, 1H, $J_1$ = 8.00 Hz, $J_2$ = 1.40 Hz), 7.65 (dd, 1H, $J_1$ = 7.94 Hz, $J_2$ = 1.22 Hz), 7.81 (d, 1H, J = 2.84 Hz), 9.11 (s, 1H) |
| I.144 | 2-Hydroxy-1-[4-(5-hydroxy-pyridin-2-yl)-piperazin-1-yl]-3-phenyl-propan-1-one | 2.82 (dd, 1H, $J_1$ = 13.56 Hz, $J_2$ = 7.92 Hz), 2.97 (dd, 1H, $J_1$ = 13.58 Hz, $J_2$ = 5.26 Hz), 3.22-3.35 (m, 4H), 3.50-3.67 (m, 4H), 4.59-4.64 (m, 1H), 5.18 (d, 1H, J = 7.92 Hz), 6.78 (d, 1H, J = 8.96 Hz), 7.12 (dd, 1H, $J_1$ = 8.96 Hz, $J_2$ = 3 Hz), 7.21-7.26 (m, 1H), 7.29-7.35 (m, 4H), 7.79 (d, 1H, J = 2.8 Hz), 9.10 (s, 1H) |
| I.145 | 3-(4-Fluoro-2-methyl-phenyl)-1-[4-(5-hydroxy-pyridin-2-yl)-piperazin-1-yl]-propan-1-one | 2.34 (s, 3H), 2.64 (t, 2H, J = 7.78 Hz), 2.84 (t, 2H, J = 7.76 Hz), 3.30 (t, 4H, J = 5.12 Hz), 3.54-3.60 (m, 4H), 6.78 (d, 1H, J = 8.96 Hz), 6.96 (td, 1H, $J_1$ = 14.4 Hz, $J_2$ = 4.3 Hz), 7.04 (dd, 1H, $J_1$ = 10.06 Hz, $J_2$ = 2.66 Hz), 7.13 (dd, 1H, $J_1$ = 8.96 Hz, $J_2$ = 3.00 Hz), 7.25 (dd, 1H, $J_1$ = 8.4 Hz, $J_2$ = 6.2 Hz), 7.80 (d, 1H, J = 2.92 Hz), 9.08 (s, 1H) |
| I.146 | 3-(2,3-Dimethyl-phenyl)-1-[4-(5-hydroxy-pyridin-2-yl)-piperazin-1-yl]-propan-1-one | 2.22 (s, 3H), 2.27 (s, 3H), 2.61 (t, 2H, J = 7.9 Hz), 2.88 (t, 2H, J = 7.9 Hz), 3.28-3.31 (m, 4H), 3.53 (t, 2H, J = 4.96 Hz), 3.60 (t, 2H, J = 5.06 Hz), 6.78 (d, 1H, J = 8.96 Hz), 7.02-7.08 (m, 3H), 7.13 (dd, 1H, $J_1$ = 8.96 Hz, $J_2$ = 3.00 Hz), 7.79 (d, 1H, J = 2.68 Hz), 9.08 (s, 1H) |
| I.147 | 3-(2,6-Dimethyl-phenyl)-1-[4-(5-hydroxy-pyridin-2-yl)-piperazin-1-yl]-propan-1-one | 2.33 (s, 6H), 2.52-2.53 (m, 2H), 2.88 (t, 2H, J = 8.26 Hz), 3.30-3.33 (m, 4H), 3.41-3.63 (m, 4H), 6.78 (d, 1H, J = 9.00 Hz), 7.03 (s, 3H), 7.13 (dd, 1H, $J_1$ = 8.96 Hz, $J_2$ = 3.00 Hz), 7.79 (d, 1H, J = 2.84 Hz), 9.06 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.148 | 2-(3,5-Difluorophenyl)-1-[4-(4-hydroxyphenyl)-piperazin-1-yl]-ethanone | 2.95 (m, 4H), 3.67 (m, 4H), 3.87 (s, 2H), 6.70-6.72 (m, 2H), 6.84-6.86 (m, 2H), 7.03 (dd, 2H, $J_1$ = 8.62 Hz, $J_2$ = 2.1 Hz), 7.14 (tt, 1H, $J_1$ = 9.48 Hz, $J_2$ = 2.34 Hz), 8.93 (s, 1H) |
| I.149 | 2-(2,4-Difluorophenyl)-1-[4-(4-hydroxyphenyl)-piperazin-1-yl]-ethanone | 2.96 (m, 2H), 3.02-3.33 (m, 2H), 3.64 (m, 2H), 3.71 (m, 2H), 3.82 (s, 2H), 6.72 (d, 2H, J = 8.8 Hz), 6.87 (d, 2H, J = 8.9 Hz), 7.08 (t, 1H, J = 7.54 Hz), 7.24 (td, 1H, $J_1$ = 9.84 Hz, $J_2$ = 2.41 Hz), 7.37 (q, 1H, $J_1$ = 15.44 Hz, $J_2$ = 8.64 Hz), 8.93 (s, 1H) |
| I.150 | 2-(5-Fluoro-1H-indol-3-yl)-1-[4-(4-hydroxyphenyl)-piperazin-1-yl]-ethanone | 2.86 (m, 2H), 2.91 (m, 2H), 3.64 (m, 2H), 3.68 (m, 2H), 3.83 (s, 2H), 6.68 (d, 2H, J = 8.93 Hz), 6.8 (d, 2H, J = 8.9 Hz), 6.96 (td, 1H, $J_1$ = 9.14 Hz, $J_2$ = 2.53 Hz), 7.35-7.40 (m, 3H), 8.9 (s, 1H), 11.05 (s, 1H) |
| I.151 | 2-(2-Bromophenylsulfanyl)-1-[4-(4-hydroxyphenyl)-piperazin-1-yl]-ethanone | 2.97 (t, 2H), 3.06 (t, 2H), 3.65 (t, 2H), 3.74 (t, 2H), 4.17 (s, 2H), 6.72 (d, 2H, J = 8.84 Hz), 6.87 (d, 2H, J = 8.84 Hz), 7.16 (t, 1H, J = 7.60 Hz), 7.42 (t, 1H, J = 7.62 Hz), 7.52 (d, 1H, J = 7.96 Hz), 7.65 (d, 1H, J = 7.88 Hz), 8.92 (s, 1H) |
| I.152 | 3-(2,4-Difluorophenyl)-1-[4-(5-hydroxypyridin-2-yl)-piperazin-1-yl]-propan-1-one | 2.70 (t, 2H, J = 7.56 Hz), 2.88 (t, 2H, J = 7.74 Hz), 3.20-3.34 (m, 4H), 3.42-3.61 (m, 4H), 6.79 (d, 1H, J = 8.96 Hz), 7.04-7.08 (m, 1H), 7.12 (dd, 1H, $J_1$ = 8.9 Hz, $J_2$ = 3.00 Hz), 7.19-7.25 (m, 1H), 7.42-7.48 (m, 1H), 7.8 (d, 1H, J = 2.80 Hz), 9.08 (s, 1H) |
| I.153 | 3-(3,4-Difluorophenyl)-1-[4-(5-hydroxypyridin-2-yl)-piperazin-1-yl]-propan-1-one | 2.73 (t, 2H, J = 7.56 Hz), 2.88 (t, 2H, J = 7.58 Hz), 3.28-3.33 (m, 4H), 3.56-3.61 (t, 4H), 6.80 (d, 1H, J = 9.0 Hz), 7.12-7.15 (m, 2H), 7.33-7.43 (m, 2H), 7.8 (d, 1H, J = 2.72 Hz), 9.10 (s, 1H) |

TABLE 2-continued

Chemical Name and ¹H NMR Data for Compound of Formula I

| Compound No. | Structure | IUPAC Name | ¹H NMR (δ ppm) in DMSO-d₆ as solvent, 500 MHz |
|---|---|---|---|
| I.154 | 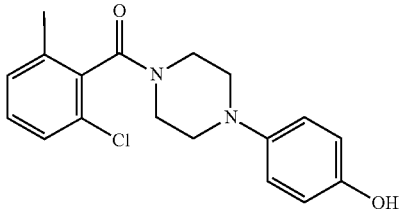 [SMILES: Cc1cccc(Cl)c1C(=O)N1CCN(c2ccc(O)cc2)CC1] | (2-Chloro-6-methylphenyl)-[4-(4-hydroxy-phenyl)-piperazin-1-yl]-methanone | 2.29 (s, 3H), 2.89-2.95 (m, 1H), 2.97-3.03 (m, 1H), 3.08 (t, 2H, J = 5.27 Hz), 3.24-3.29 (m, 2H), 3.81-3.89 (m, 2H), 6.71 (d, 2H, J = 8.96 Hz), 6.86 (d, 2H, J = 8.96 Hz), 7.32-7.36 (m, 1H), 7.39 (t, 2H, J = 3.32 Hz), 8.93 (s, 1H) |
| I.155 | 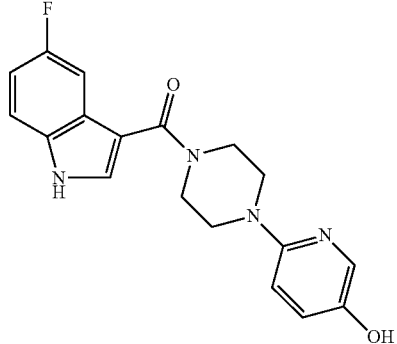 [SMILES: O=C(c1c[nH]c2ccc(F)cc12)N1CCN(c2ccc(O)cn2)CC1] | (5-Fluoro-1H-indol-3-yl)-[4-(5-hydroxy-pyridin-2-yl)-piperazin-1-yl]-methanone | 3.43 (t, 4H, J = 5.08 Hz), 3.79 (t, 4H, J = 5.08 Hz), 6.81 (d, 1H, J = 8.96 Hz), 7.04-7.09 (m, 1H), 7.13-7.16 (m, 1H), 7.47-7.51 (m, 2H), 7.81 (d, 2H, J = 2.84 Hz), 7.87 (s, 1H), 9.08 (s, 1H), 11.78 (s, 1H) |
| I.156 | 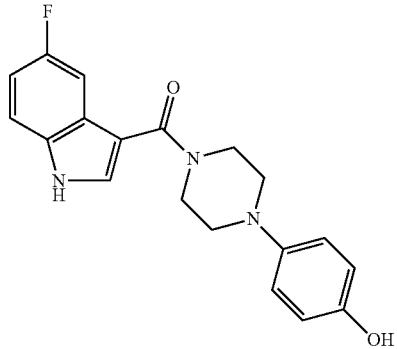 [SMILES: O=C(c1c[nH]c2ccc(F)cc12)N1CCN(c2ccc(O)cc2)CC1] | (5-Fluoro-1H-indol-3-yl)-[4-(4-hydroxy-phenyl)-piperazin-1-yl]-methanone | 3.05 (t, 4H, J = 4.94 Hz), 3.81 (t, 4H, J = 4.94 Hz), 6.72 (d, 2H, J = 8.92 Hz), 6.87 (d, 2H, J = 8.92 Hz), 7.04-7.09 (m, 1H), 7.46-7.52 (m, 2H), 8.50 (s, 1H), 8.92 (s, 1H), 11.78 (s, 1H) |
| I.157 | 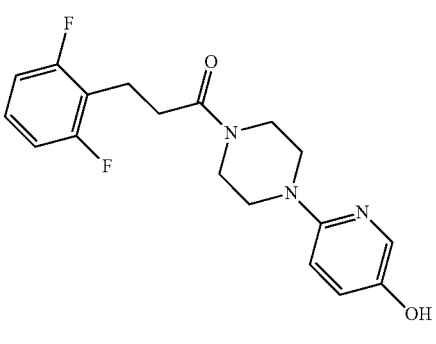 [SMILES: O=C(CCc1c(F)cccc1F)N1CCN(c2ccc(O)cn2)CC1] | 3-(2,6-Difluoro-phenyl)-1-[4-(5-hydroxy-pyridin-2-yl)-piperazin-1-yl]-propan-1-one | 2.67 (t, 2H, J = 7.94 Hz), 2.91 (t, 2H, J = 7.90 Hz), 3.32-3.38 (m, 4H), 3.55 (t, 2H, J = 4.98 Hz), 3.60 (t, 2H, J = 5.06 Hz), 6.79 (d, 1H, J = 8.96 Hz), 7.08-7.14 (m, 3H), 7.32-7.39 (m, 1H), 7.79 (d, 1H, J = 2.88 Hz), 9.08 (s, 1H) |
| I.158 | 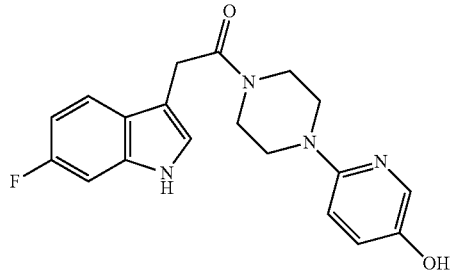 [SMILES: O=C(Cc1c[nH]c2cc(F)ccc12)N1CCN(c2ccc(O)cn2)CC1] | 2-(6-Fluoro-1H-indol-3-yl)-1-[4-(5-hydroxy-pyridin-2-yl)-piperazin-1-yl]-ethanone | 3.34 (m, 4H), 3.65-3.69 (m, 4H), 3.93 (s, 2H), 6.73 (q, 1H, J₁ = 11.4 Hz, J₂ = 7.72 Hz), 6.80 (d, 1H, J = 8.96 Hz), 7.04-7.09 (m, 1H), 7.12 (dd, 1H, J₁ = 8.98 Hz, J₂ = 2.98 Hz), 7.21 (t, 2H, J = 7.62 Hz), 7.8 (d, 1H, J = 2.92 Hz), 9.1 (s, 1H), 11.19 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.159 | 2-(5-Chloro-1H-indol-3-yl)-1-[4-(5-hydroxy-pyridin-2-yl)-piperazin-1-yl]-ethanone | 3.23-3.28 (m, 4H), 3.62-3.67 (m, 4H), 3.86 (s, 2H), 6.78 (d, 1H, J = 8.96 Hz), 7.09-7.12 (m, 2H), 7.37-7.41 (m, 2H), 7.66 (d, 1H, J = 2.04 Hz), 7.77 (d, 1H, J = 2.76 Hz), 9.09 (s, 1H), 11.16 (s, 1H) |
| I.160 | 2-(5,6-Difluoro-1H-indol-3-yl)-1-[4-(5-hydroxy-pyridin-2-yl)-piperazin-1-yl]-ethanone | 3.34-3.35 (m, 4H), 3.65-3.71 (m, 4H), 3.93 (s, 2H), 6.81 (d, 1H, , J = 9.0 Hz), 7.08-7.21 (m, 3H), 7.28 (d, 2H, J = 2.08 Hz), 7.81 (d, 1H, J = 2.88 Hz), 9.11 (s, 1H), 11.25 (s, 1H) |
| I.161 | 3-(4-Fluoro-phenyl)-1-[4-(5-hydroxy-pyridin-2-yl)-piperazin-1-yl]-3-methyl-butan-1-one | 1.45 (s, 6H), 2.56 (s, 2H), 2.73 (m, 4H), 3.48 (m, 4H), 6.75 (d, 1H, J = 9.0 Hz), 7.09-7.15 (m, 3H), 7.43-7.47 (m, 2H), 7.77 (d, 1H, J = 2.76 Hz), 9.09 (s, 1H) |
| I.162 | 2-(2-Bromo-phenyl-sulfanyl)-1-[4-(5-hydroxy-pyridin-2-yl)-piperazin-1-yl]-2-methyl-propan-1-one | 1.59 (s, 6H), 3.31 (m, 4H), 3.91 (m, 4H), 6.79 (d, 1H, J = 8.96 Hz), 7.12 (dd, 1H, J₁ = 8.94 Hz, J₂ = 2.94 Hz), 7.25-7.29 (m, 1H), 7.39-7.47 (m, 2H), 7.74 (d, 1H, J = 7.88 Hz), 7.78 (d, 1H, J = 2.84 Hz), 9.11 (s, 1H) |
| I.163 | 2-(4-Fluoro-phenyl-sulfanyl)-1-[4-(5-hydroxy-pyridin-2-yl)-piperazin-1-yl]-ethanone | 3.31-3.39 (m, 4H), 3.59-3.63 (m, 4H), 4.05 (s, 2H), 6.81 (d, 1H, J = 8.96 Hz), 7.14 (dd, 1H, J₁ = 8.9 Hz, J₂ = 2.78 Hz), 7.23 (t, 2H, J = 8.78 Hz), 7.52 (q, 1H, J₁ = 8.44 Hz, J₂ = 5.36 Hz), 7.80 (d, 1H, J = 2.68 Hz), 9.11 (s, 1H) |

TABLE 2-continued

Chemical Name and ¹H NMR Data for Compound of Formula I

| Compound No. | IUPAC Name | ¹H NMR (δ ppm) in DMSO-d₆ as solvent, 500 MHz |
|---|---|---|
| I.164 | 2-(4-Fluoro-phenoxy)-1-[4-(5-hydroxy-pyridin-2-yl)-piperazin-1-yl]-ethanone | 3.34 (m, 2H), 3.39 (m, 2H), 3.60 (t, 4H, J = 5.10 Hz), 4.90 (s, 2H), 6.82 (d, 1H, J = 9.0 Hz), 6.98-7.02 (m, 2H), 7.12-7.19 (m, 3H), 7.80 (d, 1H, J = 2.84 Hz), 9.11 (s, 1H) |
| I.165 | 2-(5-Fluoro-1-methyl-indol-3-yl)-1-[4-(5-hydroxy-pyridin-2-yl)-piperazin-1-yl]-ethanone | 3.27-3.31 (m, 4H), 3.61-3.66 (m, 4H), 3.83 (s, 3H), 3.96 (s, 2H), 6.78 (d, 1H, J = 8.99 Hz), 7.03 (td, 1H, J₁ = 15.79 Hz, J₂ = 4.59 Hz), 7.11 (dd, 1H, J₁ = 8.96 Hz, J₂ = 3.00 Hz), 7.34 (s, 1H), 7.39 (dd, 1H, J₁ = 10.08 Hz, J₂ = 2.48 Hz), 7.45 (dd, 1H, J₁ = 8.87 Hz, J₂ = 4.42 Hz), 7.78 (d, 1H, J = 2.87 Hz), 9.07 (s, 1H) |
| I.166 | 2-(5-Fluoro-2-methyl-1H-indol-3-yl)-1-[4-(5-hydroxy-pyridin-2-yl)-piperazin-1-yl]-ethanone | 2.38 (s, 3H), 3.16 (m, 2H), 3.25 (m, 2H), 3.60 (t, 4H, J = 5.01 Hz), 3.77 (s, 2H), 6.75 (d, 1H, J = 8.99 Hz), 6.82-6.86 (m, 1H), 7.10 (dd, 1H, J₁ = 8.96 Hz, J₂ = 2.96 Hz), 7.23-7.26 (m, 2H), 7.77 (d, 1H, J = 2.87 Hz), 9.09 (s, 1H), 10.97 (s, 1H) |
| I.167 | 2-(5,7-Difluoro-1H-indol-3-yl)-1-[4-(5-hydroxy-pyridin-2-yl)-piperazin-1-yl]-ethanone | 3.24-3.28 (m, 4H), 3.61 (m, 2H), 3.67 (m, 2H), 3.85 (m, 2H), 6.77 (d, 1H, J = 8.98 Hz), 6.97-7.02 (m, 1H), 7.11 (dd, 1H, J₁ = 8.94 Hz, J₂ = 2.92 Hz), 7.26 (dd, 1H, J₁ = 9.58 Hz, J₂ = 1.90 Hz), 7.44 (d, 1H, J = 1.88 Hz), 7.78 (d, 1H, J = 2.84 Hz), 9.09 (s, 1H), 11.59 (s, 1H) |
| I.168 | 1-(5-Fluoro-1H-indol-3-yl)-2-[4-(5-hydroxy-pyridin-2-yl)-piperazin-1-yl]-ethane-1,2-dione | 3.32-3.34 (m, 2H), 3.49-3.51 (m, 4H), 3.76-3.77 (m, 2H), 6.80 (d, 1H, J = 8.98 Hz), 7.14 (dd, 1H, J₁ = 8.94 Hz, J₂ = 2.89 Hz), 7.19-7.23 (m, 1H), 7.59-7.62 (m, 1H), 7.80 (d, 1H, J = 2.79 Hz), 7.85 (d, 1H, J = 7.64 Hz), 8.32 (s, 1H), 9.11 (s, 1H), 12.46 (s, 1H) |

TABLE 2-continued

Chemical Name and ¹H NMR Data for Compound of Formula I

| Compound No. | IUPAC Name | ¹H NMR (δ ppm) in DMSO-d$_6$ as solvent, 500 MHz |
|---|---|---|
| I.169 | 2-(5-Fluoro-1H-indol-3-yl)-1-[4-(5-hydroxy-pyridin-2-yl)-piperazin-1-yl]-2-methyl-propan-1-one | 1.59 (s, 6H), 3.42 (s, 8H), 6.59 (d, 1H, J = 8.98 Hz), 6.92 (t, 1H, J = 9.06 Hz), 6.98 7.03 (m, 2H), 7.38-7.41 (m, 2H), 7.68 (d, 1H, J = 2.8 Hz), 9.01 (s, 1H), 11.16 (s, 1H) |
| I.170 | 1-[4-(5-Hydroxy-pyridin-2-yl)-piperazin-1-yl]-3-(3,4,5-trifluoro-phenyl)-propan-1-one | 2.75 (t, 2H, J = 7.58 Hz), 2.87 (t, 2H, J = 7.63 Hz), 3.29 (t, 2H, J = 5.17 Hz), 3.34 (t, 2H, J = 5.12 Hz), 3.57-3.61 (m, 4H), 6.80 (d, 1H, J = 8.95 Hz), 7.13 (dd, 1H, J$_1$ = 8.96 Hz, J$_2$ = 3.00 Hz), 7.29-7.33 (m, 2H), 7.79 (d, 1H, J = 2.55 Hz), 9.09 (s, 1H) |
| I.171 | 1-[4-(4-Hydroxy-phenyl)-piperazin-1-yl]-2-(3,4,5-trifluoro-phenyl)-ethanone | 2.95-2.99 (m, 4H), 3.64-3.68 (m, 4H), 3.84 (s, 2H), 6.71 (d, 2H, J = 8.68 Hz), 6.85 (d, 2H, J = 8.72 Hz), 7.25 (t, 2H, J = 7.86 Hz), 8.99 (s, 1H) |
| I.172 | N-{3-[4-(5-Hydroxy-pyridin-2-yl)-piperazin-1-yl]-3-oxo-1-phenyl-propyl}-acrylamide | 2.87 (dd, 1H, J$_1$ = 15.40 Hz, J$_2$ = 6.44 Hz), 2.95 (dd, 1H, J$_1$ = 15.39 Hz, J$_2$ = 7.75 Hz), 3.23-3.34 (m, 4H), 3.42-3.58 (m, 4H), 5.37 (q, 1H, J$_1$ = 14.58 Hz, J$_2$ = 7.65 Hz), 5.64 (dd, 1H, J$_1$ = 10.2 Hz, J$_2$ = 2.12 Hz), 6.13 (dd, 1H, J$_1$ = 17.07 Hz, J$_2$ = 2.11 Hz), 6.29-6.34 (m, 1H), 6.78 (d, 1H, J = 8.98 Hz), 7.12 (dd, 1H, J$_1$ = 8.95 Hz, J$_2$ = 3.00 Hz), 7.26-7.29 (m, 1H), 7.35-7.40 (m, 4H), 7.79 (d, 1H, J = 2.85 Hz), 8.57 (d, 1H, J = 8.13 Hz), 9.08 (s, 1H) |
| I.173 | 1-[4-(4-Hydroxy-phenyl)-piperazin-1-yl]-3-methyl-3-phenyl-butan-1-one hydrochloride salt | 1.47 (s, 6H), 2.78 (s, 2H), 3.18 (m, 2H), 3.75-3.94 (m, 6H), 6.90 (d, 2H, J = 8.09 Hz), 7.22 (t, 1H, J = 7.24 Hz), 7.36 (t, 2H, J = 7.68 Hz), 7.45 (d, 2H, J = 7.6 Hz), 7.49-7.50 (m, 2H), 9.97 (br-s, 1H) |

TABLE 2-continued

Chemical Name and $^1$H NMR Data for Compound of Formula I

| Compound No. | Structure | IUPAC Name | $^1$H NMR (δ ppm) in DMSO-$d_6$ as solvent, 500 MHz |
|---|---|---|---|
| I.174 | 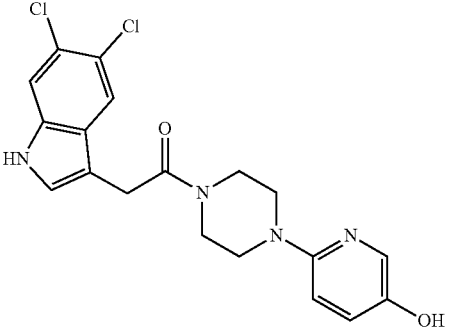 [SMILES: O=C(Cc1c[nH]c2cc(Cl)c(Cl)cc12)N1CCN(c2ccc(O)cn2)CC1] | 2-(5,6-Dichloro-1H-indol-3-yl)-1-[4-(5-hydroxy-pyridin-2-yl)-piperazin-1-yl]-ethanone | 3.25-3.28 (m, 4H), 3.61-3.67 (m, 4H), 3.87 (s, 2H), 6.78 (d, 1H, J = 8.98 Hz), 7.10 (dd, 1H, $J_1$ = 8.93 Hz, $J_2$ = 2.88 Hz), 7.42 (s, 1H), 7.64 (s, 1H), 7.78 (d, 1H, J = 2.79 Hz), 7.86 (s, 1H), 9.09 (s, 1H), 11.24 (s, 1H) |
| I.175 | 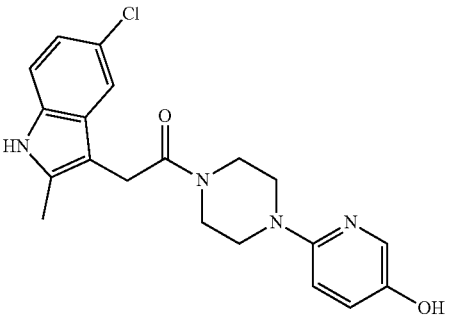 [SMILES: Cc1[nH]c2ccc(Cl)cc2c1CC(=O)N1CCN(c2ccc(O)cn2)CC1] | 2-(5-Chloro-2-methyl-1H-indol-3-yl)-1-[4-(5-hydroxy-pyridin-2-yl)-piperazin-1-yl]-ethanone | 2.38 (s, 3H), 3.19 (m, 2H), 3.26 (m, 2H), 3.61 (m, 4H), 3.79 (s, 2H), 6.77 (d, 1H, J = 9.01 Hz), 7.01 (dd, 1H, $J_1$ = 8.47 Hz, $J_2$ = 1.84 Hz), 7.10 (dd, 1H, $J_1$ = 8.93 Hz, $J_2$ = 2.92 Hz), 7.28 (d, 1H, J = 8.49 Hz), 7.52 (d, 1H, J = 1.51 Hz), 7.77 (d, 1H, J = 2.83 Hz), 9.07 (s, 1H), 11.07 (s, 1H) |
| I.176 | 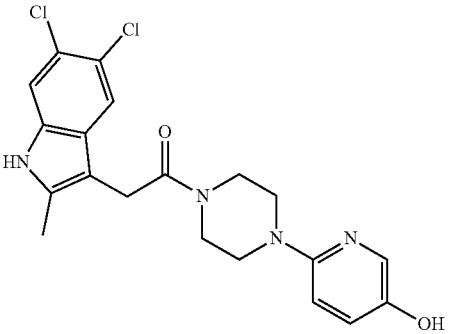 [SMILES: Cc1[nH]c2cc(Cl)c(Cl)cc2c1CC(=O)N1CCN(c2ccc(O)cn2)CC1] | 2-(5,6-Dichloro-2-methyl-1H-indol-3-yl)-1-[4-(5-hydroxy-pyridin-2-yl)-piperazin-1-yl]-ethanone | 2.37 (s, 3H), 3.22 (m, 2H), 3.27 (m, 2H), 3.61 (m, 4H), 3.80 (s, 2H), 6.77 (d, 1H, J = 8.98 Hz), 7.11 (dd, 1H, $J_1$ = 8.92 Hz, $J_2$ = 2.86 Hz), 7.50 (s, 1H), 7.72 (s, 1H), 7.77 (d, 1H, J = 2.75 Hz), 9.08 (s, 1H), 11.21 (s, 1H) |

BIOLOGICAL DATA

In-Vitro Enzyme Assay

ME3 Inhibition Assay

ME3 catalyzes the oxidative decarboxylation of malate to pyruvate with conversion of the co-factor β-NADP+ to NADPH. In the fluorescence assay, a coupled reaction is set up wherein an enzyme, Diaphorase, utilizes NADPH generated by ME3, to convert the dye resazurin to a fluorescent molecule resorufin. Resorufin has a characteristic fluorescence with excitation/emission at 540/600 nm (SLAS Discov., 2017 April 1:2472555217706649).

The enzyme activity inhibition assay is set up in a 200 μL final reaction volume in a 96-well plate. As per the experimental design, 2 μL of the test compounds at 100× the desired concentration (10 μM) in DMSO were added to the respective wells with 178 μL of assay buffer (50 mM Tris-HCl pH 7.5, 10 mM MnCl$_2$, 3 mM L-malate, 50 μM Resazurin and 0.025 mg/ml Diapharose). The 96-well plate was incubated on a plate shaker at room temperature for 15 minutes protected from light. The well contents were gently mixed by adding 10 μL of 20 nM human ME3 enzyme to the wells and the plate was incubated on a shaker at room temperature for 5 minutes protected from light. Suitable enzyme only and no enzyme controls were included in the experiment. The enzyme reaction was started by adding 10 μL of 1 mM D-NADP+. The reaction was gently mixed and the plate was initially left on a shaker at room temperature for ~7 minutes protected from light. Later, the plate was incubated without shaking at room temperature for 3 hours. At the end of 3 hours, the fluorescence of the wells was measured at excitation 540 nm and emission 600 nm. The % enzyme activity of the compounds is obtained by normalizing the data with enzyme only (100%) and no enzyme controls (0%) using GraphPad Prism software 7.04.

ME2 Inhibition Assay

ME2 catalyzes the oxidative decarboxylation of malate to pyruvate with conversion of the co-factor β-NAD+ to β-NADH. In the fluorescence assay, a coupled reaction is set up where in an enzyme, Diaphorase, utilizes NADH generated by ME2, to convert the dye resazurin to a fluorescent molecule resorufin. Resorufin has a characteristic fluorescence with excitation/emission at 540/600 nm (SLAS Discov., 2017 April 1:2472555217706649).

The enzyme activity inhibition assay is set up in a 200 µL final reaction volume in a 96-well plate. As per the experimental design, 2 µL of the compounds at 100× the desired concentration (10 µM) in DMSO were added to the respective wells with 178 µL of assay buffer (50 mM Tris-HCl pH 7.5, 10 mM $MnCl_2$, 7 mM L-malate, 50 µM Resazurin and 0.025 mg/ml Diapharose). The 96-well plate was incubated on a plate shaker at room temperature for 15 minutes protected from light. The well contents were gently mixed by adding 10 µL of 60 nM human ME2 enzyme to the wells and the plate was incubated on a shaker at room temperature for 5 minutes protected from light. Suitable 'enzyme only' and 'no enzyme' controls were included in the experiment. The enzymatic reaction was started by adding 10 µL of 2 mM β-NAD+. The reaction was gently mixed and the plate was initially left on a shaker at room temperature for ~7 minutes protected from light. Later, the plate was incubated without shaking at room temperature for 2 hours. At the end of 2 hours, the fluorescence of the wells was measured at excitation 540 nm and emission 600 nm. The % enzyme activity of the compounds is obtained by normalizing the data with enzyme only (100%) and no enzyme controls (0%) using GraphPad Prism software 7.04.

ME1 Inhibition Assay

ME1 catalyzes the oxidative decarboxylation of malate to pyruvate with conversion of the co-factor β-NADP+ to β-NADPH. In the fluorescence assay, a coupled reaction is set up where in an enzyme, Diaphorase, utilizes NADPH generated by ME1, to convert the dye resazurin to a fluorescent molecule resorufin. Resorufin has a characteristic fluorescence with excitation/emission at 540/600 nm (SLAS Discov., 2017 April 1:2472555217706649).

The enzyme activity inhibition assay is set up in a 200 µL final reaction volume in a 96-well plate. As per the experimental design, 2 µL of the compounds at 100× the desired concentration (10 µM) in DMSO were added to the respective wells with 178 µL of assay buffer (50 mM Tris-HCl pH 7.5, 10 mM $MnCl_2$, 2 mM L-malate, 10 µM Resazurin and 0.01 mg/ml Diapharose). The 96-well plate was incubated on a plate shaker at room temperature for 15 minutes protected from light. The well contents were gently mixed by adding 10 µL of 20 nM human ME1 enzyme to the wells and the plate was incubated on a shaker at room temperature for 5 minutes protected from light. Suitable 'enzyme only' and 'no enzyme' controls were included in the experiment. The enzymatic reaction was started by adding 10 µL of 0.3 mM D-NADP+. The reaction was gently mixed and the plate was initially left on a shaker at room temperature for ~7 minutes protected from light. Later, the plate was incubated without shaking at room temperature for 2 hours. At the end of 2 hours, the fluorescence of the wells was measured at excitation 540 nm and emission 600 nm. The % enzyme activity of the compounds is obtained by normalizing the data with enzyme only (100%) and no enzyme controls (0%) using GraphPad Prism software 7.04.

Results for representative compounds of the instant invention at 10 µM concentration are provided in Table 3 below.

TABLE 3

Malic Enzyme Inhibition (%) at 10 µM Concentration

| Compound No. | Malic Enzyme 3 % inhibition (10 µM) | Malic Enzyme 1 % inhibition (10 µM) | Malic Enzyme 2 % inhibition (10 µM) |
|---|---|---|---|
| I.1 | A | A | A |
| I.2 | A | A | A |
| I.3 | A | A | — |
| I.4 | A | A | — |
| I.5 | A | A | A |
| I.6 | A | A | A |
| I.7 | A | — | — |
| I.8 | A | — | — |
| I.9 | A | A | A |
| I.10 | A | — | — |
| I.11 | A | A | B |
| I.12 | A | — | — |
| I.13 | A | — | — |
| I.14 | A | — | — |
| I.15 | A | — | — |
| I.16 | A | — | — |
| I.17 | A | — | — |
| I.18 | A | — | — |
| I.19 | A | — | — |
| I.20 | A | — | — |
| I.21 | A | A | A |
| I.22 | A | — | — |
| I.23 | A | — | — |
| I.24 | A | — | — |
| I.25 | A | — | — |
| I.26 | A | — | — |
| I.27 | A | — | — |
| I.28 | A | A | — |
| I.29 | A | — | — |
| I.30 | A | — | — |
| I.31 | A | — | — |
| I.32 | B | — | — |
| I.33 | A | — | — |
| I.34 | A | — | — |
| I.35 | A | — | — |
| I.36 | A | — | — |
| I.37 | C | — | — |
| I.38 | A | — | — |
| I.39 | A | A | A |
| I.40 | A | A | A |
| I.41 | A | A | A |
| I.42 | A | A | A |
| I.43 | A | A | C |
| I.44 | A | A | C |
| I.45 | A | A | B |
| I.46 | A | A | A |
| I.47 | A | A | A |
| I.48 | A | B | B |
| I.49 | A | A | A |
| I.50 | A | A | A |
| I.51 | A | B | B |
| I.52 | A | A | A |
| I.53 | A | A | A |
| I.54 | A | B | C |
| I.55 | A | A | B |
| I.56 | A | C | B |
| I.57 | A | B | B |
| I.58 | A | B | C |
| I.59 | A | B | B |
| I.60 | A | B | B |
| I.61 | A | B | B |
| I.62 | A | B | B |
| I.63 | A | B | B |
| I.64 | A | B | C |
| I.65 | A | B | B |
| I.66 | A | B | B |
| I.67 | A | A | C |
| I.68 | A | A | B |
| I.69 | A | B | B |
| I.70 | A | B | B |
| I.71 | A | A | B |
| I.72 | A | A | B |
| I.73 | A | B | B |
| I.74 | A | A | B |

TABLE 3-continued

Malic Enzyme Inhibition (%) at 10 μM Concentration

| Compound No. | Malic Enzyme 3 % inhibition (10 μM) | Malic Enzyme 1 % inhibition (10 μM) | Malic Enzyme 2 % inhibition (10 μM) |
|---|---|---|---|
| I.75 | A | A | B |
| I.76 | A | — | — |
| I.77 | A | — | — |
| I.78 | A | — | — |
| I.79 | A | A | A |
| I.80 | A | A | A |
| I.81 | A | — | — |
| I.82 | A | A | A |
| I.83 | A | C | C |
| I.84 | A | B | B |
| I.85 | A | — | — |
| I.86 | A | — | — |
| I.87 | A | — | — |
| I.88 | A | A | B |
| I.89 | A | — | — |
| I.90 | A | — | — |
| I.91 | A | — | — |
| I.92 | A | A | A |
| I.93 | A | B | B |
| I.94 | A | B | B |
| I.95 | A | B | B |
| I.96 | A | B | B |
| I.97 | A | — | — |
| I.98 | A | — | — |
| I.99 | A | — | — |
| I.100 | A | — | — |
| I.101 | A | — | — |
| I.102 | A | — | — |
| I.103 | A | — | — |
| I.104 | B | — | — |
| I.105 | A | — | — |
| I.106 | A | — | — |
| I.107 | A | A | A |
| I.108 | A | — | — |
| I.109 | A | — | — |
| I.110 | A | — | — |
| I.111 | A | — | — |
| I.112 | A | — | — |
| I.113 | A | — | — |
| I.114 | A | — | — |
| I.115 | A | A | A |
| I.116 | A | A | A |
| I.117 | A | — | — |
| I.118 | A | — | — |
| I.119 | A | — | — |
| I.120 | A | — | — |
| I.121 | A | A | A |
| I.122 | A | A | A |
| I.123 | A | B | B |
| I.124 | A | A | A |
| I.125 | A | A | A |
| I.126 | A | A | A |
| I.127 | A | A | A |
| I.128 | A | A | A |
| I.129 | A | B | B |
| I.130 | A | B | A |
| I.131 | A | A | A |
| I.132 | A | B | A |
| I.133 | A | A | A |
| I.134 | A | A | A |
| I.135 | A | B | A |
| I.136 | A | B | A |
| I.137 | A | A | A |
| I.138 | A | A | A |
| I.139 | A | A | A |
| I.140 | A | A | A |
| I.141 | A | B | A |
| I.142 | A | B | A |
| I.143 | A | A | A |
| I.144 | A | C | A |
| I.145 | A | A | A |
| I.146 | A | A | A |
| I.147 | A | A | A |
| I.148 | A | A | A |
| I.149 | A | A | A |
| I.150 | A | A | A |
| I.151 | A | A | A |
| I.152 | A | A | A |
| I.153 | A | A | A |
| I.154 | A | A | A |
| I.155 | A | A | A |
| I.156 | A | A | A |
| I.157 | A | A | A |
| I.158 | A | A | A |
| I.159 | A | A | A |
| I.160 | A | A | A |
| I.161 | A | A | A |
| I.162 | A | A | A |
| I.163 | A | A | A |
| I.164 | A | A | A |
| I.165 | A | A | A |
| I.166 | A | A | A |
| I.167 | A | A | A |
| I.168 | A | A | A |
| I.169 | A | A | A |
| I.170 | A | A | A |
| I.171 | A | A | A |
| I.172 | A | C | A |
| I.173 | A | B | A |
| I.174 | A | A | A |
| I.175 | A | A | A |
| I.176 | A | A | A |

A = greater than 90% inhibition at the tested concentration
B = 70-89% inhibition at the tested concentration
C = 50-69% inhibition at the tested concentration.

What is claimed is:

1. A compound of Formula I

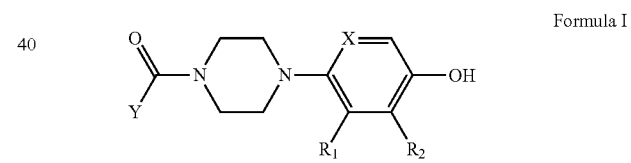

Formula I or a pharmaceutically acceptable salt, stereoisomer or deuterated analog thereof, wherein X is nitrogen;

$R_1$ is selected from hydrogen, —$CH_3$, —COOH, fluoro and —CN;

$R_2$ is selected from hydrogen, —$CH_3$, —COOH, fluoro and —CN; and

Y is selected from:

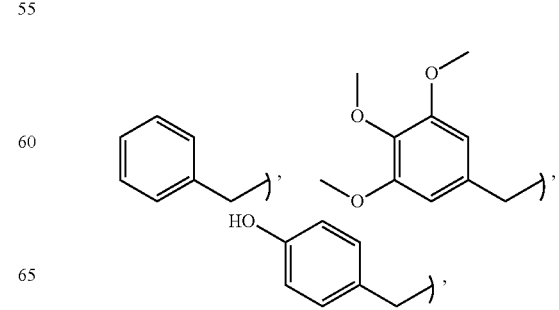

-continued
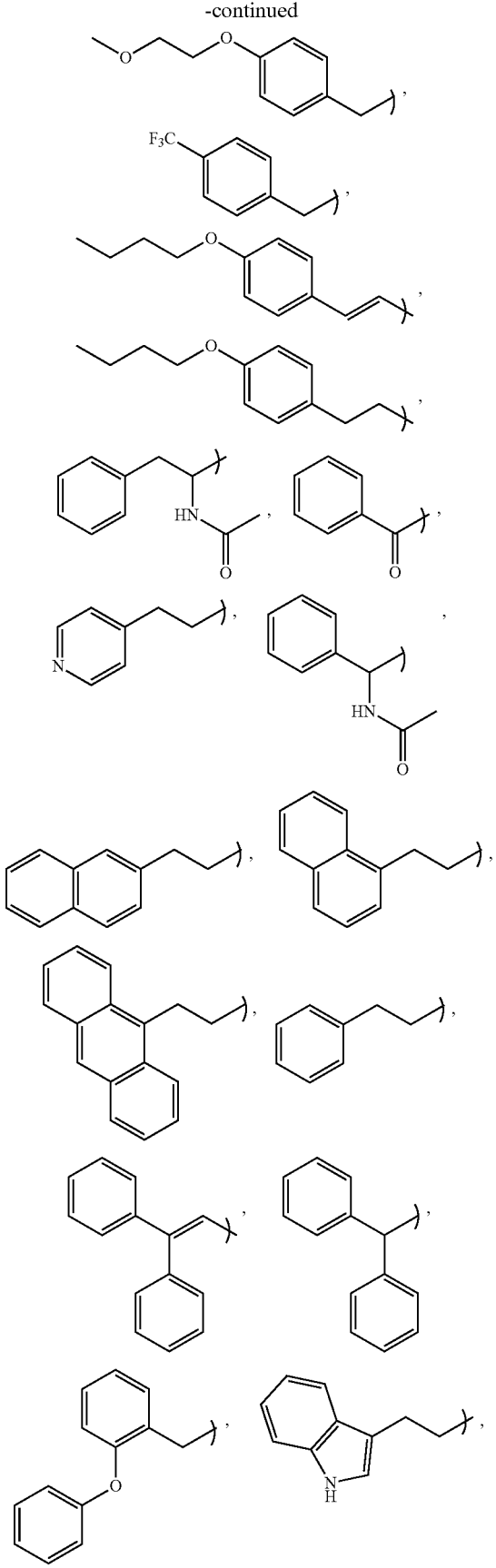
-continued
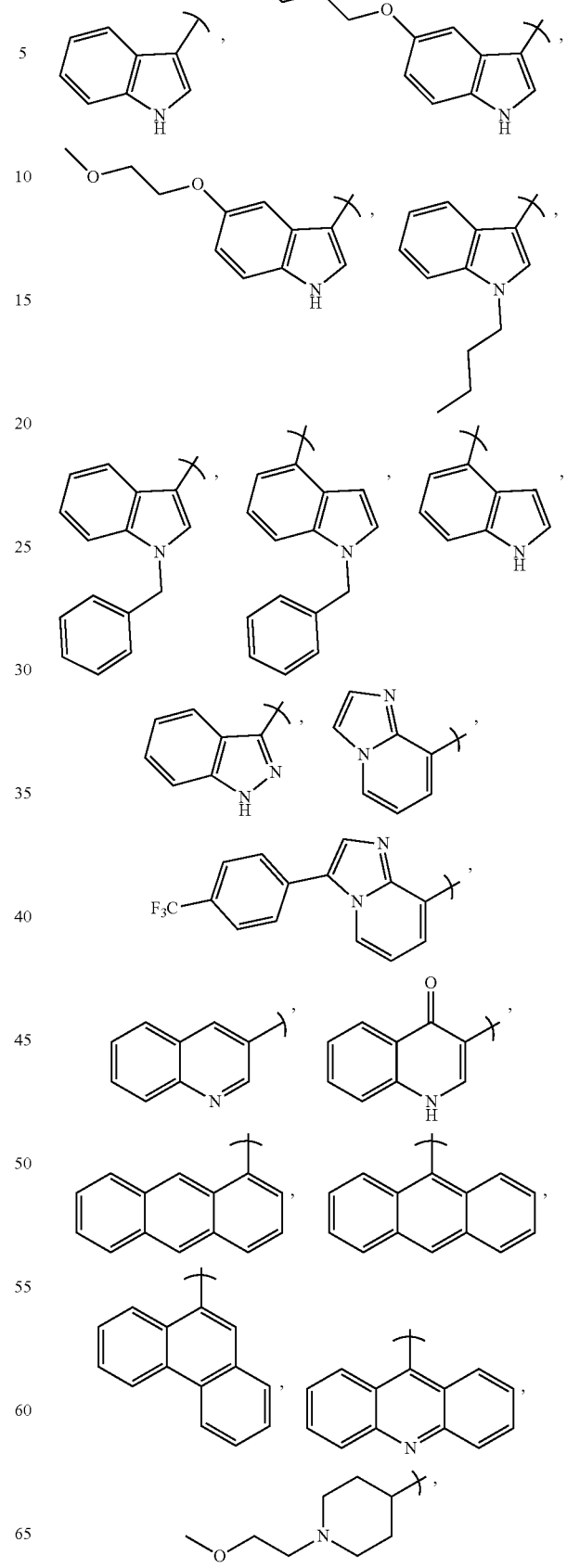

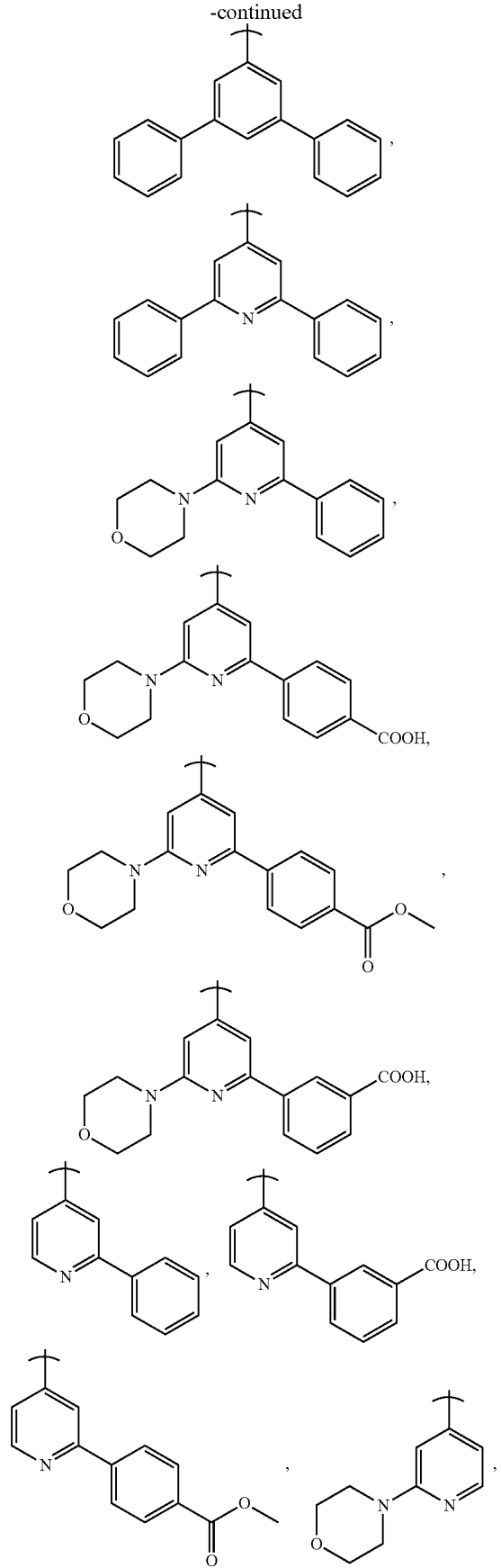
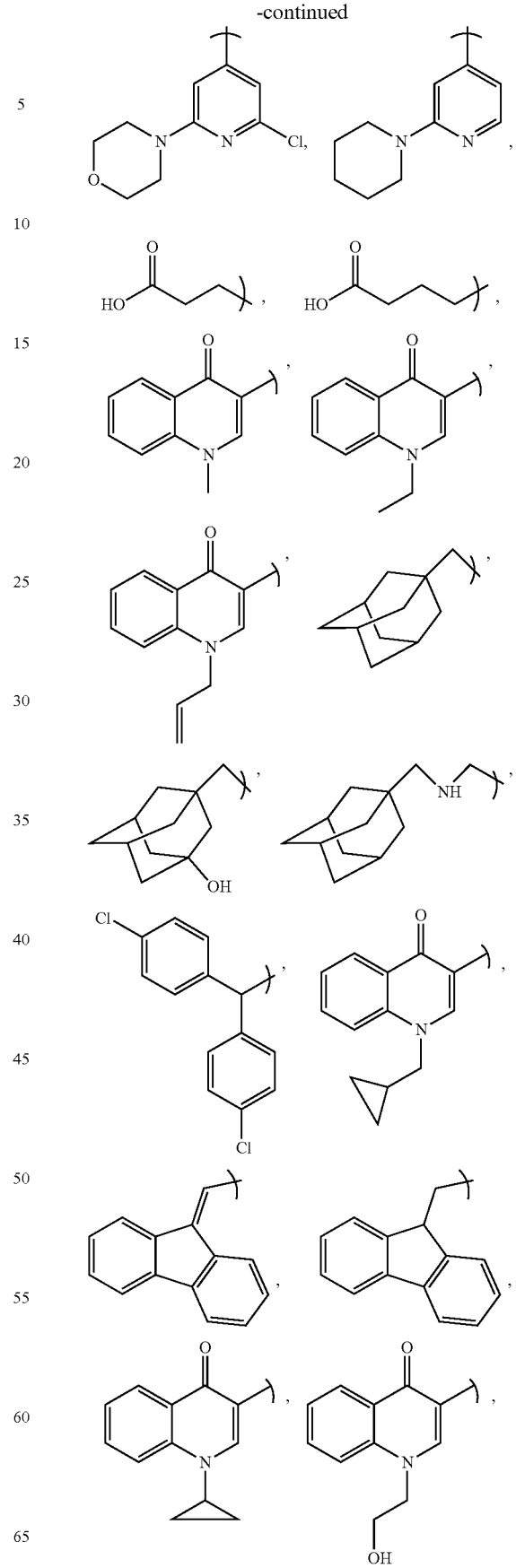

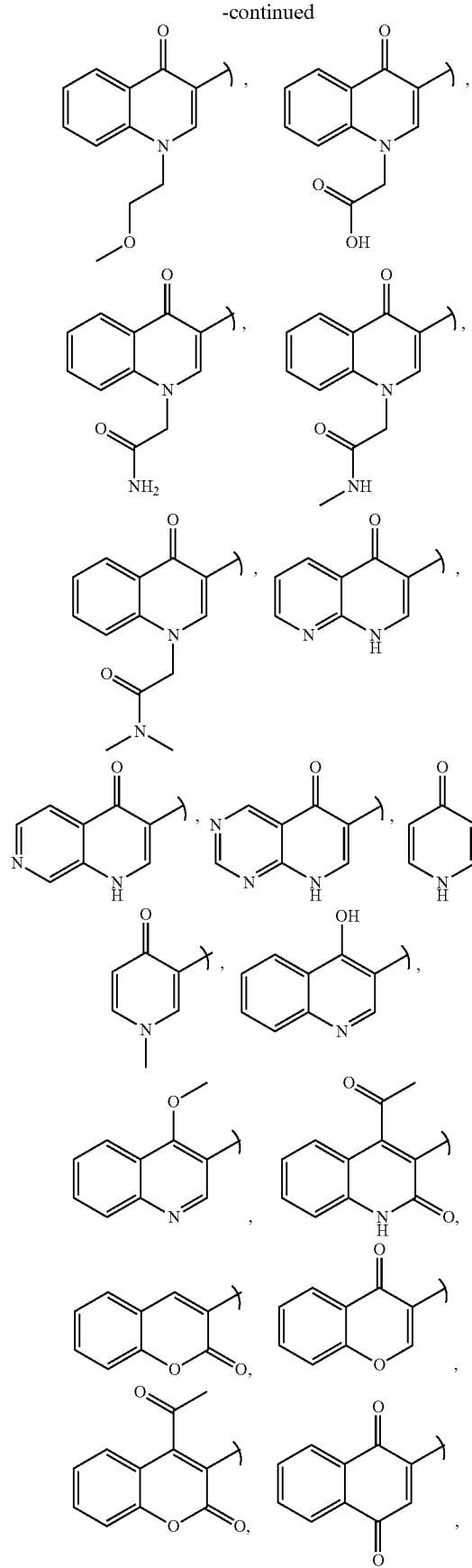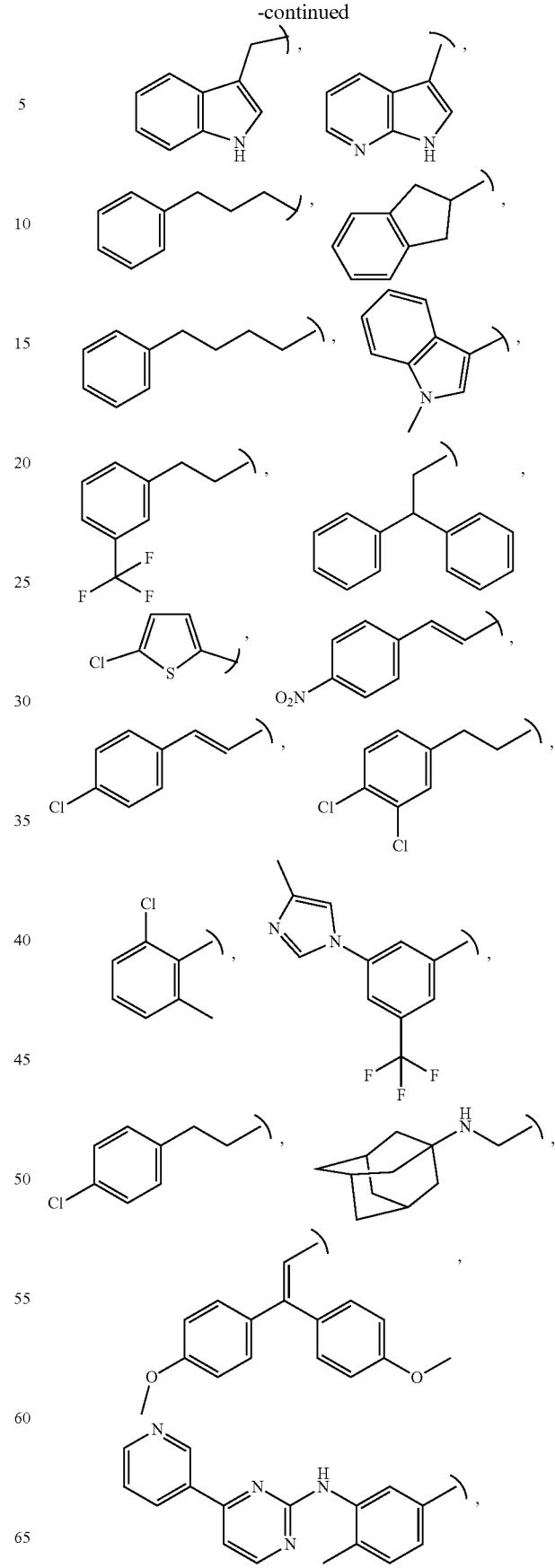

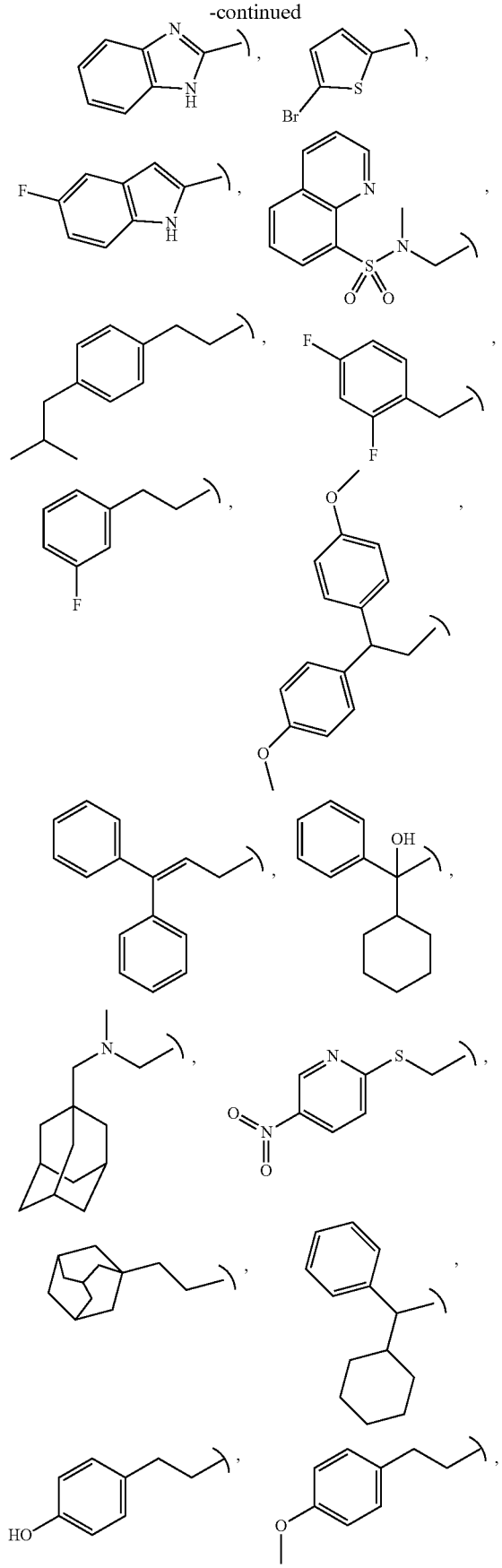
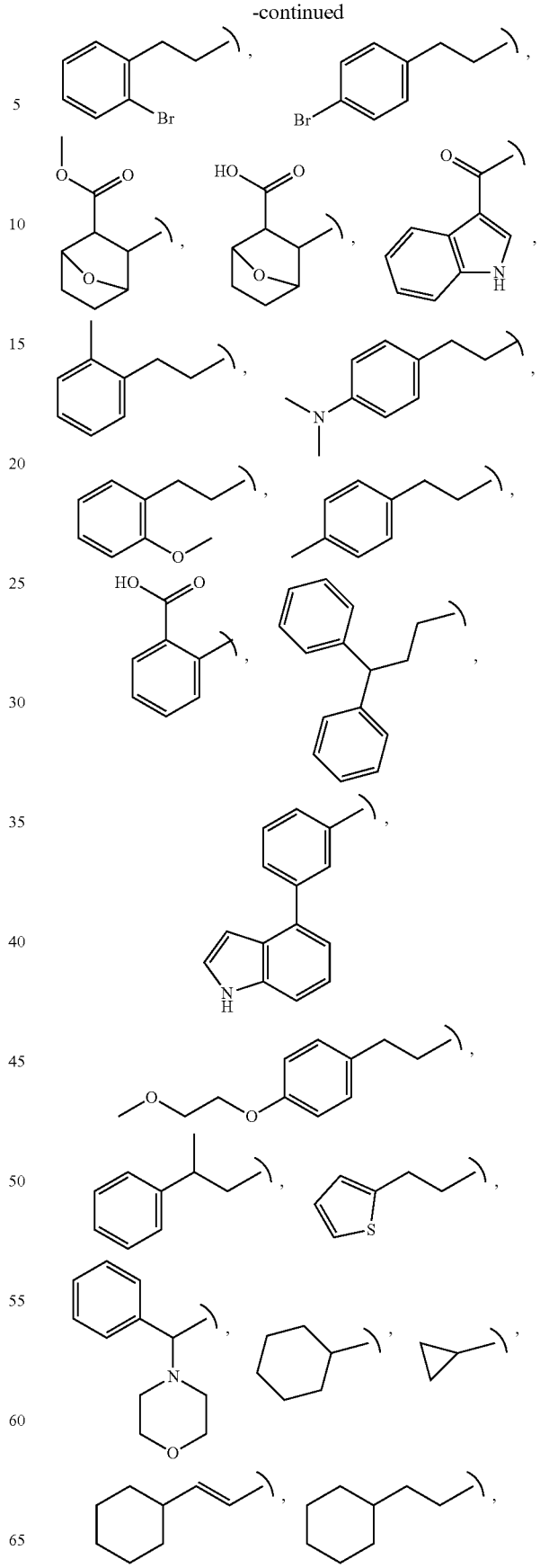

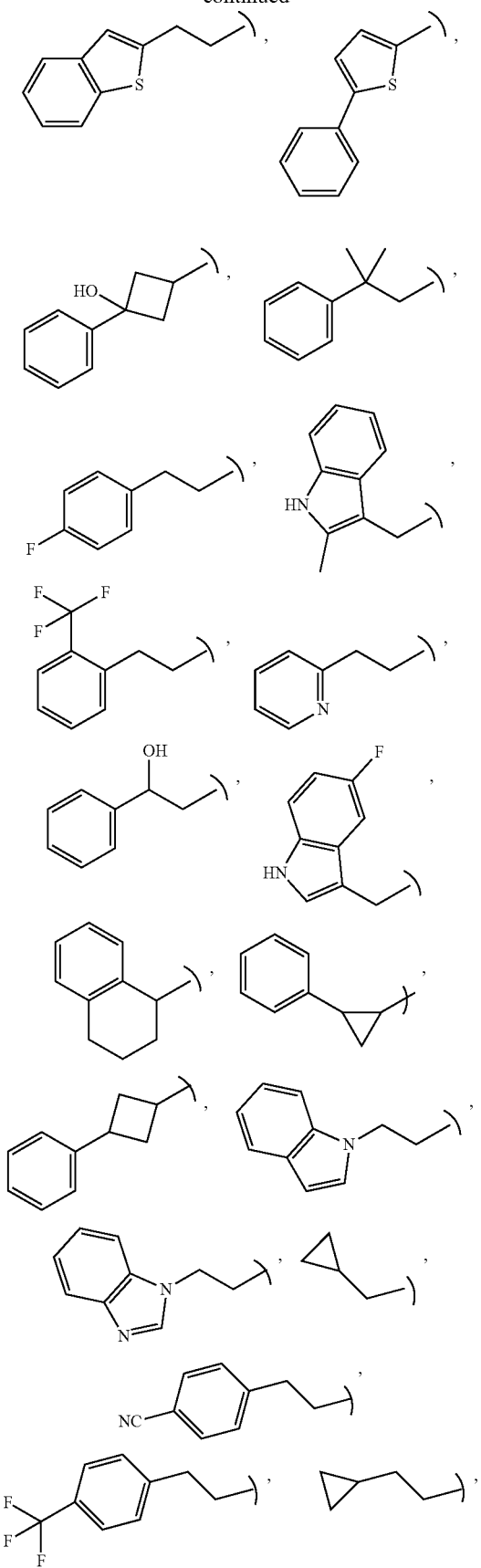
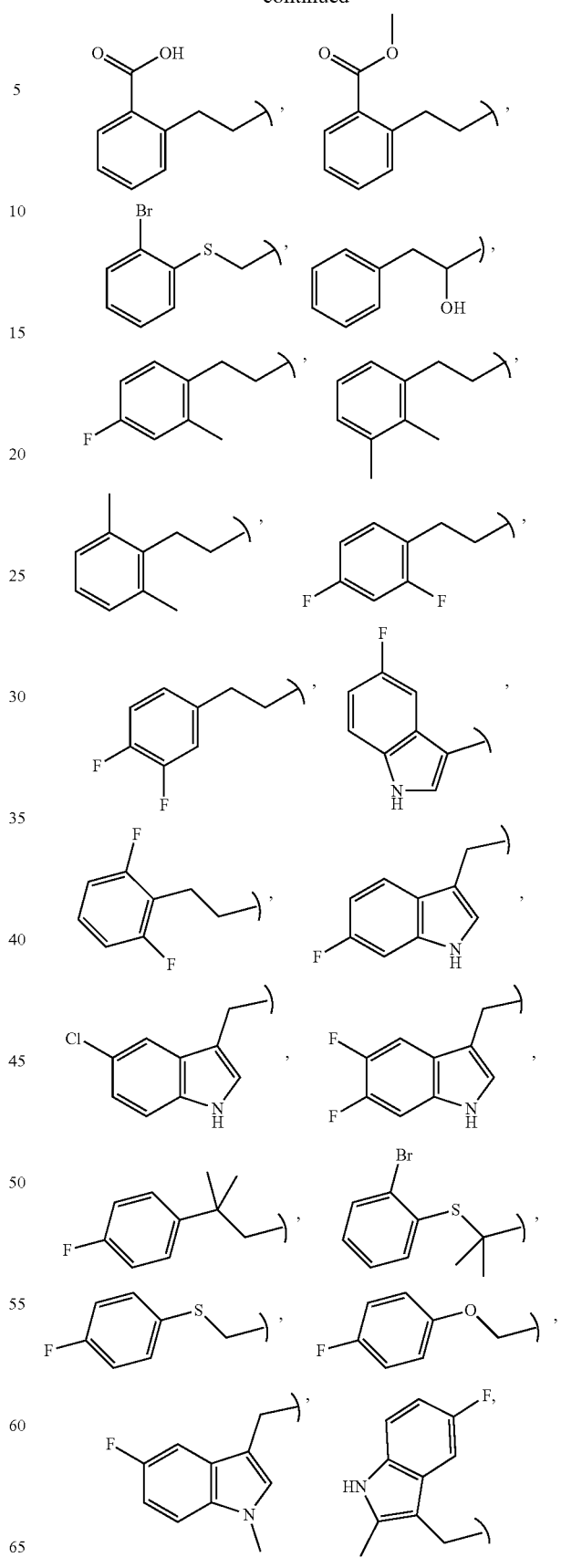

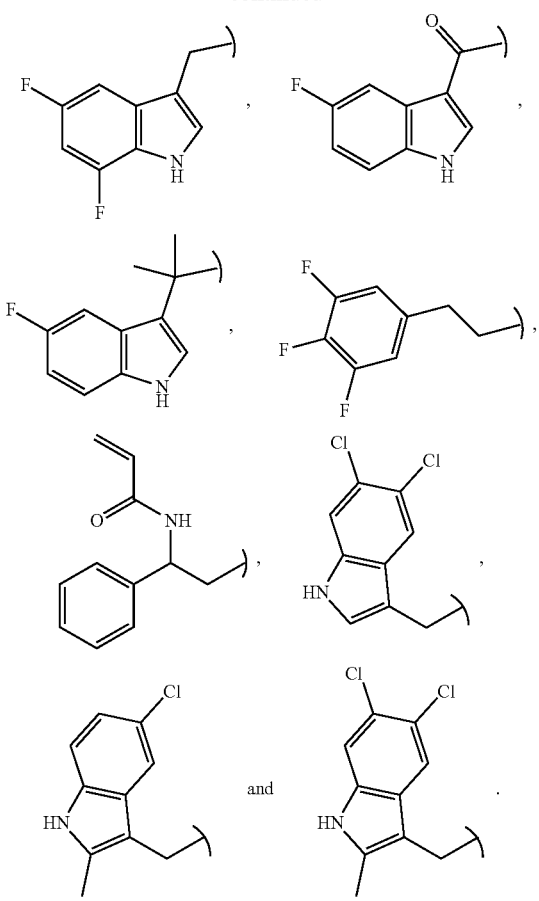
2. A compound of Formula I
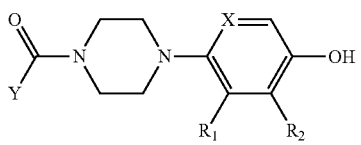
Formula I
or a pharmaceutically acceptable salt, stereoisomer or deuterated analog thereof, wherein
X is nitrogen;
$R_1$ is selected from hydrogen, —$CH_3$, —COOH, fluoro and —CN;
$R_2$ is selected from hydrogen, —$CH_3$, —COOH, fluoro and —CN; and
Y is selected from:
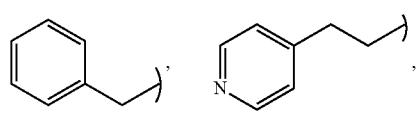
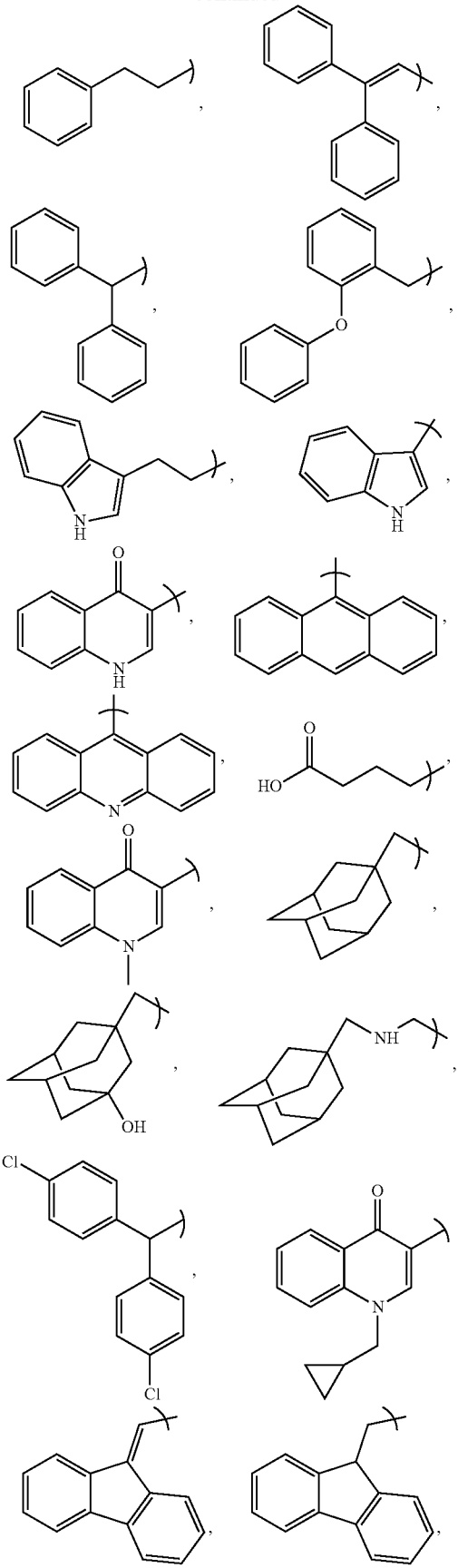

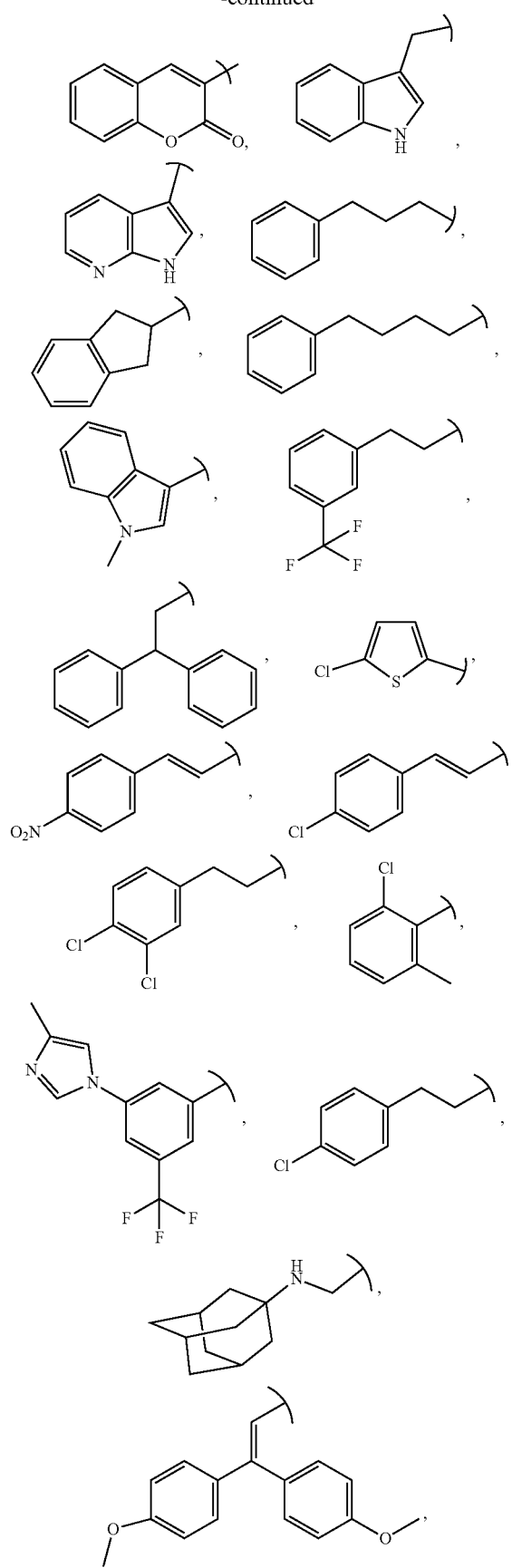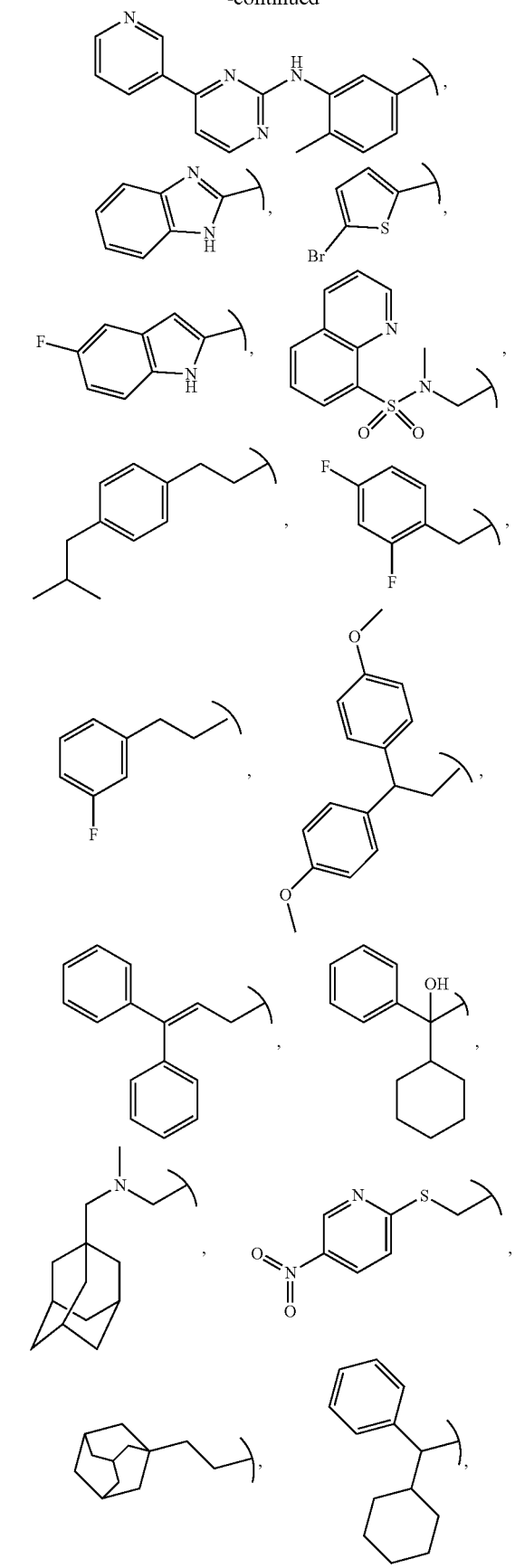

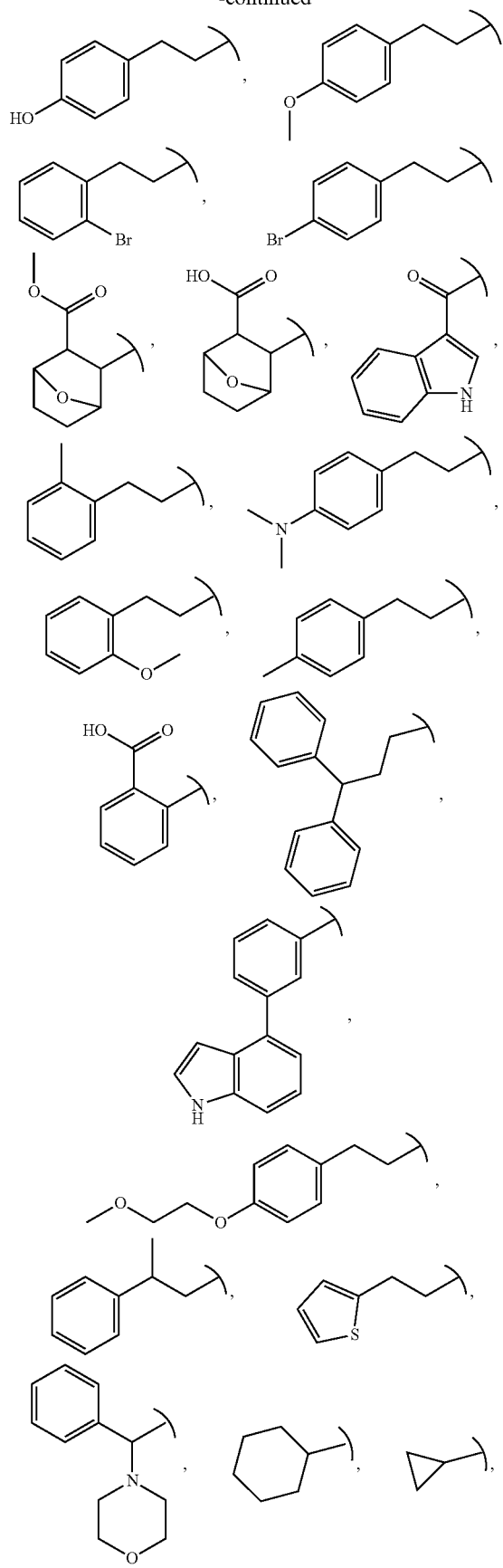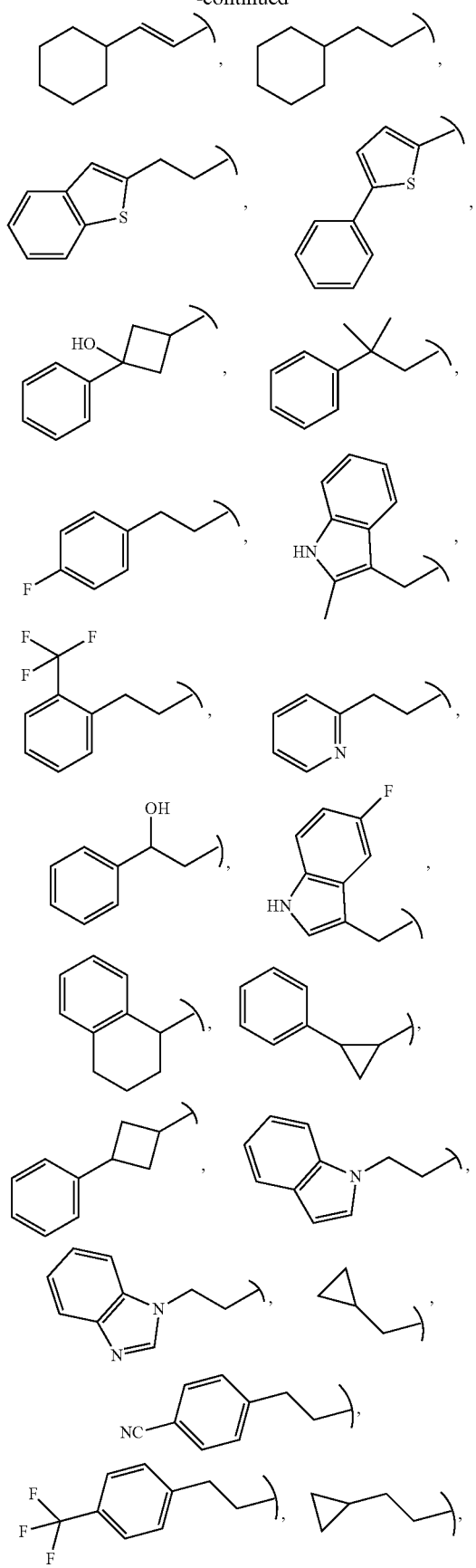

-continued
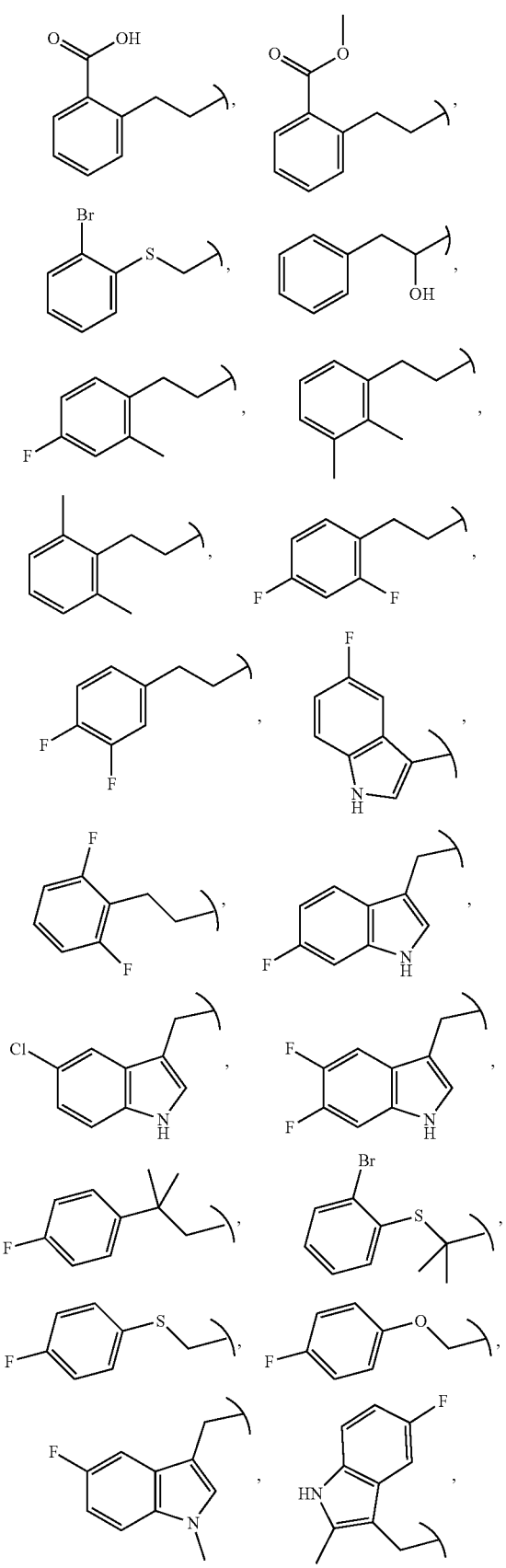
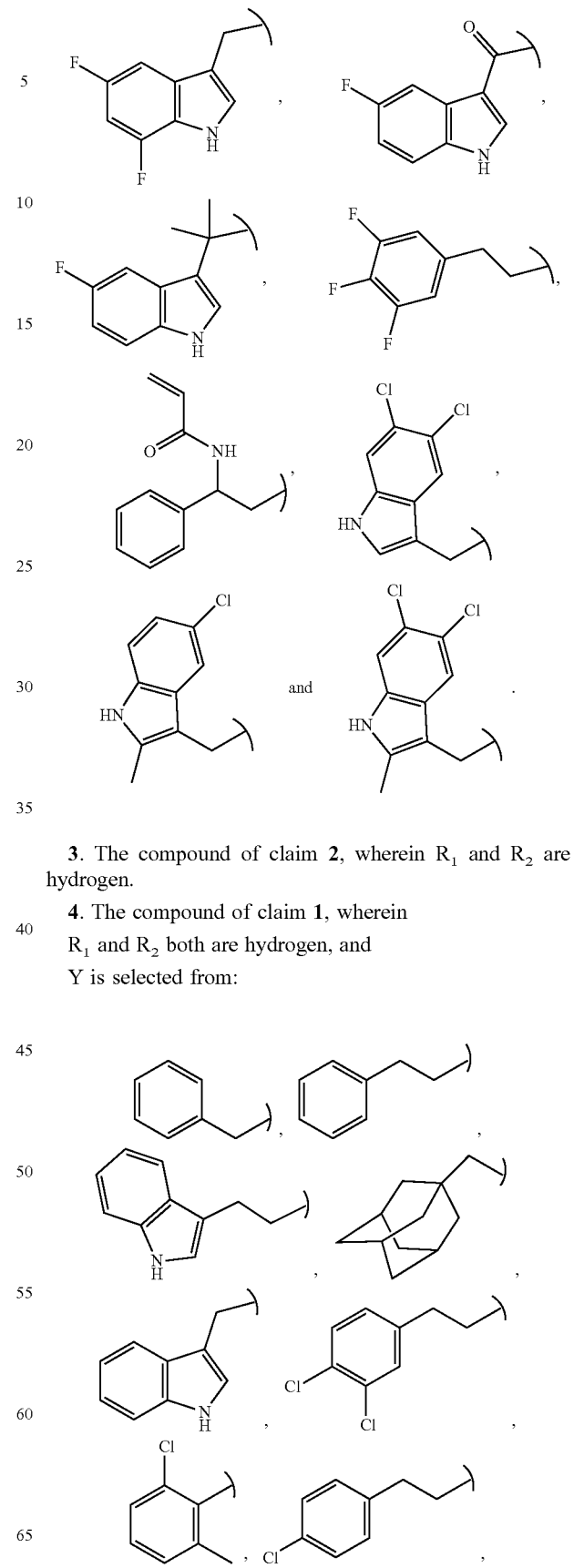
3. The compound of claim 2, wherein $R_1$ and $R_2$ are hydrogen.
4. The compound of claim 1, wherein
$R_1$ and $R_2$ both are hydrogen, and
Y is selected from:

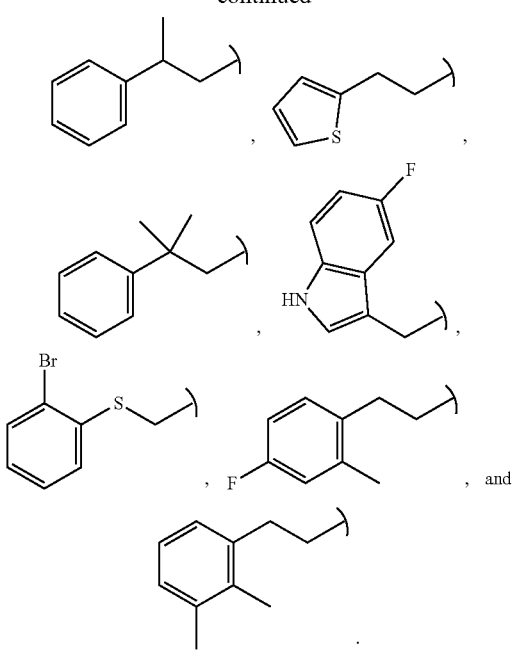
5. The compound of claim 2, wherein $R_1$ and $R_2$ both are hydrogen; and Y is selected from:
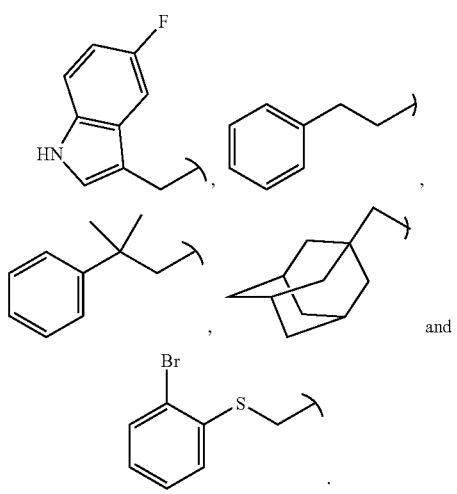
6. The compound of claim 2, wherein $R_1$ and $R_2$ both are hydrogen, and Y is selected from:
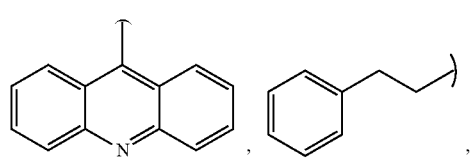
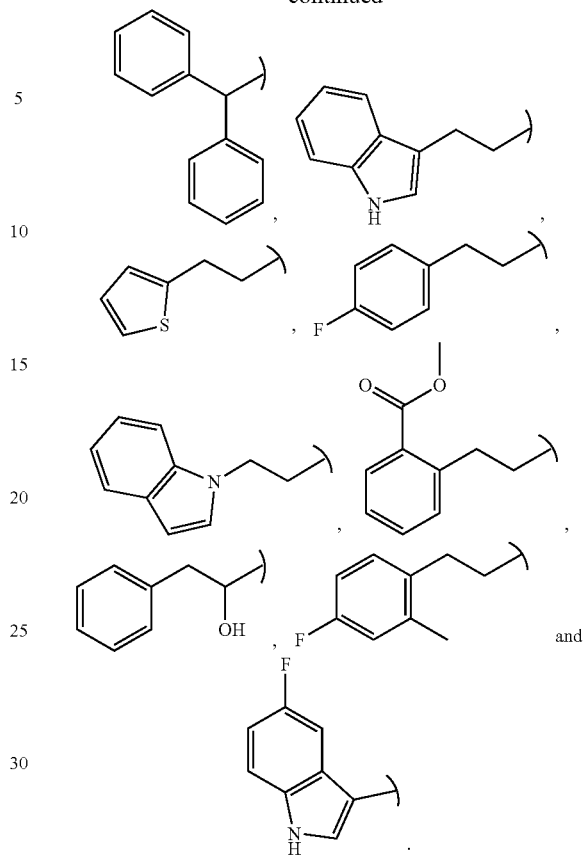
7. The compound of claim 1 wherein $R_1$ and $R_2$ both are hydrogen, and Y is selected from:
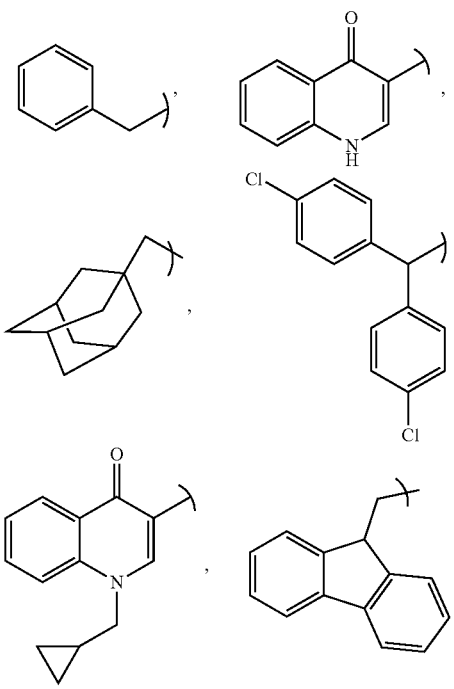

273
-continued
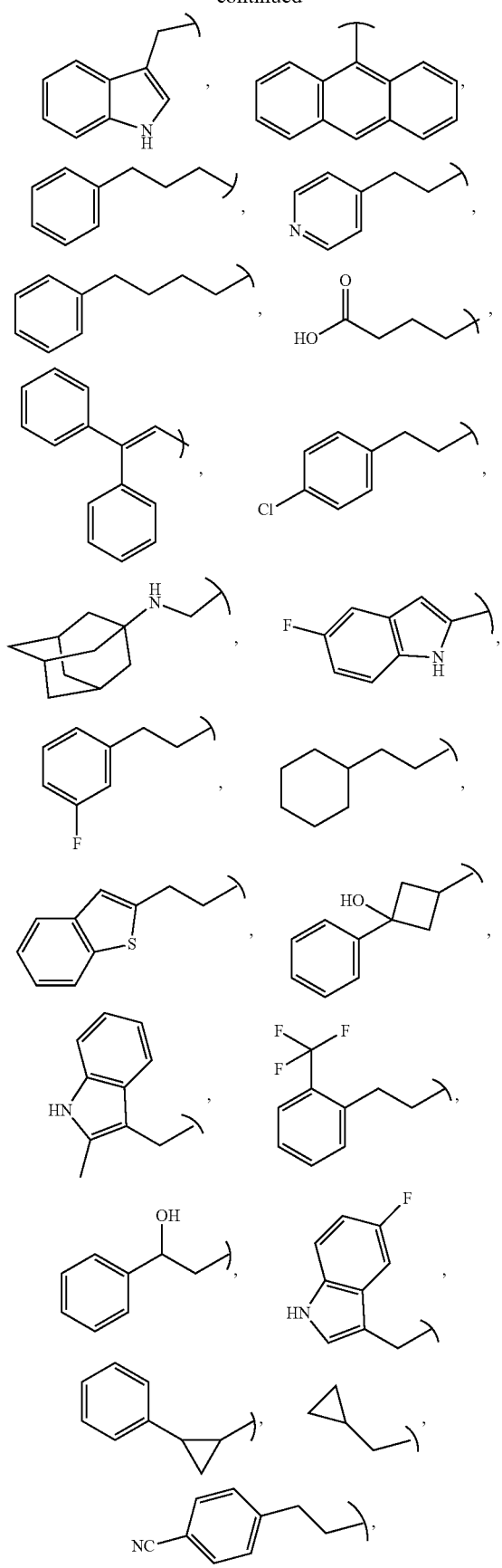
274
-continued
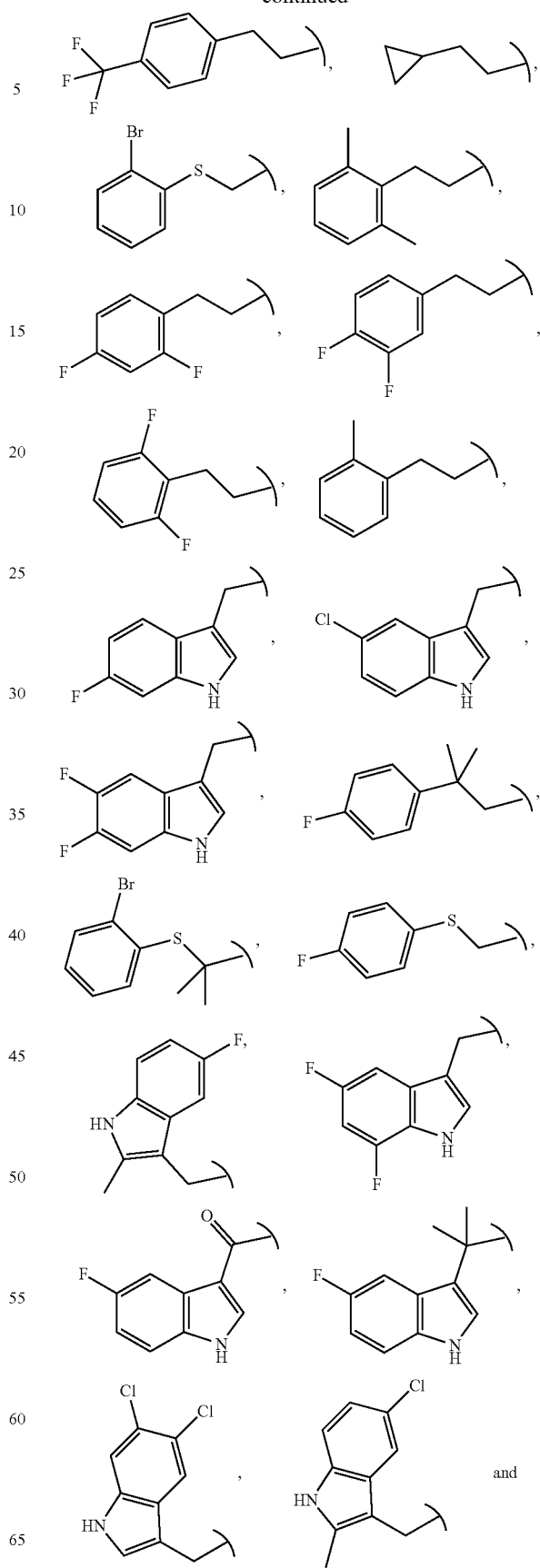

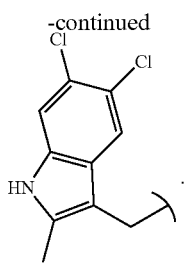

8. A compound selected from
1-[4-(5-Hydroxypyridin-2-yl)-piperazin-1-yl]-2-phenylethanone,
[4-(5-Hydroxypyridin-2-yl)-piperazin-1-yl]-(1H-indol-3-yl)-methanone,
Acridin-9-yl-[4-(5-hydroxy-pyridin-2-yl)-piperazin-1-yl]-methanone,
1-[4-(5-Hydroxypyridin-2-yl)-piperazin-1-yl]-3-phenyl-propan-1-one,
1-[4-(5-Hydroxy-2-pyridyl)piperazin-1-yl]-2,2-diphenyl-ethanone,
1-[4-(5-Hydroxypyridin-2-yl)-piperazin-1-yl]-3-(1H-indol-3-yl)-propan-1-one,
3-[4-(5-Hydroxy-2-pyridyl)piperazine-1-carbonyl]-1H-quinolin-4-one,
2-(1-Adamantyl)-1-[4-(5-hydroxy-2-pyridyl)piperazin-1-yl]ethanone,
2-(3-Hydroxy-1-adamantyl)-1-[4-(5-hydroxy-2-pyridyl)piperazin-1-yl]ethanone,
2-(1-Adamantylmethylamino)-1-[4-(5-hydroxy-2-pyridyl)piperazin-1-yl]ethanone,
2,2-Bis(4-chlorophenyl)-1-[4-(5-hydroxy-2-pyridyl)piperazin-1-yl]ethanone,
1-(Cyclopropylmethyl)-3-[4-(5-hydroxy-2-pyridyl)piperazine-1-carbonyl]quinolin-4-one,
2-Fluoren-9-ylidene-1-[4-(5-hydroxy-2-pyridyl)piperazin-1-yl]ethanone,
2-(9H-Fluoren-9-yl)-1-[4-(5-hydroxy-2-pyridyl)piperazin-1-yl]ethanone,
1-[4-(5-Hydroxypyridin-2-yl)-piperazin-1-yl]-2-(1H-indol-3-yl)-ethanone,
[4-(5-Hydroxypyridin-2-yl)-piperazin-1-yl]-(1H-pyrrolo[2,3-b]pyridin-3-yl)-methanone,
Anthracen-9-yl-[4-(5-hydroxypyridin-2-yl)-piperazin-1-yl]-methanone,
1-[4-(5-Hydroxypyridin-2-yl)-piperazin-1-yl]-4-phenylbutan-1-one,
1-[4-(5-Hydroxypyridin-2-yl)-piperazin-1-yl]-3-pyridin-4-yl-propan-1-one,
[4-(5-Hydroxypyridin-2-yl)-piperazin-1-yl]-indan-2-yl-methanone,
1-[4-(5-Hydroxypyridin-2-yl)-piperazin-1-yl]-5-phenyl-pentan-1-one,
3-[4-(5-Hydroxy-2-pyridyl)piperazine-1-carbonyl]-1-methylquinolin-4-one,
5-[4-(5-Hydroxy-2-pyridyl)piperazin-1-yl]-5-oxo-pentanoic acid,
[4-(5-Hydroxypyridin-2-yl)-piperazin-1-yl]-(1-methyl-1H-indol-3-yl)-methanone,
1-[4-(5-Hydroxypyridin-2-yl)-piperazin-1-yl]-3-(3-trifluoromethyl-phenyl)-propan-1-one,
3-[4-(5-Hydroxy-2-pyridyl)piperazine-1-carbonyl]chromen-2-one,
1-[4-(5-Hydroxy-2-pyridyl)piperazin-1-yl]-3,3-diphenyl-prop-2-en-1-one,
1-[4-(5-Hydroxy-2-pyridyl)piperazin-1-yl]-3,3-diphenyl-propan-1-one,
(5-Chlorothiophen-2-yl)-[4-(5-hydroxy-pyridin-2-yl)-piperazin-1-yl]-methanone,
(E)-1-[4-(5-Hydroxypyridin-2-yl)-piperazin-1-yl]-3-(4-nitrophenyl)-propenone,
(E)-3-(4-Chlorophenyl)-1-[4-(5-hydroxypyridin-2-yl)-piperazin-1-yl]-propenone,
3-(3,4-Dichlorophenyl)-1-[4-(5-hydroxypyridin-2-yl)-piperazin-1-yl]-propan-1-one,
(2-Chloro-6-methylphenyl)-[4-(5-hydroxypyridin-2-yl)-piperazin-1-yl]-methanone,
[4-(5-Hydroxypyridin-2-yl)-piperazin-1-yl]-[3-(4-methylimidazol-1-yl)-5-trifluoromethylphenyl]-methanone,
3-(4-Chlorophenyl)-1-[4-(5-hydroxy-pyridin-2-yl)-piperazin-1-yl]-propan-1-one,
2-(1-Adamantylamino)-1-[4-(5-hydroxy-2-pyridyl)piperazin-1-yl]ethanone,
1-[4-(5-Hydroxy-2-pyridyl)piperazin-1-yl]-3,3-bis(4-methoxyphenyl)prop-en-1-one,
[[4-(5-Hydroxypyridin-2-yl)-piperazin-1-yl]-[4-methyl-3-(4-pyridin-3-yl-pyrimidin-2-ylamino)phenyl]-methanone,
(1H-Benzoimidazol-2-yl)-[4-(5-hydroxypyridin-2-yl)-piperazin-1-yl]-methanone,
(5-Bromothiophen-2-yl)-[4-(5-hydroxypyridin-2-yl)-piperazin-1-yl]-methanone,
[(5-Fluoro-1H-indol-2-yl)-[4-(5-hydroxypyridin-2-yl)-piperazin-1-yl]-methanone,
Quinoline-8-sulfonic acid {2-[4-(5-hydroxypyridin-2-yl)-piperazin-1-yl]-2-oxo-ethyl}-methylamide,
1-[4-(5-Hydroxypyridin-2-yl)-piperazin-1-yl]-3-(4-isobutylphenyl)-propan-1-one,
2-(2,4-Difluorophenyl)-1-[4-(5-hydroxypyridine-2-yl)-piperazin-1-yl]-ethanone,
3-(3-Fluorophenyl)-1-[4-(5-hydroxypyridin-2-yl)-piperazin-1-yl]-propan-1-one,
1-[4-(5-Hydroxy-2-pyridyl)piperazin-1-yl]-3,3-bis(4-methoxyphenyl)propan-1-one,
1-[4-(5-Hydroxy-2-pyridyl)piperazin-1-yl]-4,4-diphenyl-but-3-en-1-one,
2-Cyclohexyl-2-hydroxy-1-[4-(5-hydroxy-2-pyridyl)piperazin-1-yl]-2-phenyl-ethanone,
2-[1-Adamantylmethyl(methyl)amino]-1-[4-(5-hydroxy-2-pyridyl)piperazin-1-yl]ethanone,
1-[4-(5-Hydroxypyridin-2-yl)-piperazin-1-yl]-2-(5-nitropyridin-2-ylsulfanyl)-ethanone,
3-(1-Adamantyl)-1-[4-(5-hydroxy-2-pyridyl)piperazin-1-yl]propan-1-one,
2-Cyclohexyl-1-[4-(5-hydroxy-2-pyridyl)piperazin-1-yl]-2-phenyl-ethanone,
3-(4-Hydroxyphenyl)-1-[4-(5-hydroxypyridin-2-yl)-piperazin-1-yl]-propan-1-one,
3-(4-Methoxyphenyl)-1-[4-(5-hydroxypyridin-2-yl)-piperazin-1-yl]-propan-1-one,
3-(2-Bromophenyl)-1-[4-(5-hydroxypyridin-2-yl)-piperazin-1-yl]-propan-1-one,
3-(4-Bromophenyl)-1-[4-(5-hydroxypyridin-2-yl)-piperazin-1-yl]-propan-1-one,
3-[4-(5-Hydroxypyridin-2-yl)-piperazine-1-carbonyl]-7-oxa-bicyclo[2.2.1]heptane-2-carboxylic acid methyl ester,
3-[4-(5-Hydroxypyridin-2-yl)-piperazine-1-carbonyl]-7-oxa-bicyclo[2.2.1]heptane-2-carboxylic acid,
1-[4-(5-Hydroxypyridin-2-yl)-piperazin-1-yl]-2-(1H-indol-3-yl)-ethane-1,2-dione, 1-[4-(5-Hydroxypyridin-2-yl)-piperazin-1-yl]-3-o-tolyl-propan-1-one,
3-(4-Dimethylaminophenyl)-1-[4-(5-hydroxypyridin-2-yl)-piperazin-1-yl]-propan-1-one,
1-[4-(5-Hydroxypyridin-2-yl)-piperazin-1-yl]-3-(2-methoxyphenyl)-propan-1-one,
1-[4-(5-Hydroxypyridin-2-yl)-piperazin-1-yl]-3-p-tolyl-propan-1-one,
2-[4-(5-Hydroxypyridin-2-yl)-piperazine-1-carbonyl]benzoic acid,
1-[4-(5-Hydroxy-2-pyridyl)piperazin-1-yl]-4,4-diphenylbutan-1-one,
[4-(5-Hydroxypyridin-2-yl)-piperazin-1-yl]-[3-(1H-indol-4-yl)phenyl]methanone,
1-[4-(5-Hydroxypyridin-2-yl)-piperazin-1-yl]-3-[4-(2-methoxyethoxy)phenyl]-propan-1-one,
1-[4-(5-Hydroxypyridin-2-yl)-piperazin-1-yl]-3-phenylbutan-1-one,
1-[4-(5-Hydroxypyridin-2-yl)-piperazin-1-yl]-3-thiophen-2-yl-propan-1-one,
1-[4-(5-Hydroxy-2-pyridyl)piperazin-1-yl]-2-morpholino-2-phenylethanone,
Cyclohexyl-[4-(5-hydroxy-2-pyridyl)piperazin-1-yl]methanone,
Cyclopropyl-[4-(5-hydroxy-2-pyridyl)piperazin-1-yl]methanone,
(E)-3-Cyclohexyl-1-[4-(5-hydroxy-2-pyridyl)piperazin-1-yl]prop-2-en-1-one,
3-Cyclohexyl-1-[4-(5-hydroxy-2-pyridyl)piperazin-1-yl]propan-1-one,
3-Benzo[b]thiophen-2-yl-1-[4-(5-hydroxypyridin-2-yl)-piperazin-1-yl]-propan-1-one,
[4-(5-Hydroxypyridin-2-yl)-piperazin-1-yl]-(5-phenylthiophen-2-yl)-methanone,
(3-Hydroxy-3-phenylcyclobutyl)-[4-(5-hydroxypyridin-2-yl)-piperazin-1-yl]-methanone,
1-[4-(5-Hydroxypyridin-2-yl)-piperazin-1-yl]-3-methyl-3-phenylbutan-1-one,
3-(4-Fluorophenyl)-1-[4-(5-hydroxypyridin-2-yl)-piperazin-1-yl]-propan-1-one,
1-[4-(5-Hydroxypyridin-2-yl)-piperazin-1-yl]-2-(2-methyl-1H-indol-3-yl)-ethanone,
1-[4-(5-Hydroxypyridin-2-yl)-piperazin-1-yl]-3-(2-trifluoromethylphenyl)-propan-1-one,
1-[4-(5-Hydroxypyridin-2-yl)-piperazin-1-yl]-3-pyridin-2-yl-propan-1-one,
3-Hydroxy-1-[4-(5-hydroxypyridin-2-yl)-piperazin-1-yl]-3-phenylpropan-1-one,
2-(5-Fluoro-1H-indol-3-yl)-1-[4-(5-hydroxypyridin-2-yl)-piperazin-1-yl]-ethanone,
[4-(5-Hydroxypyridin-2-yl)-piperazin-1-yl]-(1,2,3,4-tetrahydronaphthalen-1-yl)-methanone,
[4-(5-Hydroxypyridin-2-yl)-piperazin-1-yl]4(1R,2R)-2-phenylcyclopropyl)-methanone,
[4-(5-Hydroxypyridin-2-yl)-piperazin-1-yl]-(3-phenylcyclobutyl)-methanone,
1-[4-(5-Hydroxypyridin-2-yl)-piperazin-1-yl]-3-indol-1-yl-propan-1-one,
3-Benzoimidazol-1-yl-1-[4-(5-hydroxypyridin-2-yl)-piperazin-1-yl]-propan-1-one,
2-Cyclopropyl-1-[4-(5-hydroxy-2-pyridyl)piperazin-1-yl]ethanone,
3-(4-Cyanophenyl)-1-[4-(5-hydroxypyridin-2-yl)-piperazin-1-yl]-propan-1-one,
3-(4-Trifluoromethylphenyl)-1-[4-(5-hydroxypyridin-2-yl)-piperazin-1-yl]-propan-1-one,
3-Cyclopropyl-1-[4-(5-hydroxy-2-pyridyl)piperazin-1-yl]propan-1-one,
2-{3-[4-(5-Hydroxypyridin-2-yl)-piperazin-1-yl]-3-oxopropyl}-benzoic acid,
2-{3-[4-(5-Hydroxypyridin-2-yl)-piperazin-1-yl]-3-oxopropyl}-benzoic acid methyl ester,
2-(2-Bromophenylsulfanyl)-1-[4-(5-hydroxypyridin-2-yl)-piperazin-1-yl]-ethanone,
2-Hydroxy-1-[4-(5-hydroxypyridin-2-yl)-piperazin-1-yl]-3-phenyl-propan-1-one,
3-(4-Fluoro-2-methylphenyl)-1-[4-(5-hydroxypyridin-2-yl)-piperazin-1-yl]-propan-1-one,
3-(2,3-Dimethylphenyl)-1-[4-(5-hydroxypyridin-2-yl)-piperazin-1-yl]-propan-1-one,
3-(2,6-Dimethylphenyl)-1-[4-(5-hydroxypyridin-2-yl)-piperazin-1-yl]-propan-1-one,
3-(2,4-Difluorophenyl)-1-[4-(5-hydroxypyridin-2-yl)-piperazin-1-yl]-propan-1-one,
3-(3,4-Difluorophenyl)-1-[4-(5-hydroxypyridin-2-yl)-piperazin-1-yl]-propan-1-one,
(5-Fluoro-1H-indol-3-yl)-[4-(5-hydroxypyridin-2-yl)-piperazin-1-yl]-methanone,
3-(2,6-Difluorophenyl)-1-[4-(5-hydroxypyridin-2-yl)-piperazin-1-yl]-propan-1-one,
2-(6-Fluoro-1H-indol-3-yl)-1-[4-(5-hydroxy-pyridin-2-yl)-piperazin-1-yl]-ethanone,
2-(5-Chloro-1H-indol-3-yl)-1-[4-(5-hydroxy-pyridin-2-yl)-piperazin-1-yl]-ethanone,
2-(5,6-Difluoro-1H-indol-3-yl)-1-[4-(5-hydroxy-pyridin-2-yl)-piperazin-1-yl]-ethanone,
3-(4-Fluoro-phenyl)-1-[4-(5-hydroxy-pyridin-2-yl)-piperazin-1-yl]-3-methyl-butan-1-one,
2-(2-Bromo-phenylsulfanyl)-1-[4-(5-hydroxy-pyridin-2-yl)-piperazin-1-yl]-2-methyl-propan-1-one,
2-(4-Fluoro-phenylsulfanyl)-1-[4-(5-hydroxy-pyridin-2-yl)-piperazin-1-yl]-ethanone,
2-(4-Fluoro-phenoxy)-1-[4-(5-hydroxy-pyridin-2-yl)-piperazin-1-yl]-ethanone,
2-(5-Fluoro-1-methyl-indol-3-yl)-1-[4-(5-hydroxy-pyridin-2-yl)-piperazin-1-yl]-ethanone,
2-(5-Fluoro-2-methyl-1H-indol-3-yl)-1-[4-(5-hydroxy-pyridin-2-yl)-piperazin-1-yl]-ethanone,
2-(5,7-Difluoro-1H-indol-3-yl)-1-[4-(5-hydroxy-pyridin-2-yl)-piperazin-1-yl]-ethanone,
1-(5-Fluoro-1H-indol-3-yl)-2-[4-(5-hydroxy-pyridin-2-yl)-piperazin-1-yl]-ethane-1,2-dione,
2-(5-Fluoro-1H-indol-3-yl)-1-[4-(5-hydroxy-pyridin-2-yl)-piperazin-1-yl]-2-methyl-propan-1-one,
1-[4-(5-Hydroxy-pyridin-2-yl)-piperazin-1-yl]-3-(3,4,5-trifluoro-phenyl)-propan-1-one,
N-{3-[4-(5-Hydroxy-pyridin-2-yl)-piperazin-1-yl]-3-oxo-1-phenyl-propyl}-acrylamide,
2-(5,6-Dichloro-1H-indol-3-yl)-1-[4-(5-hydroxy-pyridin-2-yl)-piperazin-1-yl]-ethanone,
2-(5-Chloro-2-methyl-1H-indol-3-yl)-1-[4-(5-hydroxy-pyridin-2-yl)-piperazin-1-yl]-ethanone,
2-(5,6-Dichloro-2-methyl-1H-indol-3-yl)-1-[4-(5-hydroxy-pyridin-2-yl)-piperazin-1-yl]-ethanone, and
pharmaceutically acceptable salts, stereoisomers, and/or deuterated analogs thereof.

9. A compound selected from:
2-(5-Fluoro-1H-indol-3-yl)-1-[4-(5-hydroxypyridin-2-yl)-piperazin-1-yl]-ethanone,
1-[4-(5-Hydroxypyridin-2-yl)-piperazin-1-yl]-3-phenyl-propan-1-one,
1-[4-(5-Hydroxypyridin-2-yl)-piperazin-1-yl]-3-methyl-3-phenylbutan-1-one, 2-(1-Adamantyl)-1-[4-(5-hydroxy-2-pyridyl)piperazin-1-yl]ethanone, 2-(2-Bromophenylsulfanyl)-1-[4-(5-hydroxypyridin-2-yl)-piperazin-1-yl]-ethanone, and pharmaceutically acceptable salts, stereoisomers, and/or deuterated analogs thereof.

10. A compound selected from:

Acridin-9-yl-[4-(5-hydroxy-pyridin-2-yl)-piperazin-1-yl]-methanone,

1-[4-(5-Hydroxypyridin-2-yl)-piperazin-1-yl]-3-phenyl-propan-1-one,

1-[4-(5-Hydroxy-2-pyridyl)piperazin-1-yl]-2,2-diphenyl-ethanone,

1-[4-(5-Hydroxypyridin-2-yl)-piperazin-1-yl]-3-(1H-indol-3-yl)-propan-1-one,

1-[4-(5-Hydroxypyridin-2-yl)-piperazin-1-yl]-3-thiophen-2-yl-propan-1-one, 3-(4-Fluorophenyl)-1-[4-(5-hydroxypyridin-2-yl)-piperazin-1-yl]-propan-1-one, 1-[4-(5-Hydroxypyridin-2-yl)-piperazin-1-yl]-3-indol-1-yl-propan-1-one, 2-{3-[4-(5-Hydroxypyridin-2-yl)-piperazin-1-yl]-3-oxopropyl}-benzoic acid methyl ester, 2-Hydroxy-1-[4-(5-hydroxypyridin-2-yl)-piperazin-1-yl]-3-phenyl-propan-1-one, 3-(4-Fluoro-2-methylphenyl)-1-[4-(5-hydroxypyridin-2-yl)-piperazin-1-yl]-propan-1-one, (5-Fluoro-1H-indol-3-yl)-[4-(5-hydroxypyridin-2-yl)-piperazin-1-yl]-methanone, and pharmaceutically acceptable salts, stereoisomers, and/or deuterated analogs thereof.

11. A pharmaceutical composition comprising a compound of claim 1 and a pharmaceutically acceptable carrier, diluent, or excipient.

* * * * *